(12) United States Patent
Schuster et al.

(10) Patent No.: US 8,541,462 B2
(45) Date of Patent: Sep. 24, 2013

(54) TETRAHYDROCARBAZOLE DERIVATIVES AS LIGANDS OF G-PROTEIN COUPLED RECEPTORS

(75) Inventors: Tilmann Schuster, Grossostheim (DE); Klaus Paulini, Maintal (DE); Peter Schmidt, Schoeneck (DE); Silke Baasner, Schoeneck (DE); Emmanuel Polymeropoulos, Frankfurt (DE); Eckhard Guenther, Maintal (DE); Michael Teifel, Weiterstadt (DE)

(73) Assignee: AEterna Zentaris GmbH, Frankfurt (DE)

( * ) Notice: Subject to any disclaimer, the term of this patent is extended or adjusted under 35 U.S.C. 154(b) by 0 days.

(21) Appl. No.: 13/358,055

(22) Filed: Jan. 25, 2012

(65) Prior Publication Data

US 2012/0122763 A1 May 17, 2012

Related U.S. Application Data

(62) Division of application No. 12/109,479, filed on Apr. 25, 2008, now Pat. No. 8,148,546.

(60) Provisional application No. 60/914,424, filed on Apr. 27, 2007.

(30) Foreign Application Priority Data

Apr. 27, 2007 (EP) .................................. 07107094

(51) Int. Cl.
*A61K 31/403* (2006.01)
*C07D 209/82* (2006.01)
(52) U.S. Cl.
USPC .......................................... 514/411; 548/448

(58) Field of Classification Search
USPC .......................................... 514/411; 548/448
See application file for complete search history.

(56) References Cited

FOREIGN PATENT DOCUMENTS

| WO | 03051837 | 6/2003 |
|---|---|---|
| WO | 2006005484 | 1/2006 |

OTHER PUBLICATIONS

Koppitz et al. (WO 03051837, CAPLUS Abstract of WO 03051837).*
Kubinyi (3D QSAR in Drug Design: Ligand-Protein Interactions and Molecular Similarity, vol. 2-3, Springer, 1998, 800 pages). pp. 243-244 provided.*
Tatsuta et al. (Bioorg. Med. Chem. Lett. 15 (2005) 2265-2269).*
Wermuth, The Practice of Medicinal Chemsitry, 2d ed. (2003), 768 pages. Chapters 9-10 provided.*
Park et al. (Toxicology Lett., 120 (2001), 281-91).*
Kubinyi (3D QSAR in Drug Design: Ligand-Protein Interactions and Molecular Similarity, vol. 2-3, Springer, 1998, 800 pages), TOC, pp. 243-244 provided.
Tatsuta et al., (Bioorg. Med. Chem. Lett. 15 (2005) 2265-2269.
Wermuth, The Practice of Medicinal Chemistry, 2d ed. (2003), 768 pages,. chs. 9-10 provided.
CAPLUS Abstract of WO 03051837, (2003).

* cited by examiner

*Primary Examiner* — Robert Havlin
(74) *Attorney, Agent, or Firm* — Oblon, Spivak, McClelland, Maier & Neustadt, L.L.P.

(57) ABSTRACT

The present invention provides novel tetrahydrocarbazole compounds according to formula (I) as ligands of G-protein coupled receptors (GPCR) which are useful in the treatment and/or prophylaxis of physiological and/or pathological conditions in mammals mediated by GPCR or of physiological and/or pathological conditions which can be treated by modulation of these receptors.

20 Claims, 2 Drawing Sheets

TETRAHYDROCARBAZOLE DERIVATIVES AS LIGANDS OF G-PROTEIN COUPLED RECEPTORS

CROSS-REFERENCE TO RELATED APPLICATIONS

This application is a divisional of U.S. application Ser. No. 12/109,479 filed Apr. 25, 2008, now U.S. Pat. No. 8,148,546, and claims the benefit of U.S. application 60/914,424 filed Apr. 27, 2007.

DESCRIPTION OF THE INVENTION

1. Field of the Invention

The present invention relates to novel tetrahydrocarbazole derivatives as ligands of G-protein coupled receptors (GPCRs), in particular as ligands of the luteinizing hormone releasing hormone (LHRH) receptor, processes of manufacturing thereof and uses for the treatment and/or prophylaxis of physiological and/or pathophysiological conditions in mammals, in particular in humans.

2. Description of Related Art

G-protein coupled receptors represent a superfamily of cell membrane-associated receptors which play an important part in numerous biochemical and pathobiochemical processes in mammals and especially in humans. All GPCRs consist of seven hydrophobic, transmembrane alpha-helical domains which are connected together by three intracellular and three extracellular loops and have an extracellular amino terminus and an intracellular carboxy terminus. One or more heterotrimeric G proteins are involved in their cellular signal transduction. Diverse physiological stimuli such as photosensitivity, taste and odor, but also fundamental processes such as metabolism, reproduction and development are mediated and controlled by them. GPCRs exist for exogenous and endogenous ligands. Peptide hormones, biogenic amines, amino acids, nucleotides, lipids, $Ca^{2+}$, but also photons, have inter alia been identified as ligands; moreover one ligand may activate different receptors.

According to a recent investigation, 367 sequences have been identified in the human genome for G-protein coupled receptors (GPCRs) with endogenous ligands (Vassilatis D K et al., PNAS 2003, 100(8): 4903-4908). Of these, 284 belong to class A, 50 to class B, 17 to class C and 11 to class F/S. Examples belonging to class A are the bombesin, the dopamine and the LHRH receptors, and to class B are the VIP and the calcitonin receptors. The natural ligands for numerous GPCRs are as yet unknown.

Owing to their function, GPCRs are suitable as targets for medicaments for the therapy and prevention of a large number of pathological conditions. It is speculated that about 50% of currently known targets for active ingredients are GPCRs (Fang Y et al., DDT 2003, 8(16): 755-761). Thus, GPCRs play an important part in pathological processes such as, for example, pain (opioid receptor), asthma (beta2-adrenoceptor), migraine (serotonin 5-HT1B/1D receptor), cancer (LHRH receptor), cardiovascular disorders (angiotensin receptor), metabolic disorders (GHS receptor) or depression (serotonin 5-HT$_{1a}$ receptor) (Pierce K L et al., Nat. Rev. Mol. Cell. Biol. 2002, 3: 639-650). General information about GPCRs is to be found under http://www.gpcr.org.

The natural ligand of this receptor, the peptide hormone LHRH, is synthesized in cells of the hypothalamus and released in pulsatile fashion from the hypothalamic neurons into the capillary plexus of the ementia mediana. In the anterior lobe of the pituitary, LHRH binds to the LHRH receptors of the gonadotropic cells and stimulates certain trimeric G-proteins, which initiate a branched signal transduction cascade. The initial event is activation of phospholipase C, $A_2$ and/or D. This leads to an increased provision of the second messengers diacylglycerol and $IP_3$, followed by $Ca^{2+}$ mobilization from intracellular pools, and activation of various subordinate protein kinases. Finally, there is stimulation of the production and temporally defined pulsatile release of the gonadotropins FSH and LH. The two hormones are transported via the circulation to the target organs the testes and ovaries respectively. There they stimulate the production and release of the appropriate sex hormones. In the opposite direction there is a complex feedback mechanism by which the concentration of the sex hormones formed in turn regulates the release of LH and FSH.

In the male organism, LH binds to membrane receptors of the Leydig cells and stimulates testosterone biosynthesis. FSH acts via specific receptors on the Sertoli cells and assists the production of spermatozoa. In the female organism, LH binds to the LH receptors of the theca cells and activates the formation of androgen-synthesizing enzymes. FSH stimulates proliferation of granulosa cells of certain follicle stages via the FSH receptors thereof. The androgens which are formed are converted in the adjacent granulosa cells to the estrogens estrone and estradiol.

A number of disorders distinguished by benign or malignant tissue proliferations depend on stimulation by sex hormones such as testosterone or estradiol. Typical disorders of this type are prostate cancer and benign prostate hyperplasia (BPH) in men, and endometriosis, uterine fibroids or uterine myomas, pubertas praecox, hirsutism and polycystic ovary syndrome, and breast cancer, uterine cancer, endometrial cancer, cervical cancer and ovarian cancer in women.

Since its discovery in 1971 by Schally et al. (Schally A et al., Science 1971, 173: 1036-1038) more than 3000 synthetic analogues of natural LHRH have been synthesized and tested. Peptide agonists such as triptorelin and leuprolide have been established for many years successfully in the therapy of gynecological disorders and cancers. However, the disadvantage of agonists is generally that they stimulate LHRH receptors in the initial phase of use and thus lead to side effects via an initial increase in the sex hormone levels. Only after down-regulation of the LHRH receptor as a result of this overstimulation can the superagonists display their effect. This leads to a complete reduction in the sex hormone levels and thus to pharmacological castration with all the signs and symptoms. This disadvantage is associated with the impossibility of targeted adjustment of the level of sex hormones via the dosage. Thus, therapy of diseases which do not require a total reduction of the sex hormone levels to the castration level, such as, for example, benign tissue proliferations, with an agonist is not optimal for the patient.

This has led to the development of peptide LHRH receptor antagonists, of which, for example, cetrorelix (Cetrotide®) has been successfully introduced for controlled ovarian stimulation in the context of the treatment of female infertility. The antagonists inhibit the LHRH receptor immediately and dose-dependently, and thus lead to an immediate reduction in the plasma levels of testosterone or estradiol and progesterone. The peptide antagonists are, however, somewhat less potent than the agonists, and thus higher doses must be given.

Reviews of the clinical applications and the potential of LHRH agonists and antagonists are given by Millar R P et al. (Millar R P et al., British Med. Bull. 2000, 56: 761-772), Felberbaum R E et al. (Felberbaum R E et al., Mol. Cell. Endocrinology 2000, 166: 9-14) and Haviv F et al. (Haviv F et al., Integration of Pharmaceutical Discovery and Development: Case Studies, Chapter 7, ed. Borchardt et al., Plenum Press, New York 1998).

Besides the treatment of malignant and benign neoplastic diseases, further possible applications are controlled ovarian stimulation in the context of in vitro fertilization, fertility control (contraception), and protection from unwanted side effects of radio- or chemotherapy, the treatment of HIV infections (AIDS) and of neurological or neurodegenerative disorders such as Alzheimer's disease. Specific LHRH receptors have not only been found on pituitary cells, but also on cells in various tumors, e.g. of the breast and ovaries. These receptors might mediate a direct antiproliferative effect of LHRH receptor antagonists on the tumor.

The peptide LHRH receptor agonists and antagonists are mostly decapeptides whose bioavailability is inadequate for oral administration. They are typically given as solutions for injection or as depot formulation, subcutaneously or intramuscularly. This application is associated with inconveniences for the patient, and the compliance suffers. In addition, synthesis of the decapeptides is complicated and costly.

Compared with peptide LHRH receptor agonists and antagonists, as yet no non-peptide compound is approved and in clinical use for any of the possible indications. The current state of development in the area of LHRH receptor agonists and antagonists is described in the reviews by Zhu Y F et al., Expert Opin. Therap. Patents 2004, 14(2): 187-199, Zhu Y F et al., Ann. Rep. Med. Chem. 2004, 39: 99-110, Tucci F C et al., Curr. Opin. Drug Discovery & Development 2004, 7(6): 832-847, Armer R E, Curr. Med. Chem. 2004, 11: 3017-3028, Chengalvala M V et al., Curr. Med. Chem-Anti-Cancer Agents 2003, 3: 399-410. The former publication contains a comprehensive list of the published patent specifications describing the synthesis and use of low molecular weight LHRH receptor antagonists.

Among the first examples of non-peptide LHRH receptor antagonists is the 4-oxothieno[2,3-b]pyridine structure, which was described by Cho N et al. (Cho N et al., J. Med. Chem. 1998, 41: 4190-4195). Although these compounds, such as, for example, T-98475, have a high receptor affinity, their solubility in water is very poor and their bioavailability is low. Based on this lead structure, numerous further developments have been carried out, examples which may be mentioned being the publications of the international applications WO 95/28405, WO 96/24597, WO 97/14697 and WO 97/41126. The synthesis of thieno[2,3-d]pyrimidine-2,4-diones as orally available LHRH receptor antagonists is described by Sasaki S et al., (Sasaki S et al., J. Med. Chem. 2003, 46: 113-124).

Novel 1-arylmethyl-5-aryl-6-methyluracils are described by Guo Z et al. (Guo Z et al., J. Med. Chem. 2004, 47: 1259-1271). The preparation of N-[(hetero)arylmethyl]-benzenesulfonamides as potent non-peptide LHRH receptor antagonists is disclosed in WO 03/078398. The patent application WO 02/11732 describes tricyclic pyrrolidines as LHRH receptor antagonists. Substituted pyridin-4-ones as LHRH receptor antagonists are disclosed in WO 03/13528 and substituted 1,3,5-triazine-2,4,6-triones in WO 03/11839.

The syntheses and biological activities of erythromycin A derivatives having LHRH receptor antagonistic activity is described by Randolph J T et al. (Randolph J T et al., J. Med. Chem. 2004, 47(5): 1085-1097). Selected derivatives show an oral activity on the LH level in the castrated rats model.

Quinoline derivatives as non-peptide LHRH antagonists are disclosed for example in WO 97/14682. Substituted 2-arylindoles are described inter alia in WO 97/21435, WO 97/21703, WO 98/55116, WO 98/55470, WO 98/55479, WO 99/21553, WO 00/04013 as LHRH receptor antagonists. Correspondingly substituted aza-2-arylindoles are claimed inter alia in WO 99/51231, WO 99/51596, WO 00/53178 and WO 00/53602 as LHRH receptor antagonists. Advantageous biological or biophysical data for these compounds are not disclosed.

Patent EP 0 679 642 B1 describes fused heterocyclic compounds as LHRH receptor antagonists. However, a basic tetrahydrocarbazole structure is not the subject matter of the invention described therein.

1,2,3,4-Tetrahydrocarbazolecarboxylic acids are described in patent EP 0 239 306 B1 as prostaglandin antagonists. An LHRH receptor antagonistic effect is neither described nor obvious.

U.S. Pat. No. 3,970,757 discloses tetrahydrocarbazole derivatives as gastric anti-secretory agents. However, an LHRH receptor antagonistic effect of this type of structure is neither described nor obvious.

EP 0 603 432 B1 and U.S. Pat. No. 5,708,187 describe tetrahydrocarbazole derivatives as 5-HT1 agonists inter alia for the treatment of migraine. However, an LHRH receptor antagonistic effect is neither described nor obvious.

WO 2005/033099 A2 describes tetrahydrocarbazole derivatives as dipeptidyl peptidase IV inhibitors. However, an LHRH receptor antagonistic effect is neither described nor obvious. There is no reference to an LHRH receptor antagonistic effect, and the disclosed structures differ from the compounds of the present invention.

Davies D J et al. describe tetrahydrocarbazole derivatives having a melatonin agonistic or antagonistic effect (Davies D J et al., J. Med. Chem. 1998, 41: 451-467). However, an LHRH receptor antagonistic effect is neither described nor obvious.

Tetrahydrocarbazole derivatives are described by Shuttleworth S J et al. as partial agonists of the neuromedin B receptor (Shuttleworth S J et al., Bioorg. Med. Chem. Lett. 2004, 14: 3037-3042). However, an LHRH receptor antagonistic effect is neither described nor obvious.

Millet R et al. describe tetrahydrocarbazole derivatives as $NK_1/NK_2$ ligands. The disclosed structures differ from the compounds of the present invention (Millet R et al., Letters in Peptide Science 1999, 6: 221-233). Moreover, an LHRH receptor antagonistic effect is neither described nor obvious.

Solid-phase synthesis of 3-amino-3'-carboxytetrahydrocarbazoles described by Koppitz et al. (Koppitz et al., THL 2005, 46(6): 911-914). An LHRH receptor antagonistic effect is neither described nor obvious.

Tetrahydrocarbazole derivatives as peptidomimetic LHRH receptor antagonists having good receptor affinity are disclosed for example in WO 03/051837. The physicochemical and metabolic properties of these compounds do not, however, make them suitable in an optimal manner for an oral dosage form.

A number of publications provide an overview of the state of development of neurokinin antagonists:

Giardina G et al. provide an overview of the current patent literature (Giardina G et al., IDrugs 2003, 6(8): 758-772), Leroy V et al. (Leroy V et al., Expert Opinion on Investigational Drugs 2000, 9(4), 735-746) and Swain C et al. (Swain C et al., Annual Reports in Medicinal Chemistry 1999, 34: 51-60) describe the state of development relating to neurokinin receptor antagonists, while, for example, Navari R M et al. (Navari R M et al., Cancer Investigation 2004, 22(4): 569-576) describes the results of clinical studies in which NK1 receptor antagonists were employed to control chemotherapy-induced emesis.

Hill R G et al. describe neurokinin receptor antagonists as potential analgesics (Hill R G et al., Pain 2003, 523-530), while von Sprecher A et al. describe neurokinin receptor antagonists as potential active ingredients for the therapy of inflammations and rheumatoid arthritis (Sprecher A et al., IDrugs 1998, 1(1): 73-91). Millet R et al. describe tetrahydrocarbazole derivatives as $NK_1/NK_2$ ligands (Millet R et al., Letters in Peptide Science 1999, 6: 221-233). The disclosed structures differ from the compounds of the present invention.

WO 2006/005484 discloses tetrahydrocarbozole derivatives that are said to show improved biological action and improved solubility. These tetrahydrocarbozole derivatives act as ligands for G-protein coupled receptors, in particular LHRH receptor and NK receptors. The disclosed structures differ from the compounds of the present invention.

SUMMARY OF THE INVENTION

The present invention provides novel tetrahydrocarbazole compounds that act as ligands for G-protein coupled receptors (GPCRs) according to that described by formula (I) and other embodiments as described herein.

DETAILED DESCRIPTION OF THE INVENTION

Figure 1:
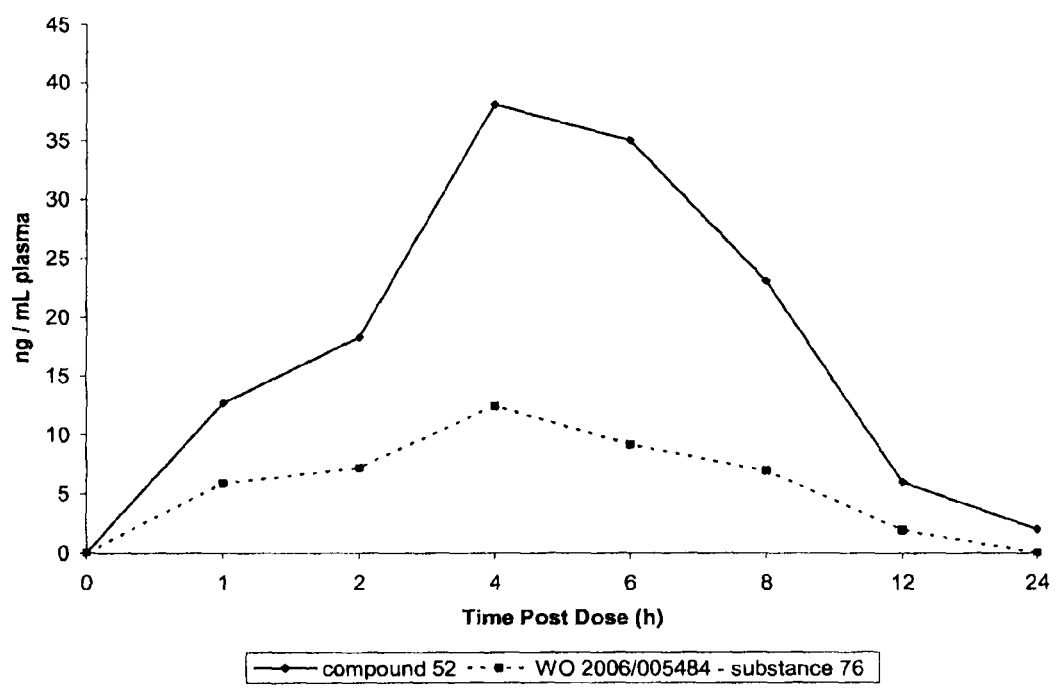
FIG. 1 depicts the results [area-under-the-curve (AUC)] of the pharmacokinetic study according to IV) of the example section for compound 52 of the invention and prior art compound WO 2006/005484—substance 76. The results are indicative for the respective bioavailability.

The object of the present invention has surprisingly been solved in one aspect by providing tetrahydrocarbazole compound according to formula (I),

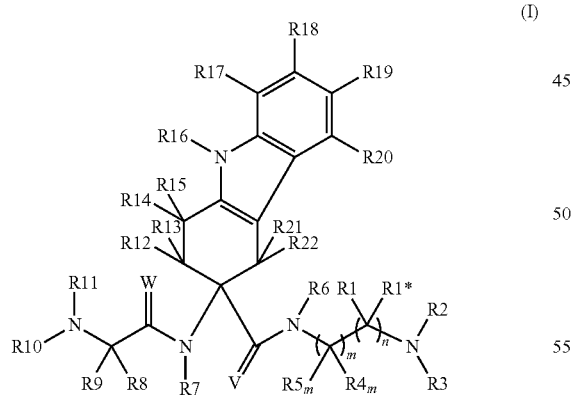

(I)

wherein:
(A) V, W are independently from each other selected from the group consisting of: "=O, =S, =S$^+$—O$^-$, geminally linked $H_2$";
R1, R1*—when present—together independently form "=O, =S or =S$^+$—O$^-$" or are independently both "hydrogen";
R2, R3 are independently from each other selected from the group consisting of:

(i) "hydrogen, alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHX1, —NX2X3, —NO$_2$, —OH, =O, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)—X4, —C(O)O—X5, —C(O)NH—X6, —C(O)NX7X8, —O—X9, —O(—X10-O)$_a$—H (a=1, 2, 3, 4, 5), —O(—X11-O)$_b$—X12 (b=1, 2, 3, 4, 5), —OC(O)—X13, —OC(O)—O—X14, —OC(O)—NHX15, —O—C(O)—NX16X17, —OP(O)(OX18)(OX19), —OSi(X20)(X21)(X22), —OS(O$_2$)—X23, —NHC(O)—NH$_2$, —NHC(O)—X24, —NX25C(O)—X26, —NH—C(O)—O—X27, —NH—C(O)—NH—X28, —NH—C(O)—NX29X30, —NX31-C(O)—O—X32, —NX33-C(O)—NH—X34, —NX35-C(O)—NX36X37, —NHS(O$_2$)—X38, —NX39S(O$_2$)—X40, —S—X41, —S(O)—X42, —S(O$_2$)—X43, —S(O$_2$)NH—X44, —S(O$_2$)NX45X46, —S(O$_2$)O—X47, —P(O)(OX48)(OX49), —Si(X50)(X51)(X52), —C(NH)—NH$_2$, —C(NX53)-NH$_2$, —C(NH)—NHX54, —C(NH)—NX55X56, —C(NX57)-NHX58, —C(NX59)-NX60X61, —NH—C(O)—NH—O—X62, —NH—C(O)—NX63-O—X64, —NX65-C(O)—NX66-O—X67, —N(—C(O)—NH—O—X68)$_2$, —N(—C(O)—NX69-O—X70)$_2$, —N(—C(O)—NH—O—X71)(—C(O)—NX72-O—X73), —C(S)—X74, —C(S)—O—X75, —C(S)—NH—X76, —C(S)—NX77X78, —C(O)—NH—O—X79, —C(O)—NX80-O—X81, —C(S)—NH—O—X82, —C(S)—NX83-O—X84, —C(O)—NH—NH—X85, —C(O)—NH—NX86X87, —C(O)—NX88-NX89X90, —C(S)—NH—NH—X91, —C(S)—NH—NX92X93, —C(S)—NX94-NX95X96, —C(O)—C(O)—O—X97, —C(O)—C(O)—NH$_2$, —C(O)—C(O)—NHX98, —C(O)—C(O)—NX99X100, —C(S)—C(O)—O—X101, —C(O)—C(S)—O—X102, —C(S)—C(S)—O—X103, —C(S)—C(O)—NH$_2$, —C(S)—C(O)—NHX104, —C(S)—C(O)—NX105X106, —C(S)—C(S)—NH$_2$, —C(S)—C(S)—NHX107, —C(S)—C(S)—NX108X109, —C(O)—C(S)—NH$_2$, —C(O)—C(S)—NHX110, —C(O)—C(S)—NX111X112";

wherein X1, X2, X3, X4, X5, X6, X7, X8, X9, X10, X11, X12, X13, X14, X15, X16, X17, X18, X19, X20, X21, X22, X23, X24, X25, X26, X27, X28, X29, X30, X31, X32, X33, X34, X35, X36, X37, X38, X39, X40, X41, X42, X43, X44, X45, X46, X47, X48, X49, X50, X51, X52, X53, X54, X55, X56, X57, X58, X59, X60, X61, X62, X63, X64, X65, X66, X67, X68, X69, X70, X71, X72, X73, X74, X75, X76, X77, X78, X79, X80, X81, X82, X83, X84, X85, X86, X87, X88, X89, X90, X91, X92, X93, X94, X95, X96, X97, X98, X99, X100, X101, X102, X103, X104, X105, X106, X107, X108, X109, X110, X111, X112 are independently from each other selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and wherein alternatively X7, X8 and/or X16, X17 and/or X29, X30 and/or X36, X37 and/or X45, X46 and/or X55, X56 and/or X60, X61 and/or X77, X78 and/or X86, X87 and/or X89, X90 and/or X92, X93 and/or X95, X96 and/or X99, X100 and/or X105, X106 and/or X108, X109 and/or X111, X112 and/or respectively together can also form heterocyclyl";

wherein optionally above substituents of substituents group (i) can in turn independently from each other be substituted with at least one substituent, identical or different, selected from the group consisting of:

(ii) "alkyl, $(C_9-C_{30})$alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHX201, —NX202X203, —NO$_2$, —OH, =O, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)—X204, —C(O)O—X205, —C(O)NH—X206, —C(O)NX207X208, —O—X209, —O(—X210-O)$_c$—H(c=1, 2, 3, 4, 5), —O(—X211-O)$_d$—X212 (d=1, 2, 3, 4, 5), —OC(O)—X213, —OC(O)—O—X214, —OC(O)—NHX215, —O—C(O)—NX216X217, —OP(O)(OX218)(OX219), —OSi(X220)(X221)(X222), —OS(O$_2$)—X223, —NHC(O)—NH$_2$, —NHC(O)—X224, —NX225C(O)—X226, —NH—C(O)—O—X227, —NH—C(O)—NH—X228, —NH—C(O)—NX229X230, —NX231-C(O)—O—X232, —NX233-C(O)—NH—X234, —NX235-C(O)—NX236X237, —NHS(O$_2$)—X238, —NX239S(O$_2$)—X240, —S—X241, —S(O)—X242, —S(O$_2$)—X243, —S(O$_2$)NH—X244, —S(O$_2$)NX245X246, —S(O$_2$)O—X247, —P(O)(OX248)(OC249), —Si(X250)(X251)(X252), —C(NH)—NH$_2$, —C(NX253)-NH$_2$, —C(NH)—NHX254, —C(NH)—NX255X256, —C(NX257)-NHX258, —C(NX259)-NX260X261, —NH—C(O)—NH—O—X262, —NH—C(O)—NX263-O—X264, —NX265-C(O)—NX266-O—X267, —N(—C(O)—NH—O—X268)$_2$, —N(—C(O)—NX269-O—X270)$_2$, —N(—C(O)—NH—O—X271)(—C(O)—NX271-O—X273), —C(S)—X274, —C(S)—O—X275, —C(S)—NH—X276, —C(S)—NX277X278, —C(O)—NH—O—X279, —C(O)—NX280-O—X281, —C(S)—NH—O—X282, —C(S)—NX283-O—X284, —C(O)—NH—NH—X285, —C(O)—NH—NX286X287, —C(O)—NX288-NX289X290, —C(S)—NH—NH—X291, —C(S)—NH—NX292X293, —C(S)—NX294-NX295X296, —C(O)—C(O)—O—X297, —C(O)—C(O)—NH$_2$, —C(O)—C(O)—NHX298, —C(O)—C(O)—NX299X300, —C(S)—C(O)—O—X301, —C(O)—C(S)—O—X302, —C(S)—C(S)—O—X303, —C(S)—C(O)—NH$_2$, —C(S)—C(O)—NHX304, —C(S)—C(O)—NX305X306, —C(S)—C(S)—NH$_2$, —C(S)—C(S)—NHX307, —C(S)—C(S)—NX308X309, —C(O)—C(S)—NH$_2$, —C(O)—C(S)—NHX310, —C(O)—C(S)—NX311X312";

wherein X201, X202, X203, X204, X205, X206, X207, X208, X209, X210, X211, X212, X213, X214, X215, X216, X217, X218, X219, X220, X221, X222, X223, X224, X225, X226, X227, X228, X229, X230, X231, X232, X233, X234, X235, X236, X237, X238, X239, X240, X241, X242, X243, X244, X245, X247, X248, X249, X250, X251, X252, X253, X254, X255, X256, X257, X258, X259, X260, X261, X262, X263, X264, X265, X266, X267, X268, X269, X270, X271, X272, X273, X274, X275, X276, X277, X278, X279, X280, X281, X282, X283, X284, X285, X286, X287, X288, X289, X290, X291, X292, X293, X294, X295, X296, X297, X298, X299, X300, X301, X302, X303, X304, X305, X306, X307, X308, X309, X310, X311, X312 are independently from each other selected from the group consisting of: "alkyl, $(C_9-C_{30})$alkyl, cycloalkyl, cycloalkyllalkyl, heterocyclyl, heterocyclylalkyl, aryl, arylalkyl, heteroaryl, heteroarylalkyl" and wherein alternatively X207, X208 and/or X216, X217 and/or X229, X230 and/or X236, X237 and/or X245, X246 and/or X255, X256 and/or X260, X261 and/or X277, X278 and/or X286, X287 and/or X289, X290 and/or X292, X293 and/or X295, X296 and/or X299, X300 and/or X305, X306 and/or X308, X309 and/or X311, X312 and/or respectively together can also form "heterocyclyl";

wherein optionally above substituents of substituents group (ii) can in turn independently from each other be substituted with at least one substituent, identical or different, selected from the group consisting of:

(iii) "alkyl, $(C_9-C_{30})$alkyl, cycloalkyl, cycloalkylalkyl, heterocyclyl, hetero-cyclylalkyl, aryl, arylalkyl, heteroaryl, heteroarylalkyl, —F, —Cl, —Br, —I, —CN, —CF$_3$, —N$_3$, —NH$_2$, —NHX401, —NX402X403, —NO$_2$, —OH, =O, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)—X404, —C(O)O—X405, —C(O)NH—X406, —C(O)NX407X408, —O—X409, —O(—X410-O)$_e$—H (e=1, 2, 3, 4, 5), —O(—X411-O)$_f$—X412 (f=1,2,3,4,5), —OC(O)—X413, —OC(O)—O—X414, —OC(O)—NHX415, —O—C(O)—NX416X417, —OP(O)(OX418)(OX419), —OSi(X420)(X421)(X422), —OS(O$_2$)—X423, —NHC(O)—NH$_2$, —NHC(O)—X424, —NX425C(O)—X426, —NH—C(O)—O—X427, —NH—C(O)—NH—X428, —NH—C(O)—NX429X430, —NX431-C(O)—O—X432, —NX433-C(O)—NH—X434, —NX435-C(O)—NX436X437, —NHS(O$_2$)—X438; —NX439S(O$_2$)—X440, —S—X441, —S(O)—X442, —S(O$_2$)—X443, —S(O$_2$)NH—X444, —S(O$_2$)NX445X446, —S(O$_2$)O—X447, —P(O)(OX448)(OX449), —Si(X450)(X451)(X452), —C(NH)—NH$_2$, —C(NX453)-NH$_2$, —C(NH)—NHX454, —C(NH)—NX455X456, —C(NX457)-NHX458, —C(NX459)-NX460X461, —NH—C(O)—NH—O—X462, —NH—C(O)—NX463-O—X464, —NX465-C(O)—NX466-O—X467, —N(—C(O)—NH—O—X468)$_2$, —N(—C(O)—NX469-O—X470)$_2$, —N(—C(O)—NH—O—X471)(—C(O)—NX472-O—X473), —C(S)—X474, —C(S)—O—X475, —C(S)—NH—X476, —C(S)—NX477X478, —C(O)—NH—O—X479, —C(O)—NX480-O—X481, —C(S)—NH—O—X482, —C(S)—NX483-O—X484, —C(O)—NH—NH—X485, —C(O)—NH—NX486X487, —C(O)—NX488-NX489X490, —C(S)—NH—NH—X491, —C(S)—NH—NX492X493, —C(S)—

NX494-NX495X496, —C(O)—C(O)—O—X497, —C(O)—C(O)—NH$_2$, —C(O)—C(O)—NHX498, —C(O)—C(O)—NX499X500, —C(S)—C(O)—O—X501, —C(O)—C(S)—O—X502, —C(S)—C(S)—O—X503, —C(S)—C(O)—NH$_2$, —C(S)—C(O)—NHX504, —C(S)—C(O)—NX505X506, —C(S)—C(S)—NH$_2$, —C(S)—C(S)—NHX507, —C(S)—C(S)—NX508X509, —C(O)—C(S)—NH$_2$, —C(O)—C(S)—NHX510, —C(O)—C(S)—NX511X512";

wherein X401, X402, X403, X404, X405, X406, X407, X408, X409, X410, X411, X412, X413, X414, X415, X416, X417, X418, X419, X420, X421, X422, X423, X424, X425, X426, X427, X428, X429, X430, X431, X432, X433, X434, X435, X436, X437, X438, X439, X440, X441, X442, X443, X444, X445, X446, X447, X448, X449, X450, X451, X452, X453, X454, X455, X456, X457, X458, X459, X460, X461, X462, X463, X464, X465, X466, X467, X468, X469, X470, X471, X472, X473, X474, X475, X476, X477, X478, X479, X480, X481, X482, X483, X484, X485, X486, X487, X488, X489, X490, X491, X492, X493, X494, X495, X496, X497, X498, X499, X500, X501, X502, X503, X504, X505, X506, X507, X508, X509, X510, X511, X512 are independently from each other selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and wherein alternatively X407, X408 and/or X416, X417 and/or X429, X430 and/or X436, X437 and/or X445, X446 and/or X455, X456 and/or X460, X461 and/or X477, X478 and/or X486, X487 and/or X489, X490 and/or X492, X493 and/or X495, X496 and/or X499, X500 and/or X505, X506 and/or X508, X509 and/or X511, X512 and/or respectively together can also form "heterocyclyl";

n independently is 0 or 1;

with the first proviso that, if R1, R1* are not present (n is 0), R2, R3 must not both be "hydrogen" at the same time;

with the second proviso that, if R1, R1* are present (n is 1) and together independently form "=O, =S or =$S^+$—$O^-$" or are independently both "hydrogen", R2, R3 must not both be "hydrogen" at the same time;

with the third proviso that, if R1, R1* are not present (n is 0), one of R2, R3 must not be "hydrogen" at the same time when the other one of R2, R3 is "—C(=NH)—NH$_2$";

with the fourth proviso that, if R1, R1* are present (n is 1) and are independently both "hydrogen", one of R2, R3 must not be "hydrogen" at the same time when the other one of R2, R3 is "—C(=NH)—NH$_2$";

with the fifth proviso that, if R1, R1* are present (n is 1) and together independently form "=O" and one of R2, R3 independently is "hydrogen" and the other one of R2, R3 independently is "alkyl, cycloalkyl, cycloalkylalkyl, aryl, arylalkyl, heteroaryl", then the other one of R2, R3 being "alkyl, cycloalkyl, cycloalkylalkyl, aryl, arylalkyl, heteroaryl" must be substituted with at least one substituent selected from the group consisting of:

(iv) "heterocyclyl, heterocyclylalkyl, —CF3, —N$_3$, —NH$_2$, —NHX600, —NX601X602, —NO$_2$, —OH, —OCF$_3$, —SH, —O—SO$_3$H, —OP(O)(OH)$_2$, —CHO, —COOH, —SO$_3$H, —P(O)(OH)$_2$, —C(O)—X603, —C(O)O—X604, —C(O)NH—X605, —C(O)NX606X607, —O-aryl, —O-arylalkyl, —O-heteroaryl, —O-heteroarylalkyl, —O-heterocyclyl, —O-heterocyclylalkyl, —O(—X608-O)$_g$—H (g=1, 2, 3, 4, 5), —O(—X609-O)$_h$—X610 (h=1, 2, 3, 4, 5), —OC(O)—X611, —OC(O)—O—X612, —OC(O)—NHX613, —O—C(O)—NX614X615, —OP(O)(OC616)(OC617), —OSi(X618)(X619)(X620), —OS(O$_2$)—X621, —NHC(O)—X622, —NX623C(O)—X624, —NH—C(O)—O—X625, —NH—C(O)—NH—X626, —NH—C(O)—NX627X628, —NX629-C(O)—O—X630, —NX631-C(O)—NH—X632, —NX633-C(O)—NX634X635, —NHS(O$_2$)—X636, —NX637S(O$_2$)—X638, —S—X639, —S(O)—X640, —S(O$_2$)—X641, —S(O$_2$)NH—X642, —S(O$_2$)NX643X644, —S(O$_2$)O—X645, —P(O)(OX646)(OX647), —Si(X648)(X649)(X650), —C(NH)—NH$_2$, —C(NX651)-NH$_2$, —C(NH)—NHX652, —C(NH)—NX653X654, —C(NX655)-NHX656, —C(NX657)-NX658X659, —NH—C(O)—NH—O—660, —NH—C(O)—NX661-O—X662, —NX663-C(O)—NX664-O—X665, —N(—C(O)—NH—O—X666)$_2$, —N(—C(O)—NX667-O—X668)$_2$, —N(—C(O)—NH—O—X669)(—C(O)—NX670-O—X671), —C(S)—X672, —C(S)—O—X673, —C(S)—NH—X674, —C(S)—NX675X676, —C(O)—NH—O—X677, —C(O)—NX678-O—X679, —C(S)—NH—O—X680, —C(S)—NX681-O—X682, —C(O)—NH—NH—X683, —C(O)—NH—NX684X685, —C(O)—NX686-NX687X688, —C(S)—NH—NH—X689, —C(S)—NH—NX690X691, —C(S)—NX692-NX693X694, —C(O)—C(O)—O—X695, —C(O)—C(O)—NH$_2$, —C(O)—C(O)—NHX696, —C(O)—C(O)—NX697X698, —C(S)—C(O)—O—X699, —C(O)—C(S)—O—X700, —C(S)—C(S)—O—X701, —C(S)—C(O)—NH$_2$, —C(S)—C(O)—NHX702, —C(S)—C(O)—NX703X704, —C(S)—C(S)—NH$_2$, —C(S)—C(S)—NHX705, —C(S)—C(S)—NX706X707, —C(O)—C(S)—NH$_2$, —C(O)—C(S)—NHX708, —C(O)—C(S)—NX709X710";

wherein X600, X601, X602, X603, X604, X605, X606, X607, X608, X609, X610, X611, X612, X613, X614, X615, X616, X617, X618, X619, X620, X621, X622, X623, X624, X625, X626, X627, X628, X629, X630, X631, X632, X633, X634, X635, X636, X637, X638, X639, X640, X641, X642, X643, X644, X645, X646, X647, X648, X649, X650, X651, X652, X653, X654, X655, X656, X657, X658, X659, X660, X661, X662, X663, X664, X665, X666, X667, X668, X669, X670, X671, X672, X673, X674, X675, X676, X677, X678, X679, X680, X681, X682, X683, X684, X685, X686, X687, X688, X689, X690, X691, X692, X693, X694, X695, X696, X697, X698, X699, X700, X701, X702, X703, X704, X705, X706, X707, X708, X709, X710, X711, X712 are independently from each other selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and wherein alternatively X606, X607 and/or X614, X615 and/or X627, X628 and/or X634, X635 and/or X643, X644 and/or X653, X654 and/or X658, X659 and/or X675, X676 and/or X684, X685 and/or X687, X688 and/or X690, X691 and/or X693, X694 and/or X697, X698 and/or X703, X704 and/or X706, X707 and/or X709, X710 and/or respectively together can also form "heterocyclyl";

with the further proviso that "—C(O)—N(alkyl)$_2$, —C(O)—N(cycloalkyl)$_2$, —C(O)—N(cycloalkylalkyl)$_2$, —C(O)—N(arylalkyl)$_2$, —C(O)—N(aryl)$_2$, —C(O)—N(heteroaryl)$_2$" are excluded from above substituents group (iv);

wherein optionally the other one of R2, R3 being "alkyl, cycloalkyl, cycloalkylalkyl, aryl, arylalkyl, heteroaryl" can in turn independently from each other be additionally substituted with at least one substituent, identical or different, selected from above substituents group (ii);

wherein optionally the other one of R2, R3 being "alkyl, cycloalkyl, cycloalkylalkyl, aryl, arylalkyl, heteroaryl" and being substituted with at least one substituent, identical or different, selected from above substituents group (iv) and, optionally, also (ii), can optionally be further substituted in their substituents selected from above substituents group (iv) and, optionally, also (ii), with at least one substituent, identical or different, selected from above substituents group (iii);

with the sixth proviso that, if R1, R1* are present (n is 1) and together independently form "=S or =S$^+$—O$^-$" and R2, R3 are independently selected from the group consisting of "hydrogen, alkyl, cycloalkyl, cycloalkylalkyl, aryl, arylalkyl", each of R2, R3 being "alkyl, cycloalkyl, cycloalkylalkyl, aryl, arylalkyl" must be substituted with at least one substituent selected from the group consisting of:

(v) "heterocyclyl, heterocyclylalkyl, heteroaryl, heteroarylalkyl, —CF3, —N$_3$, —NH$_2$, —NHX800, —NX801X802, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)—X803, —C(O)O—X804, —C(O)NH—X805, —C(O)NX806X807, —O-aryl, —O-arylalkyl, —O-heteroaryl, —O-heteroarylalkyl, —O-heterocyclyl, —O-heterocyclylalkyl, —O(—X808-O)$_i$—H (i=1, 2, 3, 4, 5), —O(—X809-O)$_j$X810 (j=1, 2, 3, 4, 5), —OC(O)—X811, —OC(O)—O—X812, —OC(O)—NHX813, —O—C(O)—NX814X815, —OP(O)(OX816)(OX817), —OSi(X818)(X819)(X820), —OS(O$_2$)—X821, —NHC(O)—X822, —NX823C(O)—X824, —NH—C(O)—O—X825, —NH—C(O)—NH—X826, —NH—C(O)—NX827X828, —NX829-C(O)—O—X830, —NX831-C(O)—NH—X832, —NX833-C(O)—NX834X835, —NHS(O$_2$)—X836, —NX837S(O$_2$)—X838, —S—X839, —S(O)—X840, —S(O$_2$)—X841, —S(O$_2$)NH—X842, —S(O$_2$)NX843X844, —S(O$_2$)O—X845, —P(O)(OX846)(OX847), —Si(X848)(X849)(X850), —C(NH)—NH$_2$, —C(NX851)-NH$_2$, —C(NH)—NHX852, —C(NH)—NX853X854, —C(NX855)-NHX856, —C(NX857)-NX858X859, —NH—C(O)—NH—O—X860, —NH—C(O)—NX861-O—X862, —NX863-C(O)—NX864-O—X865, —N(—C(O)—NH—O—X866)$_2$, —N(—C(O)—NX867-O—X868)$_2$, —N(—C(O)—NH—O—X869)(—C(O)—NX870-O—X871), —C(S)—X872, —C(S)—O—X873, —C(S)—NH—X874, —C(S)—NX875X876, —C(O)—NH—O—X877, —C(O)—NX878-O—X879, —C(S)—NH—O—X880, —C(S)—NX881-O—X882, —C(O)—NH—NH—X883, —C(O)—NH—NX884X885, —C(O)—NX886-NX887X888, —C(S)—NH—NH—X889, —C(S)—NH—NX890X891, —C(S)—NX892-NX893X894, —C(O)—C(O)—O—X895, —C(O)—C(O)—NH$_2$, —C(O)—C(O)—NHX896, —C(O)—C(O)—NX897X898, —C(S)—C(O)—O—X899, —C(O)—C(S)—O—X900, —C(S)—C(S)—O—X901, —C(S)—C(O)—NH$_2$, —C(S)—C(O)—NHX902, —C(S)—C(O)—NX903X904, —C(S)—C(S)—NH$_2$, —C(S)—C(S)—NHX905, —C(S)—C(S)—NX906X907, —C(O)—C(S)—NH$_2$, —C(O)—C(S)—NHX908, —C(O)—C(S)—NX909X910";

wherein X800, X801, X802, X803, X804, X805, X806, X807, X808, X809, X810, X811, X812, X813, X814, X815, X816, X817, X818, X819, X820, X821, X822, X823, X824, X825, X826, X827, X828, X829, X830, X831, X832, X833, X834, X835, X836, X837, X838, X839, X840, X841, X842, X843, X844, X845, X846, X847, X848, X849, X850, X851, X852, X853, X854, X855, X856, X857, X858, X859, X860, X861, X862, X863, X864, X865, X866, X867, X868, X869, X870, X871, X872, X873, X874, X875, X876, X877, X878, X879, X880, X881, X882, X883, X884, X885, X886, X887, X888, X889, X890, X891, X892, X893, X894, X895, X896, X897, X898, X899, X900, X901, X902, X903, X904, X905, X906, X907, X908, X909, X910, X911, X912 are independently from each other selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and wherein alternatively X806, X807 and/or X814, X815 and/or X827, X828 and/or X834, X835 and/or X843, X844 and/or X853, X854 and/or X858, X859 and/or X875, X876 and/or X884, X885 and/or X887, X888 and/or X890, X891 and/or X893, X894 and/or X897, X898 and/or X903, X904 and/or X906, X907 and/or X909, X910 and/or respectively together can also form "heterocyclyl";

wherein optionally each of R2, R3 being "alkyl, cycloalkyl, cycloalkylalkyl, aryl, arylalkyl" can in turn independently from each other be additionally substituted with at least one substituent, identical or different, selected from above substituents group (ii);

wherein optionally each of R2, R3 being "alkyl, cycloalkyl, cycloalkylalkyl, aryl, arylalkyl" and being substituted with at least one substituent, identical or different, selected from above substituents group (v) and, optionally, also (ii), can optionally be further substituted in their substituents selected from above substituents group (v) and, optionally, also (ii), with at least one substituent, identical or different, selected from above substituents group (iii);

m independently is 1 or 2;

$R4_m$, $R5_m$, R6, R7, R8, R9, R10, R11, R12, R13, R14, R15, R16, R17, R18, R19, R20, R21, R22 are independently from each other selected from the group consisting of:

(i) "hydrogen, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHX1001, —NX1002X1003, —NO$_2$, —OH, =O, —OCF$_3$, —SH, —O—SO$_3$H, —OP(O)(OH)$_2$, —CHO, —COON, —C(O)NH$_2$, —SO$_3$H, —P(O)(OH)$_2$, —C(O)—X1004, —C(O)O—X1005, —C(O)NH—X1006, —C(O)NX1007X1008, —O—X1009, —O(—X1010-O)$_k$—H (k=1, 2, 3, 4, 5), —O(—X1011-O)$_l$—X1012 (l=1, 2, 3, 4, 5), —OC(O)—X1013, —OC(O)—O—X1014, —OC(O)—NHX1015, —O—C(O)—NX1016X1017, —OP(O)(OX1018)(OX1019), —OSi(X1020)(X1021)(X1022), —OS(O$_2$)—X1023, —NHC(O)—NH$_2$, —NHC(O)—X1024, —NX1025C(O)—X1026, —NH—C(O)—O—X1027, —NH—C(O)—NH—X1028, —NH—C(O)—NX1029X1030, —NX1031-C(O)—O—X1032, —NX1033-C(O)—NH—X1034, —NX1035-C(O)—NX1036X1037, —NHS(O$_2$)—X1038, —NX1039S(O$_2$)—X1040, —S—X1041, —S(O)—X1042, —S(O$_2$)—X1043, —S(O$_2$)NH—X1044, —S(O$_2$)NX1045X1046, —S(O$_2$)O—X1047, —P(O)(OX1048)(OX1049), —Si(X1050)(X1051)(X1052), —C(NH)—NH$_2$, —C(NX1053)-NH$_2$, —C(NH)—NHX1054, —C(NH)—NX1055X1056, —C(NX1057)-NHX1058, —C(NX1059)-NX1060X1061, —NH—C(O)—NH—O—X1062, —NH—C(O)—NX1063-O—X1064, —NX1065-C(O)—NX1066-O—X1067, —N(—C(O)—NH—O—X1068)$_2$, —N(—C(O)—NX1069-O—X1070)$_2$, —N(—C(O)—NH—O—X1071)(—C(O)—NX1072-O—X1073), —C(S)—X1074, —C(S)—O—X1075, —C(S)—NH—X1076, —C(S)—NX1077X1078, —C(O)—NH—O—X1079, —C(O)—NX1080-O—X1081, —C(S)—NH—O—X1082, —C(S)—NX1083-O—X1084, —C(O)—NH—NH—X1085, —C(O)—NH—NX1086X1087, —C(O)—NX1088-NX1089X1090, —C(S)—NH—NH—X1091, —C(S)—NH—NX1092X1093, —C(S)—NX1094-NX1095X1096, —C(O)—C(O)—O—X1097, —C(O)—C(O)—NH$_2$, —C(O)—C(O)—NHX1098, —C(O)—C(O)—NX1099X1100, —C(S)—C(O)—O—X1101, —C(O)—C(S)—O—X1102, —C(S)—C(S)—O—X1103, —C(S)—C(O)—NH$_2$, —C(S)—C(O)—NHX1104, —C(S)—C(O)—NX1105X1106, —C(S)—C(S)—NH$_2$, —C(S)—C(S)—NHX1107, —C(S)—C(S)—NX1108X1109, —C(O)—C(S)—NH$_2$, —C(O)—C(S)—NHX1110, —C(O)—C(S)—NX1111X1112";

wherein X1001, X1002, X1003, X1004, X1005, X1006, X1007, X1008, X1009, X1010, X1011, X1012, X1013, X1014, X1015, X1016, X1017, X1018, X1019, X1020, X1021, X1022, X1023, X1024, X1025, X1026, X1027, X1028, X1029, X1030, X1031, X1032, X1033, X1034, X1035, X1036, X1037, X1038, X1039, X1040, X1041, X1042, X1043, X1044, X1045, X1046, X1047, X1048, X1049, X1050, X1051, X1052, X1053, X1054, X1055, X1056, X1057, X1058, X1059, X1060, X1061, X1062, X1063, X1064, X1065, X1066, X1067, X1068, X1069, X1070, X1071, X1072, X1073, X1074, X1075, X1076, X1077, X1078, X1079, X1080, X1081, X1082, X1083, X1084, X1085, X1086, X1087, X1088, X1089, X1090, X1091, X1092, X1093, X1094, X1095, X1096, X1097, X1098, X1099, X1100, X1101, X1102, X1103, X1104, X1105, X1106, X1107, X1108, X1109, X1110, X1111, X1112 are independently from each other selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and wherein alternatively X1007, X1008 and/or X1016, X1017 and/or X1029, X1030 and/or X1036, X1037 and/or X1045, X1046 and/or X1055, X1056 and/or X1060, X1061 and/or X1077, X1078 and/or X1086, X1087 and/or X1089, X1090 and/or X1092, X1093 and/or X1095, X1096 and/or X1099, X1100 and/or X1105, X1106 and/or X1108, X1109 and/or X1111, X1112 and/or respectively together can also form "heterocyclyl";

wherein optionally above substituents of substituents group (i) can in turn independently from each other be substituted with at least one substituent, identical or different, selected from the group consisting of:

(ii) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHX1201, —NX1202X1203, —NO$_2$, —OH, =O, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)—X1204, —C(O)O—X1205, —C(O)NH—X1206, —C(O)NX1207X1208, —O—X1209, —O(—X1210-O)$_m$—H (m=1, 2, 3, 4, 5), —O(—X1211-O)$_n$—X1212 (n=1, 2, 3, 4, 5), —OC(O)—X1213, —OC(O)—O—X1214, —OC(O)—NHX1215, —O—C(O)—NX1216X1217, —OP(O)(OX1218)(OX1219), —OSi(X1220)(X1221)(X1222), —OS(O$_2$)—X1223, —NHC(O)—NH$_2$, —NHC(O)—X1224, —NX1225C(O)—X1226, —NH—C(O)—O—X1227, —NH—C(O)—NH—X1228, —NH—C(O)—NX1229X1230, —NX1231-C(O)—O—X1232, —NX1233-C(O)—NH—X1234, —NX1235-C(O)—NX1236X1237, —NHS(O$_2$)—X1238, —NX1239S(O$_2$)—X1240, —S—X1241, —S(O)—X1242, —S(O$_2$)—X1243, —S(O$_2$)NH—X1244, —S(O$_2$)NX1245X1246, —S(O$_2$)O—X1247, —P(O)(OX1248)(OX1249), —Si(X1250)(X1251)(X1252), —C(NH)—NH$_2$, —C(NX1253)-NH$_2$, —C(NH)—NHX1254, —C(NH)—NX1255X1256, —C(NX1257)-NHX1258, —C(NX1259)-NX1260X1261, —NH—C(O)—NH—O—X1262, —NH—C(O)—NX1263-O—X1264, —NX1265-C(O)—NX1266-O—X1267, —N(—C(O)—NH—O—X1268)$_2$, —N(—C(O)—NX1269-O—X1270)$_2$, —N(—C(O)—NH—O—X1271)(—C(O)—NX1272-O—X1273), —C(S)—X1274, —C(S)—O—X1275, —C(S)—NH—X1276, —C(S)—NX1277X1278, —C(O)—NH—O—X1279, —C(O)—NX1280-O—X1281, —C(S)—NH—O—X1282, —C(S)—NX1283-O—X1284, —C(O)—NH—NH—X1285, —C(O)—NH—NX1286X1287, —C(O)—NX1288-NX1289X1290, —C(S)—NH—NH—X1291, —C(S)—NH—NX1292X1293, —C(S)—NX1294-NX1295X1296, —C(O)—C(O)—O—X1297, —C(O)—C(O)—NH$_2$, —C(O)—C(O)—

NHX1298, —C(O)—C(O)—NX1299X1300, —C(S)—C(O)—O—X1301, —C(O)—C(S)—O—X1302, —C(S)—C(S)—O—X1303, —C(S)—C(O)—NH$_2$, —C(S)—C(O)—NHX1304, —C(S)—C(O)—NX1305X1306, —C(S)—C(S)—NH$_2$, —C(S)—C(S)—NHX1307, —C(S)—C(S)—NX1308X1309, —C(O)—C(S)—NH$_2$, —C(O)—C(S)—NHX1310, —C(O)—C(S)—NX1311X1312";

wherein X1201, X1202, X1203, X1204, X1205, X1206, X1207, X1208, X1209, X1210, X1211, X1212, X1213, X1214, X1215, X1216, X1217, X1218, X1219, X1220, X1221, X1222, X1223, X1224, X1225, X1226, X1227, X1228, X1229, X1230, X1231, X1232, X1233, X1234, X1235, X1236, X1237, X1238, X1239, X1240, X1241, X1242, X1243, X1244, X1245, X1246, X1247, X1248, X1249, X1250, X1251, X1252, X1253, X1254, X1255, X1256, X1257, X1258, X1259, X1260, X1261, X1262, X1263, X1264, X1265, X1266, X1267, X1268, X1269, X1270, X1271, X1272, X1273, X1274, X1275, X1276, X1277, X1278, X1279, X1280, X1281, X1282, X1283, X1284, X1285, X1286, X1287, X1288, X1289, X1290, X1291, X1292, X1293, X1294, X1295, X1296, X1297, X1298, X1299, X1300, X1301, X1302, X1303, X1304, X1305, X1306, X1307, X1308, X1309, X1310, X1311, X1312 are independently from each other selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and wherein alternatively X1207, X1208 and/or X1216, X1217 and/or X1229, X1230 and/or X1236, X1237 and/or X1245, X1246 and/or X1255, X1256 and/or X1260, X1261 and/or X1277, X1278 and/or X1286, X1287 and/or X1289, X1290 and/or X1292, X1293 and/or X1295, X1296 and/or X1299, X1300 and/or X1305, X1306 and/or X1308, X1309 and/or X1311, X1312 and/or respectively together can also form "heterocyclyl";

wherein optionally above substituents of substituents group (ii) can in turn independently from each other be substituted with at least one substituent, identical or different, selected from the group consisting of:

(iii) "alkyl, (C$_9$-C$_{30}$)alkyl, cycloalkyl, cycloalkylalkyl, heterocyclyl, hetero-cyclylalkyl, aryl, arylalkyl, heteroaryl, heteroarylalkyl, —F, —Cl, —Br, —I, —CN, —CF$_3$, —N$_3$, —NH$_2$, —NHX1401, —NX1402X1403, —NO$_2$, —OH, =O, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)—X1404, —C(O)O—X1405, —C(O)NH—X1406, —C(O)NX1407X1408, —O—X1409, —O(—X1410-O)$_o$—H (o=1, 2, 3, 4, 5), —O(—X1411-O)$_p$—X1412 (p=1, 2, 3, 4, 5), —OC(O)—X1413, —OC(O)—O—X1414, —OC(O)—NHX1415, —O—C(O)—NX1416X1417, —OP(O)(OX1418)(OX1419), —OSi(X1420)(X1421)(X1422), —OS(O$_2$)—X1423, —NHC(O)—NH$_2$, —NHC(O)—X1424, —NX1425C(O)—X1426, —NH—C(O)—O—X1427, —NH—C(O)—NH—X1428, —NH—C(O)—NX1429X1430, —NX1431-C(O)—O—X1432, —NX1433-C(O)—NH—X1434, —NX1435-C(O)—NX1436X1437, —NHS(O$_2$)—X1438, —NX1439S(O$_2$)—X1440, —S—X1441, —S(O)—X1442, —S(O$_2$)—X1443, —S(O$_2$)NH—X1444, —S(O$_2$)NX1445X1446, —S(O$_2$)O—X1447, —P(O)(OX1448)(OX1449), —Si(X1450)(X1451)(X1452), —C(NH)—NH$_2$, —C(NX1453)-NH$_2$, —C(NH)—NHX1454, —C(NH)—NX1455X1456, —C(NX1457)-NHX1458, —C(NX1459)-NX1460X1461, —NH—C(O)—NH—O—X1462, —NH—C(O)—NX1463-O—X1464, —NX1465-C(O)—NX1466-O—X1467, —N(—C(O)—NH—O—X1468)$_2$, —N(—C(O)—NX1469-O—X1470)$_2$, —N(—C(O)—NH—O—X1471)(—C(O)—NX1472-O—X1473), —C(S)—X1474, —C(S)—O—X1475, —C(S)—NH—X1476, —C(S)—NX1477X1478, —C(O)—NH—O—X1479, —C(O)—NX1480-O—X1481, —C(S)—NH—O—X1482, —C(S)—NX1483-O—X1484, —C(O)—NH—NH—X1485, —C(O)—NH—NX1486X1487, —C(O)—NX1488-NX1489X1490, —C(S)—NH—NH—X1491, —C(S)—NH—NX1492X1493, —C(S)—NX1494-NX1495X1496, —C(O)—C(O)—O—X1497, —C(O)—C(O)—NH$_2$, —C(O)—C(O)—NHX1498, —C(O)—C(O)—NX1499X1500, —C(S)—C(O)—O—X1501, —C(O)—C(S)—O—X1502, —C(S)—C(S)—O—X1503, —C(S)—C(O)—NH$_2$, —C(S)—C(O)—NHX1504, —C(S)—C(O)—NX1505X1506, —C(S)—C(S)—NH$_2$, —C(S)—C(S)—NHX1507, —C(S)—C(S)—NX1508X1509, —C(O)—C(S)—NH$_2$, —C(O)—C(S)—NHX1510, —C(O)—C(S)—NX1511X1512";

wherein X1401, X1402, X1403, X1404, X1405, X1406, X1407, X1408, X1409, X1410, X1411, X1412, X1413, X1414, X1415, X1416, X1417, X1418, X1419, X1420, X1421, X1422, X1423, X1424, X1425, X1426, X1427, X1428, X1429, X1430, X1431, X1432, X1433, X1434, X1435, X1436, X1437, X1438, X1439, X1440, X1441, X1442, X1443, X1444, X1445, X1446, X1447, X1448, X1449, X1450, X1451, X1452, X1453, X1454, X1455, X1456, X1457, X1458, X1459, X1460, X1461, X1462, X1463, X1464, X1465, X1466, X1467, X1468, X1469, X1470, X1471, X1472, X1473, X1474, X1475, X1476, X1477, X1478, X1479, X1480, X1481, X1482, X1483, X1484, X1485, X1486, X1487, X1488, X1489, X1490, X1491, X1492, X1493, X1494, X1495, X1496, X1497, X1498, X1499, X1500, X1501, X1502, X1503, X1504, X1505, X1506, X1507, X1508, X1509, X1510, X1511, X1512 are independently from each other selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and wherein alternatively X1407, X1408 and/or X1416, X1417 and/or X1429, X1430 and/or X1436, X1437 and/or X1445, X1446 and/or X1455, X1456 and/or X1460, X1461 and/or X1477, X1478 and/or X1495, X1496 and/or X1499, X1500 and/or X1505, X1506 and/or X1508, X1509 and/or X1511, X1512 and/or respectively together can also form "heterocyclyl";

or (B) V, W are independently from each other selected from the group consisting of: "=O, =S, =S$^+$—O$^-$, geminally linked H$_2$";

R1*, R2 together independently form "heterocyclyl" or together independently form "heteroaryl"; where "heterocyclyl" and "heteroaryl" can optionally be substituted with at least one substituent selected from below substituents group (i);

R1, R3 are independently from each other selected from the group consisting of:

(i) "hydrogen, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHZ1, —NZ2Z3, —NO$_2$, —OH, =O, —OCF$_3$, —SH, —O—SO$_3$H, —OP(O)(OH)$_2$, —CHO, —COOH, —C(O)NH$_2$, —SO$_3$1-1, —P(O)(OH)$_2$, —C(O)—Z4, —C(O)O—Z5, —C(O)NH—Z6, —C(O)NZ7Z8, —O—Z9, —O(—Z10-O)$_a$—H (a=1, 2, 3, 4, 5), —O(—Z11-O)$_b$—Z12 (b=1, 2, 3, 4, 5), —OC(O)—Z13, —OC(O)—O—Z14, —OC(O)—NHZ15, —O—C(O)—NZ16Z17, —OP(O)(OZ18)(OZ19), —OSi(Z20)(Z21)(Z22), —OS(O$_2$)—Z23, —NHC(O)—NH$_2$, —NHC(O)—Z24, —NZ25C(O)—Z26, —NH—C(O)—O—Z27, —NH—C(O)—NH—Z28, —NH—C(O)—NZ29Z30, —NZ31-C(O)—O—Z32, —NZ33-C(O)—NH—Z34, —NZ35-C(O)—NZ36Z37, —NHS(O$_2$)—Z38, —NZ39S(O$_2$)—Z40, —S—Z41, —S(O)—Z42, —S(O$_2$)—Z43, —S(O$_2$)NH—Z44, —S(O$_2$)NZ45Z46, —S(O$_2$)O—Z47, —P(O)(OZ48)(OZ49), —Si(Z50)(Z51)(Z52), —C(NH)—NH$_2$, —C(NZ53)-NH$_2$, —C(NH)—NHZ54, —C(NH)—NZ55Z56, —C(NZ57)-NHZ58, —C(NZ59)-NZ60Z61, —NH—C(O)—NH—O—Z62, —NH—C(O)—NZ63-O—Z64, —NZ65-C(O)—NZ66-O—Z67, —N(—C(O)—NH—O—Z68)$_2$, —N(—C(O)—NZ69-O—Z70)$_2$, —N(—C(O)—NH—O—Z71)(—C(O)—NZ72-O—Z73), —C(S)—Z74, —C(S)O—Z75, —C(S)—NH—Z76, —C(S)—NZ77Z78, —C(O)—NH—O—Z79, —C(O)—NZ80-O—Z81, —C(S)—NH—O—Z82, —C(S)—NZ83-O—Z84, —C(O)—NH—NH—Z85, —C(O)—NH—NZ86Z87, —C(O)—NZ88-NZ89Z90, —C(S)—NH—NH—Z91, —C(S)—NH—NZ92Z93, —C(S)—NZ94-NZ95Z96, —C(O)—C(O)—O—Z97, —C(O)—C(O)—NH$_2$, —C(O)—C(O)—NHZ98, —C(O)—C(O)—NZ99Z100, —C(S)—C(O)—O—Z101, —C(O)—C(S)—O—Z102, —C(S)—C(S)—O—Z103, —C(S)—C(O)—NH$_2$, —C(S)—C(O)—NHZ104, —C(S)—C(O)—NZ105Z106, —C(S)—C(S)—NH$_2$, —C(S)—C(S)—NHZ107, —C(S)—C(S)—NZ108Z109, —C(O)—C(S)—NH$_2$, —C(O)—C(S)—NHZ110, —C(O)—C(S)—NZ111Z112";

wherein Z1, Z2, Z3, Z4, Z5, Z6, Z7, Z8, Z9, Z10, Z11, Z12, Z13, Z14, Z15, Z16, Z17, Z18, Z19, Z20, Z21, Z22, Z23, Z24, Z25, Z26, Z27, Z28, Z29, Z30, Z31, Z32, Z33, Z34, Z35, Z36, Z37, Z38, Z39, Z40, Z41, Z42, Z43, Z44, Z45, Z46, Z47, Z48, Z49, Z50, Z51, Z52, Z53, Z54, Z55, Z56, Z57, Z58, Z59, Z60, Z61, Z62, Z63, Z64, Z65, Z66, Z67, Z68, Z69, Z70, Z71, Z72, Z73, Z74, Z75, Z76, Z77, Z78, Z79, Z80, Z81, Z82, Z83, Z84, Z85, Z86, Z87, Z88, Z89, Z90, Z91, Z92, Z93, Z94, Z95, Z96, Z97, Z98, Z99, Z100, Z101, Z102, Z103, Z104, Z105, Z106, Z107, Z108, Z109, Z110, Z111, Z112 are independently from each other selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and wherein alternatively Z7, Z8 and/or Z16, Z17 and/or Z29, Z30 and/or Z36, Z37 and/or Z45, Z46 and/or Z55, Z56 and/or Z60, Z61 and/or Z77, Z78 and/or Z86, Z87 and/or Z89, Z90 and/or Z92, Z93 and/or Z95, Z96 and/or Z99, Z100 and/or Z105, Z106 and/or Z108, Z109 and/or Z111, Z112 and/or respectively together can also form "heterocyclyl";

wherein optionally above substituents of substituents group (i) can in turn independently from each other be substituted with at least one substituent, identical or different, selected from the group consisting of:

(ii) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHZ201, —NZ202Z203, —NO$_2$, —OH, =O, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)—Z204, —C(O)O—Z205, —C(O)NH—Z206, —C(O)NZ207Z208, —O—Z209, —O(—Z210-O)$_c$—H (c=1, 2, 3, 4, 5), —O(—Z211-O)$_d$—Z212 (d=1, 2, 3, 4, 5), —OC(O)—Z213, —OC(O)—O—Z214, —OC(O)—NHZ215, —O—C(O)—NZ216Z217, —OP(O)(OZ218)(OZ219), —OSi(Z220)(Z221)(Z222), —S(O$_2$)—Z223, —NHC(O)—NH$_2$, —NHC(O)—Z224, —NZ225C(O)—Z226, —NH—C(O)—O—Z227, —NH—C(O)—NH—Z228, —NH—C(O)—NZ229Z230, —NZ231-C(O)—O—Z232, —NZ233-C(O)—NH—Z234, —NZ235-C(O)—NZ236Z237, —NHS(O$_2$)—Z238, —NZ239S(O$_2$)—Z240, —S—Z241, —S(O)—Z242, —S(O$_2$)—Z243, —S(O$_2$)NH—Z244, —S(O$_2$)NZ245Z246, —S(O$_2$)O—Z247, —P(O)(OZ248)(OZ249), —Si(Z250)(Z251)(Z252), —C(NH)—NH$_2$, —C(NZ253)-NH$_2$, —C(NH)—NHZ254, —C(NH)—NZ255Z256, —C(NZ257)-NHZ258, —C(NZ259)-NZ260Z261, —NH—C(O)—NH—O—Z262, —NH—C(O)—NZ263-O—Z264, —NZ265-C(O)—NZ266-O—Z267, —N(—C(O)—NH—O—Z268)$_2$, —N(—C(O)—NZ269-O—Z270)$_2$, —N(—C(O)—NH—O—Z271)(—C(O)—NZ272-O—Z273), —C(S)—Z274, —C(S)—O—Z275, —C(S)—NH—Z276, —C(S)—NZ277Z278, —C(O)—NH—O—Z279, —C(O)—NZ280-O—Z281, —C(S)—NH—O—Z282, —C(S)—NZ283-O—Z284, —C(O)—NH—NH—Z285, —C(O)—NH—NZ286Z287, —C(O)—NZ288-NZ289Z290, —C(S)—NH—NH—Z291, —C(S)—NH—NZ292Z293, —C(S)—NZ294-NZ295Z296, —C(O)—C(O)—O—Z297, —C(O)—C(O)—NH$_2$, —C(O)—C(O)—NHZ298, —C(O)—C(O)—NZ299Z300, —C(S)—C(O)—O—Z301, —C(O)—C(S)—O—Z302, —C(S)—C(S)—O—Z303, —C(S)—C(O)—NH$_2$, —C(S)—C(O)—NHZ304, —C(S)—C(O)—NZ305Z306, —C(S)—C(S)—NH$_2$, —C(S)—C(S)—NHZ307, —C(S)—C(S)—

NZ308Z309, —C(O)—C(S)—NH$_2$, —C(O)—C(S)—NHZ310, —C(O)—C(S)—NZ311Z312";

wherein Z201, Z202, Z203, Z204, Z205, Z206, Z207, Z208, Z209, Z210, Z211, Z212, Z213, Z214, Z215, Z216, Z217, Z218, Z219, Z220, Z221, Z222, Z223, Z224, Z225, Z226, Z227, Z228, Z229, Z230, Z231, Z232, Z233, Z234, Z235, Z236, Z237, Z238, Z239, Z240, Z241, Z242, Z243, Z244, Z245, Z246, Z247, Z248, Z249, Z250, Z251, Z252, Z253, Z254, Z255, Z256, Z257, Z258, Z259, Z260, Z261, Z262, Z263, Z264, Z265, Z266, Z267, Z268, Z269, Z270, Z271, Z272, Z273, Z274, Z275, Z276, Z277, Z278, Z279, Z280, Z281, Z282, Z283, Z284, Z285, Z286, Z287, Z288, Z289, Z290, Z291, Z292, Z293, Z294, Z295, Z296, Z297, Z298, Z299, Z300, Z301, Z302, Z303, Z304, Z305, Z306, Z307, Z308, Z309, Z310, Z311, Z312 are independently from each other selected from the group consisting of: "alkyl, (C$_9$-C$_{30}$) alkyl, cycloalkyl, cycloalkylalkyl, heterocyclyl, heterocyclylalkyl, aryl, arylalkyl, heteroaryl, heteroarylalkyl" and wherein alternatively Z207, Z208 and/or Z216, Z217 and/or Z229, Z230 and/or Z236, Z237 and/or Z245, Z246 and/or Z255, Z256 and/or Z260, Z261 and/or Z277, Z278 and/or Z286, Z287 and/or Z289, Z290 and/or Z292, Z293 and/or Z295, Z296 and/or Z299, Z300 and/or Z305, Z306 and/or Z308, Z309 and/or Z311, Z312 and/or respectively together can also form "heterocyclyl";

wherein optionally above substituents of substituents group (ii) can in turn independently from each other be substituted with at least one substituent, identical or different, selected from the group consisting of:

(iii) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHZ401, —NZ402Z403, —NO$_2$, —OH, =O, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)—Z404, —C(O)O—Z405, —C(O)NH—Z406, —C(O)NZ407Z408, —O—Z409, —O(—Z410-O)$_e$—H (e=1, 2, 3, 4, 5), —O(—Z411-O)$_f$—Z412 (f=1, 2, 3, 4, 5), —OC(O)—Z413, —OC(O)—O—Z414, —OC(O)—NHZ415, —O—C(O)—NZ416Z417, —OP(O)(OZ418)(OZ419), —OSi(Z420)(Z421)(Z422), —OS(O$_2$)—Z423, —NHC(O)—NH$_2$, —NHC(O)—Z424, —NZ425C(O)—Z426, —NH—C(O)—O—Z427, —NH—C(O)—NH—Z428, —NH—C(O)—NZ429Z430, —NZ431-C(O)—O—Z432, —NZ433-C(O)—NH—Z434, —NZ435-C(O)—NZ436Z437, —NHS(O$_2$)—Z438, —NZ439S(O$_2$)—Z440, —S—Z441, —S(O)—Z442, —S(O$_2$)—Z443, —S(O$_2$)NH—Z444, —S(O$_2$)NZ445Z446, —S(O$_2$)O—Z447, —P(O)(OZ448)(OZ449), —Si(Z450)(Z451)(Z452), —C(NH)—NH$_2$, —C(NZ453)-NH$_2$, —C(NH)—NHZ454, —C(NH)—NZ455Z456, —C(NZ457)-NHZ458, —C(NZ459)-NZ460Z461, —NH—C(O)—NH—O—Z462, —NH—C(O)—NZ463-O—Z464, —NZ465-C(O)—NZ466-O—Z467, —N(—C(O)—NH—O—Z468)$_2$, —N(—C(O)—NZ469-O—Z470)$_2$, —N(—C(O)—NH—O—Z471)(—C(O)—NZ472-O—Z473), —C(S)—Z474, —C(S)—O—Z475, —C(S)—NH—Z476, —C(S)—NZ477Z478, —C(O)—NH—O—Z479, —C(O)—NZ480-O—Z481, —C(S)—NH—O—Z482, —C(S)—NZ483-O—Z484, —C(O)—NH—NH—Z485, —C(O)—NH—NZ486Z487, —C(O)—NZ488-NZ489Z490, —C(S)—NH—NH—Z491, —C(S)—NH—NZ492Z493, —C(S)—NZ494-NZ495Z496, —C(O)—C(O)—O—Z497, —C(O)—C(O)—NH$_2$, —C(O)—C(O)—NHZ498, —C(O)—C(O)—NZ499Z500, —C(S)—C(O)—O—Z501, —C(O)—C(S)—O—Z502, —C(S)—C(S)—O—Z503, —C(S)—C(O)—NH$_2$, —C(S)—C(O)—NHZ504, —C(S)—C(O)—NZ505Z506, —C(S)—C(S)—NH$_2$, —C(S)—C(S)—NHZ507, —C(S)—C(S)—NZ508Z509, —C(O)—C(S)—NH$_2$, —C(O)—C(S)—NHZ510, —C(O)—C(S)—NZ511Z512";

wherein Z401, Z402, Z403, Z404, Z405, Z406, Z407, Z408, Z409, Z410, Z411, Z412, Z413, Z414, Z415, Z416, Z417, Z418, Z419, Z420, Z421, Z422, Z423, Z424, Z425, Z426, Z427, Z428, Z429, Z430, Z431, Z432, Z433, Z434, Z435, Z436, Z437, Z438, Z439, Z440, Z441, Z442, Z443, Z444, Z445, Z446, Z447, Z448, Z449, Z450, Z451, Z452, Z453, Z454, Z455, Z456, Z457, Z458, Z459, Z460, Z461, Z462, Z463, Z464, Z465, Z466, Z467, Z468, Z469, Z470, Z471, Z472, Z473, Z474, Z475, Z476, Z477, Z478, Z479, Z480, Z481, Z482, Z483, Z484, Z485, Z486, Z487, Z488, Z489, Z490, Z491, Z492, Z493, Z494, Z495, Z496, Z497, Z498, Z499, Z500, Z501, Z502, Z503, Z504, Z505, Z506, Z507, Z508, Z509, Z510, Z511, Z512 are independently from each other selected from the group consisting of: "alkyl, (C$_9$-C$_{30}$) alkyl, cycloalkyl, cycloalkylalkyl, heterocyclyl, heterocyclylalkyl, aryl, arylalkyl, heteroaryl, heteroarylalkyl" and wherein alternatively Z407, Z408 and/or Z416, Z417 and/or Z429, Z430 and/or Z436, Z437 and/or Z445, Z446 and/or Z455, Z456 and/or Z460, Z461 and/or Z477, Z478 and/or Z486, Z487 and/or Z489, Z490 and/or Z492, Z493 and/or Z495, Z496 and/or Z499, Z500 and/or Z505, Z506 and/or Z508, Z509 and/or Z511, Z512 and/or respectively together can also form "heterocyclyl";

alternatively, R1, R3 can also independently from each other be "no substituent";

n independently is 1;

m independently is 1 or 2;

R4$_m$, R5$_m$, R6, R7, R8, R9, R10, R11, R12, R13, R14, R15, R16, R17, R18, R19, R20, R21, R22 are independently from each other selected from the group consisting of:

(i) "hydrogen, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHZ1001, —NZ1002Z1003, —NO$_2$, —OH, =O, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)—Z1004, —C(O)O—Z1005, —C(O)NH—Z1006, —C(O)NZ1007Z1008, —O—Z1009, —O(—Z1010-O)$_k$—H (k=1, 2, 3, 4, 5), —O(—Z1011-O)$_l$—Z101$^2$ (l=1, 2, 3, 4, 5), —OC(O)—Z1013, —OC(O)—O—Z1014, —OC(O)—NHZ1015, —O—C(O)—NZ1016Z1017, —OP(O)(OZ1018)(OZ1019), —OSi(Z1020)(Z1021)(Z1022), —OS(O$_2$)—Z1023, —NHC(O)—NH$_2$, —NHC(O)—Z1024, —NZ1025C(O)—Z1026, —NH—C(O)—O—Z1027, —NH—C(O)—NH—Z1028, —NH—C(O)—NZ1029Z1030, —NZ1031-C(O)—O—Z1032, —NZ1033-C(O)—NH—Z1034, —NZ1035-C(O)—NZ1036Z1037, —NHS(O$_2$)—Z1038, —NZ1039S(O$_2$)—Z1040, —S—Z1041, —S(O)—Z1042, —S(O$_2$)—Z1043, —S(O$_2$)NH—Z1044, —S(O$_2$)NZ1045Z1046, —S(O$_2$)O—Z1047, —P(O)(OZ1048)(OZ1049), —Si(Z1050)(Z1051)(Z1052), —C(NH)—NH$_2$, —C(NZ1053)-NH$_2$, —C(NH)—NHZ1054, —C(NH)—NZ1055Z1056, —C(NZ1057)-NHZ1058, —C(NZ1059)-NZ1060Z1061, —NH—C(O)—NH—O—Z1062, —NH—C(O)—NZ1063-O—Z1064, —NZ1065-C(O)—NZ1066-O—Z1067, —N(—C(O)—NH—O—Z1068)$_2$, —N(—C(O)—NZ1069-O—Z1070)$_2$, —N(—C(O)—NH—O—Z1071)(—C(O)—NZ1072-O—Z1073), —C(S)—Z1074, —C(S)—O—Z1075, —C(S)—NH—Z1076, —C(S)—NZ1077Z1078, —C(O)—NH—O—Z1079, —C(O)—NZ1080-O—Z1081, —C(S)—NH—O—Z1082, —C(S)—NZ1083-O—Z1084, —C(O)—NH—NH—Z1085, —C(O)—NH—NZ1086Z1087, —C(O)—NZ1088-NZ1089Z1090, —C(S)—NH—NH—Z1091, —C(S)—NH—NZ1092Z1093, —C(S)—NZ1094-NZ1095Z1096, —C(O)—C(O)—O—Z1097, —C(O)—C(O)—NH$_2$, —C(O)—C(O)—NHZ1098, —C(O)—C(O)—NZ1099Z1100, —C(S)—C(O)—O—Z1101, —C(O)—C(S)—O—Z1102, —C(S)—C(S)—O—Z1103, —C(S)—C(O)—NH$_2$, —C(S)—C(O)—NHZ1104, —C(S)—C(O)—NZ1105Z1106, —C(S)—C(S)—NH$_2$, —C(S)—C(S)—NHZ1107, —C(S)—C(S)—NZ1108Z1109, —C(O)—C(S)—NH$_2$, —C(O)—C(S)—NHZ1110, —C(O)—C(S)—NZ1111Z1112";

wherein X1001, X1002, X1003, X1004, X1005, X1006, X1007, X1008, X1009, X1010, X1011, X1012, X1013, X1014, X1015, X1016, X1017, X1018, X1019, X1020, X1021, X1022, X1023, X1024, X1025, X1026, X1027, X1028, X1029, X1030, X1031, X1032, X1033, X1034, X1035, X1036, X1037, X1038, X1039, X1040, X1041, X1042, X1043, X1044, X1045, X1046, X1047, X1048, X1049, X1050, X1051, X1052, X1053, X1054, X1055, X1056, X1057, X1058, X1059, X1060, X1061, X1062, X1063, X1064, X1065, X1066, X1067, X1068, X1069, X1070, X1071, X1072, X1073, X1074, X1075, X1076, X1077, X1078, X1079, X1080, X1081, X1082, X1083, X1084, X1085, X1086, X1087, X1088, X1089, X1090, X1091, X1092, X1093, X1094, X1095, X1096, X1097, X1098, X1099, X1100, X1101, X1102, X1103, X1104, X1105, X1106, X1107, X1108, X1109, X1110, X1111, X1112 are independently from each other selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl" and wherein alternatiVely X1007, X1008 and/or X1016, X1017 and/or X1029, X1030 and/or X1036, X1037 and/or X1045, X1046 and/or X1055, X1056 and/or X1060, X1061 and/or X1077, X1078 and/or X1086, X1087 and/or X1089, X1090 and/or X1092, X1093 and/or X1095, X1096 and/or X1099, X1100 and/or X1105, X1106 and/or X1108, X1109 and/or X1111, X1112 and/or respectively together can also form "heterocyclyl";

wherein optionally above substituents of substituents group (i) can in turn independently from each other be substituted with at least one substituent, identical or different, selected from the group consisting of:

(ii) "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF$_3$, —N$_3$, —NH$_2$, —NHZ1201, —NZ1202Z1203, —NO$_2$, —OH, =O, —OCF$_3$, —SH, —O—SO$_3$H, —OP(O)(OH)$_2$, —CHO, —COON, —C(O)NH$_2$, —SO$_3$H, —P(O)(OH)$_2$, —C(O)—Z1204, —C(O)O—Z1205, —C(O)NH-Z1206, —C(O)NZ1207Z1208, —O—Z1209, —O(—Z1210-O)$_m$—H (m=1, 2, 3, 4, 5), —O(—Z1211-O)$_n$—Z1212 (n=1, 2, 3, 4, 5), —OC(O)—Z1213, —OC(O)—O—Z1214, —OC(O)—NHZ1215, —O—C(O)—NZ1216Z1217, —OP(O)(OZ1218)(OZ1219), —OSi(Z1220)(Z1221)(Z1222), —OS(O$_2$)—Z1223, —NHC(O)—NH$_2$, —NHC(O)—Z1224, —NZ1225C(O)—Z1226, —NH—C(O)—O—Z1227, —NH—C(O)—NH—Z1228, —NH—C(O)—NZ1229Z1230, —NZ1231-C(O)—O—Z1232, —NZ1233-C(O)—NH—Z1234, —NZ1235-C(O)—NZ1236Z1237, —NHS(O$_2$)—Z1238, —NZ1239S(O$_2$)—Z1240, —S—Z1241, —S(O)—Z1242, —S(O$_2$)—Z1243, —S(O$_2$)NH—Z1244, —S(O$_2$)NZ1245Z1246, —S(O$_2$)O—Z1247, —P(O)(OZ1248)(OZ1249), —Si(Z1250)(Z1251)(Z1252), —C(NH)—NH$_2$, —C(NZ1253)-NH$_2$, —C(NH)—NHZ1254, —C(NH)—NZ1255Z1256, —C(NZ1257)-NHZ1258, —C(NZ1259)-NZ1260Z1261, —NH—C(O)—NH—O—Z1262, —NH—C(O)—NZ1263-O—Z1264, —NZ1265—C(O)—NZ1266-O—Z1267, —N(—C(O)—NH—O—Z1268)$_2$, —N(—C(O)—NZ1269-O—Z1270)$_2$, —N(—C(O)—NH—O—Z1271)(—C(O)—NZ1272-O—Z1273), —C(S)—Z1274, —C(S)—O—Z1275, —C(S)—NH—Z1276, —C(S)—NZ1277Z1278, —C(O)—NH—O—Z1279, —C(O)—NZ1280-O—Z1281, —C(S)—NH—O—Z1282, —C(S)—NZ1283-O—Z1284, —C(O)—NH—NH—Z1285, —C(O)—NH—NZ1286Z1287, —C(O)—NZ1288-NZ1289Z1290, —C(S)—NH—NH—Z1291, —C(S)—NH—NZ1292Z1293, —C(S)—NZ1294-NZ1295Z1296, —C(O)—C(O)—O—Z1297, —C(O)—C(O)—NH$_2$, —C(O)—C(O)—NHZ1298, —C(O)—C(O)—NZ1299Z1300, —C(S)—C(O)—O—Z1301, —C(O)—C(S)—O—Z1302, —C(S)—C(S)—O—Z1303, —C(S)—C(O)—NH$_2$, —C(S)—C(O)—NHZ1304, —C(S)—C(O)—NZ1305Z1306, —C(S)—C(S)—NH$_2$, —C(S)—C(S)—NHZ1307, —C(S)—C(S)—NZ1308Z1309, —C(O)—C(S)—NH$_2$, —C(O)—C(S)—NHZ1310, —C(O)—C(S)—NZ1311Z1312";

wherein Z1201, Z1202, Z1203, Z1204, Z1205, Z1206, Z1207, Z1208, Z1209, Z1210, Z1211, Z1212, Z1213, Z1214, Z1215, Z1216, Z1217, Z1218, Z1219, Z1220, Z1221, Z1222, Z1223, Z1224, Z1225, Z1226, Z1227, Z1228, Z1229, Z1230, Z1231, Z1232, Z1233, Z1234, Z1235, Z1236, Z1237, Z1238, Z1239, Z1240, Z1241, Z1242, Z1243, Z1244, Z1245, Z1246, Z1247, Z1248, Z1249, Z1250, Z1251, Z1252, Z1253, Z1254, Z1255, Z1256, Z1257, Z1258, Z1259, Z1260, Z1261, Z1262, Z1263, Z1264, Z1265, Z1266, Z1267, Z1268, Z1269, Z1270, Z1271, Z1272, Z1273, Z1274, Z1275, Z1276, Z1277, Z1278, Z1279, Z1280, Z1281, Z1282, Z1283, Z1284, Z1285, Z1286, Z1287, Z1288, Z1289, Z1290, Z1291, Z1292, Z1293, Z1294, Z1295, Z1296, Z1297, Z1298, Z1299, Z1300, Z1301, Z1302, Z1303, Z1304, Z1305, Z1306, Z1307, Z1308, Z1309, Z1310, Z1311, Z1312 are independently from each other selected from the group consisting of: "alkyl, $(C_9-C_{30})$alkyl, cycloalkyl, cycloalkylalkyl, heterocyclyl, heterocyclylalkyl, aryl, arylalkyl, heteroaryl, heteroarylalkyl" and wherein alternatively Z1207, Z1208 and/or Z1216, Z1217 and/or Z1229, Z1230 and/or Z1236, Z1237 and/or Z1245, Z1246 and/or Z1255, Z1256 and/or Z1260, Z1261 and/or Z1277, Z1278 and/or Z1286, Z1287 and/or Z1289, Z1290 and/or Z1292, Z1293 and/or Z1295, Z1296 and/or Z1299, Z1300 and/or Z1305, Z1306 and/or Z1308, Z1309 and/or Z1311, Z1312 and/or respectively together can also form "heterocyclyl";

wherein optionally above substituents of substituents group (ii) can in turn independently from each other be substituted with at least one substituent, identical or different, selected from the group consisting of:

(iii) "alkyl, $(C_9-C_{30})$alkyl, cycloalkyl, cycloalkylalkyl, heterocyclyl, heterocyclylalkyl, aryl, arylalkyl, heteroaryl, heteroarylalkyl, —F, —Cl, —Br, —I, —CN, —CF₃, —N₃, —NH₂, —NHZ1401, —NZ1402Z1403, —NO₂, —OH, =O, —OCF₃, —SH, —O—SO₃H, —OP(O)(OH)₂, —CHO, —COOH, —C(O)NH₂, —SO₃H, —P(O)(OH)₂, —C(O)—Z1404, —C(O)O—Z1405, —C(O)NH—Z1406, —C(O)NZ1407Z1408, —O—Z1409, —O(—Z1410-O)$_o$H (o=1, 2, 3, 4, 5), —O(—Z1411-O)$_p$—Z1412 (p=1, 2, 3, 4, 5), —OC(O)—Z1413, —OC(O)—O—Z1414, —OC(O)—NHZ1415, —O—C(O)—NZ1416Z1417, —OP(O)(OZ1418)(OZ1419), —OSi(Z1420)(Z1421)(Z1422), —OS(O₂)—Z1423, —NHC(O)—NH₂, —NHC(O)—Z1424, —NZ1425C(O)—Z1426, —NH—C(O)—O—Z1427, —NH—C(O)—NH—Z1428, —NH—C(O)—NZ1429Z1430, —NZ1431-C(O)—O—Z1432, —NZ1433-C(O)—NH—Z1434, —NZ1435-C(O)—NZ1436Z1437, —NHS(O₂)—Z1438, —NZ1439S(O₂)—Z1440, —S—Z1441, —S(O)—Z1442, —S(O₂)—Z1443, —S(O₂)NH—Z1444, —S(O₂)NZ1445Z1446, —S(O₂)O—Z1447, —P(O)(OZ1448)(OZ1449), —Si(Z1450)(Z1451)(Z1452), —C(NH)—NH₂, —C(NZ1453)-NH₂, —C(NH)—NHZ1454, —C(NH)—NZ1455Z1456, —C(NZ1457)-NHZ1458, —C(NZ1459)-NZ1460Z1461, —NH—C(O)—NH—O—Z1462, —NH—C(O)—NZ1463-O—Z1464, —NZ1465-C(O)—NZ1466-O—Z1467, —N(—C(O)—NH—O—Z1468)₂, —N(—C(O)—NZ1469-O—Z1470)₂, —N(—C(O)—NH—O—Z1471)(—C(O)—NZ1472-O—Z1473), —C(S)—Z1474, —C(S)—O—Z1475, —C(S)—NH—Z1476, —C(S)—NZ1477Z1478, —C(O)—NH—O—Z1479, —C(O)—NZ1480-O—Z1481, —C(S)—NH—O—Z1482, —C(S)—NZ1483-O—Z1484, —C(O)—NH—NH—Z1485, —C(O)—NH—NZ1486Z1487, —C(O)—NZ1488-NZ1489Z1490, —C(S)—NH—NH—Z1491, —C(S)—NH—NZ1492Z1493, —C(S)—NZ1494-NZ1495Z1496, —C(O)—C(O)—O—Z1497, —C(O)—C(O)—NH₂, —C(O)—C(O)—NHZ1498, —C(O)—C(O)—NZ1499Z1500, —C(S)—C(O)—O—Z1501, —C(O)—C(S)—O—Z1502, —C(S)—C(S)—O—Z1503, —C(S)—C(O)—NH₂, —C(S)—C(O)—NHZ1504, —C(S)—C(O)—NZ1505Z1506, —C(S)—C(S)—NH₂, —C(S)—C(S)—NHZ1507, —C(S)—C(S)—NZ1508Z1509, —C(O)—C(S)—NH₂, —C(O)—C(S)—NHZ1510, —C(O)—C(S)—NZ1511Z1512";

wherein Z1401, Z1402, Z1403; Z1404, Z1405, Z1406, Z1407, Z1408, Z1409, Z1410, Z1411, Z1412, Z1413, Z1414, Z1415, Z1416, Z1417, Z1418, Z1419, Z1420, Z1421, Z1422, Z1423, Z1424, Z1425, Z1426, Z1427, Z1428, Z1429, Z1430, Z1431, Z1432, Z1433, Z1434, Z1435, Z1436, Z1437, Z1438, Z1439, Z1440, Z1441, Z1442, Z1443, Z1444, Z1445, Z1446, Z1447, Z1448, Z1449, Z1450, Z1451, Z1452, Z1453, Z1454, Z1455, Z1456, Z1457, Z1458, Z1459, Z1460, Z1461, Z1462, Z1463, Z1464, Z1465, Z1466, Z1467, Z1468, Z1469, Z1470, Z1471, Z1472, Z1473, Z1474, Z1475, Z1476, Z1477, Z1478, Z1479, Z1480, Z1481, Z1482, Z1483, Z1484, Z1485, Z1486, Z1487, Z1488, Z1489, Z1490, Z1491, Z1492, Z1493, Z1494, Z1495, Z1496, Z1497, Z1498, Z1499, Z1500, Z1501, Z1502, Z1503, Z1504, Z1505, Z1506, Z1507, Z1508, Z1509, Z1510, Z1511, Z1512 are independently from each other selected from the group consisting of: "alkyl, $(C_9-C_{30})$alkyl, cycloalkyl, cycloalkylalkyl, heterocyclyl, heterocyclylalkyl, aryl, arylalkyl, heteroaryl, heteroarylalkyl" and wherein alternatively Z1407, Z1408 and/or Z1416, Z1417 and/or Z1429, Z1430 and/or Z1436, Z1437 and/or Z1445, Z1446 and/or Z1455, Z1456 and/or Z1460, Z1461 and/or Z1477, Z1478 and/or Z1486, Z1487 and/or Z1489, Z1490 and/or Z1492, Z1493 and/or Z1495, Z1496 and/or Z1499, Z1500 and/or Z1505, Z1506 and/or Z1508, Z1509 and/or Z1511, Z1512 and/or respectively together can also form "heterocyclyl".

With regard to the alternative embodiment "no substituent" for R1 and R3, it is understood in the course of the present invention that R1 and/or R3 are not present and that the valences of the respective carbon and/or nitrogen atom, of which R1 and R3 are ligands and that are part of "heterocyclyl" or "heteroaryl", are fully used up by means of double and/or triple bonds.

With regard to R1, R1* and n, it is understood in the course of the present invention that if n is 0 substituents R1, R1* and the corresponding harbouring carbon atom are not present, i.e. the nitrogen atom harbouring R2, R3 is directly attached to the carbon atom harbouring $R4_m$, $R5_m$. If n is 1, then one carbon atom harbouring R1, R1* is pre-sent between the carbon atom harbouring $R4_m$, $R5_m$ and the nitrogen atom harbouring R2, R3.

With regard to $R4_m$, $R5_m$, and m, it is understood in the course of the present invention that if m is 1, one carbon atom harbouring one radical $R4_m$ and one radical $R5_m$ is present. If m is 2, then two carbon atoms each harbouring one radical $R4_m$ and one radical $R5_m$ are present, where all four radicals $R4_{m1}$, $R5_{m1}$, $R4_{m2}$, $R5_{m2}$ can independently from each other be identical or different.

In a preferred embodiment, tetrahydrocarbazole compounds according to formula (I) are provided, where according to (A)

V, W are independently "=O";
R1, R1* together independently form "=O or =S" or are independently both "hydrogen";
n is 1;
m is 1 or 2;
R2 is independently selected from the group consisting of: "—$NH_2$, —NH-aryl, —CO-heterocyclyl, —CO-heterocyclylalkyl, —CO-heteroarylalkyl, —CO—NH-heterocyclylalkyl, —NH—CO-alkyl, —NH—CO-aryl, —NH—CO—$NH_2$, alkyl, cycloalkyl, aryl, arylalkyl, heterocyclyl, heterocyclylalkyl, heteroaryl, heteroarylalkyl, —O-alkyl", where "alkyl", "cycloalkyl", "aryl", "heteroaryl" and "arylalkyl" must be independently from each other substituted with at least one substituent selected from the group consisting of: "heterocyclyl, —OH, —COOH, —N(alkyl)$_2$, —P(O)(O-alkyl)$_2$, —P(O)(OH)$_2$, —OP(O)(O-alkyl)$_2$, —OP(O)(OH)$_2$, —OC(O)-alkyl, —OC(O)O-alkyl" and where "NH-aryl", "—CO-heterocyclyl", "—CO-heterocyclylalkyl", "—CO-heteroarylalkyl", "—CO—NH-heterocyclylalkyl", "—NH—CO-alkyl", "—NH—CO-aryl", "alkyl", "cycloalkyl", "aryl", "arylalkyl", "heterocyclyl", "heterocyclylalkyl", "heteroaryl", "heteroarylalkyl", and "—O-alkyl" are optionally independently from each other (further) substituted with at least one substituent selected from the group consisting of: "alkyl, —F, —Cl, —OH, —COOH, —CHO, —O-alkyl, —C(O)-alkyl, —N(alkyl)$_2$, —O(-alkyl-O)$_2$-alkyl";
$R4_m$, R8 are independently "alkyl";
R3, $R5_m$, R6, R7, R9, R11, R12, R13, R14, R15, R16, R21, R22 are independently "hydrogen";
R10 independently is selected from the group consisting of "—C(O)O-arylalkyl, —C(O)-arylalkyl, —C(S)-arylalkyl", where "arylalkyl" is optionally substituted with at least one substituent selected from the group consisting of: "—F, —Cl";
R17, R18, R19, R20 are independently from each other selected from the group consisting of "hydrogen, —F, —Cl, —$CF_3$".

In a further preferred embodiment of the foregoing embodiment,
R1, R1* are not present;
n is 0.

In another preferred embodiment, tetrahydrocarbazole compounds according to formula (I) are provided, where according to (A)
V, W are independently "=O";
n is 1;
m is 1 or 2;
R1, R1* together independently form "=O or =S" or are independently both "hydrogen";

R2 is independently selected from the group consisting of: "amino, N'-(acetyl)-amino, N'-(aminocarbonyl)-amino, N'-phenyl-amino, N'-(4-hydroxy-phenyl)-amino, N'-(4-methoxy-phenyl)-amino, N'-(3-hydroxy-4-methoxy-benzyl)-amino, N'-(4-hydroxy-3-methoxy-benzyl)-amino, N'-(4-hydroxy-benzoyl)-amino, 2-hydroxy-ethyl, 2-diethylamino-ethyl, 3-hydroxy-propyl, 4-hydroxy-butyl, 5-hydroxy-pentyl, 2,3,4,5,6-pentahydroxy-hexan-1-yl, 2-(3,4,5,6-tetrahydroxy)-hexanoic acid, 4-butyl-phosphonic acid diethyl ester, 4-butyl-phosphonic acid, dimethylamino-acetic acid 4-butyl ester, carbonic acid 4-butyl ester 2-[2-(2-methoxy-ethoxy)-ethoxy]-ethyl ester, phosphoric acid mono-4-butyl ester, phosphonic acid diethyl ester 4-(2-methoxy)-phenyl ester, methoxy, ethoxy, 4-hydroxy-cyclohexyl, 4-hydroxy-phenyl, 4-methoxy-phenyl, 3-fluoro-4-hydroxy-phenyl, 4-hydroxy-3-methoxy-phenyl, 2-hydroxy-4-methoxy-phenyl, 3-hydroxy-4-methoxy-phenyl, 2,4-dihydroxy-phenyl, benzyl, 4-hydroxy-benzyl, 3-hydroxy-4-methoxy-benzyl, 2-(5-methoxy)-benzoic acid, 5-(2-methoxy)-benzoic acid, 5-(2-hydroxy)-benzoic acid, furan-2-yl-methyl, furan-3-yl-methyl, 2-furan-2-yl-ethyl, 2-imidazol-1-yl-ethyl, 3-imidazol-1-yl-propyl, 3-imidazol-1-yl-propionyl, 2-thiophen-2-yl-ethyl, 2-pyrazol-1-yl-ethyl, 2-(1,2,4)triazol-1-yl-ethyl, 3-(1,2,4)triazol-1-yl-propyl, 4-(1,2,4)triazol-1-yl-butyl, 5-methyl-(1,3,4)oxadiazol-2-yl-methyl, 2-methoxy-pyridin-4-yl-methyl, pyridin-3-yl-methyl, pyridin-4-yl-methyl, pyridin-4-yl-ethyl, 6-chloro-pyridin-3-yl-methyl, 2-pyridin-3-yl-ethyl, pyrimidin-4-yl-methyl, pyrimidin-5-yl-methyl, pyrazin-2-yl-methyl, pyrrolidin-1-yl-methyl, morpholin-4-yl, morpholin-4-yl-methyl, morpholin-4-yl-ethyl, morpholin-4-yl-propyl, 3-morpholin-4-yl-propionyl, tetrahydro-puran-3-yl-methyl, tetrahydro-puran-4-yl-methyl, tetrahydro-puran-4-yl, tetrahydro-puran-4-carbonyl, 2-(tetrahydro-puran-4-yl)-ethyl, 2-(tetrahydro-puran-4-yl)-acetyl, tetrahydro-puran-4-yl-methyl-carbamoyl, 3,4,5-trihydroxy-6-hydroxymethyl-tetrahydro-puran-2-yl, piperidin-4-yl-methyl, 1-methyl-piperidin-4-yl-methyl, 1-formyl-piperidin-4-yl-methyl, 1-acetyl-piperidin-4-yl-methyl";
$R4_m$, R8 are independently "1-methyl-propan-1-yl";
R3, $R5_m$, R6, R7, R9, R11, R12, R13, R14, R15, R16, R21, R22 are independently "hydrogen";
R10 independently is selected from the group consisting of "benzyloxycarbonyl, 2,6-difluoro-phenyl-acetyl, 2-fluoro-phenyl-acetyl, 2-fluoro-phenyl-thioacetyl";
R17, R18, R19, R20 are independently from each other selected from the group consisting of "hydrogen, —F, —Cl, —$CF_3$".

In a further preferred embodiment of the foregoing embodiment,
R1, R1* are not present;
n is 0.

In a further preferred embodiment, tetrahydrocarbazole compounds according to formula (I) are provided, where according to (B)
V, W are independently "=O";
n is 1;
m is 1 or 2;
R1*, R2 together independently form "heteroaryl" or "heterocyclyl", where "heteroaryl" and "heterocyclyl" are optionally substituted with at least one substituent selected from the group consisting of: "alkyl, —CN, —$NH_2$, =O, —C(O)O-alkyl, —C(O)$NH_2$, —C(O)N(alkyl)$_2$, —NH—C(O)-alkyl, —NH—C(O)—NH-alkyl, —NH—C(O)—NH—O-alkyl, —N(C(O)—NH—O-alkyl)$_2$";
R1, R3 are independently "no substituent";

R4$_m$, R8 are independently "alkyl";
R5$_m$, R6, R7, R9, R11, R12, R13, R14, R15, R16, R21, R22 are independently "hydrogen";
R10 independently is selected from the group consisting of "—C(O)O-arylalkyl, —C(O)arylalkyl, —C(S)-arylalkyl", where "arylalkyl" is optionally substituted with at least one substituent selected from the group consisting of: "—F, —Cl";
R17, R18, R19, R20 are independently from each other selected from the group consisting of "hydrogen, —F, —Cl, —CF$_3$".

In a yet further preferred embodiment, tetrahydrocarbazole compounds according to formula (I) are provided, where according to (B)
V, W are independently "=O";
n is 1;
m is 1 or 2;
R1*, R2 together independently form "(1,3,4)oxadiazol-2-yl, 5-amino-(1,3,4)oxadiazol-2-yl, 3-methyl-(1,2,4)oxadiazol-5-yl, 5-methyl-(1,3,4)oxadiazol-2-yl, 5-(1,2,4)oxadiazole-3-carboxylic acid methyl ester, 5-(1,2,4)oxadiazole-3-carboxylic acid ethyl ester, 5-(1,3,4)oxadiazole-2-carboxylic acid ethyl ester, 5-oxo-4,5-dihydro-(1,3,4)-oxadiazol-2-yl, 3-carbamoyl-(1,2,4)oxadiazol-5-yl, 3-diethylcarbamoyl-(1,2,4)oxadiazol-5-yl, 5-acetylamino-(1,3,4)-oxadiazol-2-yl, 5-(1,2,4)oxadiazole-3-carboxylic acid propyl ester, 3-cyano-(1,2,4)oxadiazol-5-yl, 5-(3-ethyl-ureido)-(1,3,4)oxadiazol-2-yl, 5-(3-methoxy-ureido)-(1,3,4)oxadiazol-2-yl, 5-[1-(methoxy-amino-carbonyl)-3-methoxy-ureido]-(1,3,4)oxadiazol-2-yl or 1H-tetrazol-5-yl";
R1, R3 are independently "no substituent";
R4$_m$, R8 are independently "1-methyl-propan-1-yl";
R5$_m$, R6, R7, R9, R11, R12, R13, R14, R15, R16, R21, R22 are independently "hydrogen";
R10 independently is selected from the group consisting of "benzyloxycarbonyl, 2,6-difluoro-phenyl-acetyl, 2-fluoro-phenyl-acetyl, 2-fluoro-phenyl-thioacetyl";
R17, R18, R19, R20 are independently from each other selected from the group consisting of "hydrogen, —F, —Cl, —CF$_3$".

In another preferred embodiment, tetrahydrocarbazole compounds according to formula (I) and above preferred embodiments are provided that are selected from the group consisting of:

Compound 1 ((S)-14(R)-3-[(R)-1-(5-Amino-[1,3,4] oxadiazol-2-yl)-2-methyl-butylcarbarnoyl]-6,8-dichloro-2,3,4,9-tetrahydro-1H-carbazol-3-ylcarbamoyl)-2-methyl-butyl)-carbamic acid benzyl ester

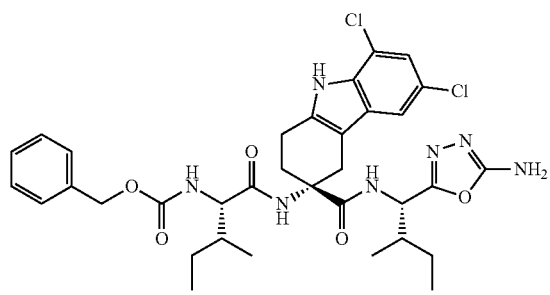 [SMILES: CCC(C)[C@H](NC(=O)OCc1ccccc1)C(=O)N[C@]1(C(=O)N[C@H](c2nnc(N)o2)C(C)CC)CCc2[nH]c3c(Cl)cc(Cl)cc3c2C1]

Compound 2 ((S)-1-{(S)-3-[(R)-1-(5-Amino-[1,3,4] oxadiazol-2-yl)-2-methyl-butylcarbamoyl]-6,8-dichloro-2,3,4,9-tetrahydro-1H-carbazol-3-ylcarbarnoyl}-2-methyl-butyl)-carbamic acid benzyl ester

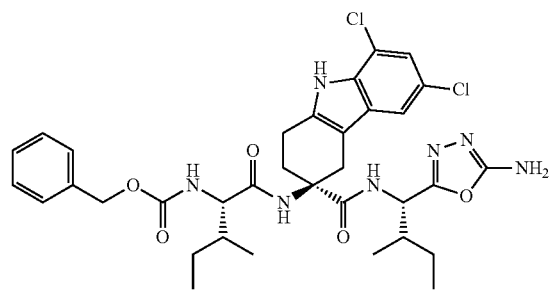 [SMILES: CCC(C)[C@H](NC(=O)OCc1ccccc1)C(=O)N[C@@]1(C(=O)N[C@H](c2nnc(N)o2)C(C)CC)CCc2[nH]c3c(Cl)cc(Cl)cc3c2C1]

Compound 3 ((S)-1-{(R)-6,8-Dichloro-3-[(S)-2-methyl-1-(3-methyl-[1,2,4]oxadiazol-5-yl)-butylcarbamoyl]-2,3,4,9-tetrahydro-1H-carbazol-3-ylcarbamoyl}-2-methyl-butyl)-carbamic acid benzyl ester

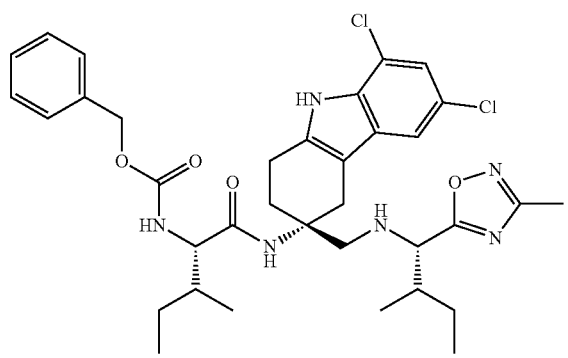 [SMILES: CCC(C)[C@H](NC(=O)OCc1ccccc1)C(=O)N[C@]1(CN[C@H](c2nc(C)no2)C(C)CC)CCc2[nH]c3c(Cl)cc(Cl)cc3c2C1]

Compound 4 ((S)-1-{(S)-6,8-Dichloro-3-[(S)-2-methyl-1-(3-methyl-[1,2,4]oxadiazol-5-yl)-butylcarbamoyl]-2,3,4,9-tetrahydro-1H-carbazol-3-ylcarbamoyl}-2-methyl-butyl)-carbamic acid benzyl ester

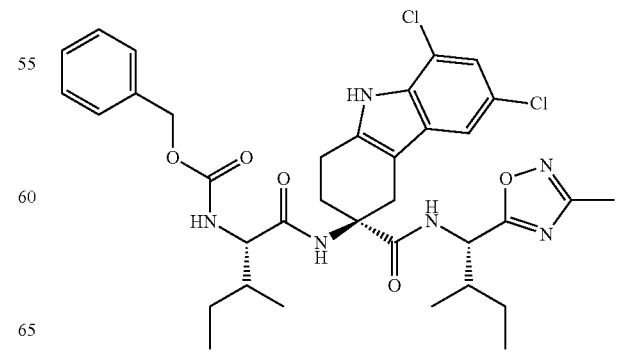

Compound 5 5-((S)-1-{[(R)-3-((S)-2-Benzyloxycarbonylamino-3-methyl-pentanoylamino)-6,8-dichloro-2,3,4,9-tetrahydro-1H-carbazole-3-carbonyl]-amino}-2-methyl-butyl)-[1,2,4]oxadiazole-3-carboxylic acid ethyl ester

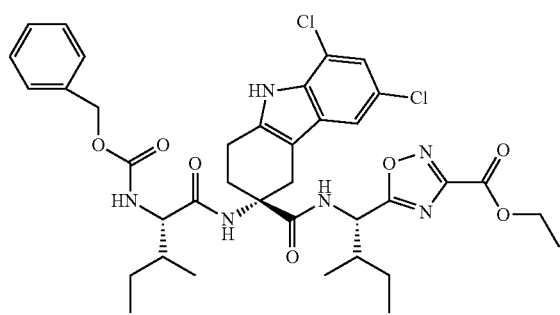 [SMILES: CCOC(=O)c1noc([C@@H](NC(=O)[C@@]2(NC(=O)[C@@H](NC(=O)OCc3ccccc3)C(C)CC)CCc3[nH]c4c(Cl)cc(Cl)cc4c3C2)C(C)CC)n1]

Compound 6 5-((S)-1-{[(S)-3-((S)-2-Benzyloxycarbonylamino-3-methyl-pentanoylamino)-6,8-dichloro-2,3,4,9-tetrahydro-1H-carbazole-3-carbonyl]-amino}-2-methyl-butyl)-[1,2,4]oxadiazole-3-carboxylic acid ethyl ester

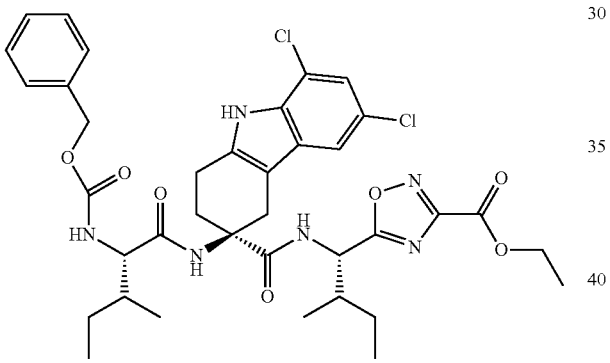

Compound 7 ((S)-1-{(S)-6,8-Dichloro-3-[(S)-2-methyl-1-(5-oxo-4,5-dihydro-[1,3,4]oxadiazol-2-yl)-butylcarbamoyl]-2,3,4,9-tetrahydro-1H-carbazol-3-ylcarbamoyl}-2-methyl-butyl)-carbamic acid benzyl ester

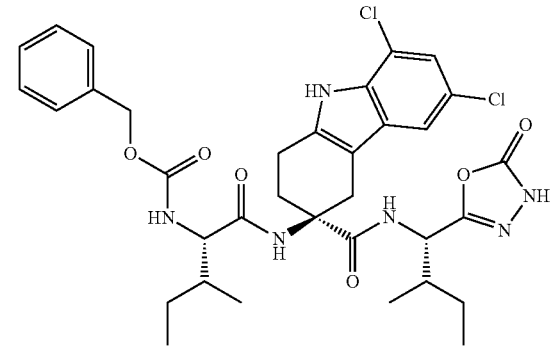 [SMILES: CCC(C)[C@H](NC(=O)OCc1ccccc1)C(=O)N[C@@]1(C(=O)N[C@H](c2n[nH]c(=O)o2)C(C)CC)CCc2[nH]c3c(Cl)cc(Cl)cc3c2C1]

Compound 8 {(S)-1-[(R)-6,8-Dichloro-3-((S)-2-methyl-1-[1,3,4]oxadiazol-2-yl-butylcarbamoyl)-2,3,4,9-tetrahydro-1H-carbazol-3-ylcarbamoyl]-2-methyl-butyl}-carbamic acid benzyl ester

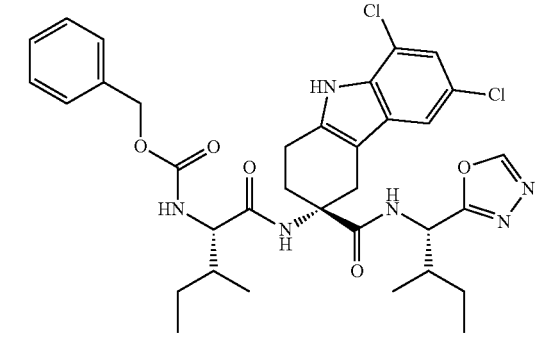 [SMILES: CCC(C)[C@H](NC(=O)OCc1ccccc1)C(=O)N[C@]1(C(=O)N[C@H](c2nnco2)C(C)CC)CCc2[nH]c3c(Cl)cc(Cl)cc3c2C1]

Compound 9 {(S)-1-[(S)-6,8-Dichloro-3-((S)-2-methyl-[1,3,4]oxadiazol-2-yl-butylcarbamoyl)-2,3,4,9-tetrahydro-1H-carbazol-3-ylcarbamoyl]-2-methyl-butyl}-carbamic acid benzyl ester

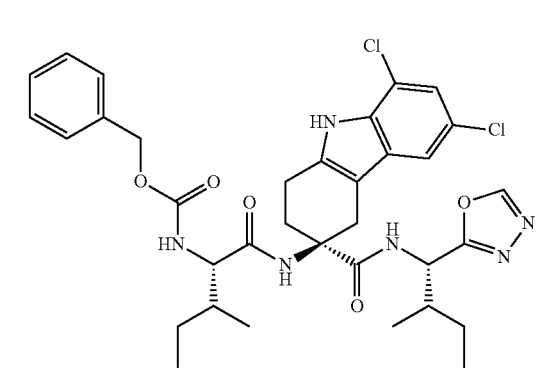 [SMILES: CCC(C)[C@H](NC(=O)OCc1ccccc1)C(=O)N[C@@]1(C(=O)N[C@H](c2nnco2)C(C)CC)CCc2[nH]c3c(Cl)cc(Cl)cc3c2C1]

Compound 10 ((S)-1-{(R)-3-[(S)-1-(3-Carbamoyl-[1,2,4]oxadiazol-5-yl)-2-methyl-butylcarbamoyl]-6,8-dichloro-2,3,4,9-tetrahydro-1H-carbazol-3-ylcarbamoyl}-2-methyl-butyl)-carbamic acid benzyl ester

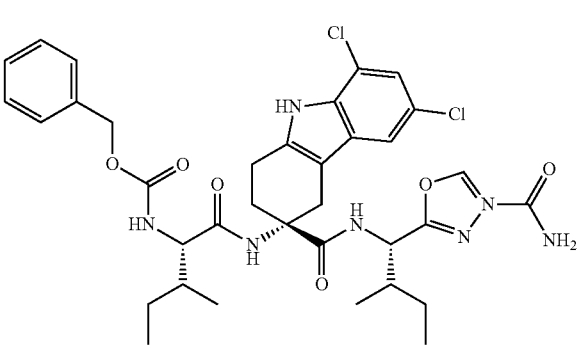

Compound 11 ((S)-1-{(S)-3-[(S)-1-(3-Carbamoyl-[1,2,4]oxadiazol-5-yl)-2-methyl-butylcarbamoyl]-6,8-dichloro-2,3,4,9-tetrahydro-1H-carbazol-3-ylcarbamoyl}-2-methyl-butyl)-carbamic acid benzyl ester

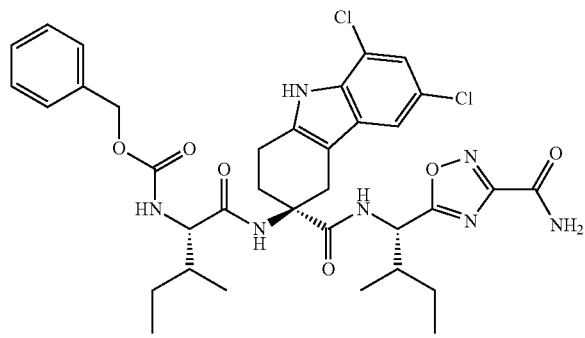 [SMILES: CCC(C)[C@H](NC(=O)OCc1ccccc1)C(=O)N[C@@]1(C(=O)N[C@H](c2nc(C(N)=O)no2)C(C)CC)CCc2[nH]c3c(Cl)cc(Cl)cc3c2C1]

Compound 12 5-{(S)-1-[((R)-3-{(S)-2-[2-(2,6-Difluoro-phenyl)-acetylamino]-3-methyl-pentanoylamino}-8-trifluoromethyl-2,3,4,9-tetrahydro-1H-carbazole-3-carbonyl)-amino]-2-methyl-butyl}-[1,2,4]oxadiazole-3-carboxylic acid ethyl ester

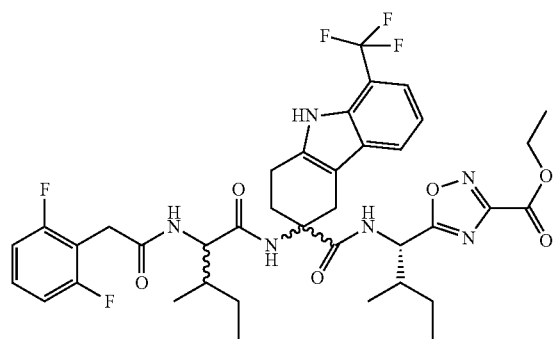

Compound 13 5-((S)-1-{[(R)-3-((S)-2-Benzyloxycarbonylamino-3-methyl-pentanoylamino)-6,8-dichloro-2,3,4,9-tetrahydro-1H-carbazole-3-carbonyl]-amino}-2-methyl-butyly[1,3,4]oxadiazole-2-carboxylic acid ethyl ester

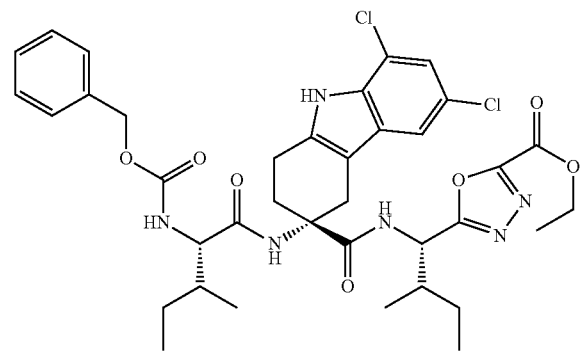 [SMILES: CCOC(=O)c1nnc([C@@H](NC(=O)[C@@]2(NC(=O)[C@@H](NC(=O)OCc3ccccc3)C(C)CC)CCc3[nH]c4c(Cl)cc(Cl)cc4c3C2)C(C)CC)o1]

Compound 14 ((S)-1-{(R)-3-[(S)-1-(5-Acetylamino-[1,3,4]oxadiazol-2-yl)-2-methyl-butylcarbamoyl]-6,8-dichloro-2,3,4,9-tetrahydro-1H-carbazol-3-ylcarbamoyl}-2-methyl-butyl)-carbamic acid benzyl ester

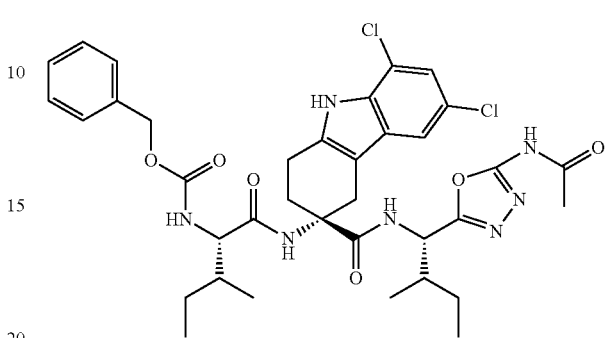

Compound 15 5-((S)-1-{[(S)-3-((S)-2-Benzyloxycarbonylamino-3-methyl-pentanoylamino)-6,8-dichloro-2,3,4,9-tetrahydro-1H-carbazole-3-carbonyl]-amino}-2-methyl-butyl)-[1,3,4]oxadiazole-2-carboxylic acid ethyl ester

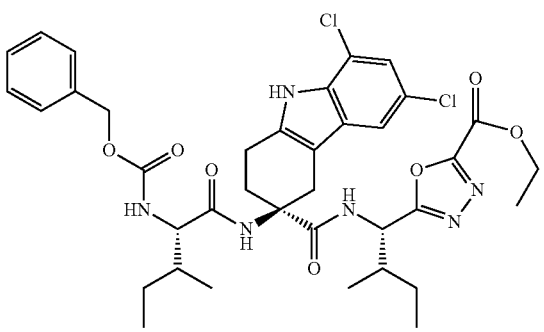 [SMILES: CCOC(=O)c1nnc([C@@H](NC(=O)[C@]2(NC(=O)[C@@H](NC(=O)OCc3ccccc3)C(C)CC)CCc3[nH]c4c(Cl)cc(Cl)cc4c3C2)C(C)CC)o1]

Compound 16 ((S)-1-{(S)-3-[(S)-1-(5-Acetylamino-[1,3,4]oxadiazol-2-yl)-2-methyl-butylcarbamoyl]-6,8-dichloro-2,3,4,9-tetrahydro-1H-carbazol-3-ylcarbamoyl}-2-methyl-butyl)-carbamic acid benzyl ester

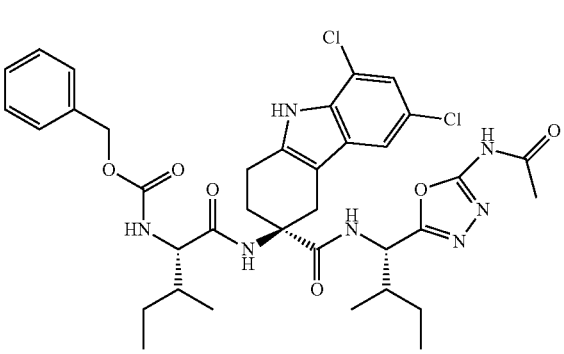 [SMILES: CCC(C)[C@H](NC(=O)OCc1ccccc1)C(=O)N[C@@]1(C(=O)N[C@H](c2nnc(NC(C)=O)o2)C(C)CC)CCc2[nH]c3c(Cl)cc(Cl)cc3c2C1]

Compound 17 ((S)-1{(R)-6,8-Dichloro-3-[(S)-2-methyl-1-(5-oxo-4,5-dihydro-[1,3,4]oxadiazol-2-yl)-butylcarbamoyl]-2,3,4,9-tetrahydro-1H-carbazol-3-ylcarbamoyl}-2-methyl-butyl)-carbamic acid benzyl ester

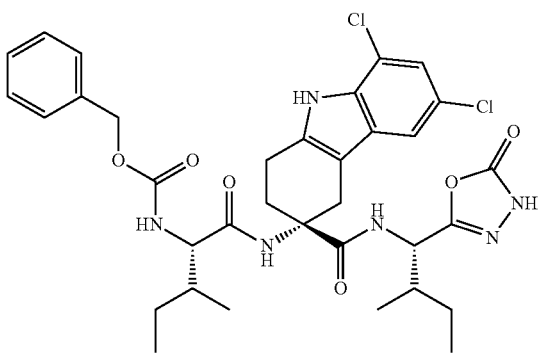 [SMILES: CCC(C)[C@H](NC(=O)OCc1ccccc1)C(=O)N[C@]1(C(=O)N[C@H](c2n[nH]c(=O)o2)C(C)CC)CCc2[nH]c3c(Cl)cc(Cl)cc3c2C1]

Compound 18 5-((S)-1-{[(R)-3-((S)-2-Benzyloxycarbonylamino-3-methyl-pentanoylamino)-6,8-dichloro-2,3,4,9-tetrahydro-1H-carbazole-3-carbonyl]-amino}-2-methyl-butyl)-[1,2,4]oxadiazole-3-carboxylic acid propyl ester

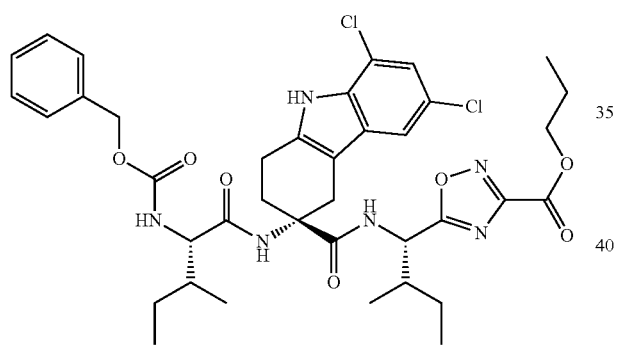

Compound 19 5-((S)-1-{[(S)-3-((S)-2-Benzyloxycarbonylamino-3-methyl-pentanoylamino)-6,8-dichloro-2,3,4,9-tetrahydro-1H-carbazole-3-carbonyl]-amino}-2-methyl-butyl)-[1,2,4]oxadiazole-3-carboxylic acid propyl ester

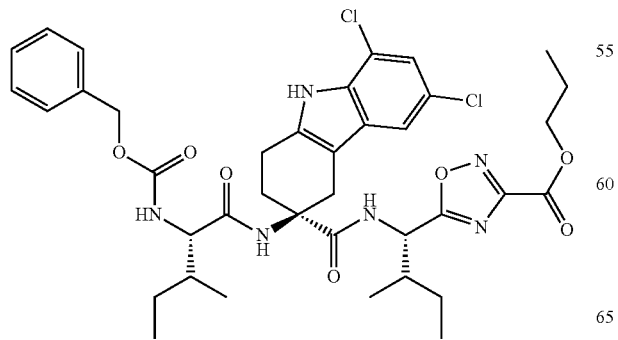

Compound 20 ((S)-1-{(R)-6,8-Dichloro-3-[(S)-1-(3-diethylcarbamoyl-[1,2,4]oxadiazol-5-yl)-2-methyl-butylcarbamoyl]-2,3,4,9-tetrahydro-1H-carbazol-3-ylcarbamoyl}-2-methyl-butyl)-carbamic acid benzyl ester

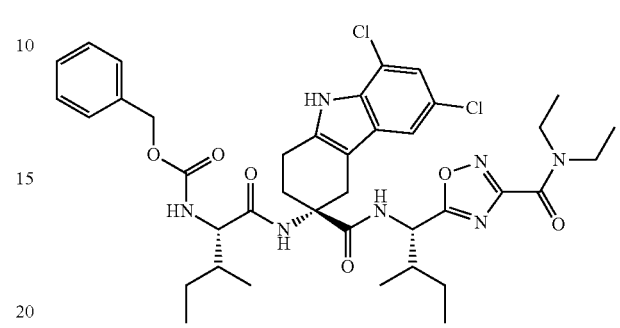

Compound 21 ((S)-1-{(R)-6,8-Dichloro-3-[(S)-1-(3-cyano-[1,2,4]oxadiazol-5-yl)-2-methyl-butylcarbamoyl]-2,3,4,9-tetrahydro-1H-carbazol-3-ylcarbamoyl}-2-methyl-butyl)-carbamic acid benzyl ester

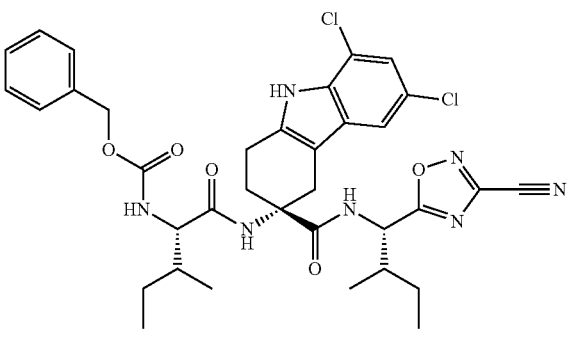 [SMILES: CCC(C)[C@H](NC(=O)OCc1ccccc1)C(=O)N[C@]1(C(=O)N[C@H](c2nc(C#N)no2)C(C)CC)CCc2[nH]c3c(Cl)cc(Cl)cc3c2C1]

Compound 22 ((S)-1-{(S)-6,8-Dichloro-3-[(S)-1-(3-cyano-[1,2,4]oxadiazol-5-yl)-2-methyl-butylcarbamoyl]-2,3,4,9-tetrahydro-1H-carbazol-3-ylcarbamoyl}-2-methyl-butyl)-carbamic acid benzyl ester

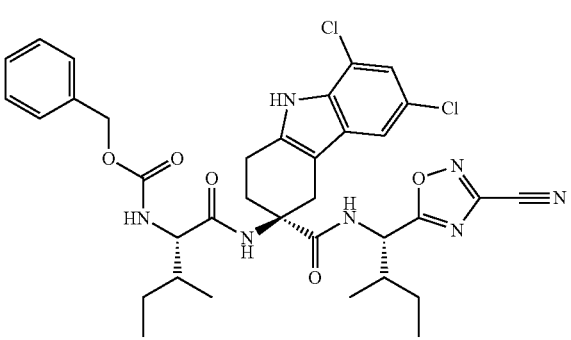 [SMILES: CCC(C)[C@H](NC(=O)OCc1ccccc1)C(=O)N[C@@]1(C(=O)N[C@H](c2nc(C#N)no2)C(C)CC)CCc2[nH]c3c(Cl)cc(Cl)cc3c2C1]

Compound 23 ((S)-1-{(R)-6,8-Dichloro-3-[(S)-2-methyl-1-(5-methyl-[1,3,4]oxadiazol-2-yl)-butylcarbamoyl]-2,3,4,9-tetrahydro-1H-carbazol-3-ylcarbamoyl}-2-methyl-butyl)-carbamic acid benzyles-ter Compound 26 5-((S)-1-{[(S)-3-((S)-2-Benzyloxycarbonylamino-3-methyl-pentanoylamino)-6,8-dichloro-2,3,4,9-tetrahydro-1H-carbazole-3-carbonyl]-amino}-2-methyl-butyl)-[1,2,4]oxadiazole-3-carboxylic acid methyl ester

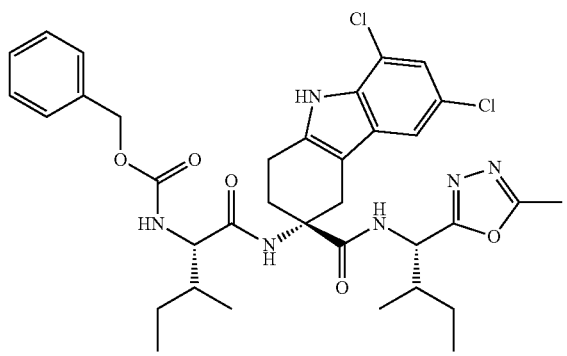 [SMILES: CCC(C)[C@H](NC(=O)OCc1ccccc1)C(=O)N[C@]1(C(=O)N[C@H](c2nnc(C)o2)C(C)CC)CCc2[nH]c3c(Cl)cc(Cl)cc3c2C1]

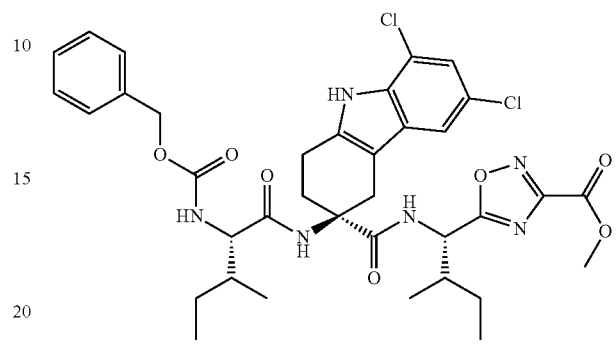

Compound 24 ((S)-1-{(S)-6,8-Dichloro-3-[(S)-2-methyl-1-(5-methyl-[1,3,4]oxadiazol-2-yl)-butylcarbamoyl]-2,3,4,9-tetrahydro-1H-carbazol-3-ylcarbamoyl}-2-methyl-butyl)-carbamic acid benzyl ester Compound 27 [(S)-1-((R)-6,8-Dichloro-3-{(S)-1-[5-(3-ethyl-ureido)-[1,3,4]oxadiazol-2-yl]-2-methyl-butylcarbamoyl}-2,3,4,9-tetrahydro-1H-carbazol-3-ylcarbamoyl)-2-methyl-butyl]-carbamic acid benzyl ester

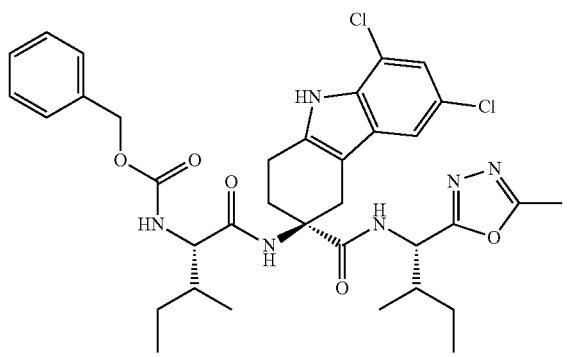 [SMILES: CCC(C)[C@H](NC(=O)OCc1ccccc1)C(=O)N[C@@]1(C(=O)N[C@H](c2nnc(C)o2)C(C)CC)CCc2[nH]c3c(Cl)cc(Cl)cc3c2C1]

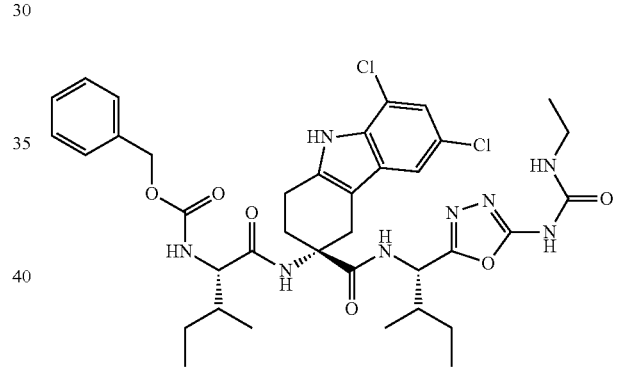

Compound 25 5((S)-1-{[(R)-3-((S)-2-Benzyloxycarbonylamino-3-methyl-pentanoylamino)-6,8-dichloro-2,3,4,9-tetrahydro-1H-carbazole-3-carbonyl]-amino}-2-methyl-butyl)-[1,2,4]oxadiazole-3-carboxylic acid methyl ester Compound 28 5-{(S)-1-[((R)-3-{(S)-2-[2-(2-Fluorophenyl)-acetylamino]-3-methyl-pentanoylamino}-8-trifluoromethyl-2,3,4,9-tetrahydro-1H-carbazole-3-carbonyl)-amino]-2-methyl-butyl}-[1,2,4]oxadiazole-3-carboxylic acid ethyl ester

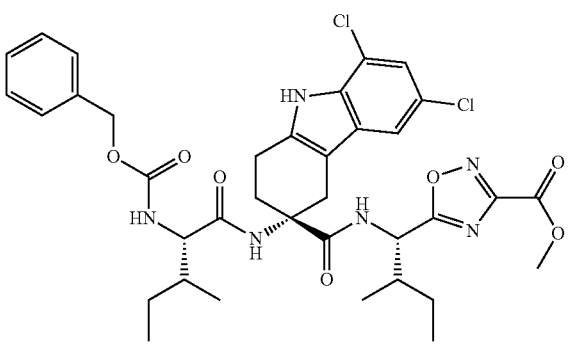 [SMILES: CCC(C)[C@H](NC(=O)OCc1ccccc1)C(=O)N[C@]1(C(=O)N[C@H](c2nc(C(=O)OC)no2)C(C)CC)CCc2[nH]c3c(Cl)cc(Cl)cc3c2C1]

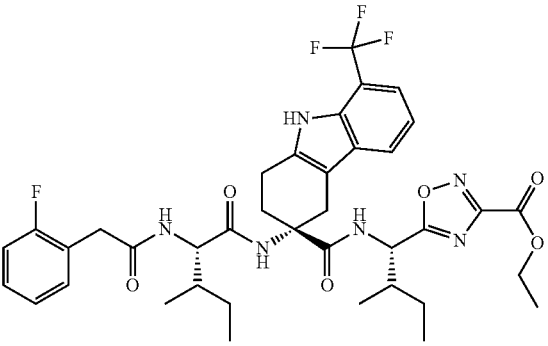 [SMILES: CCOC(=O)c1noc([C@@H](NC(=O)[C@@]2(NC(=O)[C@@H](NC(=O)Cc3ccccc3F)C(C)CC)CCc3[nH]c4c(C(F)(F)F)cccc4c3C2)C(C)CC)n1]

Compound 29 5-{(S)-1-[((S)-3-{(S)-2-[2-(2-Fluoro-phenyl)-acetylamino]-3-methyl-pentanoylamino}-8-trifluoromethyl-2,3,4,9-tetrahydro-1H-carbazole-3-carbonyl)-amino]-2-methyl-butyl}[1,2,4]oxadiazole-3-carboxylic acid ethyl ester

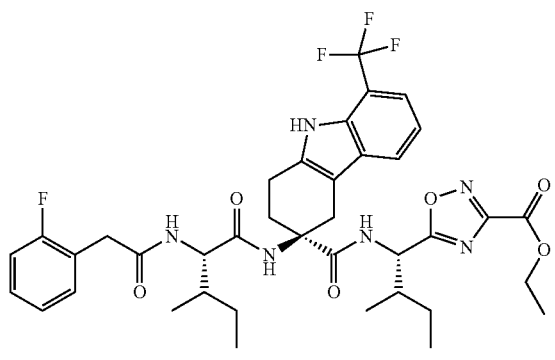 [SMILES: CCOC(=O)c1noc([C@@H](NC(=O)[C@]2(NC(=O)[C@@H](NC(=O)Cc3ccccc3F)C(C)CC)CCc3[nH]c4c(C(F)(F)F)cccc4c3C2)C(C)CC)n1]

Compound 30 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[5-(3-ethyl-ureido)-[1,3,4]oxadiazol-2-yl]-2-methyl-butyl}-amide

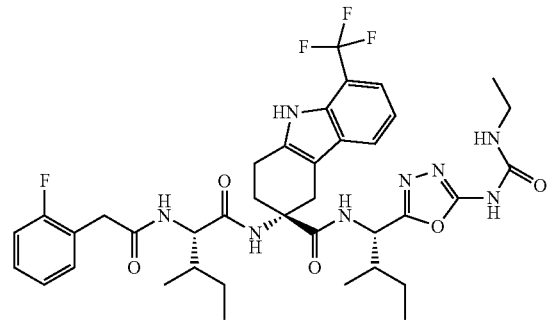 [SMILES: CCNC(=O)Nc1nnc([C@@H](NC(=O)[C@@]2(NC(=O)[C@@H](NC(=O)Cc3ccccc3F)C(C)CC)CCc3[nH]c4c(C(F)(F)F)cccc4c3C2)C(C)CC)o1]

Compound 31 (S)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[5-(3-ethyl-ureido)-[1,3,4]oxadiazol-2-yl]-2-methyl-butyl}-amide

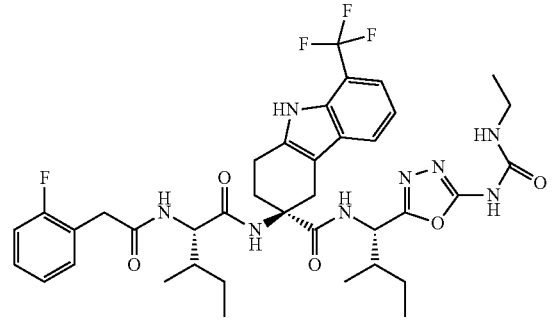 [SMILES: CCNC(=O)Nc1nnc([C@@H](NC(=O)[C@]2(NC(=O)[C@@H](NC(=O)Cc3ccccc3F)C(C)CC)CCc3[nH]c4c(C(F)(F)F)cccc4c3C2)C(C)CC)o1]

Compound 32 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(5-amino-[1,3,4]oxadiazol-2-yl)-2-methyl-butyl]-amide

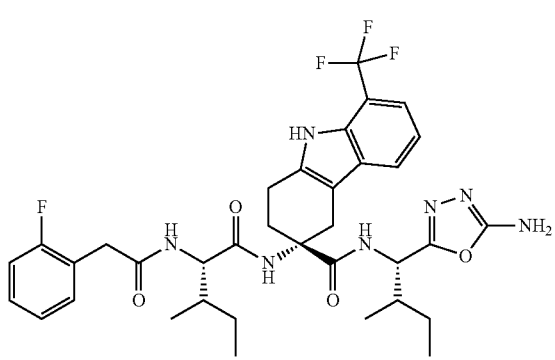 [SMILES: CCC(C)[C@H](NC(=O)Cc1ccccc1F)C(=O)N[C@]1(C(=O)N[C@H](c2nnc(N)o2)C(C)CC)CCc2[nH]c3c(C(F)(F)F)cccc3c2C1]

Compound 33

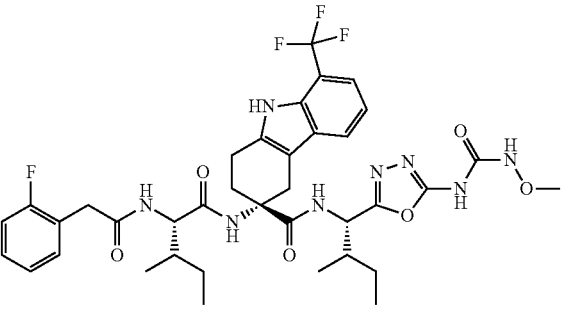 [SMILES: CCC(C)[C@H](NC(=O)Cc1ccccc1F)C(=O)N[C@]1(C(=O)N[C@H](c2nnc(NC(=O)NOC)o2)C(C)CC)CCc2[nH]c3c(C(F)(F)F)cccc3c2C1]

Compound 34

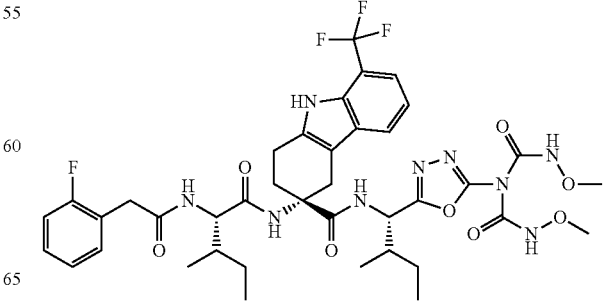

Compound 35 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(pyrrolidin-1-ylmethyl)-carbamoyl]-butyl}-amide

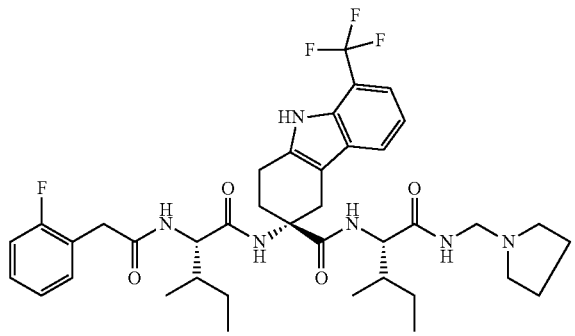 [SMILES: CCC(C)[C@H](NC(=O)Cc1ccccc1F)C(=O)N[C@]1(C(=O)N[C@H](C(=O)NCN2CCCC2)C(C)CC)CCc2[nH]c3c(C(F)(F)F)cccc3c2C1]

Compound 36 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[morpholin-4-ylmethyl)-carbamoyl]-butyl}-amide

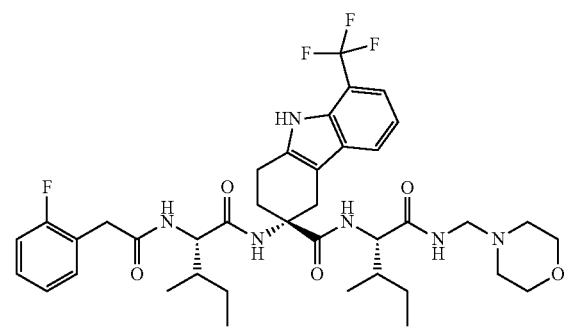 [SMILES: CCC(C)[C@H](NC(=O)Cc1ccccc1F)C(=O)N[C@]1(C(=O)N[C@H](C(=O)NCN2CCOCC2)C(C)CC)CCc2[nH]c3c(C(F)(F)F)cccc3c2C1]

Compound 37 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[morpholin-4-ylmethyl)-thiocarbamoy]-butyl}-amide

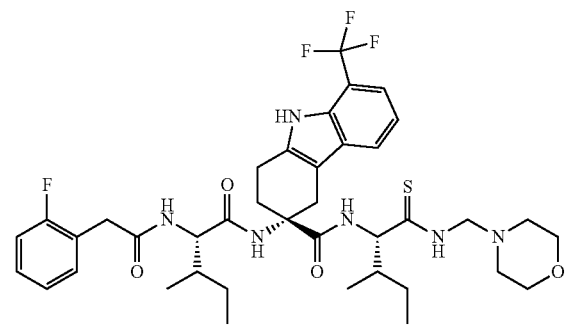 [SMILES: CCC(C)[C@H](NC(=O)Cc1ccccc1F)C(=O)N[C@]1(C(=O)N[C@H](C(=S)NCN2CCOCC2)C(C)CC)CCc2[nH]c3c(C(F)(F)F)cccc3c2C1]

Compound 38 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid ((S)-1-methoxycarbamoyl-2-methyl-butyl)-amide

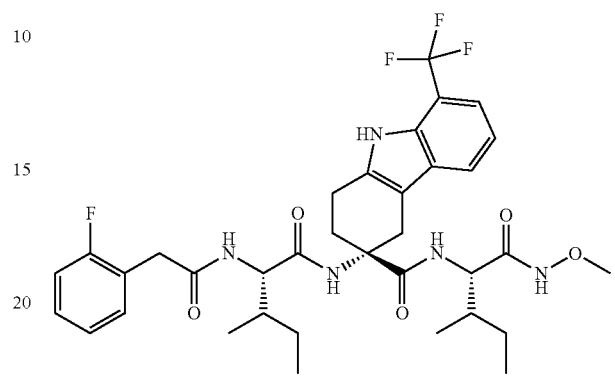

Compound 39 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(morpholine-4-carbonyl)-butyl]-amide

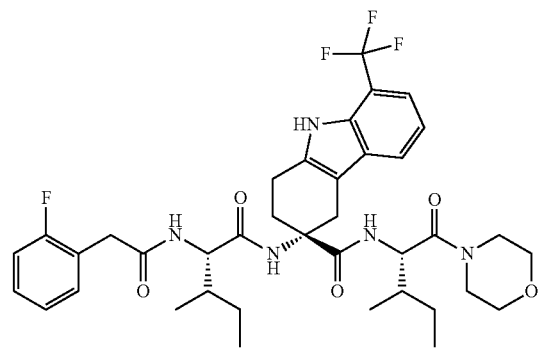

Compound 40 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid ((S)-1-ethylcarbamoyl-2-methyl-butyl)-amide

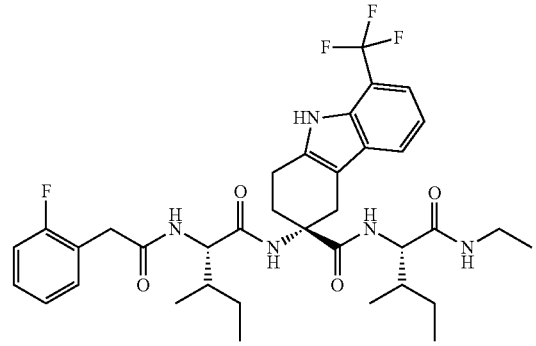 [SMILES: CCC(C)[C@H](NC(=O)Cc1ccccc1F)C(=O)N[C@]1(C(=O)N[C@H](C(=O)NOC)C(C)CC)CCc2[nH]c3c(C(F)(F)F)cccc3c2C1]

41

Compound 41 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid ((S)-1-ethoxycarbamoyl-2-methyl-butyl)-amide

42

Compound 44 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(3-morpholin-4-yl-propylcarbamoyl)-butyl]-amide

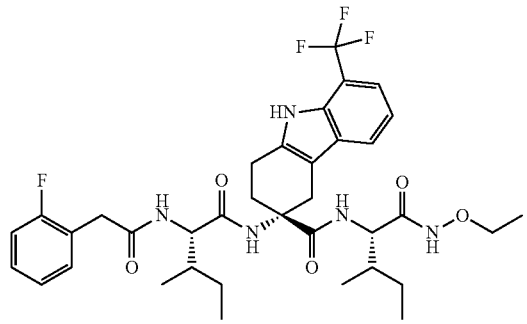 [SMILES: CCONC(=O)[C@@H](NC(=O)[C@@]1(NC(=O)[C@@H](NC(=O)Cc2ccccc2F)C(C)CC)CCc2[nH]c3c(C(F)(F)F)cccc3c2C1)C(C)CC]

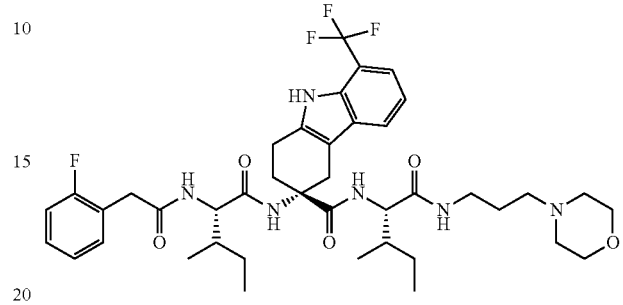

Compound 42 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(2-morpholin-4-yl-ethylcarbamoyl)-butyl]-amide Compound 45 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(1-methyl-piperidin-4-ylmethyl)-carbamoyl]-butyl}-amide

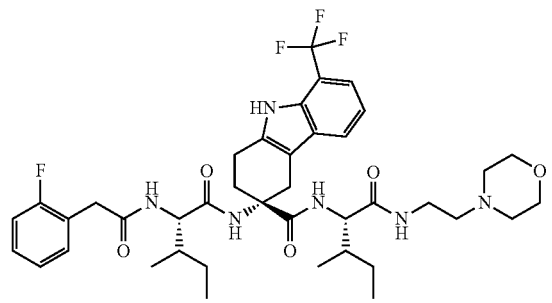 [SMILES: CCC(C)[C@H](NC(=O)Cc1ccccc1F)C(=O)N[C@]1(C(=O)N[C@H](C(=O)NCCN2CCOCC2)C(C)CC)CCc2[nH]c3c(C(F)(F)F)cccc3c2C1]

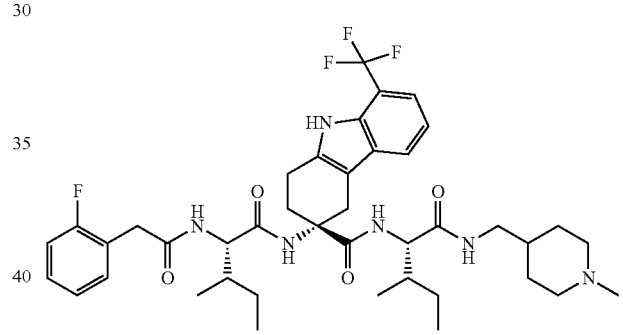

Compound 43 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(4-hydroxy-butylcarbamoyl)-2-methyl-butyl]-amide Compound 46 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[tetrahydro-pyran-4-ylmethyl)-carbamoyl]-butyl}-amide

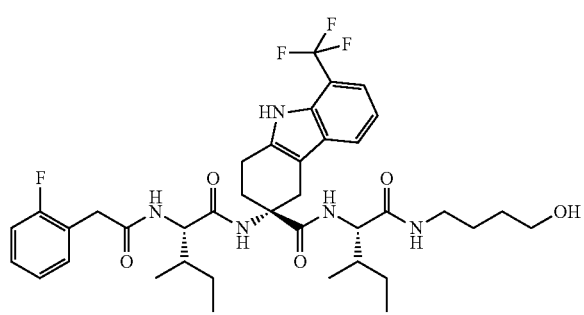 [SMILES: CCC(C)[C@H](NC(=O)Cc1ccccc1F)C(=O)N[C@]1(C(=O)N[C@H](C(=O)NCCCCO)C(C)CC)CCc2[nH]c3c(C(F)(F)F)cccc3c2C1]

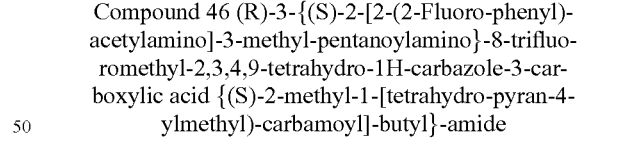

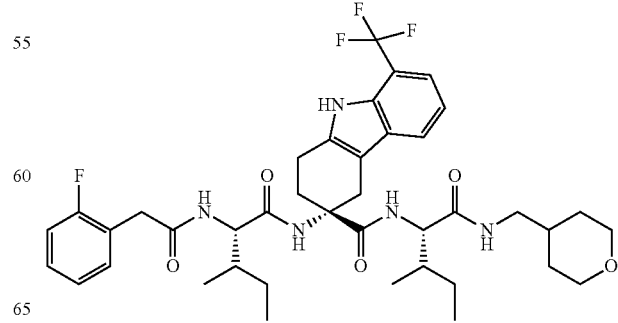

Compound 47 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(2-morpholin-4-yl-ethylthiocarbamoyl)-butyl]-amide Compound 50 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(pyridin-4-ylmethyl)-carbamoyl]-butyl}-amide

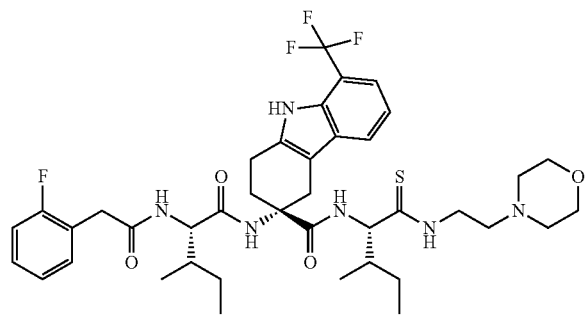 [SMILES: CCC(C)[C@H](NC(=O)Cc1ccccc1F)C(=O)N[C@]1(C(=O)N[C@H](C(=S)NCCN2CCOCC2)C(C)CC)CCc2[nH]c3c(C(F)(F)F)cccc3c2C1]

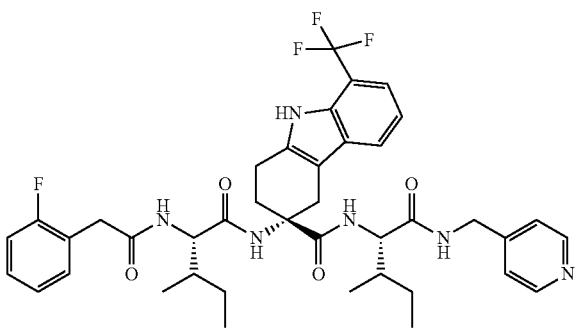

Compound 48 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[(1-formyl-piperidin-4-ylmethyl)-carbamoyl]-2-methyl-butyl}-amide Compound 51 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(2-diethylamino-ethylcarbamoyl)-2-methyl-butyl]-amide

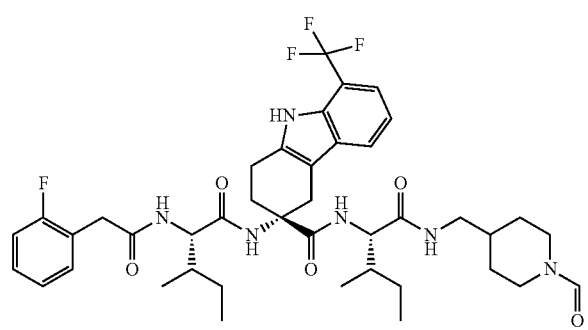 [SMILES: CCC(C)[C@H](NC(=O)Cc1ccccc1F)C(=O)N[C@]1(C(=O)N[C@H](C(=O)NCC2CCN(C=O)CC2)C(C)CC)CCc2[nH]c3c(C(F)(F)F)cccc3c2C1]

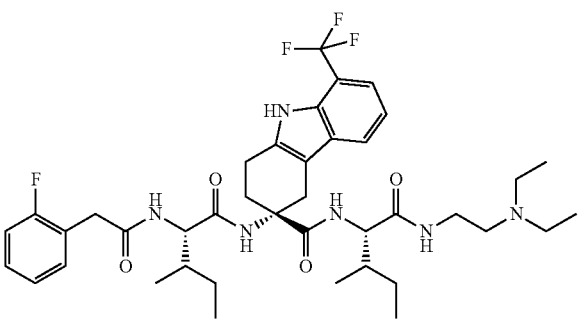

Compound 49 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[(1-acetyl-piperidin-4-ylmethyl)-carbamoyl]-2-methyl-butyl}-amide Compound 52 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(tetrahydro-pyran-4-ylmethyl)-thiocarbamoyl]-butyl}-amide

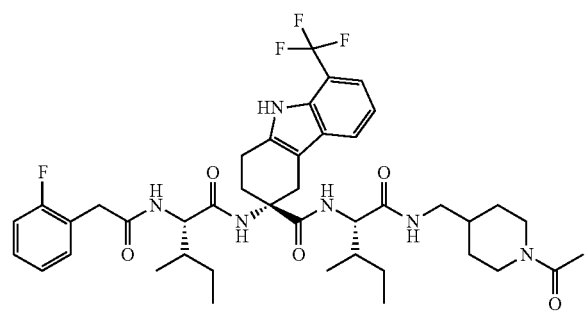 [SMILES: CCC(C)[C@H](NC(=O)Cc1ccccc1F)C(=O)N[C@]1(C(=O)N[C@H](C(=O)NCC2CCN(C(C)=O)CC2)C(C)CC)CCc2[nH]c3c(C(F)(F)F)cccc3c2C1]

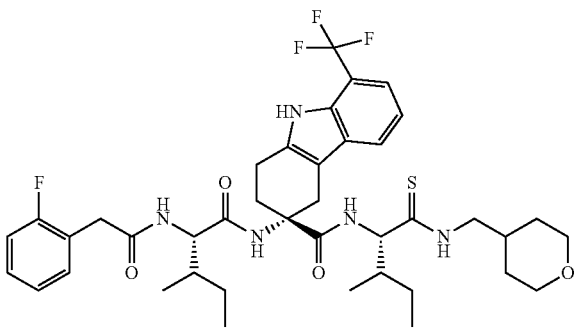 [SMILES: CCC(C)[C@H](NC(=O)Cc1ccccc1F)C(=O)N[C@]1(C(=O)N[C@H](C(=S)NCC2CCOCC2)C(C)CC)CCc2[nH]c3c(C(F)(F)F)cccc3c2C1]

Compound 53 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(4-hydroxy-butylthiocarbamoyl)-2-methyl-butyl]-amide Compound 56 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(piperidin-4-ylmethyl)-carbamoyl]-butyl}-amide

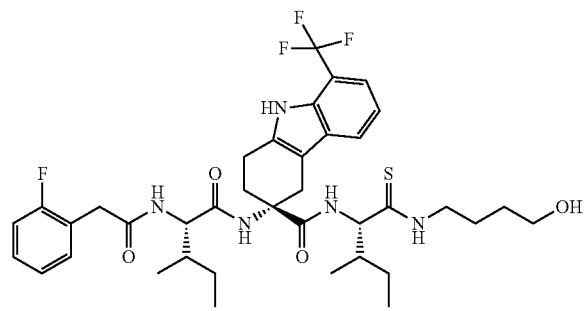 [SMILES: CCC(C)[C@H](NC(=O)Cc1ccccc1F)C(=O)N[C@]1(C(=O)N[C@H](C(=S)NCCCCO)C(C)CC)CCc2[nH]c3c(C(F)(F)F)cccc3c2C1]

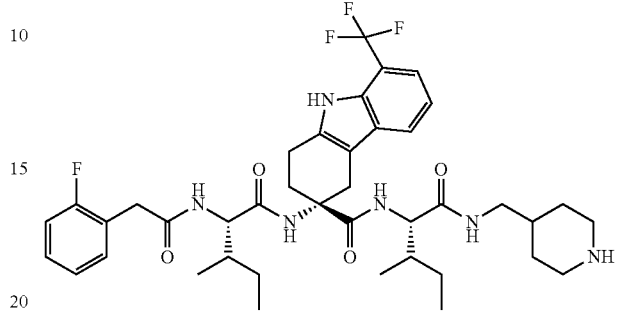

Compound 54 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(2-morpholin-4-yl-ethylthiocarbamoyl)-butyl]-amide Compound 57 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(2-hydroxy-ethylcarbamoyl)-2-methyl-butyl]-amide

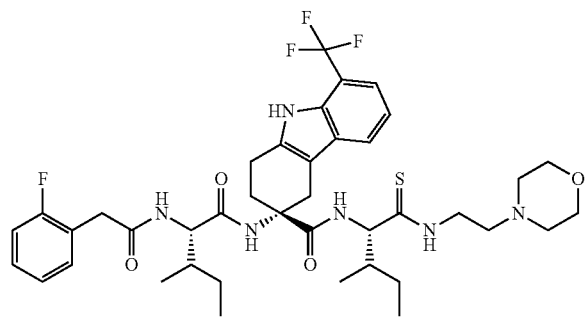 [SMILES: CCC(C)[C@H](NC(=O)Cc1ccccc1F)C(=O)N[C@]1(C(=O)N[C@H](C(=S)NCCN2CCOCC2)C(C)CC)CCc2[nH]c3c(C(F)(F)F)cccc3c2C1]

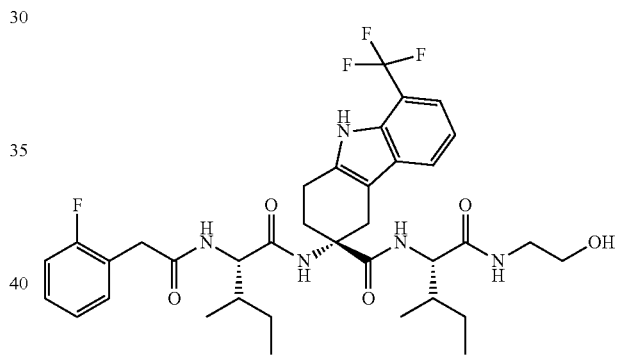

Compound 55 (R)-8-Chloro-6-fluoro-3-{(S)-2-[2-(2-fluoro-phenyl)-acetylamino]-3-methyl-pentanoylamino}-2,3,4,9-tetrahydro-1H-carbazole-3-carboxylic acid [(S)-2-methyl-1-(2-morpholin-4-yl-ethylcarbamoyl)-butyl]-amide Compound 58 (R)-8-Chloro-6-fluoro-3-{(S)-2-[2-(2-fluoro-phenyl)-acetylamino]-3-methyl-pentanoylamino}-2,3,4,9-tetrahydro-1H-carbazole-3-carboxylic acid {(S)-2-methyl-1-[(pyridin-4-ylmethyl)-carbamoyl]-butyl}-amide

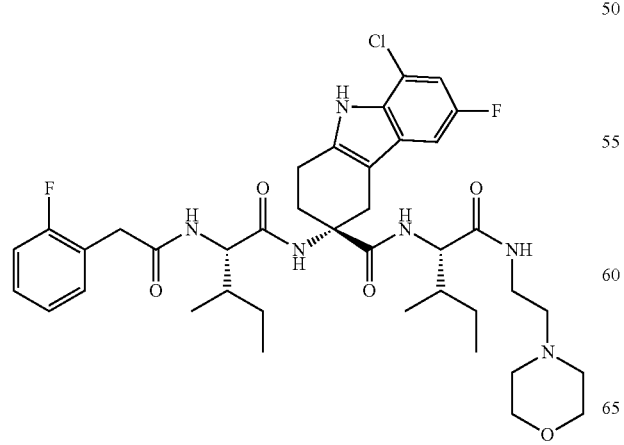

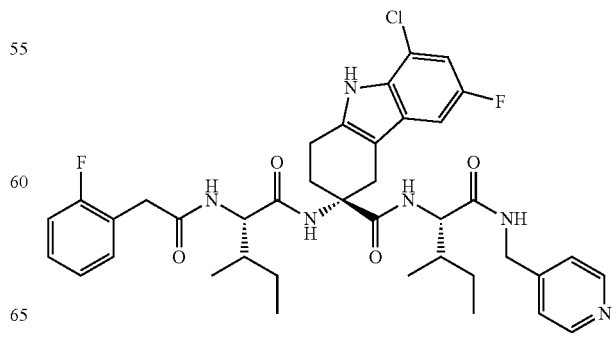

Compound 59 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(5-hydroxy-pentylcarbamoyl)-2-methyl-butyl]-amide

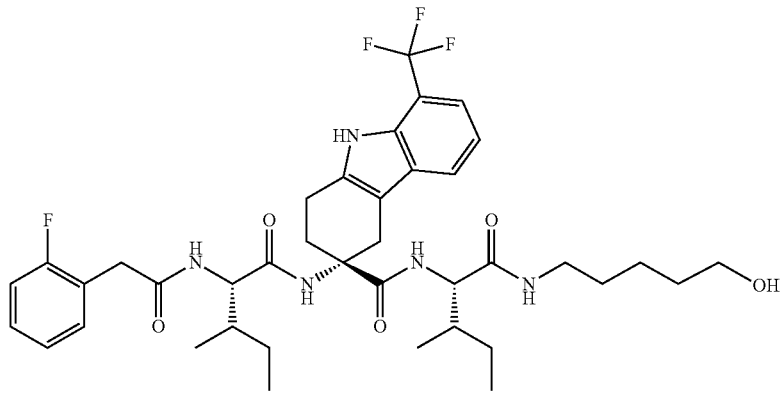 [SMILES: CCC(C)[C@H](NC(=O)Cc1ccccc1F)C(=O)N[C@]1(C(=O)N[C@H](C(=O)NCCCCCO)C(C)CC)CCc2[nH]c3c(C(F)(F)F)cccc3c2C1]

Compound 60 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(pyridin-4-ylmethyl)-thiocarbamoyl]-butyl}-amide Compound 62 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid ((S)-2-methyl-1-{[(tetrahydro-pyran-4-ylmethyl)-amino]-methyl}-butyl)-amide

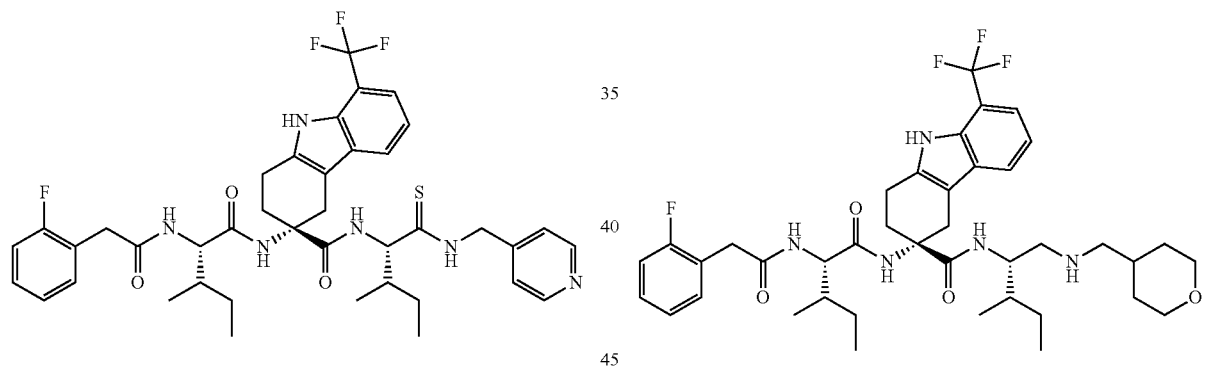

Compound 61 (R)-8-Chloro-6-fluoro-3-{(S)-2-[2-(2-fluoro-phenyl)-acetylamino]-3-methyl-pentanoylamino}-2,3,4,9-tetrahydro-1H-carbazole-3-carboxylic acid [(S)-2-methyl-1-(2-morpholin-4-yl-ethylthiocarbamoyl)-butyl]-amide

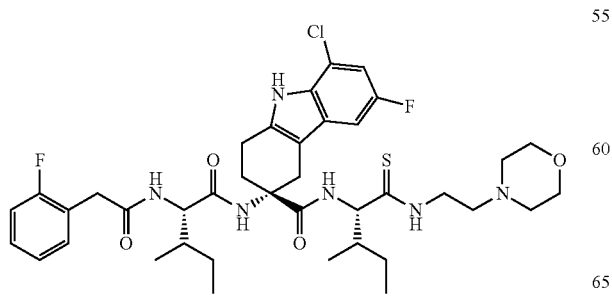

Compound 63 (4-{(S)-2-[((R)-3-{(S)-2-[2-(2-Fluoro-phenyl)-acetylamino]-3-methyl-pentanoylamino}-8-trifluoromethyl-2,3,4,9-tetrahydro-1H-carbazole-3-carbonyl)-amino]-3-methyl-pentanoylamino}-butyl)-phosphonic acid diethyl ester

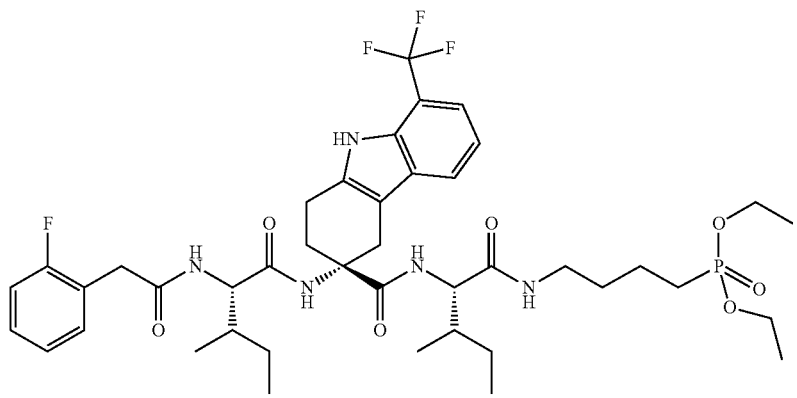 [SMILES: CCOP(=O)(CCCCNC(=O)[C@@H](NC(=O)[C@@]1(NC(=O)[C@@H](NC(=O)Cc2ccccc2F)C(C)CC)CCc2[nH]c3c(C(F)(F)F)cccc3c2C1)C(C)CC)OCC]

Compound 64 (4-{(S)-2-[((R)-3-{(S)-2-[2-(2-Fluoro-phenyl)-acetylamino]-3-methyl-pentanoylamino}-8-trifluoromethyl-2,3,4,9-tetrahydro-1H-carbazole-3-carbonyl)-amino]-3-methyl-pentanoylamino}-butyl)-phosphonic acid

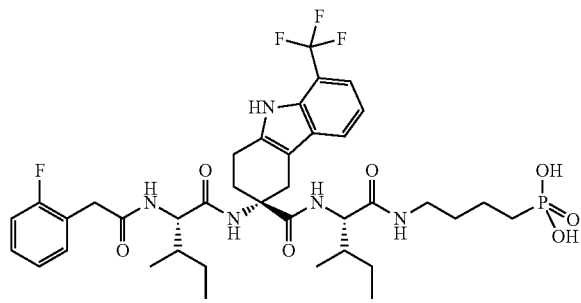 [SMILES: CCC(C)[C@H](NC(=O)Cc1ccccc1F)C(=O)N[C@]1(C(=O)N[C@H](C(=O)NCCCCP(=O)(O)O)C(C)CC)CCc2[nH]c3c(C(F)(F)F)cccc3c2C1]

Compound 66 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(2-morpholin-4-yl-ethylarnino)-methyl-]-butyl}-amide

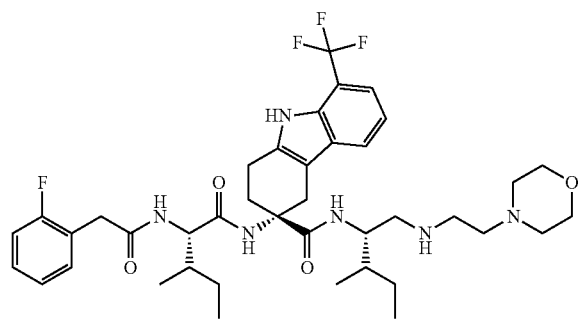 [SMILES: CCC(C)[C@H](NC(=O)Cc1ccccc1F)C(=O)N[C@]1(C(=O)N[C@H](CNCCN2CCOCC2)C(C)CC)CCc2[nH]c3c(C(F)(F)F)cccc3c2C1]

Compound 67 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(4-hydroxy-phenylcarbamoyl)-2-methyl-butyl]-amide

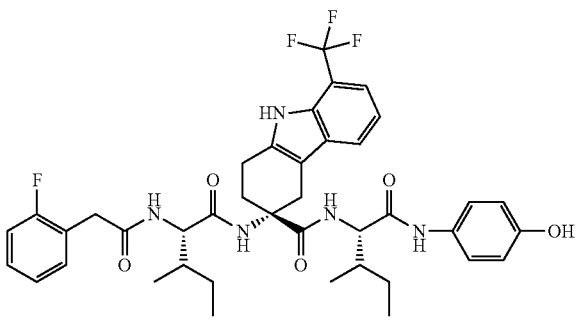 [SMILES: CCC(C)[C@H](NC(=O)Cc1ccccc1F)C(=O)N[C@]1(C(=O)N[C@H](C(=O)Nc2ccc(O)cc2)C(C)CC)CCc2[nH]c3c(C(F)(F)F)cccc3c2C1]

Compound 68 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(4-methoxy-phenylcarbamoyl)-2-methyl-butyl]-amide

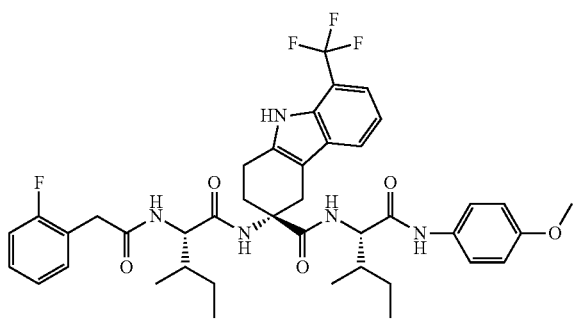 [SMILES: CCC(C)[C@H](NC(=O)Cc1ccccc1F)C(=O)N[C@]1(C(=O)N[C@H](C(=O)Nc2ccc(OC)cc2)C(C)CC)CCc2[nH]c3c(C(F)(F)F)cccc3c2C1]

Compound 69 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(3-hydroxy-4-methoxy-phenylcarbamoyl)-2-methyl-butyl]-amide Compound 72 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(2,4,6-trimethoxy-phenylcarbamoyl)-butyl]-amide

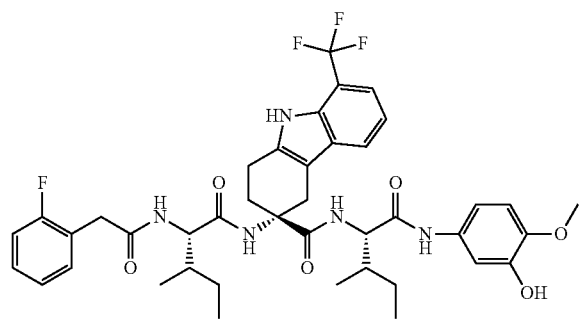 [SMILES: CCC(C)[C@H](NC(=O)Cc1ccccc1F)C(=O)N[C@]1(C(=O)N[C@H](C(=O)Nc2ccc(OC)c(O)c2)C(C)CC)CCc2[nH]c3c(C(F)(F)F)cccc3c2C1]

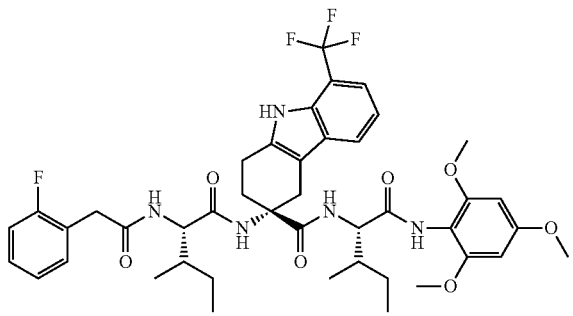

Compound 70 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(2,4-dihydroxy-phenylcarbamoyl)-2-methyl-butyl]-amide Compound 73 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(4-hydroxy-cyclohexylcarbamoyl)-2-methyl-butyl]-amide

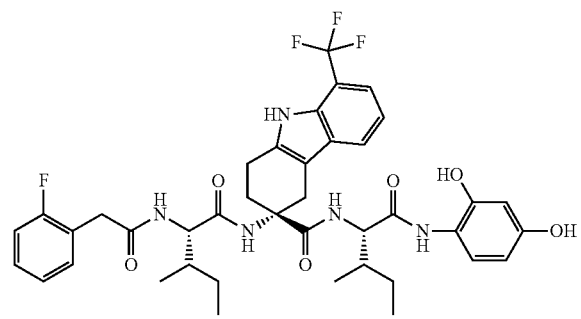 [SMILES: CCC(C)[C@H](NC(=O)Cc1ccccc1F)C(=O)N[C@]1(C(=O)N[C@H](C(=O)Nc2ccc(O)cc2O)C(C)CC)CCc2[nH]c3c(C(F)(F)F)cccc3c2C1]

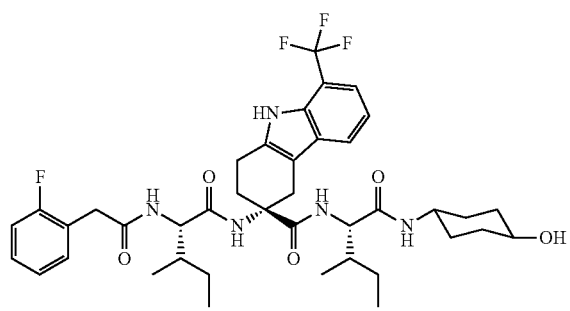

Compound 71 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(2-hydroxy-4-methoxy-phenylcarbarnoyl)-2-methyl-butyl]-amide Compound 74 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(3-imidazol-1-yl-propylthiocarbamoyl)-2-methyl-butyl]-amide

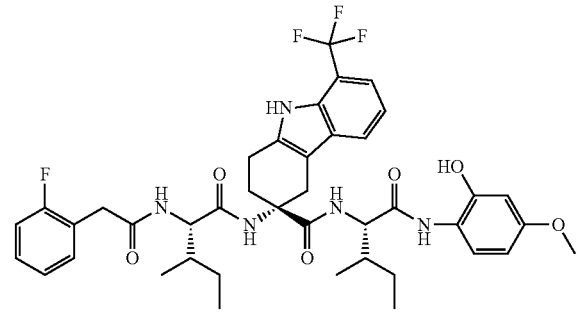 [SMILES: CCC(C)[C@H](NC(=O)Cc1ccccc1F)C(=O)N[C@]1(C(=O)N[C@H](C(=O)Nc2ccc(OC)cc2O)C(C)CC)CCc2[nH]c3c(C(F)(F)F)cccc3c2C1]

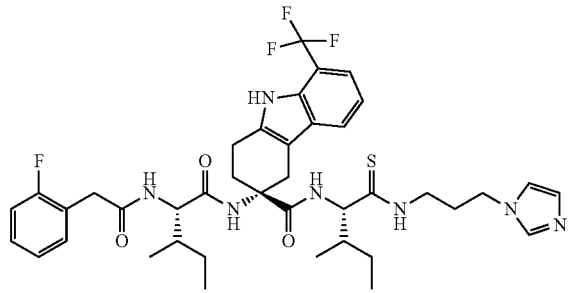 [SMILES: CCC(C)[C@H](NC(=O)Cc1ccccc1F)C(=O)N[C@]1(C(=O)N[C@H](C(=S)NCCCn2ccnc2)C(C)CC)CCc2[nH]c3c(C(F)(F)F)cccc3c2C1]

Compound 75 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(R)-1-(3-imidazol-1-yl-propylthiocarbamoyl)-2-methyl-butyl]-amide

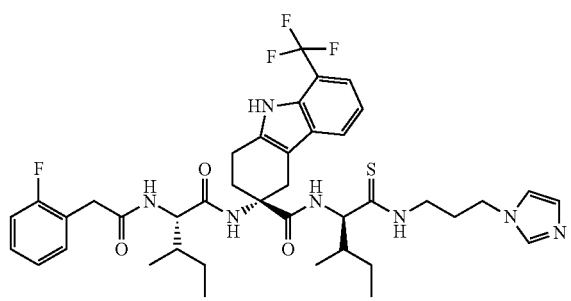 [SMILES: CCC(C)[C@H](NC(=O)Cc1ccccc1F)C(=O)N[C@]1(C(=O)N[C@@H](C(=S)NCCCn2ccnc2)C(C)CC)CCc2[nH]c3c(C(F)(F)F)cccc3c2C1]

Compound 76 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(2-thiophen-2-yl-ethylthiocarbamoyl)-butyl]-amide

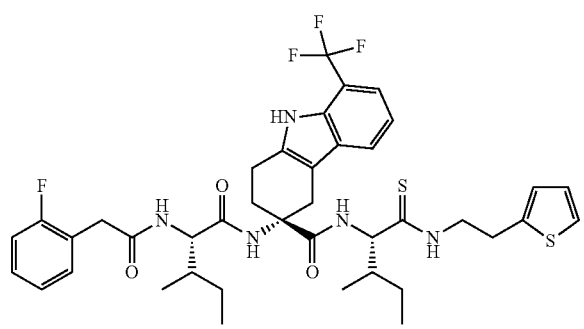 [SMILES: CCC(C)[C@H](NC(=O)Cc1ccccc1F)C(=O)N[C@]1(C(=O)N[C@H](C(=S)NCCc2cccs2)C(C)CC)CCc2[nH]c3c(C(F)(F)F)cccc3c2C1]

Compound 77 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(pyridin-3-ylmethyl)-thiocarbamoyl]-butyl}-amide

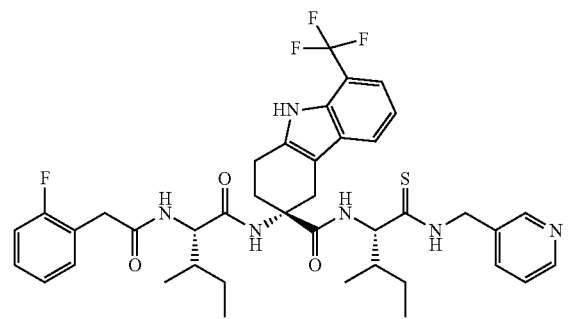 [SMILES: CCC(C)[C@H](NC(=O)Cc1ccccc1F)C(=O)N[C@]1(C(=O)N[C@H](C(=S)NCc2cccnc2)C(C)CC)CCc2[nH]c3c(C(F)(F)F)cccc3c2C1]

Compound 78 ((S)-1-{(R)-6,8-Dichloro-3-[(S)-3-methyl-1-(1H-tetrazol-5-yl)-butylcarbamoyl]-2,3,4,9-tetrahydro-1H-carbazol-3-ylcarbamoyl}-2-methyl-butyl)-carbamic acid benzyl ester

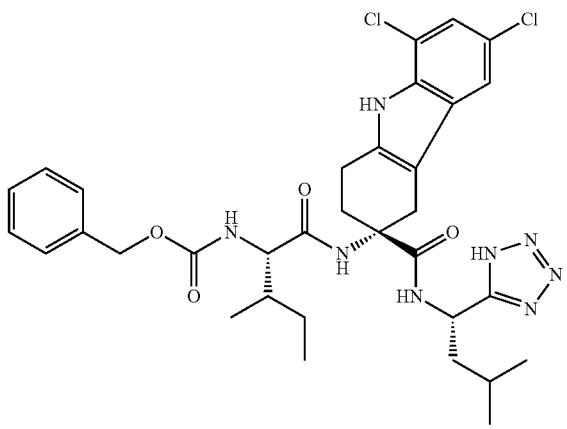 [SMILES: CCC(C)[C@H](NC(=O)OCc1ccccc1)C(=O)N[C@]1(C(=O)N[C@@H](CC(C)C)c2nnn[nH]2)CCc2[nH]c3c(Cl)cc(Cl)cc3c2C1]

Compound 80 5-{(S)-1-[(3-{2-[2-(2-Fluoro-phenyl)-acetylamino]-3-methyl-pentanoylamino}-8-trifluoromethyl-2,3,4,9-tetrahydro-1H-carbazole-3-carbonyl)-amino]-2-methyl-butyl}[1,2,4]oxadiazole-3-carboxylic acid ethyl ester

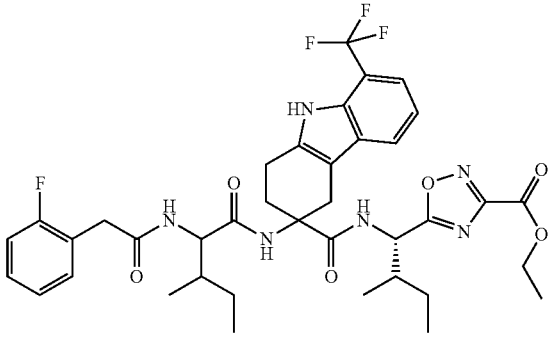 [SMILES: CCOC(=O)c1noc([C@@H](NC(=O)C2(NC(=O)C(NC(=O)Cc3ccccc3F)C(C)CC)CCc3[nH]c4c(C(F)(F)F)cccc4c3C2)C(C)CC)n1]

Compound 81 5-{(S)-1-[((R)-3-{(R)-2-[2-(2-Fluoro-phenyl)-acetylamino]-3-methyl-pentanoylamino}-8-trifluoromethyl-2,3,4,9-tetrahydro-1H-carbazole-3-carbonyl)-amino]-2-methyl-butyl}-[1,2,4]oxadiazole-3-carboxylic acid ethyl ester

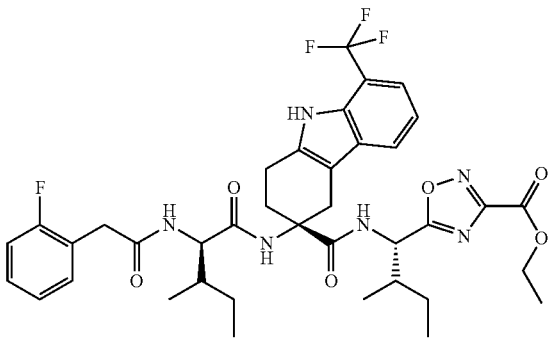 [SMILES: CCOC(=O)c1noc([C@@H](NC(=O)[C@@]2(NC(=O)[C@H](NC(=O)Cc3ccccc3F)C(C)CC)CCc3[nH]c4c(C(F)(F)F)cccc4c3C2)C(C)CC)n1]

Compound 82 (R)-3-{(R)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[5-(3-ethyl-ureido)-[1,3,4]oxadiazol-2-yl]-2-methyl-butyl}-amide

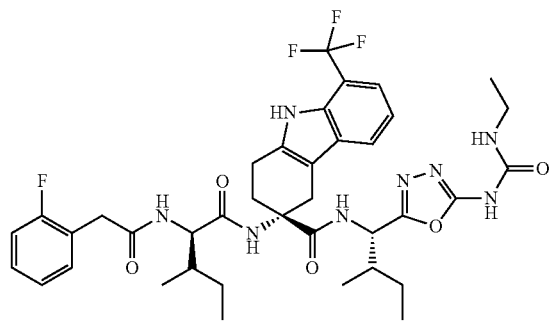 [SMILES: CCNC(=O)Nc1nnc([C@@H](NC(=O)[C@@]2(NC(=O)[C@H](NC(=O)Cc3ccccc3F)C(C)CC)CCc3[nH]c4c(C(F)(F)F)cccc4c3C2)C(C)CC)o1]

Compound 83 (S)-3-{(R)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[5-(3-ethyl-ureido)-[1,3,4]oxadiazol-2-yl]-2-methyl-butyl}-amide

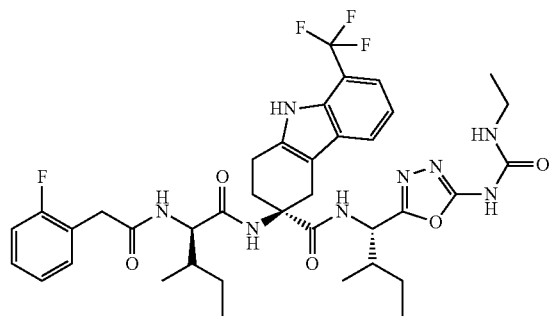 [SMILES: CCNC(=O)Nc1nnc([C@@H](NC(=O)[C@]2(NC(=O)[C@H](NC(=O)Cc3ccccc3F)C(C)CC)CCc3[nH]c4c(C(F)(F)F)cccc4c3C2)C(C)CC)o1]

Compound 85 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(2-diethylamino-ethylcarbamoyl)-methyl]-amide

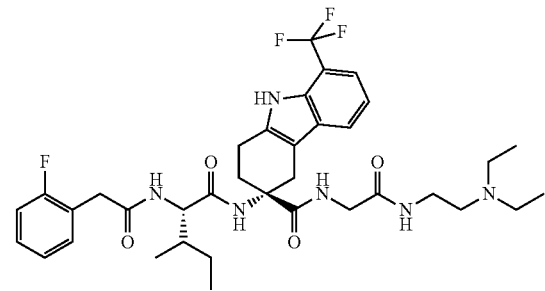 [SMILES: CCC(C)[C@H](NC(=O)Cc1ccccc1F)C(=O)N[C@]1(C(=O)NCC(=O)NCCN(CC)CC)CCc2[nH]c3c(C(F)(F)F)cccc3c2C1]

Compound 86 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(2-morpholin-4-yl-ethylcarbamoyl)-methyl]-amide

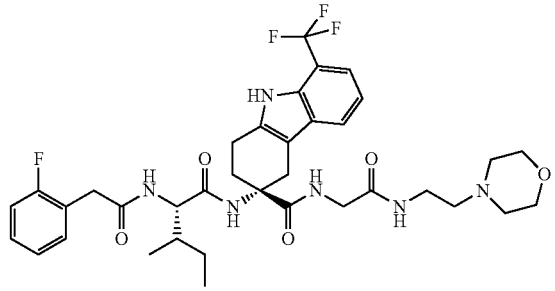 [SMILES: CCC(C)[C@H](NC(=O)Cc1ccccc1F)C(=O)N[C@]1(C(=O)NCC(=O)NCCN2CCOCC2)CCc2[nH]c3c(C(F)(F)F)cccc3c2C1]

Compound 87 (S)-8-Chloro-6-fluoro-3-{(S)-2-[2-(2-fluoro-phenyl)-acetylamino]-3-methyl-pentanoylamino}-2,3,4,9-tetrahydro-1H-carbazole-3-carboxylic acid {(S)-2-methyl-1-[(pyridin-4-ylmethyl)-carbamoyl]-butyl}-amide

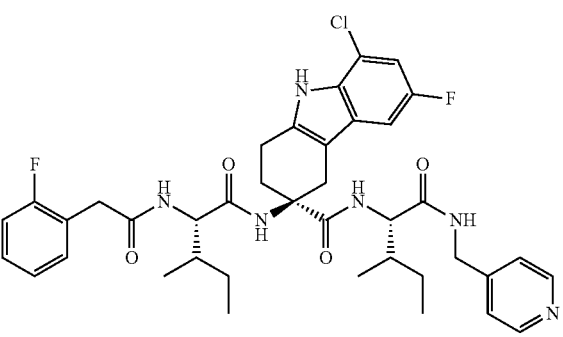 [SMILES: CCC(C)[C@H](NC(=O)Cc1ccccc1F)C(=O)N[C@@]1(C(=O)N[C@H](C(=O)NCc2ccncc2)C(C)CC)CCc2[nH]c3c(Cl)cc(F)cc3c2C1]

Compound 88 (R)-8-Chloro-6-fluoro-3-{(S)-2-[2-(2-fluoro-phenyl)-thioacetylamino]-3-methyl-pentanoylamino}-2,3,4,9-tetrahydro-1H-carbazole-3-carboxylic acid {(S)-2-methyl-1-[(pyridin-4-ylmethyl)-carbamoyl]-butyl}-amide

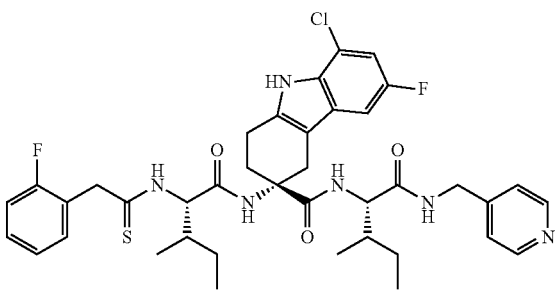 [SMILES: CCC(C)[C@H](NC(=O)[C@@]1(NC(=O)[C@@H](NC(=S)Cc2ccccc2F)C(C)CC)CCc2[nH]c3c(Cl)cc(F)cc3c2C1)C(=O)NCc1ccncc1]

Compound 89 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(2-pyridin-4-yl-ethylthiocarbarnoyl)-butyl]-amide Compound 91 2-{(S)-2-[((R)-3-{(S)-2-[2-(2-Fluoro-phenyl)-acetylamino]-3-methyl-pentanoylamino}-8-trifluoromethyl-2,3,4,9-tetrahydro-1H-carbazole-3-carbonyl)-amino]-3-methyl-pentanoylamino}-5-methoxy-benzoic acid

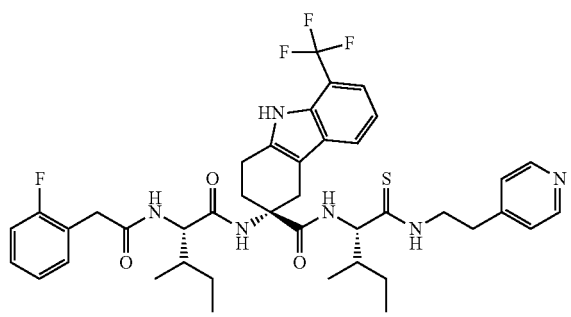 [SMILES: CCC(C)[C@H](NC(=O)Cc1ccccc1F)C(=O)N[C@]1(C(=O)N[C@H](C(=S)NCCc2ccncc2)C(C)CC)CCc2[nH]c3c(C(F)(F)F)cccc3c2C1]

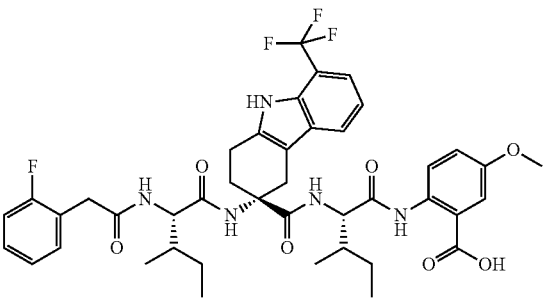

Compound 90 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(4-hydroxy-cyclohexylthiocarbamoyl)-2-methyl-butyl]-amide Compound 92 Phosphoric acid diethyl ester 5-{(S)-2-[((R)-3-{(S)-2-[2-(2-fluoro-phenyl)-acetylamino]-3-methyl-pentanoylamino}-8-trifluoromethyl-2,3,4,9-tetrahydro-1H-carbazole-3-carbonyl)-amino]-3-methyl-pentanoylamino}-2-methoxy-phenyl ester

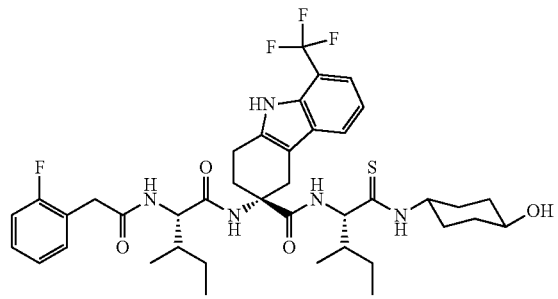 [SMILES: CCC(C)[C@H](NC(=O)Cc1ccccc1F)C(=O)N[C@]1(C(=O)N[C@H](C(=S)NC2CCC(O)CC2)C(C)CC)CCc2[nH]c3c(C(F)(F)F)cccc3c2C1]

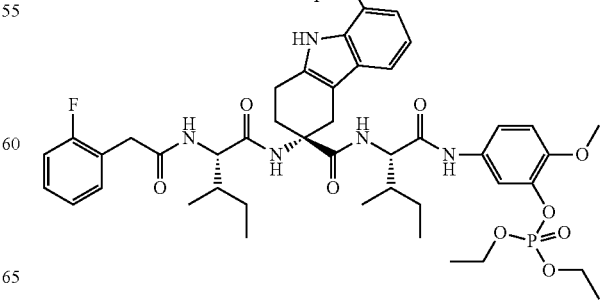

Compound 93 Dimethylamino-acetic acid 4-{(S)-2-[((R)-3-{(S)-2-[2-(2-fluoro-phenyl)-acetylamino]-3-methyl-pentanoylamino}-8-trifluoromethyl-2,3,4,9-tetrahydro-1H-carbazole-3-carbonyl)-amino]-3-methyl-pentanoylamino}-butyl ester

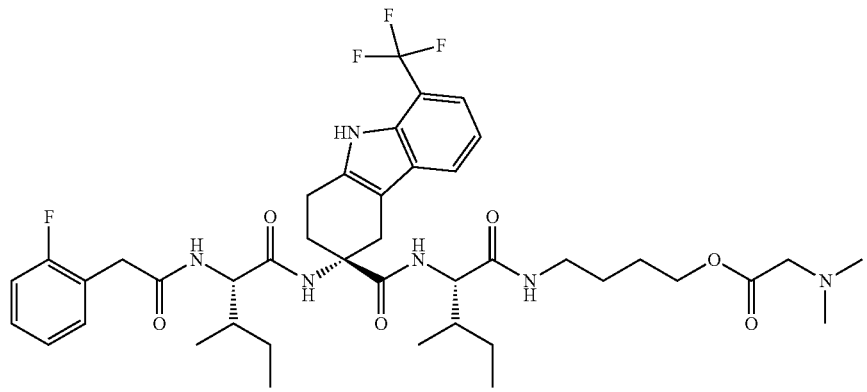 [SMILES: CCC(C)[C@H](NC(=O)Cc1ccccc1F)C(=O)N[C@]1(C(=O)N[C@H](C(=O)NCCCCOC(=O)CN(C)C)C(C)CC)CCc2[nH]c3c(C(F)(F)F)cccc3c2C1]

Compound 94 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(4-hydroxy-benzylcarbamoyl)-2-methyl-butyl]-amide

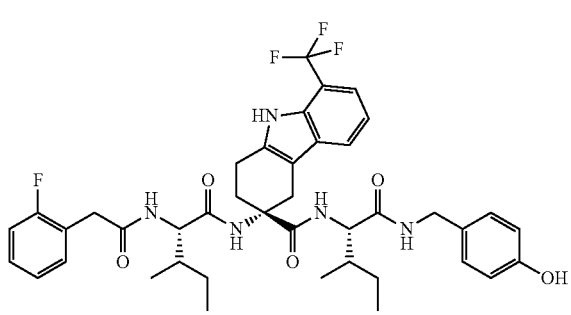 [SMILES: CCC(C)[C@H](NC(=O)Cc1ccccc1F)C(=O)N[C@]1(C(=O)N[C@H](C(=O)NCc2ccc(O)cc2)C(C)CC)CCc2[nH]c3c(C(F)(F)F)cccc3c2C1]

Compound 95 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(3-hydroxy-4-methoxy-benzylcarbamoyl)-2-methyl-butyl]-amide

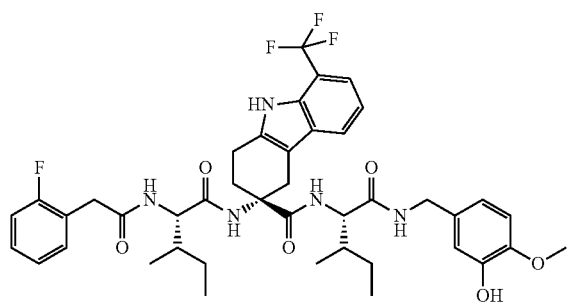 [SMILES: CCC(C)[C@H](NC(=O)Cc1ccccc1F)C(=O)N[C@]1(C(=O)N[C@H](C(=O)NCc2ccc(OC)c(O)c2)C(C)CC)CCc2[nH]c3c(C(F)(F)F)cccc3c2C1]

Compound 96 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(4-hydroxy-3-methoxy-benzylcarbamoyl)-2-methyl-butyl]-amide Compound 97 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(4-methoxy-phenylthiocarbamoyl)-2-methyl-butyl]-amide

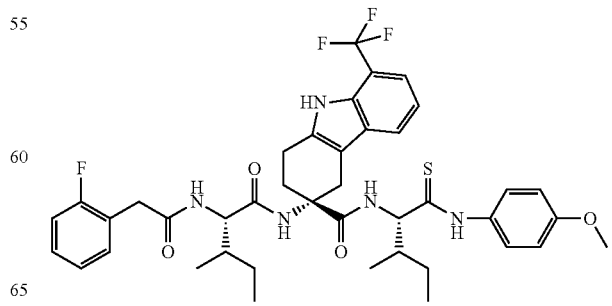

61

Compound 98 5-{(S)-2-[((R)-3-{(S)-2-[2-(2-Fluoro-phenyl)-acetylamino]-3-methyl-pentanoylamino}-8-trifluoromethyl-2,3,4,9-tetrahydro-1H-carbazole-3-carbonyl)-amino]-3-methyl-pentanoylamino}-2-methoxy-benzoic acid

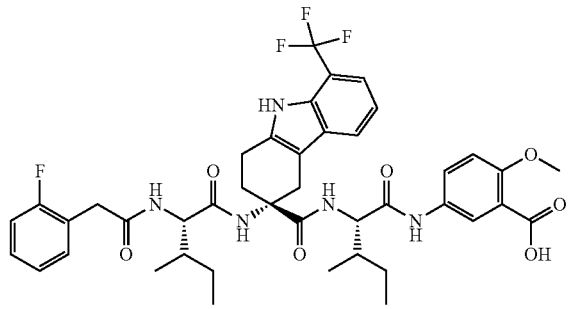 [SMILES: CCC(C)[C@H](NC(=O)Cc1ccccc1F)C(=O)N[C@]1(C(=O)N[C@H](C(=O)Nc2ccc(OC)c(C(=O)O)c2)C(C)CC)CCc2[nH]c3c(C(F)(F)F)cccc3c2C1]

62

Compound 99 5-{(S)-2-[((R)-3-{(S)-2-[2-(2-Fluoro-phenyl)-acetylamino]-3-methyl-pentanoylamino}-8-trifluoromethyl-2,3,4,9-tetrahydro-1H-carbazole-3-carbonyl)-amino]-3-methyl-pentanethioylamino}-2-methoxy-benzoic acid

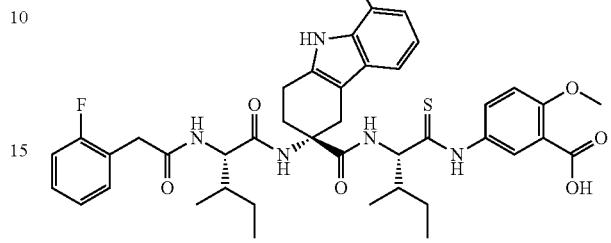

Compound 100 Carbonic acid 4-{(S)-2-[((R)-3-{(S)-2-[2-(2-fluoro-phenyl)-acetylamino]-3-methyl-pentanoylamino}-8-trifluoromethyl-2,3,4,9-tetrahydro-1H-carbazole-3-carbonyl)-amino]-3-methyl-pentanoylamino}-butyl ester 2-[2-(2-methoxy-ethoxy)-ethoxy]-ethyl ester

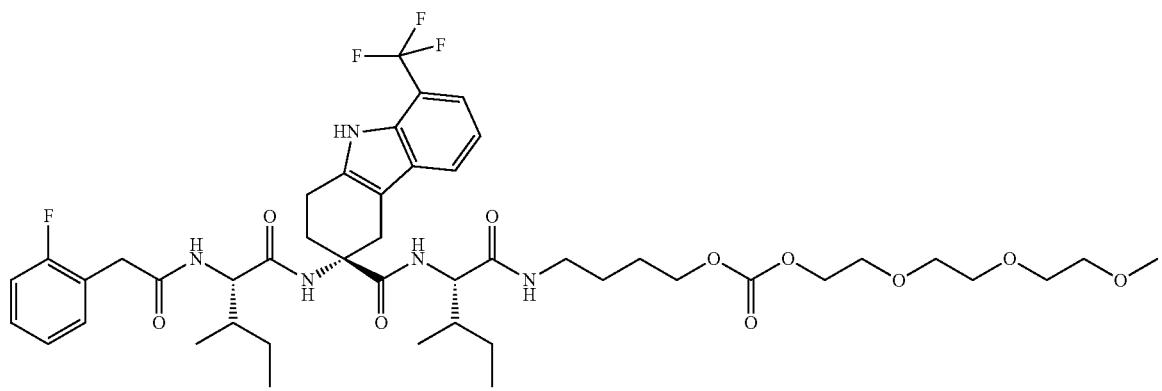 [SMILES: CCC(C)[C@H](NC(=O)Cc1ccccc1F)C(=O)N[C@]1(C(=O)N[C@H](C(=O)NCCCCOC(=O)OCCOCCOCCOC)C(C)CC)CCc2[nH]c3c(C(F)(F)F)cccc3c2C1]

Compound 101 Phosphoric acid mono-(4-{(S)-2-[((R)-3-{(S)-2-[2-(2-fluoro-phenyl)-acetylamino]-3-methyl-pentanoylamino}-8-trifluoromethyl-2,3,4,9-tetrahydro-1H-carbazole-3-carbonyl)-amino]-3-methyl-pentanoylamino}-butyl) ester

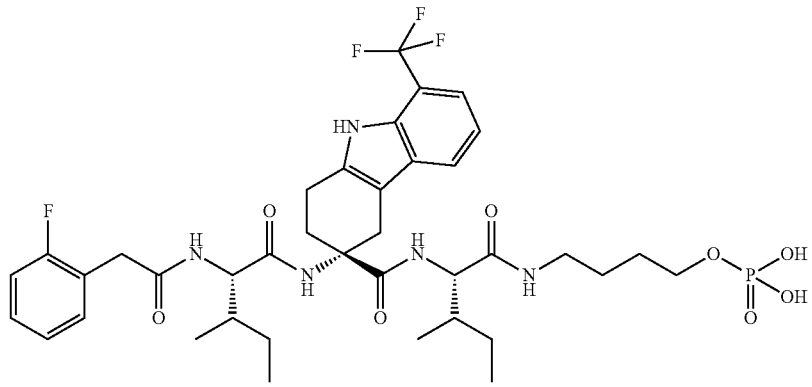 [SMILES: CCC(C)[C@H](NC(=O)Cc1ccccc1F)C(=O)N[C@]1(C(=O)N[C@H](C(=O)NCCCCOP(=O)(O)O)C(C)CC)CCc2[nH]c3c(C(F)(F)F)cccc3c2C1]

Compound 102 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(3-hydroxy-propylcarbamoyl)-2-methyl-butyl]-amide

Compound 105 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(pyrimidin-5-ylmethyl)-thiocarbamoyl]-butyl}-amide

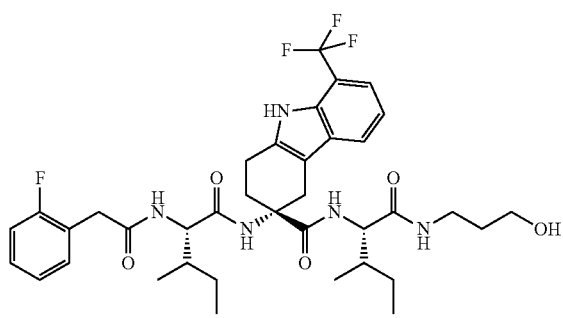 [SMILES: CCC(C)[C@H](NC(=O)Cc1ccccc1F)C(=O)N[C@]1(C(=O)N[C@H](C(=O)NCCCO)C(C)CC)CCc2[nH]c3c(C(F)(F)F)cccc3c2C1]

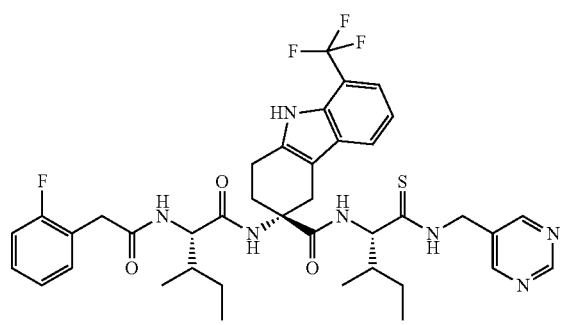

Compound 103 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid ((S)-1-benzylthiocarbamoyl-2-methyl-butyl)-amide

Compound 106 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(pyrazin-2-ylmethyl)-thiocarbamoyl]-butyl}-amide

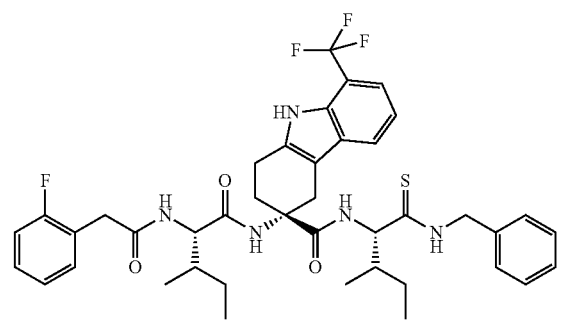 [SMILES: CCC(C)[C@H](NC(=O)Cc1ccccc1F)C(=O)N[C@]1(C(=O)N[C@H](C(=S)NCc2ccccc2)C(C)CC)CCc2[nH]c3c(C(F)(F)F)cccc3c2C1]

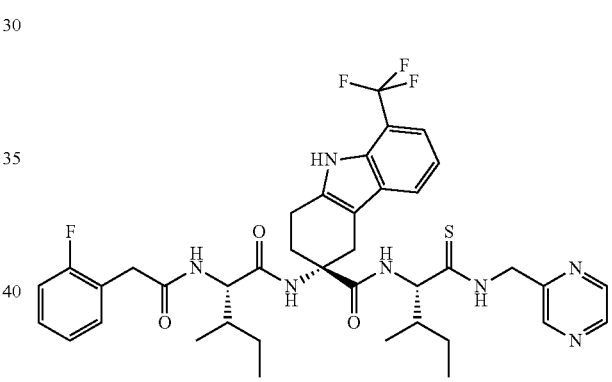

Compound 104 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[(2-methoxy-pyridin-4-ylmethyl)-thiocarbamoyl]-2-methyl-butyl}-amide

Compound 107 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[(6-chloro-pyridin-3-ylmethyl)-thiocarbamoyl]-2-methyl-butyl}-amide

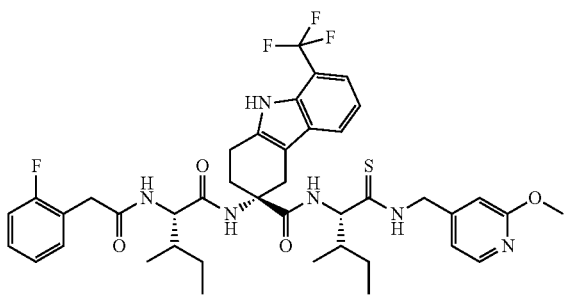 [SMILES: CCC(C)[C@H](NC(=O)Cc1ccccc1F)C(=O)N[C@]1(C(=O)N[C@H](C(=S)NCc2ccnc(OC)c2)C(C)CC)CCc2[nH]c3c(C(F)(F)F)cccc3c2C1]

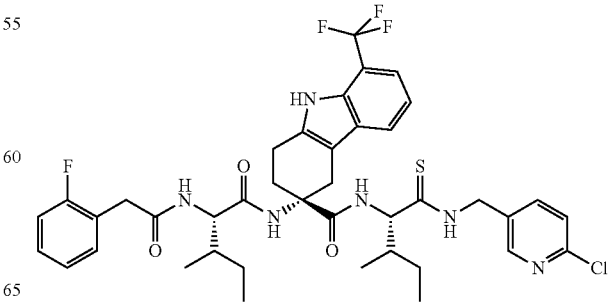

Compound 108 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(2-pyridin-3-yl-ethylthiocarbamoyl)-butyl]-amide Compound 111 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(2-pyrazol-1-yl-ethylthiocarbamoyl)-butyl]-amide

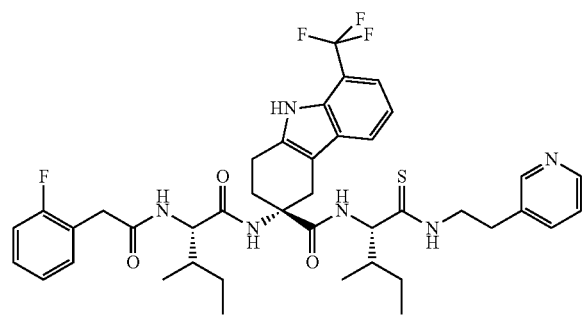 [SMILES: CCC(C)[C@H](NC(=O)Cc1ccccc1F)C(=O)N[C@]1(C(=O)N[C@H](C(=S)NCCc2cccnc2)C(C)CC)CCc2[nH]c3c(C(F)(F)F)cccc3c2C1]

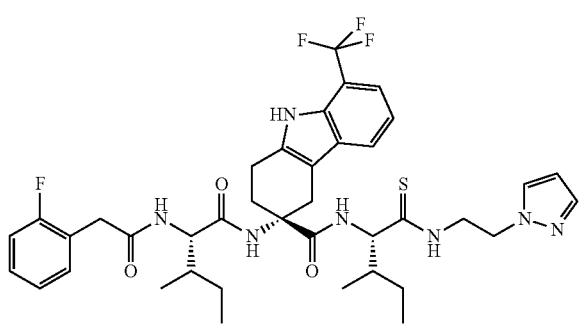

Compound 109 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(pyrimidin-4-ylmethyl)-thiocarbamoyl]-butyl}-amide Compound 112 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(2-[1,2,4]triazol-1-yl-ethylthiocarbamoyl)-butyl]-amide

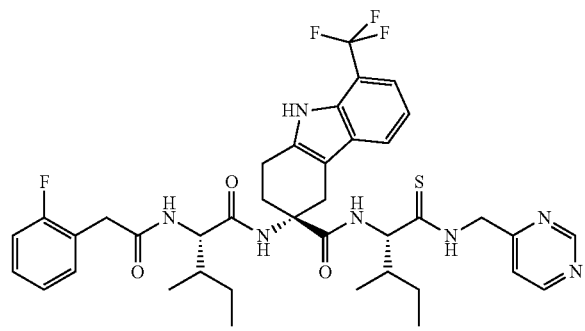 [SMILES: CCC(C)[C@H](NC(=O)Cc1ccccc1F)C(=O)N[C@]1(C(=O)N[C@H](C(=S)NCc2ccncn2)C(C)CC)CCc2[nH]c3c(C(F)(F)F)cccc3c2C1]

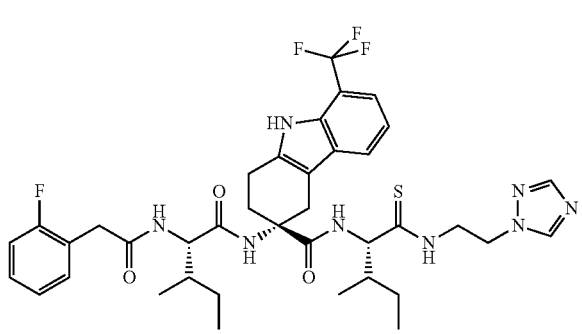

Compound 110 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(2-imidazol-1-yl-ethylthiocarbamoyl)-2-methyl-butyl]-amide Compound 113 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(3-[1,2,4]triazol-1-yl-propylthiocarbamoyl)-butyl]-amide

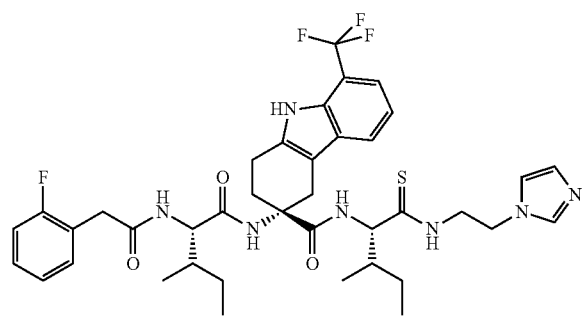 [SMILES: CCC(C)[C@H](NC(=O)Cc1ccccc1F)C(=O)N[C@]1(C(=O)N[C@H](C(=S)NCCn2ccnc2)C(C)CC)CCc2[nH]c3c(C(F)(F)F)cccc3c2C1]

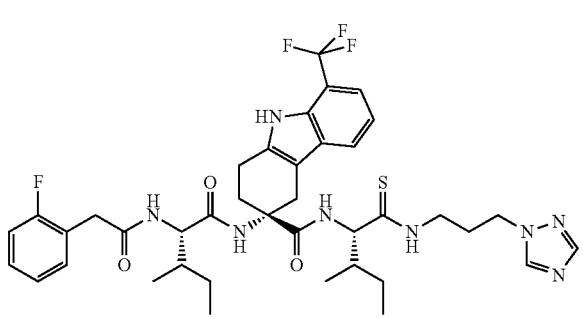 [SMILES: CCC(C)[C@H](NC(=O)Cc1ccccc1F)C(=O)N[C@]1(C(=O)N[C@H](C(=S)NCCCn2cncn2)C(C)CC)CCc2[nH]c3c(C(F)(F)F)cccc3c2C1]

Compound 114 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-1(4-[1,2,4]triazol-1-yl butylthiocarbamoyl)-butyl]-amide

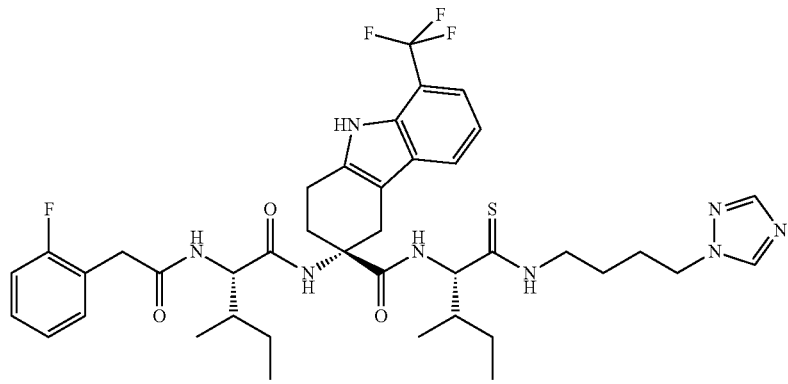 [SMILES: CCC(C)[C@H](NC(=O)Cc1ccccc1F)C(=O)N[C@]1(C(=O)N[C@H](C(=S)NCCCCn2cncn2)C(C)CC)CCc2[nH]c3c(C(F)(F)F)cccc3c2C1]

Compound 115 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[(furan-2-ylmethyl)-thiocarbamoyl]-2-methyl-butyl}-amide

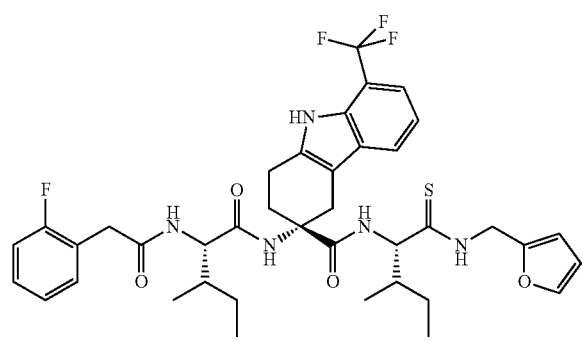 [SMILES: CCC(C)[C@H](NC(=O)Cc1ccccc1F)C(=O)N[C@]1(C(=O)N[C@H](C(=S)NCc2ccco2)C(C)CC)CCc2[nH]c3c(C(F)(F)F)cccc3c2C1]

Compound 116 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[(furan-3-ylmethyl)-thiocarbamoyl]-2-methyl-butyl}-amide

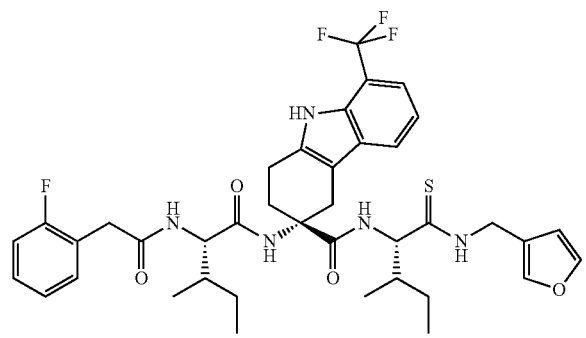 [SMILES: CCC(C)[C@H](NC(=O)Cc1ccccc1F)C(=O)N[C@]1(C(=O)N[C@H](C(=S)NCc2ccoc2)C(C)CC)CCc2[nH]c3c(C(F)(F)F)cccc3c2C1]

Compound 117 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(2-furan-2-yl-ethylthiocarbamoyl)-2-methyl-butyl]-amide

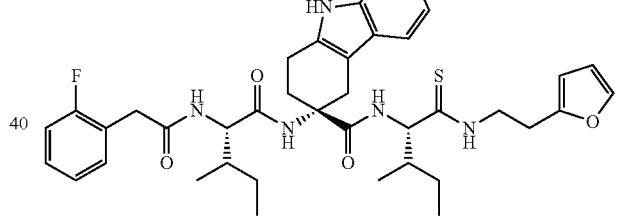

Compound 118 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(5-methyl-[1,3,4]oxadiazol-2-ylmethyl)-thiocarbamoyl]-butyl}-amide

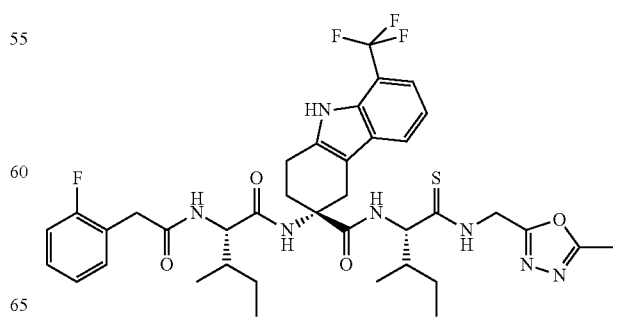

Compound 119 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[2-(tetrahydro-pyran-4-yl)-ethylthiocarbamoyl]-butyl}-amide

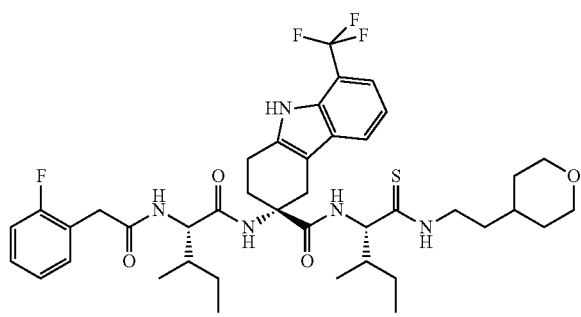 [SMILES: CCC(C)[C@H](NC(=O)Cc1ccccc1F)C(=O)N[C@]1(C(=O)N[C@H](C(=S)NCCC2CCOCC2)C(C)CC)CCc2[nH]c3c(C(F)(F)F)cccc3c2C1]

Compound 120 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(tetrahydro-pyran-4-ylthiocarbamoyl)-butyl]-amide

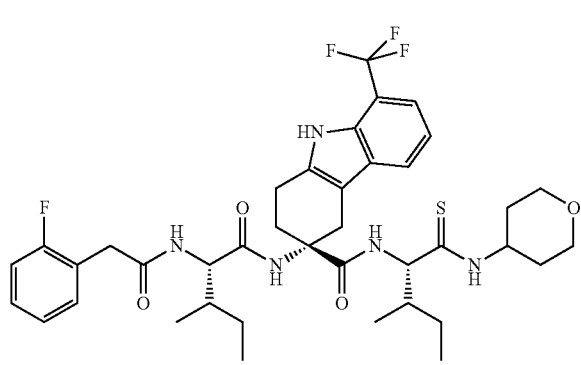 [SMILES: CCC(C)[C@H](NC(=O)Cc1ccccc1F)C(=O)N[C@]1(C(=O)N[C@H](C(=S)NC2CCOCC2)C(C)CC)CCc2[nH]c3c(C(F)(F)F)cccc3c2C1]

Compound 121 5-{(S)-2-[((R)-3-{(S)-2-[2-(2-Fluoro-phenyl)-acetylamino]-3-methyl-pentanoylamino}-8-trifluoromethyl-2,3,4,9-tetrahydro-1H-carbazole-3-carbonyl)-amino]-3-methyl-pentanoylamino}-2-hydroxy-benzoic acid

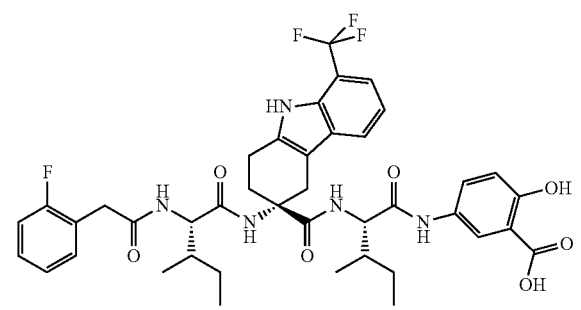 [SMILES: CCC(C)[C@H](NC(=O)Cc1ccccc1F)C(=O)N[C@]1(C(=O)N[C@H](C(=O)Nc2ccc(O)c(C(=O)O)c2)C(C)CC)CCc2[nH]c3c(C(F)(F)F)cccc3c2C1]

Compound 122 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(3-fluoro-4-hydroxy-phenylcarbamoyl)-2-methyl-butyl]-amide

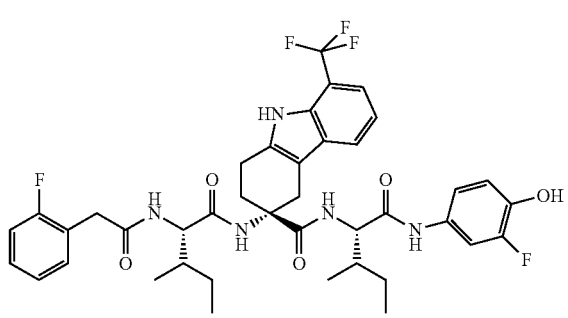 [SMILES: CCC(C)[C@H](NC(=O)Cc1ccccc1F)C(=O)N[C@]1(C(=O)N[C@H](C(=O)Nc2ccc(O)c(F)c2)C(C)CC)CCc2[nH]c3c(C(F)(F)F)cccc3c2C1]

Compound 123 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(3-hydroxy-4-methoxy-benzylthiocarbamoyl)-2-methyl-butyl]-amide

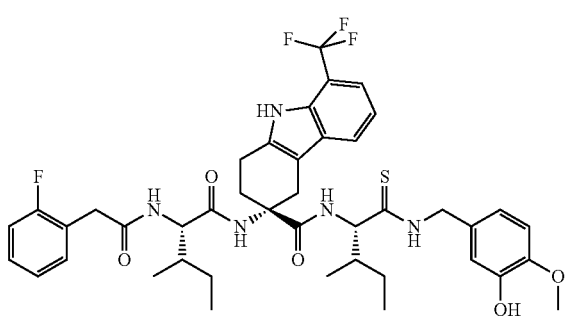 [SMILES: CCC(C)[C@H](NC(=O)Cc1ccccc1F)C(=O)N[C@]1(C(=O)N[C@H](C(=S)NCc2ccc(OC)c(O)c2)C(C)CC)CCc2[nH]c3c(C(F)(F)F)cccc3c2C1]

Compound 124 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid ((S)-1-hydrazinocarbonyl-2-methyl-butyl)-amide

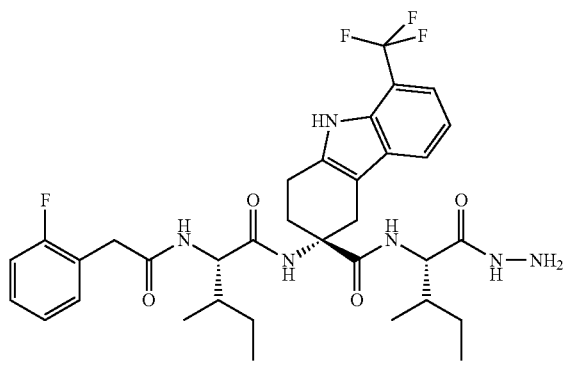 [SMILES: CCC(C)[C@H](NC(=O)Cc1ccccc1F)C(=O)N[C@]1(C(=O)N[C@H](C(=O)NN)C(C)CC)CCc2[nH]c3c(C(F)(F)F)cccc3c2C1]

71

Compound 125 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(3-hydroxy-4-methoxy-phenylthiocarbamoyl)-2-methyl-butyl]-amide

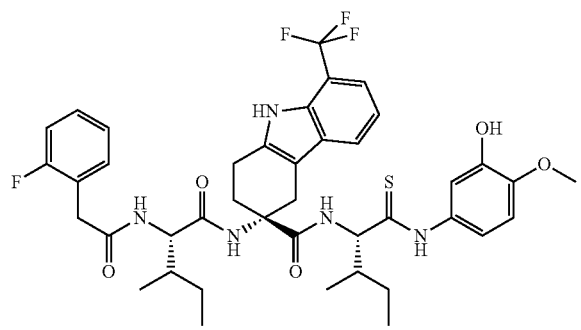 [SMILES: CCC(C)[C@H](NC(=O)Cc1ccccc1F)C(=O)N[C@]1(C(=O)N[C@H](C(=S)Nc2ccc(OC)c(O)c2)C(C)CC)CCc2[nH]c3c(C(F)(F)F)cccc3c2C1]

Compound 126 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid ((S)-2-oxo-pyrrolidin-3-yl)-amide

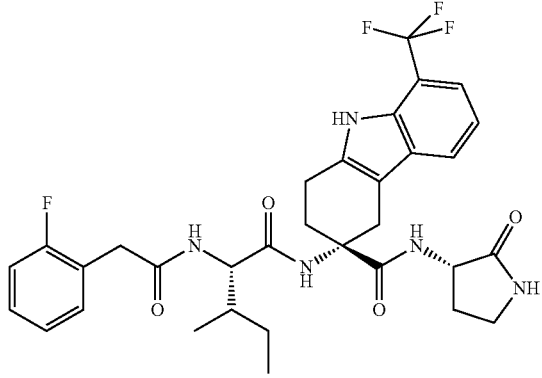 [SMILES: CCC(C)[C@H](NC(=O)Cc1ccccc1F)C(=O)N[C@]1(C(=O)N[C@H]2CCNC2=O)CCc2[nH]c3c(C(F)(F)F)cccc3c2C1]

72

Compound 127 (S)-2-[((R)-3-{(S)-2-[2-(2-Fluoro-phenyl)-acetylamino]-3-methyl-pentanoylamino}-8-trifluoromethyl-2,3,4,9-tetrahydro-1H-carbazole-3-carbonyl)-amino]-3-methyl-pentanoic acid 3-imidazol-1-yl-propyl ester

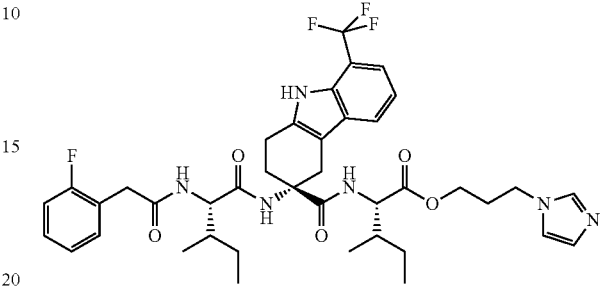

Compound 128 (R)-2-[((R)-3-{(S)-2-[2-(2-Fluoro-phenyl)-acetylamino]-3-methyl-pentanoylamino}-8-trifluoromethyl-2,3,4,9-tetrahydro-1H-carbazole-3-carbonyl)-amino]-3-methyl-pentanoic acid 3-imidazol-1-yl-propyl ester Compound 129 ((S)-1-{(R)-6,8-Dichloro-3-[(S)-1-(4-hydroxy-benzylcarbamoyl)-2-methyl-butylcarbamoyl]-2,3,4,9-tetrahydro-11-1carbazol-3-ylcarbamoyl}-2-methyl-butyl)-carbamic acid benzyl ester

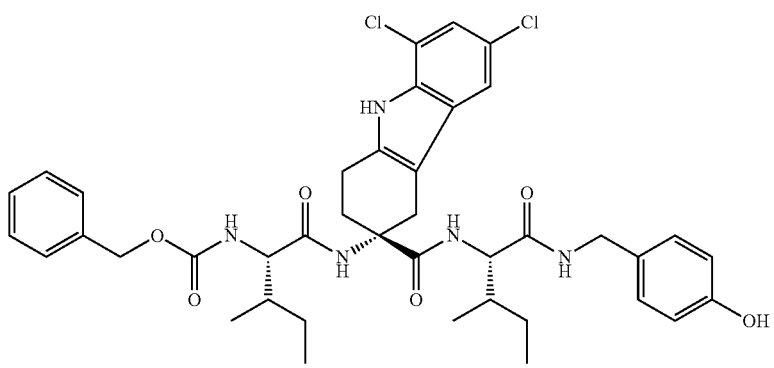 [SMILES: CCC(C)[C@H](NC(=O)OCc1ccccc1)C(=O)N[C@]1(C(=O)N[C@H](C(=O)NCc2ccc(O)cc2)C(C)CC)CCc2[nH]c3c(Cl)cc(Cl)cc3c2C1]

Compound 130 ((S)-1-{(S)-6,8-Dichloro-3-[(S)-1-(4-hydroxy-benzylcarbamoyl)-2-methyl-butylcarbamoyl]-2,3,4,9-tetrahydro-1H-carbazol-3-ylcarbamoyl}-2-methyl-butyl)-carbamic acid benzyl ester

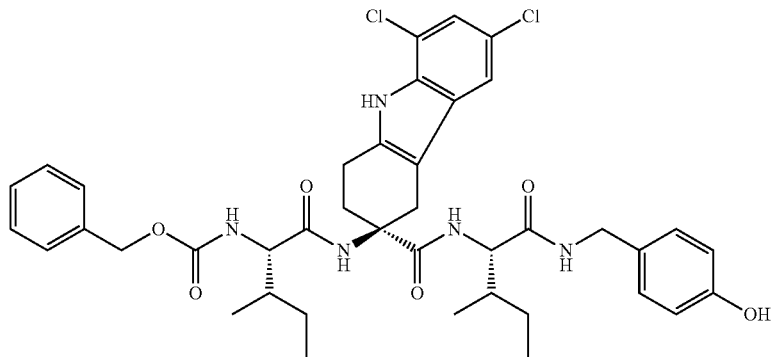 [SMILES: CCC(C)[C@H](NC(=O)OCc1ccccc1)C(=O)N[C@@]1(C(=O)N[C@H](C(=O)NCc2ccc(O)cc2)C(C)CC)CCc2[nH]c3c(Cl)cc(Cl)cc3c2C1]

Compound 131 (S)-2-[((R)-3-{(S)-2-[2-(2-Fluorophenyl)-acetylamino]-3-methyl-pentanoylamino}-8-trifluoromethyl-2,3,4,9-tetrahydro-1H-carbazole-3-carbonyl)-amino]-3-methyl-pentanoic acid pyridin-4-ylmethyl ester Compound 133 2-[((R)-3-{(S)-2-[2-(2-Fluoro-phenyl)-acetylamino]-3-methyl-pentanoylamino}-8-trifluoromethyl-2,3,4,9-tetrahydro-1H-carbazole-3-carbonyl)-amino]-3-methyl-pentanoic acid 2-dimethylamino-ethyl ester

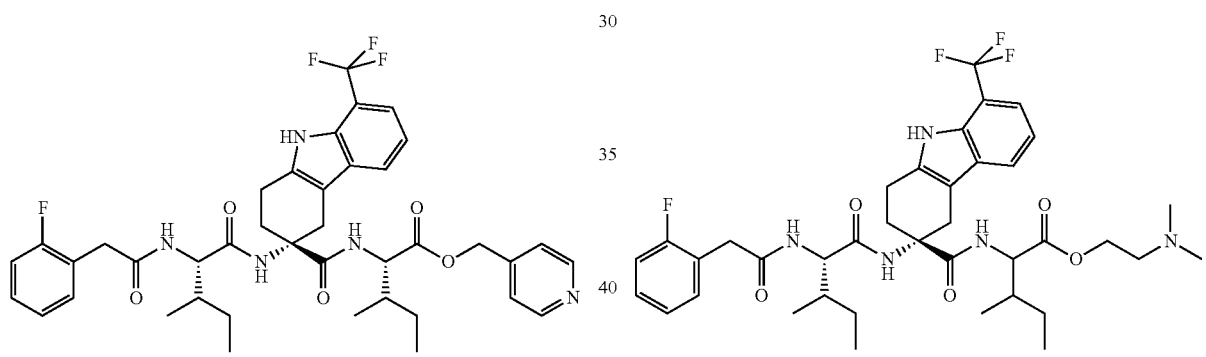

Compound 132 (R)-2-[((R)-3-{(S)-2-[2-(2-Fluorophenyl)-acetylamino]-3-methyl-pentanoylamino}-8-trifluoromethyl-2,3,4,9-tetrahydro-1H-carbazole-3-carbonyl)-amino]-3-methyl-pentanoic acid pyridin-4-ylmethyl ester Compound 134 (S)-2-[((R)-3-{(S)-2-[2-(2-Fluoro-phenyl)-acetylamino]-3-methyl-pentanoylamino}-8-trifluoromethyl-2,3,4,9-tetrahydro-1H-carbazole-3-carbonyl)-amino]-3-methyl-pentanoic acid 3-hydroxy-4-methoxy-benzyl ester

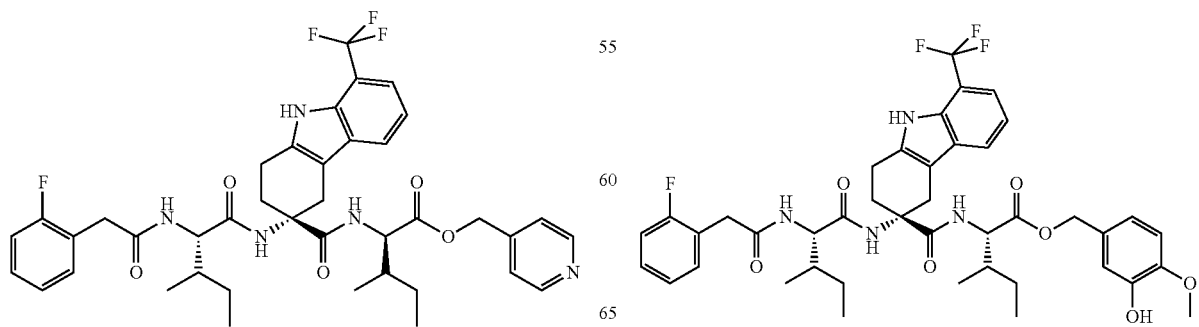

Compound 135 (R)-2-[((R)-3-{(S)-2-[2-(2-Fluoro-phenyl)-acetylamino]-3-methyl-pentanoylamino}-8-trifluoromethyl-2,3,4,9-tetrahydro-1H-carbazole-3-carbonyl)-amino]-3-methyl-pentanoic acid 3-hydroxy-4-methoxy-benzyl ester Compound 138 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(R)-2-methyl-1-(quinolin-6-ylcarbamoyl)-butyl]-amide

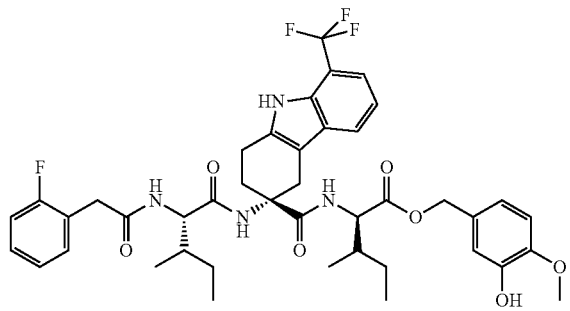 [SMILES: CCC(C)[C@H](NC(=O)Cc1ccccc1F)C(=O)N[C@]1(C(=O)N[C@@H](C(=O)OCc2ccc(OC)c(O)c2)C(C)CC)CCc2[nH]c3c(C(F)(F)F)cccc3c2C1]

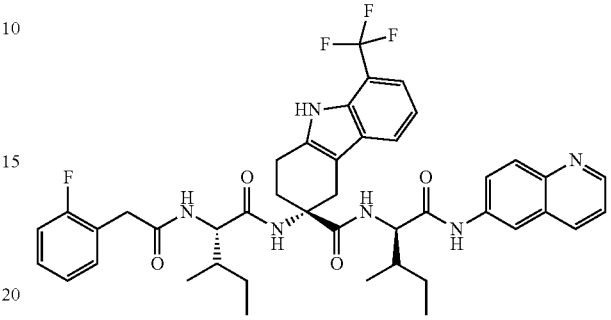

Compound 136 [(S)-1-((S)-6,8-Dichloro-3-{(S)-2-methyl-1-[(tetrahydro-pyran-4-ylmethyl)-carbamoyl]-butylcarbamoyl}-2,3,4,9-tetrahydro-1H-carbazol-3-ylcarbamoyl)-2-methyl-butyl]-carbamic acid benzyl ester Compound 139 [(S)-1-((R)-6,8-Dichloro-3-{(S)-2-methyl-1-[(tetrahydro-pyran-4-ylmethyl)-thiocarbamoyl]-butylcarbamoyl}-2,3,4,9-tetrahydro-1H-carbazol-3-ylcarbamoyl)-2-methyl-butyl]-carbamic acid benzyl ester

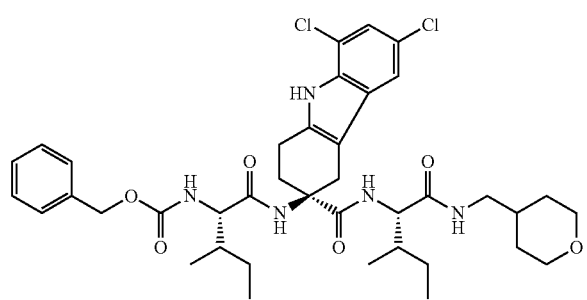 [SMILES: CCC(C)[C@H](NC(=O)OCc1ccccc1)C(=O)N[C@@]1(C(=O)N[C@H](C(=O)NCC2CCOCC2)C(C)CC)CCc2[nH]c3c(Cl)cc(Cl)cc3c2C1]

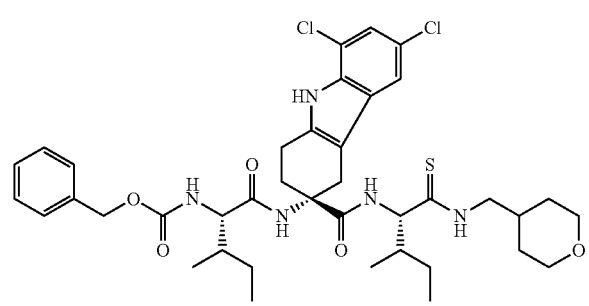

Compound 137 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(quinolin-6-ylcarbamoyl)-butyl]-amide Compound 140 ((S)-1-{(R)-6,8-Dichloro-3-[(S)-1-(4-hydroxy-3-methoxy-phenylcarbamoyl)-2-methyl-butylcarbamoyl]-2,3,4,9-tetrahydro-1H-carbazol-3-ylcarbamoyl}-2-methyl-butyl)-carbamic acid benzyl ester

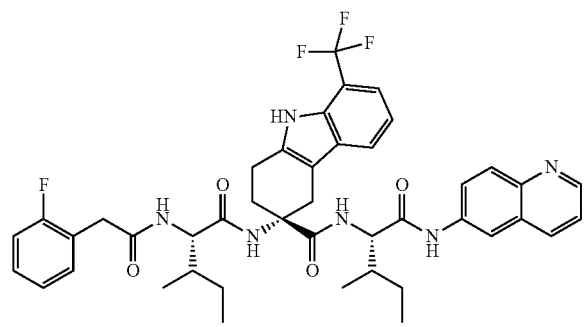 [SMILES: CCC(C)[C@H](NC(=O)Cc1ccccc1F)C(=O)N[C@]1(C(=O)N[C@H](C(=O)Nc2ccc3ncccc3c2)C(C)CC)CCc2[nH]c3c(C(F)(F)F)cccc3c2C1]

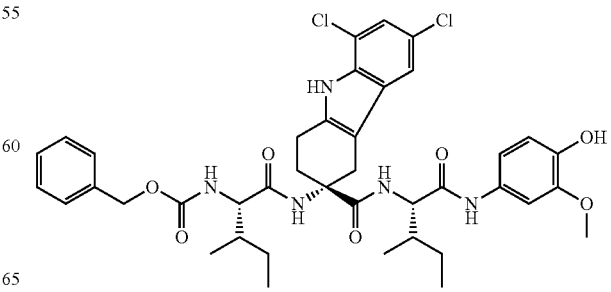

Compound 141 ((S)-1{(S)-6,8-Dichloro-3-[(S)-1(4-hydroxy-3-methoxy-phenylcarbamoyl)-2-methyl-butylcarbamoyl]-2,3,4,9-tetrahydro-1H-carbazol-3-ylcarbamoyl}-2-methyl-butyl)-carbamic acid benzyl ester

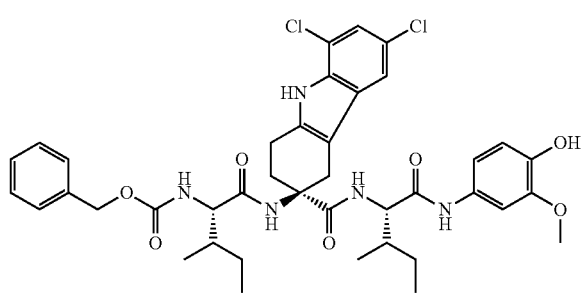 [SMILES: CCC(C)[C@H](NC(=O)OCc1ccccc1)C(=O)N[C@@]1(C(=O)N[C@H](C(=O)Nc2ccc(O)c(OC)c2)C(C)CC)CCc2[nH]c3c(Cl)cc(Cl)cc3c2C1]

Compound 142 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid ((S)-2-oxo-piperidin-3-yl)-amide

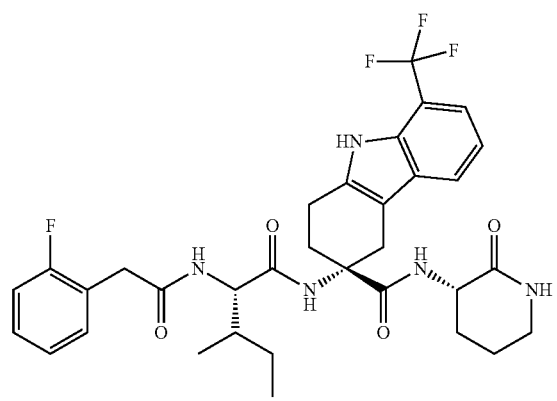 [SMILES: CCC(C)[C@H](NC(=O)Cc1ccccc1F)C(=O)N[C@]1(C(=O)N[C@H]2CCCNC2=O)CCc2[nH]c3c(C(F)(F)F)cccc3c2C1]

Compound 143 [(S)-1-((R)-6,8-Dichloro-3-{(S)-2-methyl-1-[(tetrahydro-pyran-4-ylmethyl)-carbamoyl]-butylcarbamoyl}-2,3,4,9-tetrahydro-1H-carbazol-3-ylcarbamoyl)-2-methyl-butyl]-carbamic acid benzyl ester

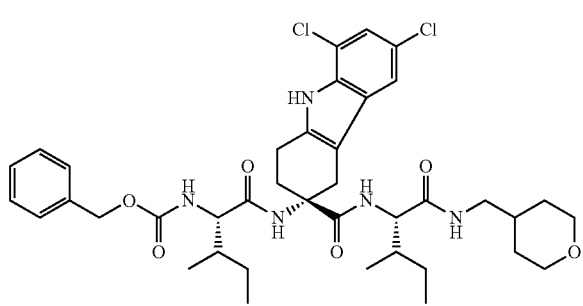 [SMILES: CCC(C)[C@H](NC(=O)OCc1ccccc1)C(=O)N[C@]1(C(=O)N[C@H](C(=O)NCC2CCOCC2)C(C)CC)CCc2[nH]c3c(Cl)cc(Cl)cc3c2C1]

Compound 144 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(N'-phenyl-hydrazinocarbonyl)-butyl]-amide

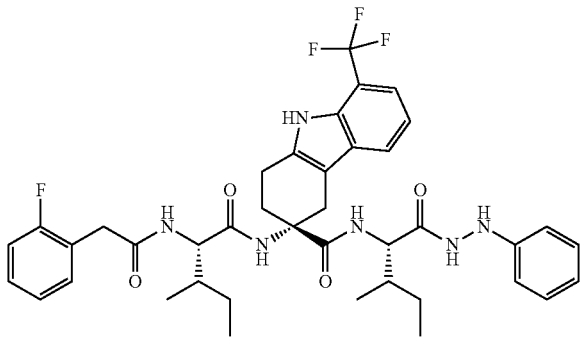 [SMILES: CCC(C)[C@H](NC(=O)Cc1ccccc1F)C(=O)N[C@]1(C(=O)N[C@H](C(=O)NNc2ccccc2)C(C)CC)CCc2[nH]c3c(C(F)(F)F)cccc3c2C1]

Compound 145 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid ((S)-3-methylsulfanyl-1-thiocarbamoyl-propyl)-amide

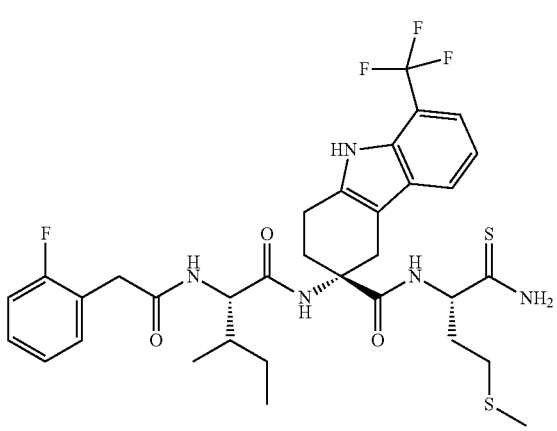 [SMILES: CCC(C)[C@H](NC(=O)Cc1ccccc1F)C(=O)N[C@]1(C(=O)N[C@@H](CCSC)C(N)=S)CCc2[nH]c3c(C(F)(F)F)cccc3c2C1]

Compound 146 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(quinolin-5-ylcarbamoyl)-butyl]-amide

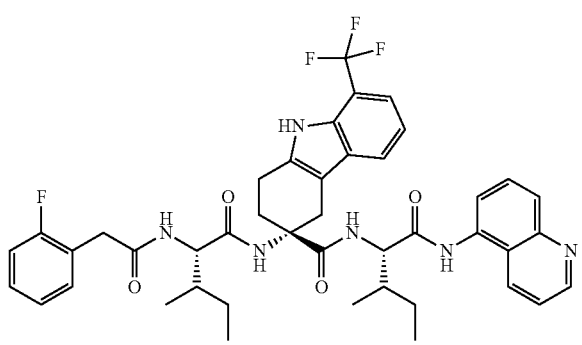 [SMILES: CCC(C)[C@H](NC(=O)Cc1ccccc1F)C(=O)N[C@]1(C(=O)N[C@H](C(=O)Nc2cccc3ncccc23)C(C)CC)CCc2[nH]c3c(C(F)(F)F)cccc3c2C1]

Compound 147 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(isoquinolin-5-ylcarbamoyl)-2-methyl-butyl]-amide

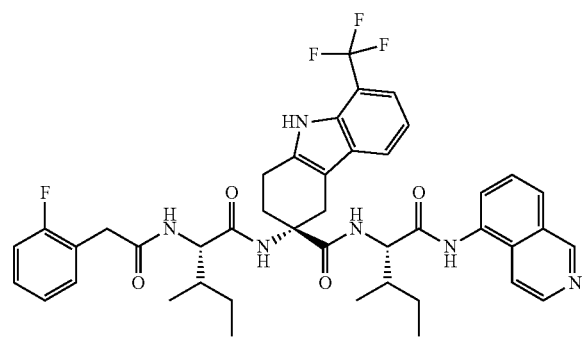 [SMILES: CCC(C)[C@H](NC(=O)Cc1ccccc1F)C(=O)N[C@]1(C(=O)N[C@H](C(=O)Nc2cccc3cnccc23)C(C)CC)CCc2[nH]c3c(C(F)(F)F)cccc3c2C1]

Compound 148 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(2-tetrahydro-pyran-4-yl-acetylamino)-methyl]-butyl}-amide

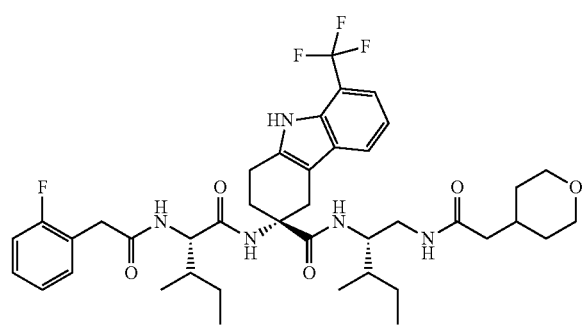 [SMILES: CCC(C)[C@H](NC(=O)Cc1ccccc1F)C(=O)N[C@]1(C(=O)N[C@H](CNC(=O)CC2CCOCC2)C(C)CC)CCc2[nH]c3c(C(F)(F)F)cccc3c2C1]

Compound 149 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid ((S)-2-methyl-1-{[(tetrahydro-pyran-4-carbonyl)-amino]-methyl}-butyl)-amide

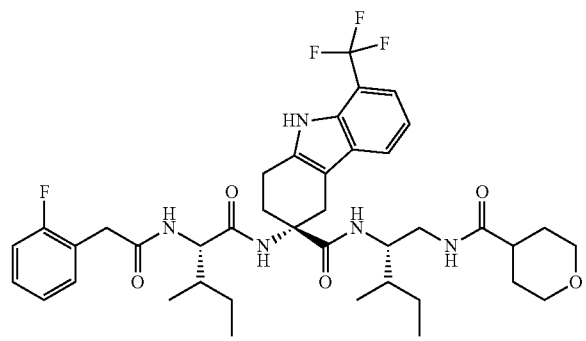 [SMILES: CCC(C)[C@H](NC(=O)Cc1ccccc1F)C(=O)N[C@]1(C(=O)N[C@H](CNC(=O)C2CCOCC2)C(C)CC)CCc2[nH]c3c(C(F)(F)F)cccc3c2C1]

Compound 150 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(3-morpholin-4-yl-propionylamino)-methyl]-butyl}-amide

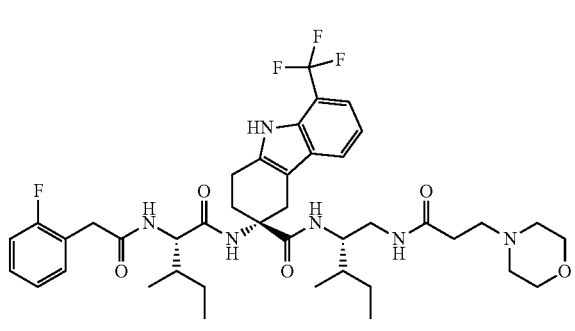 [SMILES: CCC(C)[C@H](NC(=O)Cc1ccccc1F)C(=O)N[C@]1(C(=O)N[C@H](CNC(=O)CCN2CCOCC2)C(C)CC)CCc2[nH]c3c(C(F)(F)F)cccc3c2C1]

Compound 151 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[(3-imidazol-1-yl-propionylamino)-methyl]-2-methyl-butyl}-amide

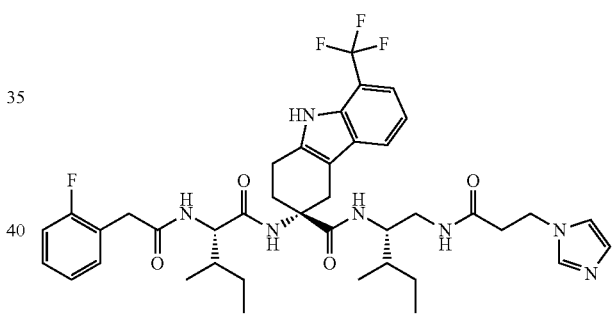

Compound 152 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[3-(tetrahydro-pyran-4-ylmethyl)-ureidomethyl]-butyl}-amide

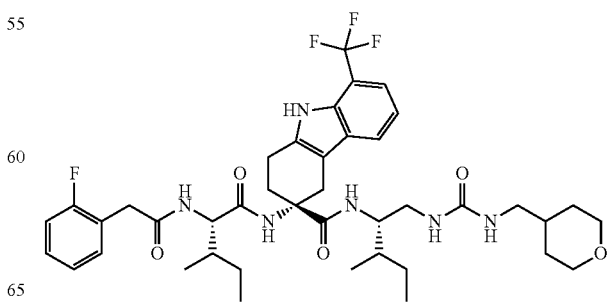

Compound 153 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(2-tetrahydro-pyran-4-yl-acetylamino)-butyl]-amide Compound 156 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(3-imidazol-1-yl-propionylamino)-2-methyl-butyl]-amide

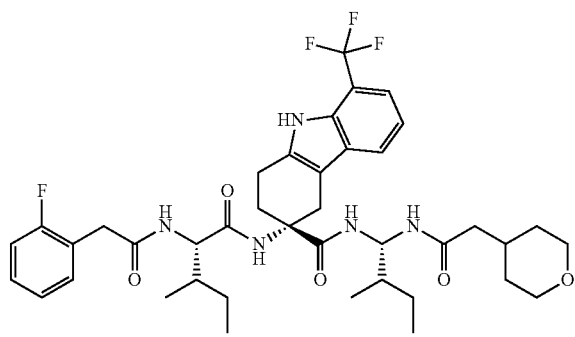 [SMILES: CCC(C)[C@@H](NC(=O)CC1CCOCC1)NC(=O)[C@@]1(NC(=O)[C@@H](NC(=O)Cc2ccccc2F)C(C)CC)CCc2[nH]c3c(C(F)(F)F)cccc3c2C1]

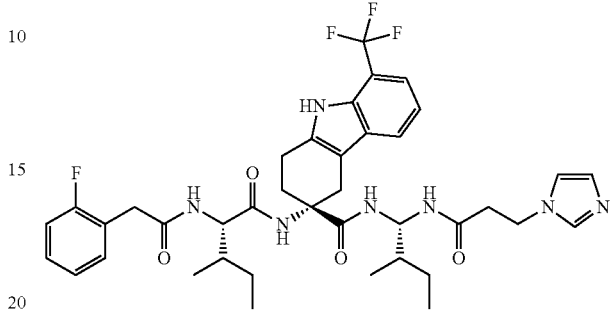

Compound 154 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(tetrahydro-pyran-4-carbonyl)-amino]-butyl}-amide Compound 157 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(R)-2-methyl-1-[3-(tetrahydro-pyran-4-ylmethyl)-ureido]-butyl}-amide

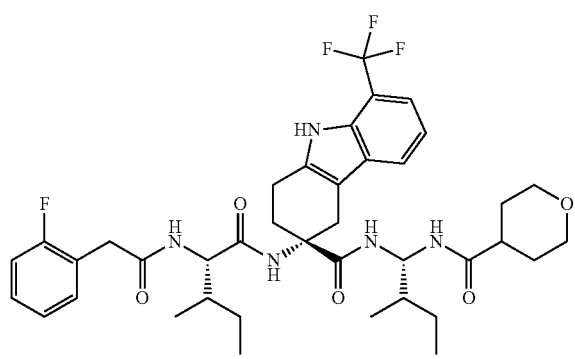 [SMILES: CCC(C)[C@@H](NC(=O)C1CCOCC1)NC(=O)[C@@]1(NC(=O)[C@@H](NC(=O)Cc2ccccc2F)C(C)CC)CCc2[nH]c3c(C(F)(F)F)cccc3c2C1]

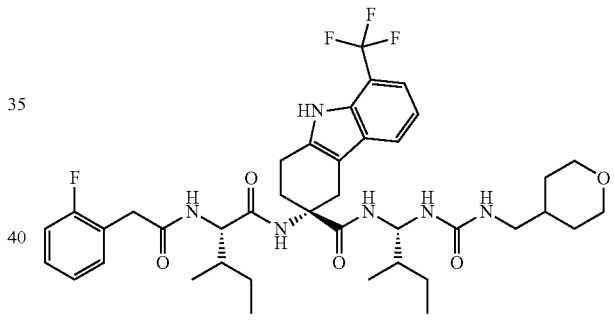

Compound 155 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(3-morpholin-4-yl-propionylamino)-butyl]-amide Compound 158 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid ((R)-2-methyl-1-{[tetrahydro-pyran-4-ylmethyl)-carbamoyl]-methyl}-butyl)-amide

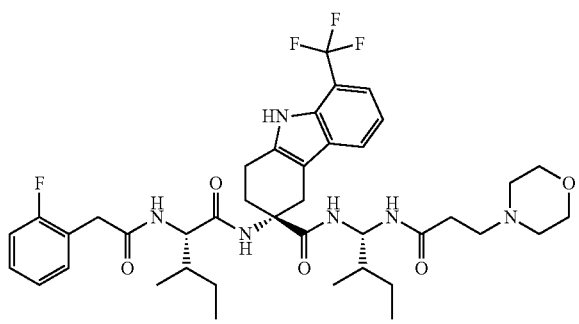 [SMILES: CCC(C)[C@@H](NC(=O)CCN1CCOCC1)NC(=O)[C@@]1(NC(=O)[C@@H](NC(=O)Cc2ccccc2F)C(C)CC)CCc2[nH]c3c(C(F)(F)F)cccc3c2C1]

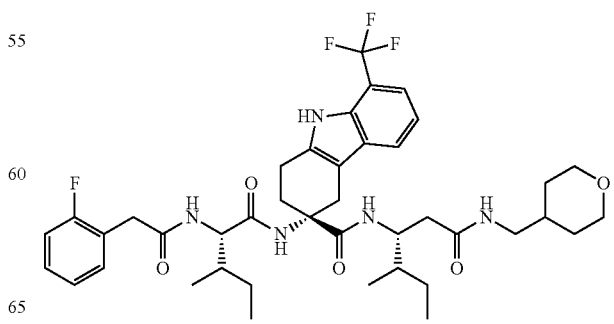

Compound 159 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[N'-(4-hydroxy-phenyl)-hydrazinocarbonyl]-2-methyl-butyl}-amide Compound 160 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[N'-(4-methoxy-phenyl)-hydrazinocarbonyl]-2-methyl-butyl}-amide

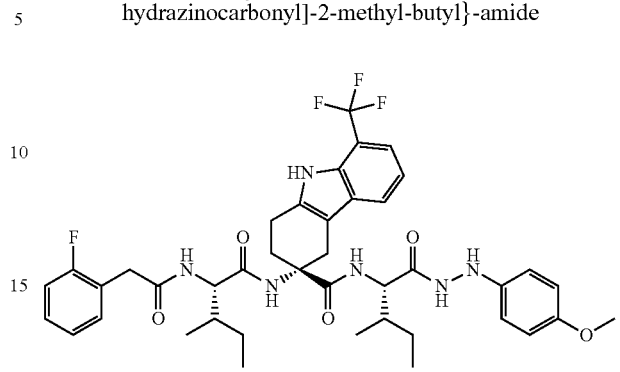

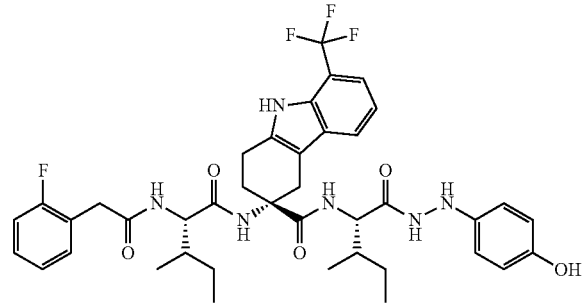 [SMILES: CCC(C)[C@H](NC(=O)Cc1ccccc1F)C(=O)N[C@]1(C(=O)N[C@H](C(=O)NNc2ccc(O)cc2)C(C)CC)CCc2[nH]c3c(C(F)(F)F)cccc3c2C1]

Compound 161 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[N'-(3-hydroxy-4-methoxy-benzyl)-hydrazinocarbonyl]-2-methyl-butyl}-amide

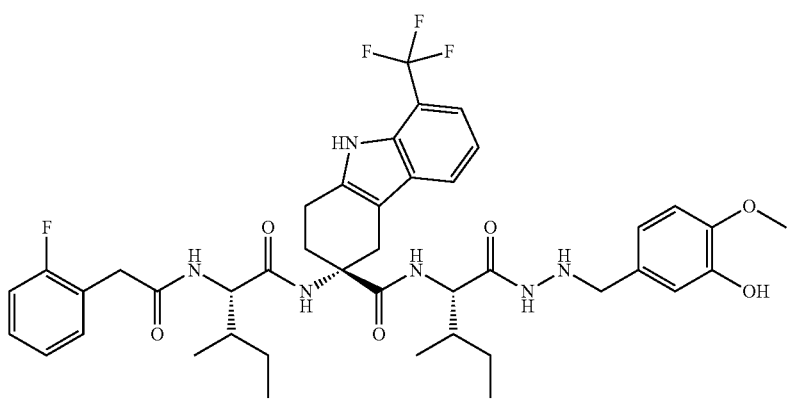 [SMILES: CCC(C)[C@H](NC(=O)Cc1ccccc1F)C(=O)N[C@]1(C(=O)N[C@H](C(=O)NNCc2ccc(OC)c(O)c2)C(C)CC)CCc2[nH]c3c(C(F)(F)F)cccc3c2C1]

Compound 162 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[N'-(4-hydroxy-3-methoxy-benzyl)-hydrazinocarbonyl]-2-methyl-butyl}-amide

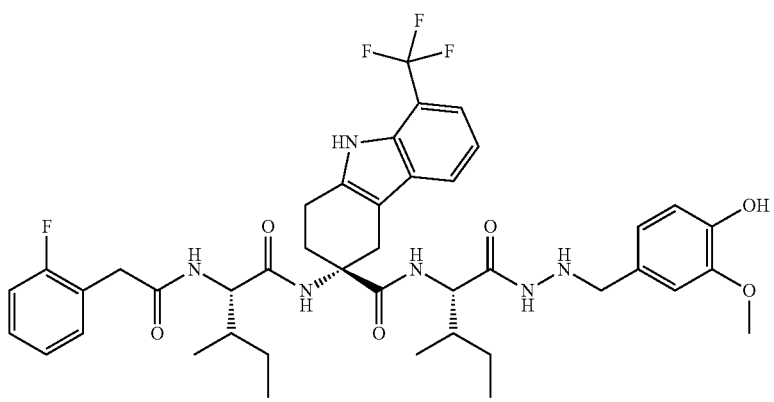 [SMILES: CCC(C)[C@H](NC(=O)Cc1ccccc1F)C(=O)N[C@]1(C(=O)N[C@H](C(=O)NNCc2ccc(O)c(OC)c2)C(C)CC)CCc2[nH]c3c(C(F)(F)F)cccc3c2C1]

85

Compound 163 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(N'-acetyl-hydrazinocarbonyl)-2-methyl-butyl]-amide

86

Compound 164

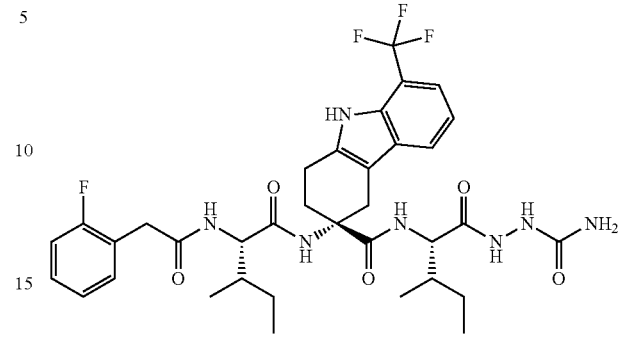

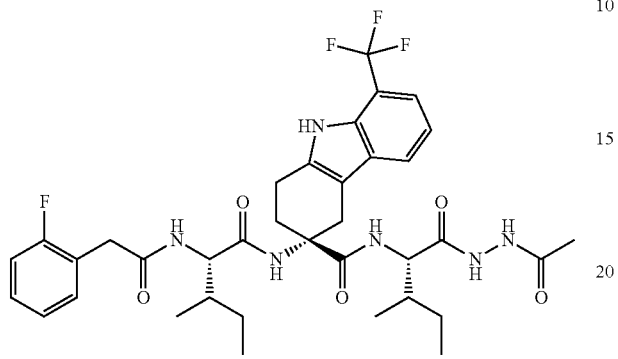

Compound 165 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[N'-(4-hydroxy-benzoyl)-hydrazinocarbonyl]-2-methyl-butyl}-amide

| Compound | Structure | Chemical name |
|---|---|---|
| 166 | 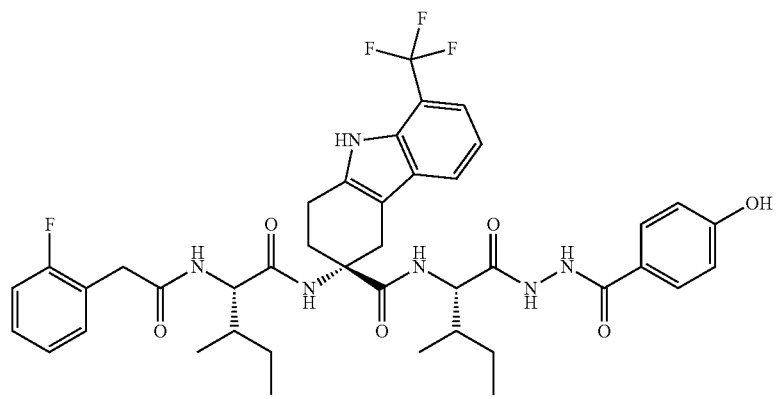 [SMILES: CCC(C)[C@H](NC(=O)Cc1ccccc1F)C(=O)N[C@]1(C(=O)N[C@H](C(=O)NNC(=O)c2ccc(O)cc2)C(C)CC)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(acetylamino-methyl)-2-methyl-butyl]-amide |

| Compound | Structure | Chemical name |
|---|---|---|
| 167 | 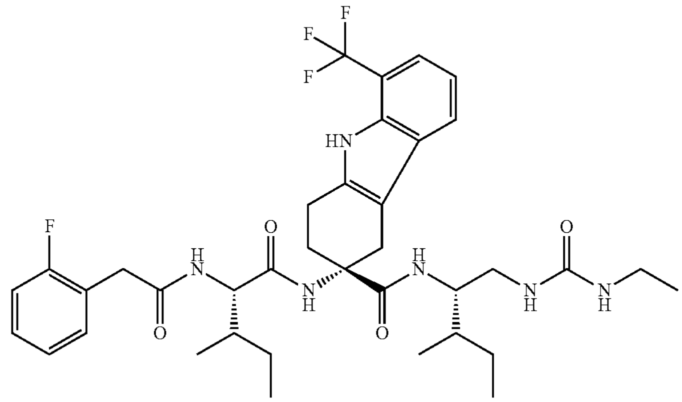 [SMILES: CCNC(=O)NC[C@@H](NC(=O)[C@@]1(NC(=O)[C@@H](NC(=O)Cc2ccccc2F)C(C)CC)CCc2[nH]c3c(C(F)(F)F)cccc3c2C1)C(C)CC] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[(3-ethyl-ureido)-methyl]-2-methyl-butyl}-amide |
| 168 | 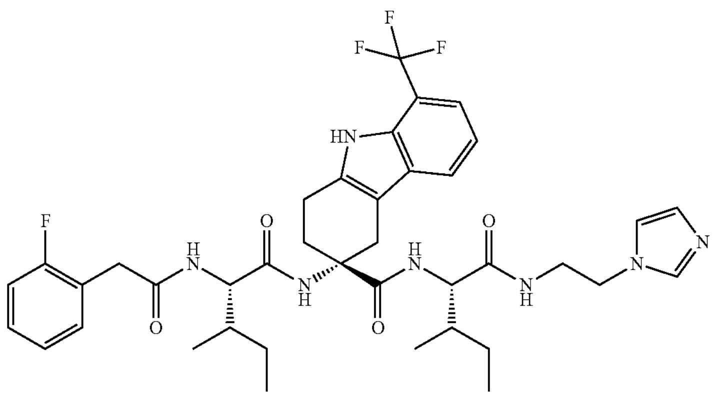 [SMILES: CCC(C)[C@H](NC(=O)Cc1ccccc1F)C(=O)N[C@]1(C(=O)N[C@H](C(=O)NCCn2ccnc2)C(C)CC)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(2-imidazol-1-yl-ethylcarbamoyl)-2-methyl-butyl]-amide |
| 169 | 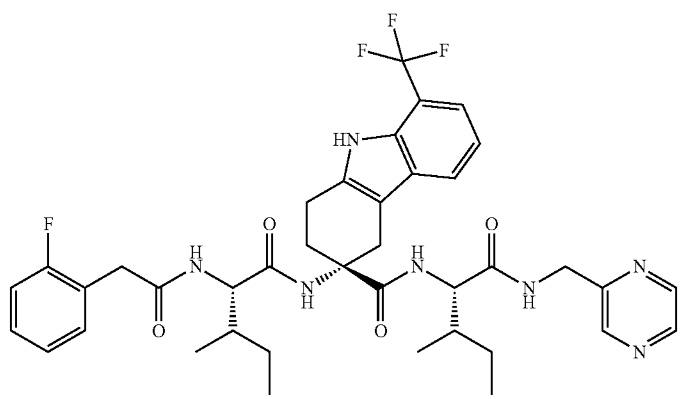 [SMILES: CCC(C)[C@H](NC(=O)Cc1ccccc1F)C(=O)N[C@]1(C(=O)N[C@H](C(=O)NCc2cnccn2)C(C)CC)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(pyrazin-2-ylmethyl)-carbamoyl]-butyl}-amide |
| 170 | 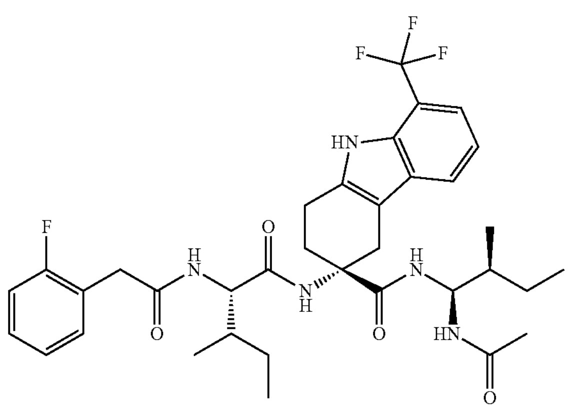 [SMILES: CCC(C)[C@H](NC(=O)Cc1ccccc1F)C(=O)N[C@]1(C(=O)N[C@H](NC(C)=O)[C@@H](C)CC)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid ((1S,2S)-1-acetylamino-2-methyl-butyl)-amide |

-continued

| Compound | Structure | Chemical name |
|---|---|---|
| 171 | 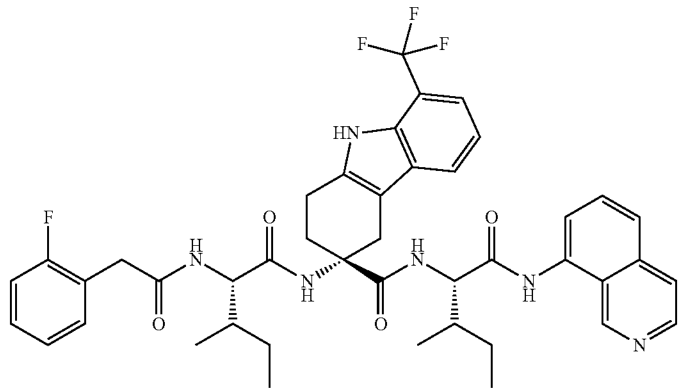 [SMILES: CCC(C)[C@H](NC(=O)Cc1ccccc1F)C(=O)N[C@]1(C(=O)N[C@H](C(=O)Nc2cccc3ccncc23)C(C)CC)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(isoquinolin-8-ylcarbamoyl)-2-methyl-butyl]-amide |
| 172 | 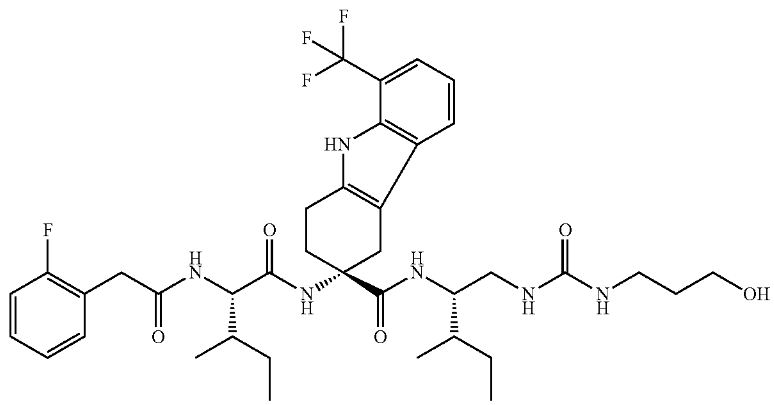 [SMILES: CCC(C)[C@H](NC(=O)Cc1ccccc1F)C(=O)N[C@]1(C(=O)N[C@H](CNC(=O)NCCCO)C(C)CC)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[3-(3-hydroxy-propyl)-ureidomethyl]-2-methyl-butyl}-amide |
| 173 | 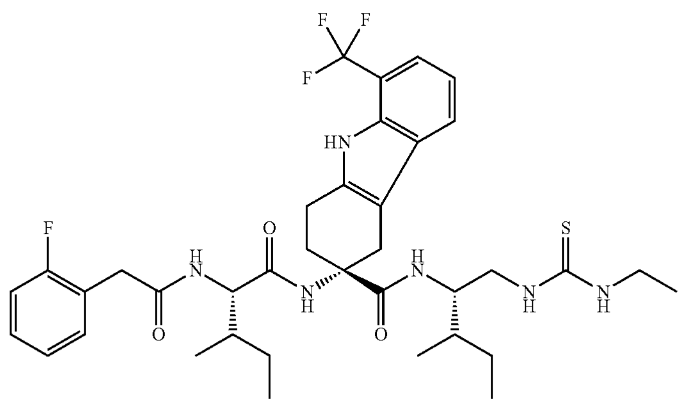 [SMILES: CCNC(=S)NC[C@@H](NC(=O)[C@@]1(NC(=O)[C@@H](NC(=O)Cc2ccccc2F)C(C)CC)CCc2[nH]c3c(C(F)(F)F)cccc3c2C1)C(C)CC] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[(3-ethyl-thioureido)-methyl]-2-methyl-butyl}-amide |
| 174 | 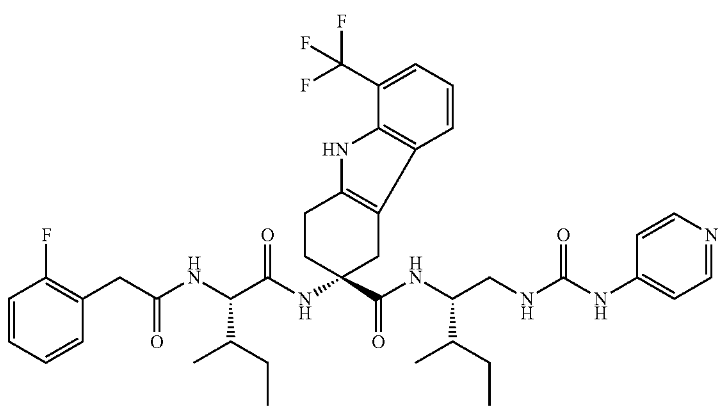 [SMILES: CCC(C)[C@H](NC(=O)Cc1ccccc1F)C(=O)N[C@]1(C(=O)N[C@H](CNC(=O)Nc2ccncc2)C(C)CC)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(3-pyridin-4-yl-ureido)-methyl]-butyl}-amide |

| Compound | Structure | Chemical name |
|---|---|---|
| 175 | 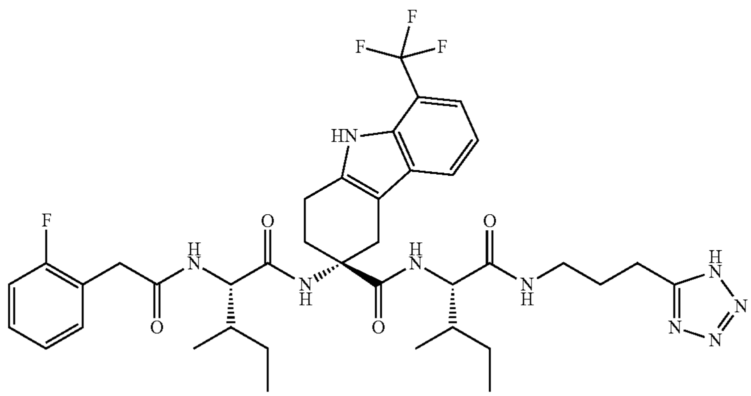 [SMILES: CCC(C)[C@H](NC(=O)Cc1ccccc1F)C(=O)N[C@]1(C(=O)N[C@H](C(=O)NCCCc2nnn[nH]2)C(C)CC)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[3-(1H-tetrazol-5-yl)-propylcarbamoyl]-butyl}-amide |
| 176 | 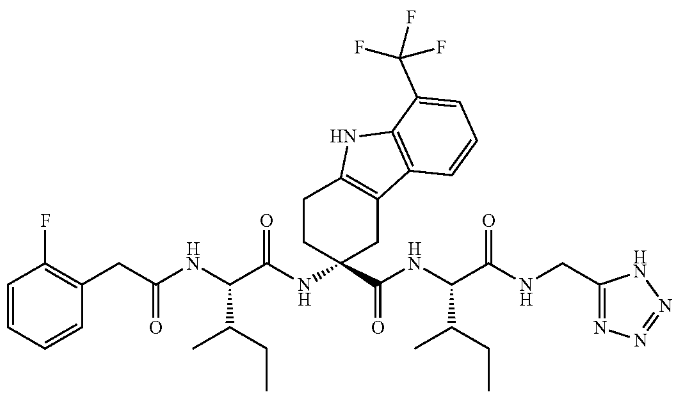 [SMILES: CCC(C)[C@H](NC(=O)Cc1ccccc1F)C(=O)N[C@]1(C(=O)N[C@H](C(=O)NCc2nnn[nH]2)C(C)CC)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(1H-tetrazol-5-ylmethyl)-carbamoyl]-butyl}-amide |
| 177 | 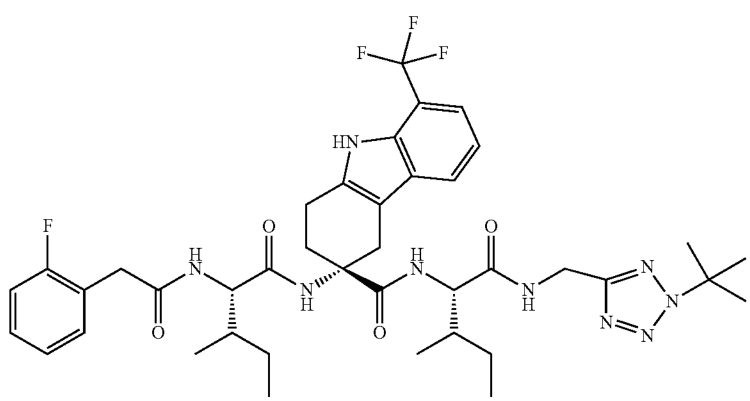 [SMILES: CCC(C)[C@H](NC(=O)Cc1ccccc1F)C(=O)N[C@]1(C(=O)N[C@H](C(=O)NCc2nnn(C(C)(C)C)n2)C(C)CC)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[(2-tert-butyl-2H-tetrazol-5-ylmethyl)-carbamoyl]-2-methyl-butyl}-amide |
| 178 | 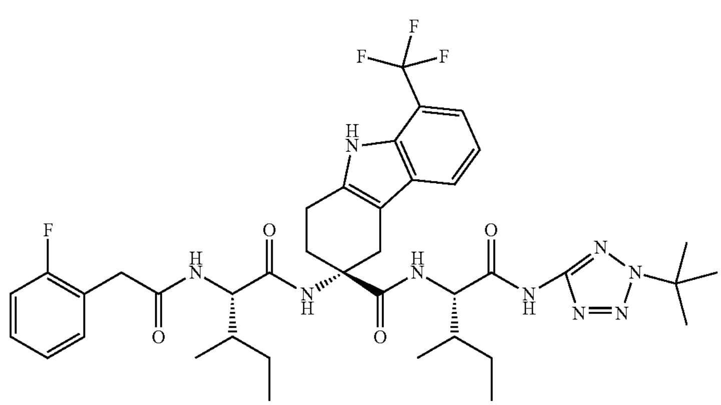 [SMILES: CCC(C)[C@H](NC(=O)Cc1ccccc1F)C(=O)N[C@]1(C(=O)N[C@H](C(=O)Nc2nnn(C(C)(C)C)n2)C(C)CC)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(2-tert-butyl-2H-tetrazol-5-ylcarbamoyl)-2-methyl-butyl]-amide |

| Compound | Structure | Chemical name |
|---|---|---|
| 179 | 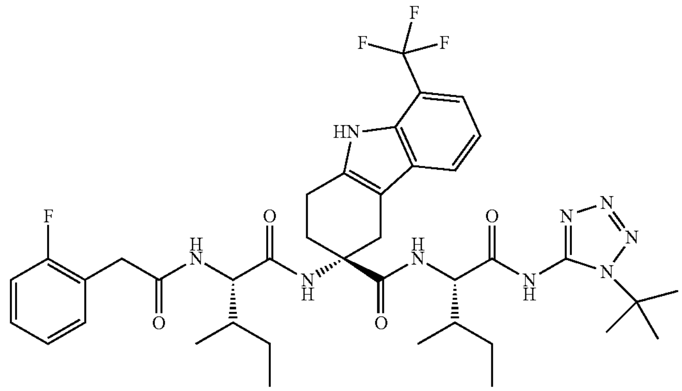 [SMILES: CCC(C)[C@H](NC(=O)Cc1ccccc1F)C(=O)N[C@]1(C(=O)N[C@H](C(=O)Nc2nnnn2C(C)(C)C)C(C)CC)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(1-tert-butyl-1H-tetrazol-5-ylcarbamoyl)-2-methyl-butyl]-amide |
| 180 | 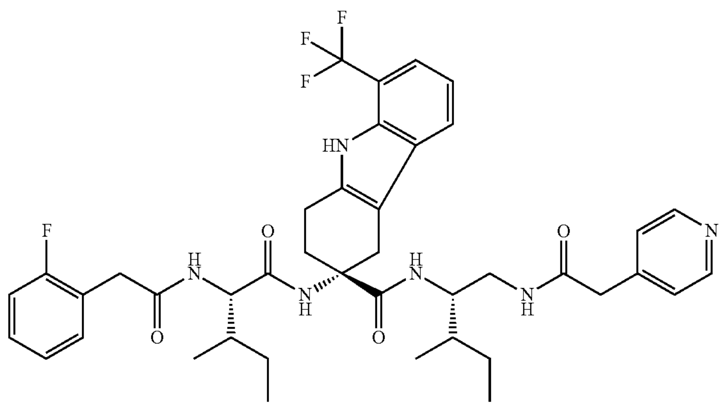 [SMILES: CCC(C)[C@H](NC(=O)Cc1ccccc1F)C(=O)N[C@]1(C(=O)N[C@H](CNC(=O)Cc2ccncc2)C(C)CC)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(2-pyridin-4-yl-acetylamino)-methyl]-butyl}-amide |
| 181 | 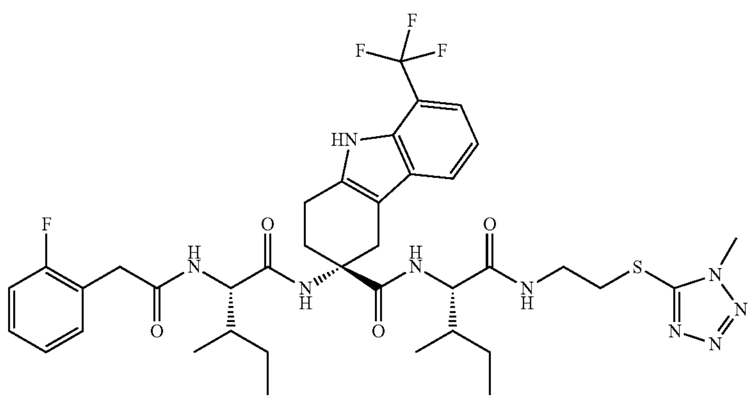 [SMILES: CCC(C)[C@H](NC(=O)Cc1ccccc1F)C(=O)N[C@]1(C(=O)N[C@H](C(=O)NCCSc2nnnn2C)C(C)CC)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[2-(1-methyl-1H-tetrazol-5-ylsulfanyl)-ethylcarbamoyl]-butyl}-amide |
| 182 | 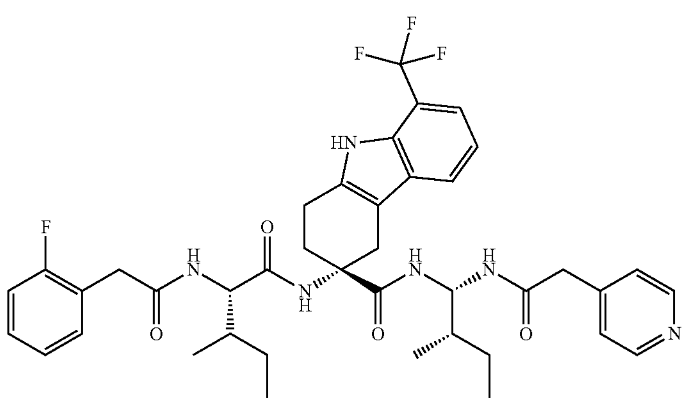 [SMILES: CCC(C)[C@H](NC(=O)Cc1ccccc1F)C(=O)N[C@]1(C(=O)N[C@H](NC(=O)Cc2ccncc2)[C@@H](C)CC)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(1S,2S)-2-methyl-1-(2-pyridin-4-yl-acetylamino)-butyl]-amide |

| Compound | Structure | Chemical name |
|---|---|---|
| 183 | 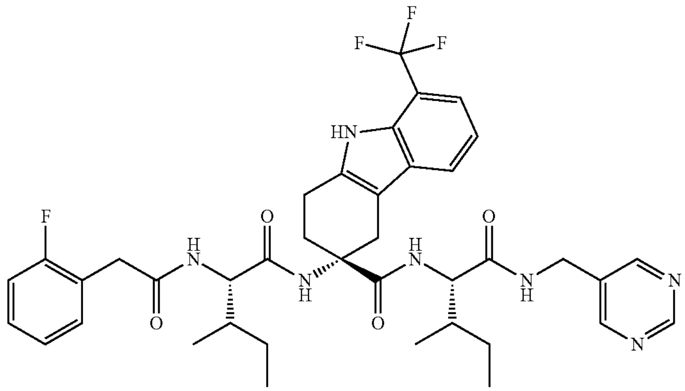 [SMILES: CCC(C)[C@H](NC(=O)Cc1ccccc1F)C(=O)N[C@]1(C(=O)N[C@H](C(=O)NCc2cncnc2)C(C)CC)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid (S)-2-methyl-1-[(pyrimidin-5-ylmethyl)-carbamoyl]-butyl}-amide |
| 184 | 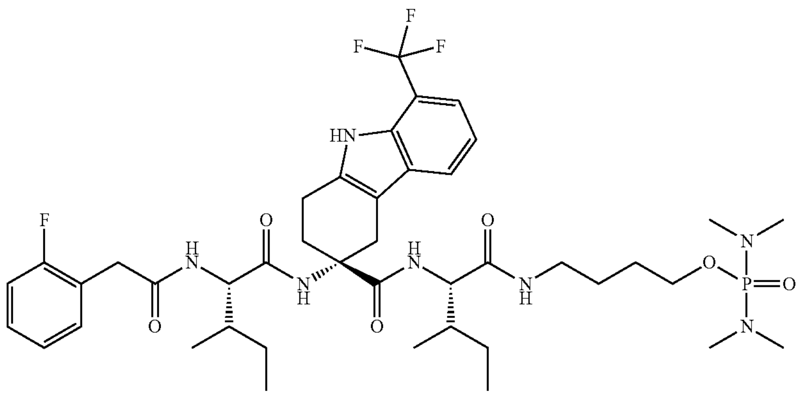 [SMILES: CCC(C)[C@H](NC(=O)Cc1ccccc1F)C(=O)N[C@]1(C(=O)N[C@H](C(=O)NCCCCOP(=O)(N(C)C)N(C)C)C(C)CC)CCc2[nH]c3c(C(F)(F)F)cccc3c2C1] | |
| 185 | 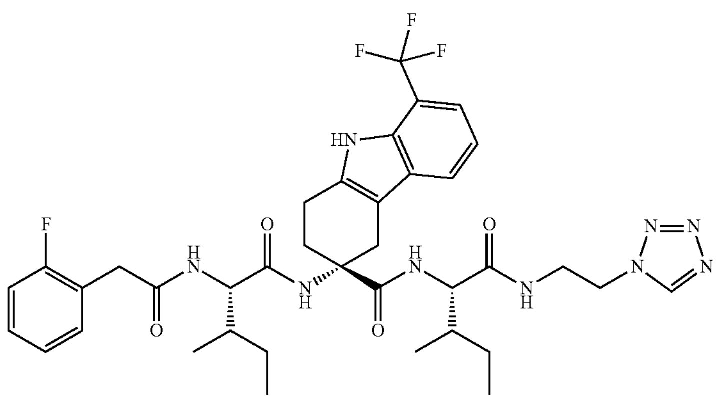 [SMILES: CCC(C)[C@H](NC(=O)Cc1ccccc1F)C(=O)N[C@]1(C(=O)N[C@H](C(=O)NCCn2cnnn2)C(C)CC)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(2-tetrazol-1-yl-ethylcarbamoyl)-butyl]-amide |
| 186 | 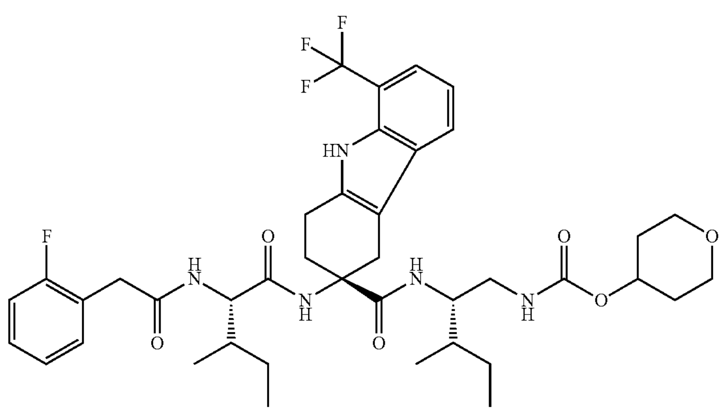 [SMILES: CCC(C)[C@H](NC(=O)Cc1ccccc1F)C(=O)N[C@]1(C(=O)N[C@H](CNC(=O)OC2CCOCC2)C(C)CC)CCc2[nH]c3c(C(F)(F)F)cccc3c2C1] | {(S)-2-[((R)-3-{(S)-2-[2-(2-Fluoro-phenyl)-acetylamino]-3-methyl-pentanoylamino}-8-trifluoromethyl-2,3,4,9-tetrahydro-1H-carbazole-3-carbonyl)-amino]-3-methyl-pentyl}-carbamic acid tetrahydro-pyran-4-yl ester |

| Compound | Structure | Chemical name |
|---|---|---|
| 187 | 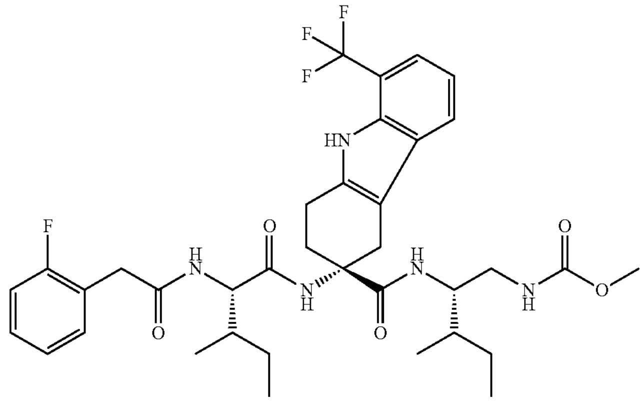 [SMILES: CCC(C)[C@H](NC(=O)Cc1ccccc1F)C(=O)N[C@]1(C(=O)N[C@H](CNC(=O)OC)C(C)CC)CCc2[nH]c3c(C(F)(F)F)cccc3c2C1] | {(S)-2-[((R)-3-{(S)-2-[2-(2-Fluoro-phenyl)-acetylamino]-3-methyl-pentanoylamino}-8-trifluoromethyl-2,3,4,9-tetrahydro-1H-carbazole-3-carbonyl)-amino]-3-methyl-pentyl}-carbamic acid methyl ester |
| 188 | 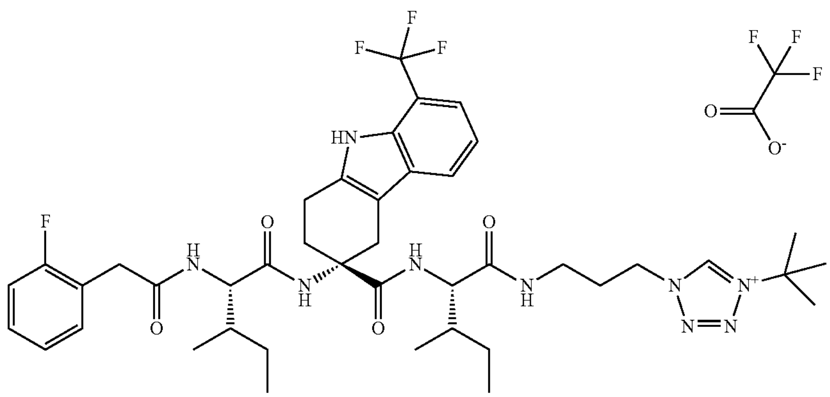 [SMILES: CCC(C)[C@H](NC(=O)Cc1ccccc1F)C(=O)N[C@]1(C(=O)N[C@H](C(=O)NCCCn2c[n+](C(C)(C)C)nn2)C(C)CC)CCc2[nH]c3c(C(F)(F)F)cccc3c2C1 ; O=C([O-])C(F)(F)F] | 1-tert-butyl-4-(3-{(S)-2-[((R)-3-{(S)-2-[2-(2-fluoro-phenyl)-acetylamino]-3-methyl-pentanoylamino}-8-trifluoromethyl-2,3,4,9-tetrahydro-1H-carbazole-3-carbonyl)-amino]-3-methyl-pentanoylamino}-propyl)-4H-tetrazol-1-ium; Trifluoro-acetate |
| 189 | 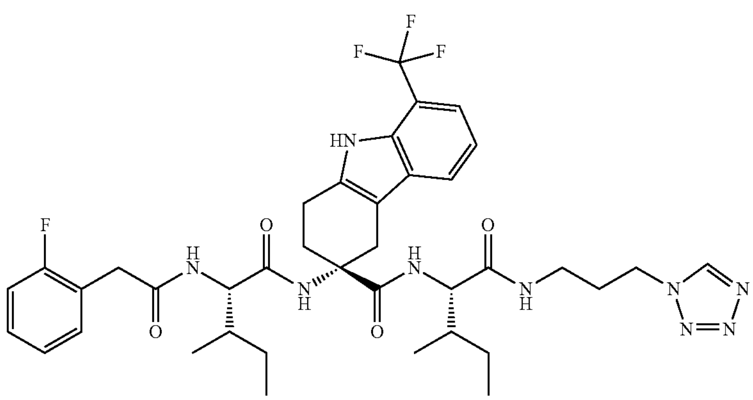 [SMILES: CCC(C)[C@H](NC(=O)Cc1ccccc1F)C(=O)N[C@]1(C(=O)N[C@H](C(=O)NCCCn2cnnn2)C(C)CC)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(3-tetrazol-1-yl-propylcarbamoyl)-butyl]-amide |
| 190 | 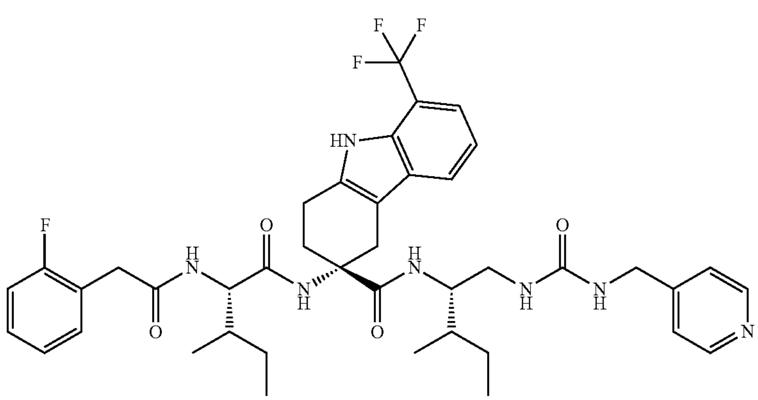 [SMILES: CCC(C)[C@H](NC(=O)Cc1ccccc1F)C(=O)N[C@]1(C(=O)N[C@H](CNC(=O)NCc2ccncc2)C(C)CC)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(3-pyridin-4-ylmethyl-ureidomethyl)-butyl]-amide |

-continued

| Compound | Structure | Chemical name |
|---|---|---|
| 191 | 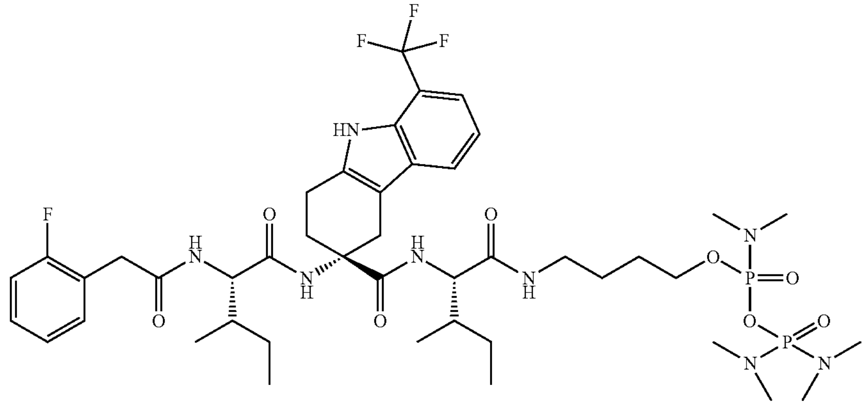 [SMILES: CCC(C)[C@H](NC(=O)Cc1ccccc1F)C(=O)N[C@]1(C(=O)N[C@H](C(=O)NCCCCOP(=O)(OP(=O)(N(C)C)N(C)C)N(C)C)C(C)CC)CCc2[nH]c3c(C(F)(F)F)cccc3c2C1] | |
| 192 | 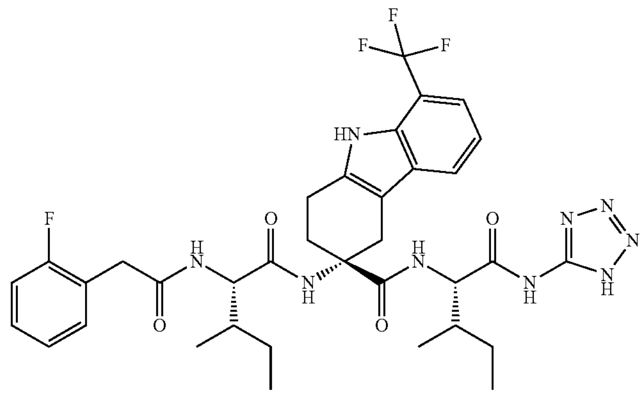 [SMILES: CCC(C)[C@H](NC(=O)Cc1ccccc1F)C(=O)N[C@]1(C(=O)N[C@H](C(=O)Nc2nnn[nH]2)C(C)CC)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(1H-tetrazol-5-ylcarbamoyl)-butyl]-amide |
| 193 | 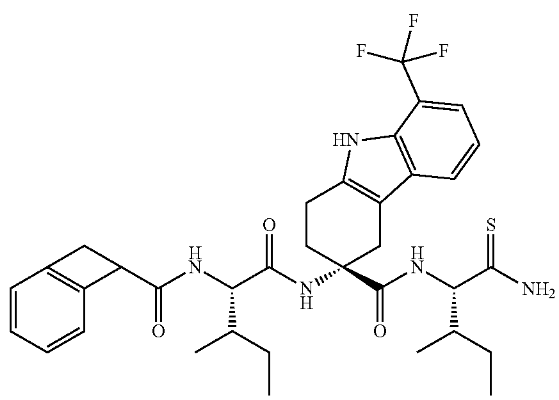 [SMILES: CCC(C)[C@H](NC(=O)C1Cc2ccccc21)C(=O)N[C@]1(C(=O)N[C@H](C(N)=S)C(C)CC)CCc2[nH]c3c(C(F)(F)F)cccc3c2C1] | (R)-3-{(S)-2-[(Bicyclo[4.2.0]octa-1(6),2,4-triene-7-carbonyl)-amino]-3-methyl-pentanoylamino}-8-trifluoromethyl-2,3,4,9-tetrahydro-1H-carbazole-3-carboxylic acid ((S)-2-methyl-1-thiocarbamoyl-butyl)-amide |
| 194 | 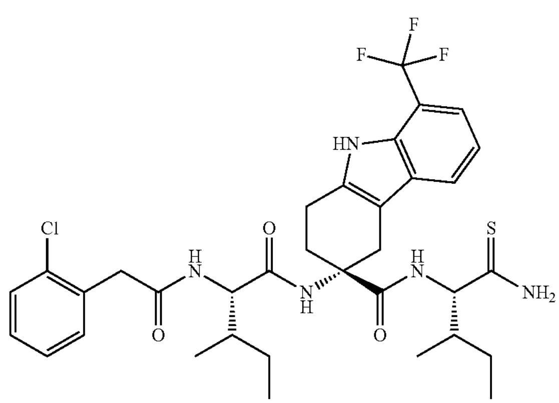 [SMILES: CCC(C)[C@H](NC(=O)Cc1ccccc1Cl)C(=O)N[C@]1(C(=O)N[C@H](C(N)=S)C(C)CC)CCc2[nH]c3c(C(F)(F)F)cccc3c2C1] | (R)-3-{(S)-2-[2-(2-Chloro-phenyl)-acetylamino]-3-methyl-pentanoylamino}-8-trifluoromethyl-2,3,4,9-tetrahydro-1H-carbazole-3-carboxylic acid ((S)-2-methyl-1-thiocarbamoyl-butyl)-amide |

-continued

| Compound | Structure | Chemical name |
|---|---|---|
| 195 | 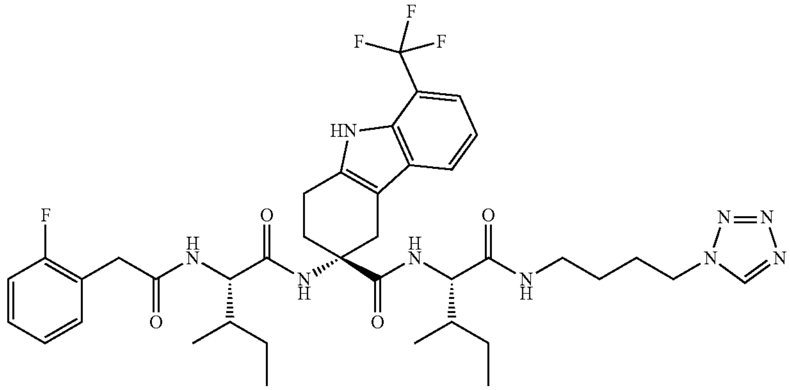 [SMILES: CCC(C)[C@H](NC(=O)Cc1ccccc1F)C(=O)N[C@]1(C(=O)N[C@H](C(=O)NCCCCn2cnnn2)C(C)CC)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(4-tetrazol-1-yl-butylcarbamoyl)-butyl]-amide |
| 196 | 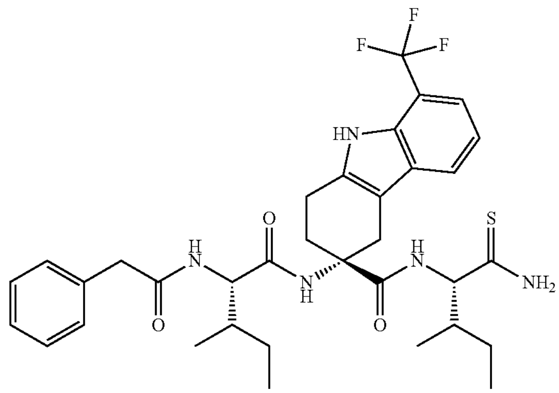 [SMILES: CCC(C)[C@H](NC(=O)Cc1ccccc1)C(=O)N[C@]1(C(=O)N[C@H](C(N)=S)C(C)CC)CCc2[nH]c3c(C(F)(F)F)cccc3c2C1] | (R)-3-((S)-3-Methyl-2-phenylacetylamino-pentanoylamino)-8-trifluoromethyl-2,3,4,9-tetrahydro-1H-carbazole-3-carboxylic acid ((S)-2-methyl-1-thiocarbamoyl-butyl)-amide |
| 197 | 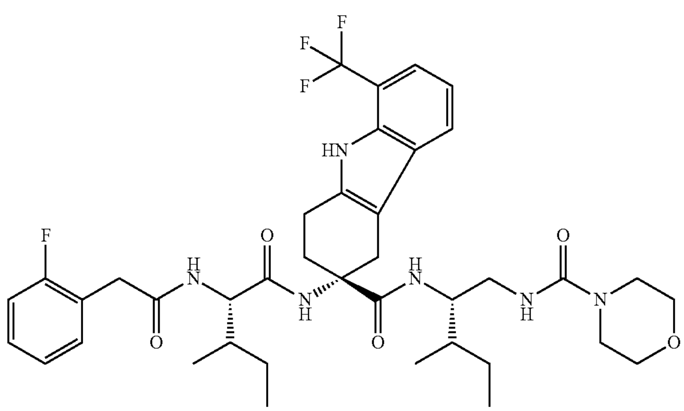 [SMILES: CCC(C)[C@H](NC(=O)Cc1ccccc1F)C(=O)N[C@]1(C(=O)N[C@H](CNC(=O)N2CCOCC2)C(C)CC)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid ((S)-2-methyl-1-{[(morpholine-4-carbonyl)-amino]-methyl}-butyl)-amide |
| 198 | 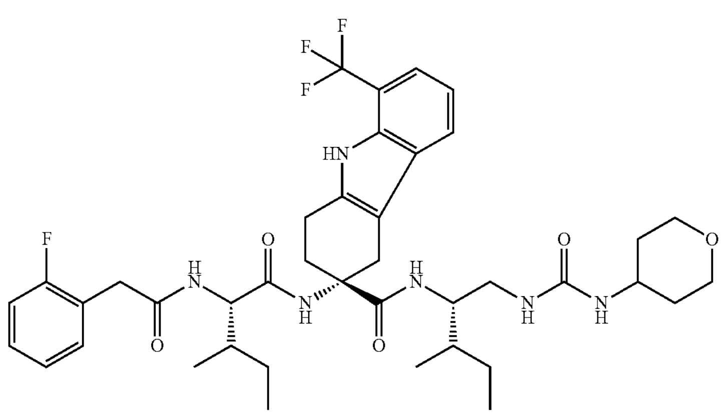 [SMILES: CCC(C)[C@H](NC(=O)Cc1ccccc1F)C(=O)N[C@]1(C(=O)N[C@H](CNC(=O)NC2CCOCC2)C(C)CC)CCc2[nH]c3c(C(F)(F)F)cccc3c2C1] | R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid ((S)-2-methyl-1-{[3-(tetrahydro-pyran-4-yl)-ureido]-methyl}-butyl)-amide |

-continued

| Compound | Structure | Chemical name |
|---|---|---|
| 199 | 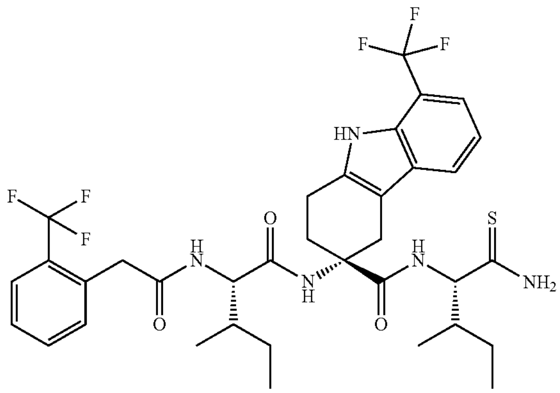 [SMILES: CCC(C)[C@H](NC(=O)Cc1ccccc1C(F)(F)F)C(=O)N[C@]1(C(=O)N[C@H](C(N)=S)C(C)CC)CCc2[nH]c3c(C(F)(F)F)cccc3c2C1] | (R)-3-{(S)-3-Methyl-2-[2-(2-trifluoromethyl-phenyl)-acetylamino]-pentanoylamino}-8-trifluoromethyl-2,3,4,9-tetrahydro-1H-carbazole-3-carboxylic acid ((S)-2-methyl-1-thiocarbamoyl-butyl)-amide |
| 200 | 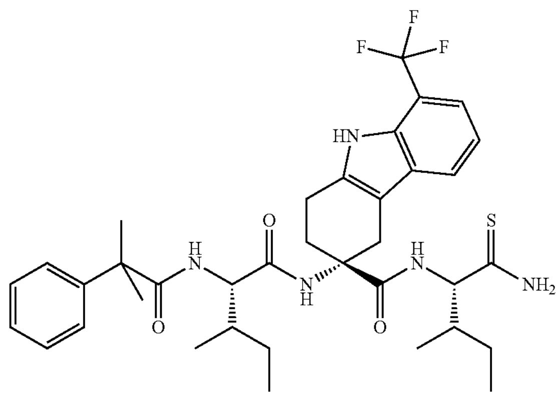 [SMILES: CCC(C)[C@H](NC(=O)C(C)(C)c1ccccc1)C(=O)N[C@]1(C(=O)N[C@H](C(N)=S)C(C)CC)CCc2[nH]c3c(C(F)(F)F)cccc3c2C1] | (R)-3-[(S)-3-Methyl-2-(2-methyl-2-phenyl-propionylamino)-pentanoylamino]-8-trifluoromethyl-2,3,4,9-tetrahydro-1H-carbazole-3-carboxylic acid ((S)-2-methyl-1-thiocarbamoyl-butyl)-amide |
| 201 | 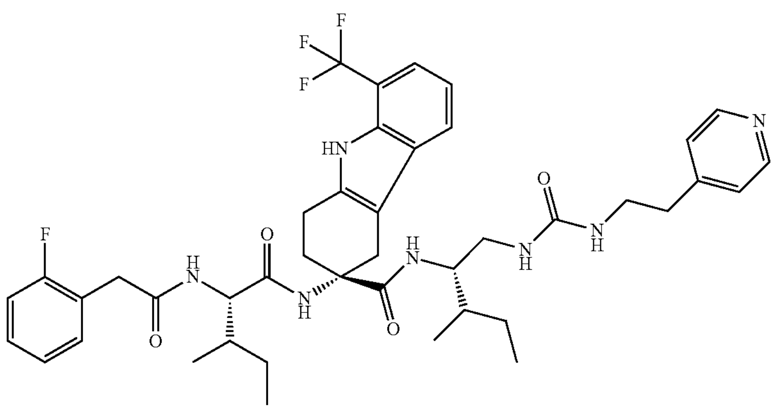 [SMILES: CCC(C)[C@H](NC(=O)Cc1ccccc1F)C(=O)N[C@]1(C(=O)N[C@H](CNC(=O)NCCc2ccncc2)C(C)CC)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[3-(2-pyridin-4-yl-ethyl)-ureidomethyl]-butyl}-amide |
| 202 | 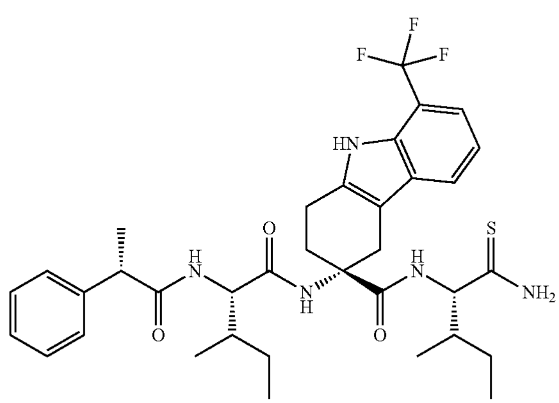 [SMILES: CCC(C)[C@H](NC(=O)[C@@H](C)c1ccccc1)C(=O)N[C@]1(C(=O)N[C@H](C(N)=S)C(C)CC)CCc2[nH]c3c(C(F)(F)F)cccc3c2C1] | (R)-3-[(S)-3-Methyl-2-((S)-2-phenyl-propionylamino)-pentanoylamino]-8-trifluoromethyl-2,3,4,9-tetrahydro-1H-carbazole-3-carboxylic acid ((S)-2-methyl-1-thiocarbamoyl-butyl)-amide |

-continued

| Compound | Structure | Chemical name |
|---|---|---|
| 203 | 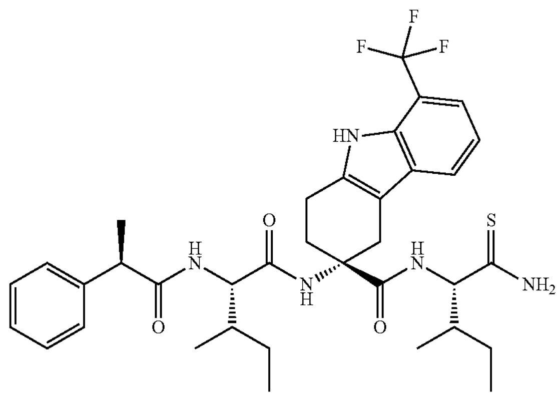 [SMILES: CCC(C)[C@H](NC(=O)[C@H](C)c1ccccc1)C(=O)N[C@]1(C(=O)N[C@H](C(N)=S)C(C)CC)CCc2[nH]c3c(C(F)(F)F)cccc3c2C1] | (R)-3-[(S)-3-Methyl-2-((R)-2-phenyl-propionylamino)-pentanoylamino]-8-trifluoromethyl-2,3,4,9-tetrahydro-1H-carbazole-3-carboxylic acid ((S)-2-methyl-1-thiocarbamoyl-butyl)-amide |
| 204 | 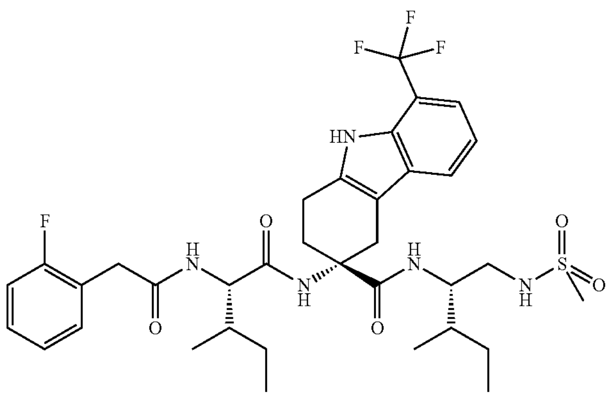 [SMILES: CCC(C)[C@H](NC(=O)Cc1ccccc1F)C(=O)N[C@]1(C(=O)N[C@H](CNS(C)(=O)=O)C(C)CC)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(methanesulfonylamino-methyl)-2-methyl-butyl]-amide |
| 205 | 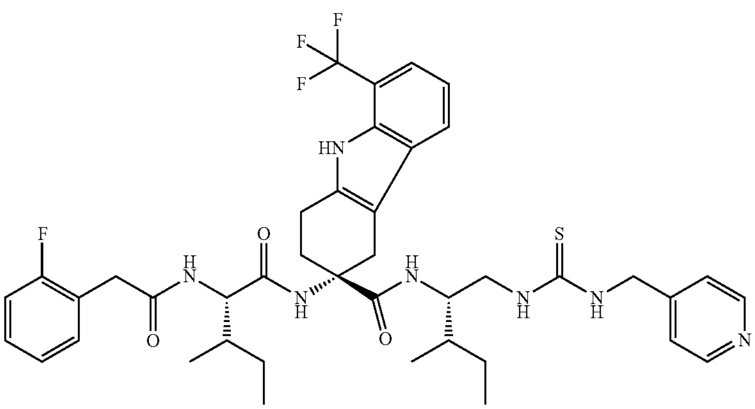 [SMILES: CCC(C)[C@H](NC(=O)Cc1ccccc1F)C(=O)N[C@]1(C(=O)N[C@H](CNC(=S)NCc2ccncc2)C(C)CC)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(3-pyridin-4-ylmethyl-thioureidomethyl)-butyl]-amide |
| 206 | 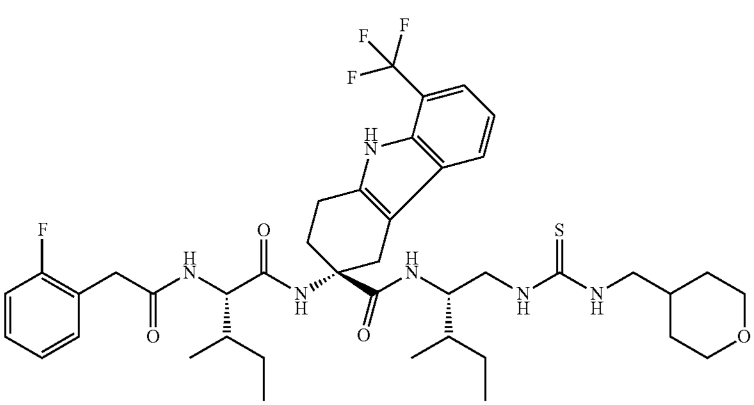 [SMILES: CCC(C)[C@H](NC(=O)Cc1ccccc1F)C(=O)N[C@]1(C(=O)N[C@H](CNC(=S)NCC2CCOCC2)C(C)CC)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[3-(tetrahydro-pyran-4-ylmethyl)-thioureidomethyl]-butyl}-amide |

| Compound | Structure | Chemical name |
|---|---|---|
| 207 | 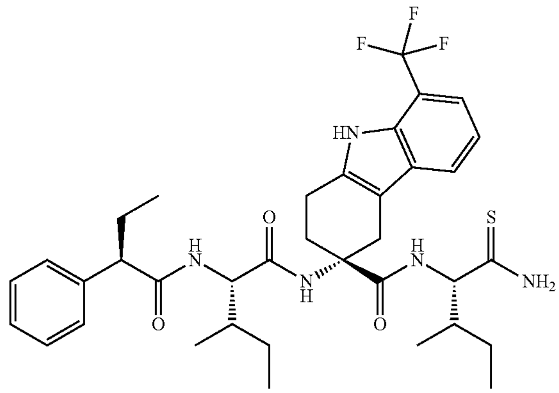 [SMILES: CCC(C)[C@H](NC(=O)[C@H](CC)c1ccccc1)C(=O)N[C@]1(C(=O)N[C@H](C(N)=S)C(C)CC)CCc2[nH]c3c(C(F)(F)F)cccc3c2C1] | (R)-3-[(S)-3-Methyl-2-((R)-2-phenyl-butyrylamino)-pentanoylamino]-8-trifluoromethyl-2,3,4,9-tetrahydro-1H-carbazole-3-carboxylic acid ((S)-2-methyl-1-thiocarbamoyl-butyl)-amide |
| 208 | 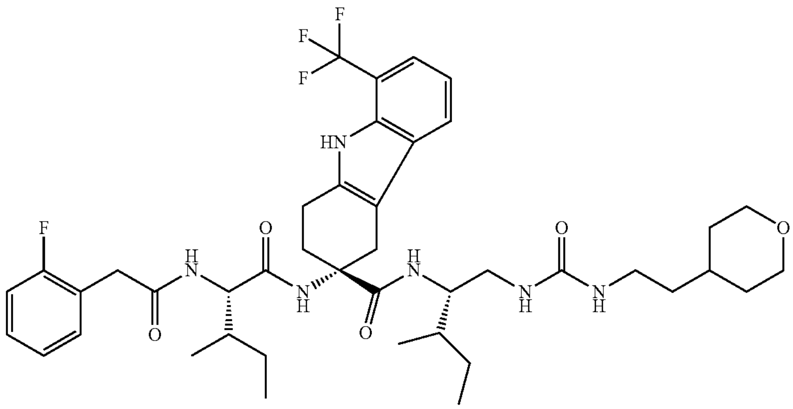 [SMILES: CCC(C)[C@H](NC(=O)Cc1ccccc1F)C(=O)N[C@]1(C(=O)N[C@H](CNC(=O)NCCC2CCOCC2)C(C)CC)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboylic acid ((S)-2-methyl-1-{3-[2-(tetrahydro-pyran-4-yl)-ethyl]-ureidomethyl}-butyl)-amide |
| 209 | 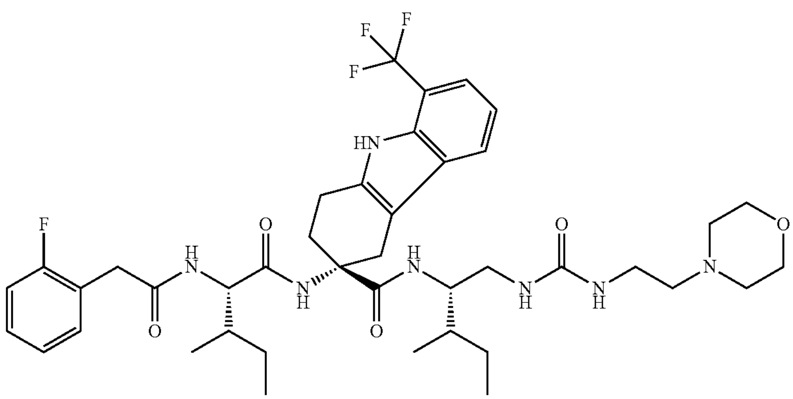 [SMILES: CCC(C)[C@H](NC(=O)Cc1ccccc1F)C(=O)N[C@]1(C(=O)N[C@H](CNC(=O)NCCN2CCOCC2)C(C)CC)CCc2[nH]c3c(C(F)(F)F)cccc3c2C1] | R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[3-(2-morpholin-4-yl-ethyl)-ureidomethyl]-butyl}-amide |
| 210 | 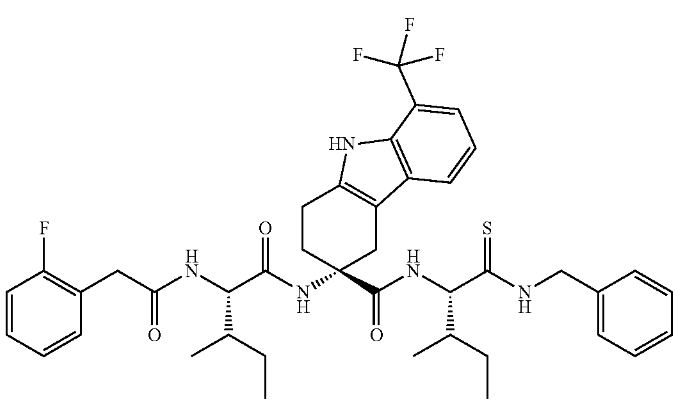 [SMILES: CCC(C)[C@H](NC(=O)Cc1ccccc1F)C(=O)N[C@]1(C(=O)N[C@H](C(=S)NCc2ccccc2)C(C)CC)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid ((S)-1-benzylthiocarbamoyl-2-methyl-butyl)-amide |

-continued

| Compound | Structure | Chemical name |
|---|---|---|
| 211 | 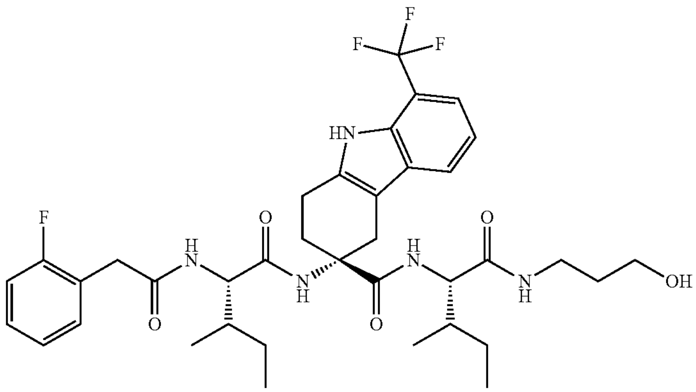 [SMILES: CCC(C)[C@H](NC(=O)Cc1ccccc1F)C(=O)N[C@]1(C(=O)N[C@H](C(=O)NCCCO)C(C)CC)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(3-hydroxy-propylcarbamoyl)-2-methyl-butyl]-amide |
| 212 | 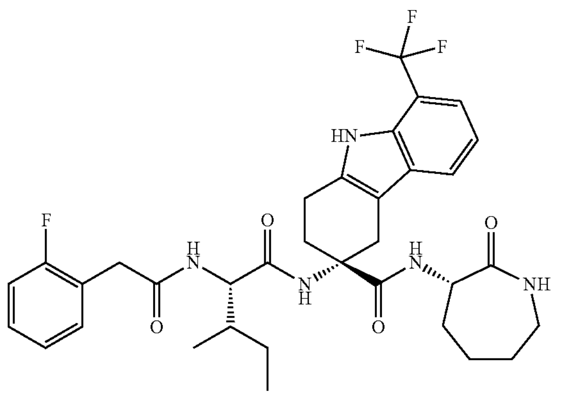 [SMILES: CCC(C)[C@H](NC(=O)Cc1ccccc1F)C(=O)N[C@]1(C(=O)N[C@H]2CCCCNC2=O)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid ((S)-2-oxo-azepan-3-yl)-amide |
| 213 | 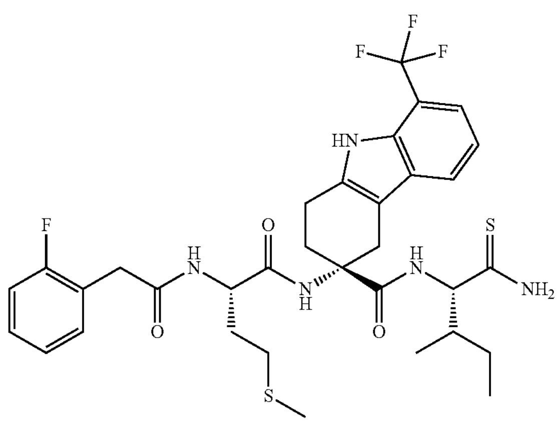 [SMILES: CCC(C)[C@H](NC(=O)[C@@]1(NC(=O)[C@H](CCSC)NC(=O)Cc2ccccc2F)CCc2[nH]c3c(C(F)(F)F)cccc3c2C1)C(N)=S] | (R)-3-{(S)-2-[2-(2-Fluoro-phenyl)-acetylamino]-4-methylsulfanyl-butyrylamino}-8-trifluoromethyl-2,3,4,9-tetrahydro-1H-carbazole-3-carboxylic acid ((S)-2-methyl-1-thiocarbamoyl-butyl)-amide |
| 214 | 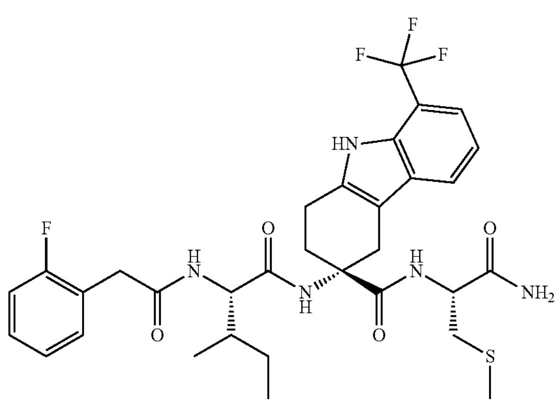 [SMILES: CCC(C)[C@H](NC(=O)Cc1ccccc1F)C(=O)N[C@]1(C(=O)N[C@@H](CSC)C(N)=O)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid ((R)-1-carbamoyl-2-methylsulfanyl-ethyl)-amide |

-continued

| Compound | Structure | Chemical name |
|---|---|---|
| 215 | 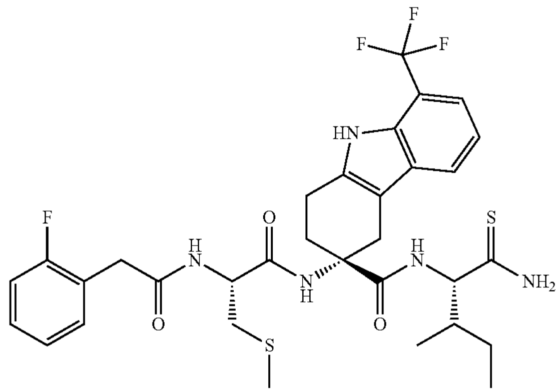 [SMILES: CCC(C)[C@H](NC(=O)[C@@]1(NC(=O)[C@H](CSC)NC(=O)Cc2ccccc2F)CCc2[nH]c3c(C(F)(F)F)cccc3c2C1)C(N)=S] | (R)-3-{(R)-2-[2-(2-Fluoro-phenyl)-acetylamino]-3-methylsulfanyl-propionylamino}-8-trifluoromethyl-2,3,4,9-tetrahydro-1H-carbazole-3-carboxylic acid ((S)-2-methyl-1-thiocarbamoyl-butyl)-amide |
| 216 | 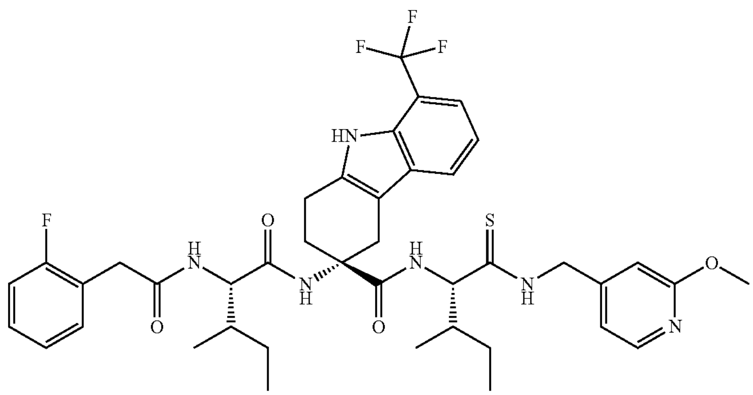 [SMILES: CCC(C)[C@H](NC(=O)Cc1ccccc1F)C(=O)N[C@]1(C(=O)N[C@H](C(=S)NCc2ccnc(OC)c2)C(C)CC)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[(2-methoxy-pyridin-4-ylmethyl)-thiocarbamoyl]-2-methyl-butyl}-amide |
| 217 | 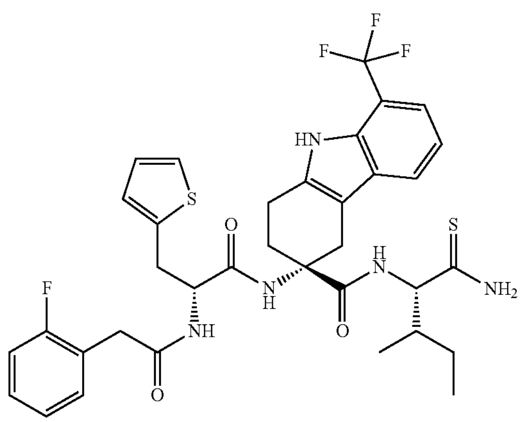 [SMILES: CCC(C)[C@H](NC(=O)[C@@]1(NC(=O)[C@@H](Cc2cccs2)NC(=O)Cc2ccccc2F)CCc2[nH]c3c(C(F)(F)F)cccc3c2C1)C(N)=S] | (R)-3-{(R)-2-[2-(2-Fluoro-phenyl)-acetylamino]-3-thiophen-2-yl-propionylamino}-8-trifluoromethyl-2,3,4,9-tetrahydro-1H-carbazole-3-carboxylic acid ((S)-2-methyl-1-thiocarbamoyl-butyl)-amide |
| 218 | 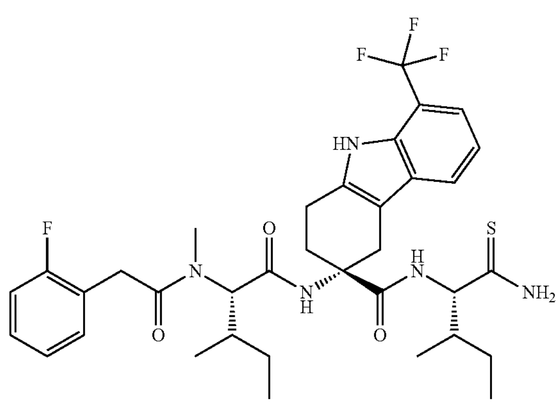 [SMILES: CCC(C)[C@H](NC(=O)[C@@]1(NC(=O)[C@H](C(C)CC)N(C)C(=O)Cc2ccccc2F)CCc2[nH]c3c(C(F)(F)F)cccc3c2C1)C(N)=S] | (R)-3-((S)-2-{[2-(2-Fluoro-phenyl)-acetyl]-methyl-amino}-3-methyl-pentanoylamino)-8-trifluoromethyl-2,3,4,9-tetrahydro-1H-carbazole-3-carboxylic acid ((S)-2-methyl-1-thiocarbamoyl-butyl)-amide |

-continued

| Compound | Structure | Chemical name |
|---|---|---|
| 219 | 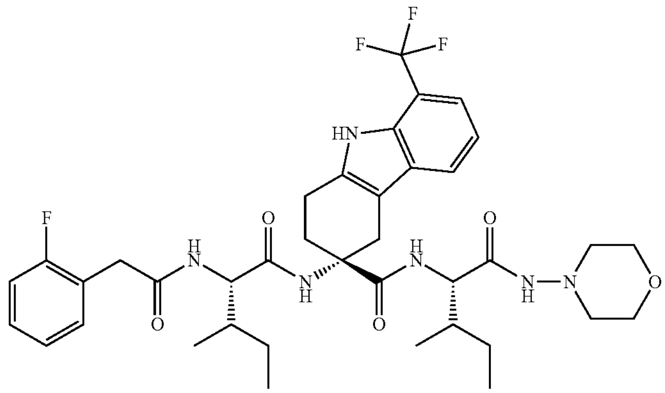 [SMILES: CCC(C)[C@H](NC(=O)Cc1ccccc1F)C(=O)N[C@]1(C(=O)N[C@H](C(=O)NN2CCOCC2)C(C)CC)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(morpholin-4-ylcarbamoyl)-butyl]-amide |
| 220 | 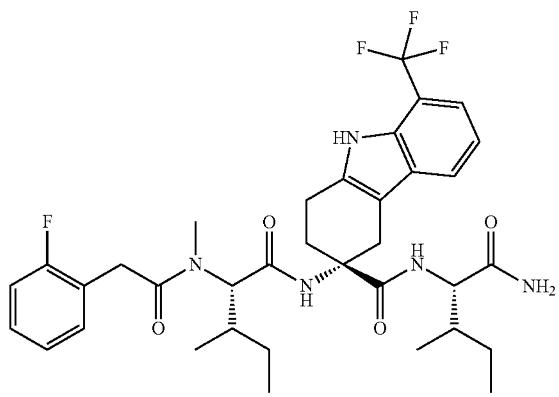 [SMILES: CCC(C)[C@H](NC(=O)[C@@]1(NC(=O)[C@H](C(C)CC)N(C)C(=O)Cc2ccccc2F)CCc2[nH]c3c(C(F)(F)F)cccc3c2C1)C(N)=O] | (R)-3-((S)-2-{[2-(2-Fluoro-phenyl)-acetyl]-methyl-amino}-3-methyl-pentanoylamino)-8-trifluoromethyl-2,3,4,9-tetrahydro-1H-carbazole-3-carboxylic acid ((S)-1-carbamoyl-2-methyl-butyl)-amide |
| 221 | 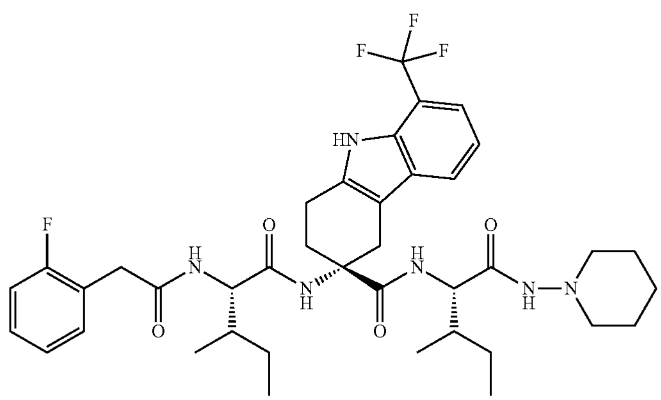 [SMILES: CCC(C)[C@H](NC(=O)Cc1ccccc1F)C(=O)N[C@]1(C(=O)N[C@H](C(=O)NN2CCCCC2)C(C)CC)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(piperidin-1-ylcarbamoyl)-butyl]-amide |
| 222 | 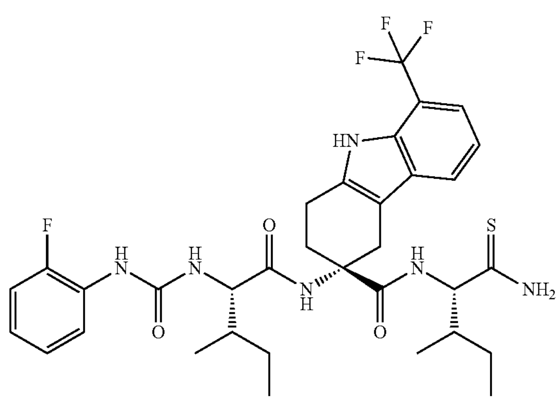 [SMILES: CCC(C)[C@H](NC(=O)Nc1ccccc1F)C(=O)N[C@]1(C(=O)N[C@H](C(N)=S)C(C)CC)CCc2[nH]c3c(C(F)(F)F)cccc3c2C1] | (R)-3-{(S)-2-[3-(2-Fluoro-phenyl)-ureido]-3-methyl-pentanoylamino}-8-trifluoromethyl-2,3,4,9-tetrahydro-1H-carbazole-3-carboxylic acid ((S)-2-methyl-1-thiocarbamoyl-butyl)-amide |

-continued

| Compound | Structure | Chemical name |
|---|---|---|
| 223 | 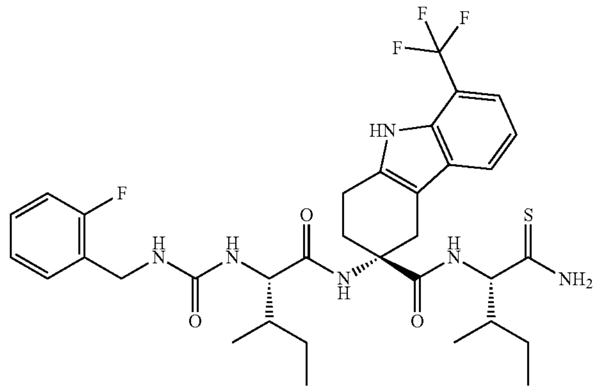 [SMILES: CCC(C)[C@H](NC(=O)NCc1ccccc1F)C(=O)N[C@]1(C(=O)N[C@H](C(N)=S)C(C)CC)CCc2[nH]c3c(C(F)(F)F)cccc3c2C1] | (R)-3-{(S)-2-[3-(2-Fluoro-benzyl)-ureido]-3-methyl-pentanoylamino}-8-trifluoromethyl-2,3,4,9-tetrahydro-1H-carbazole-3-carboxylic acid ((S)-2-methyl-1-thiocarbamoyl-butyl)-amide |
| 224 | 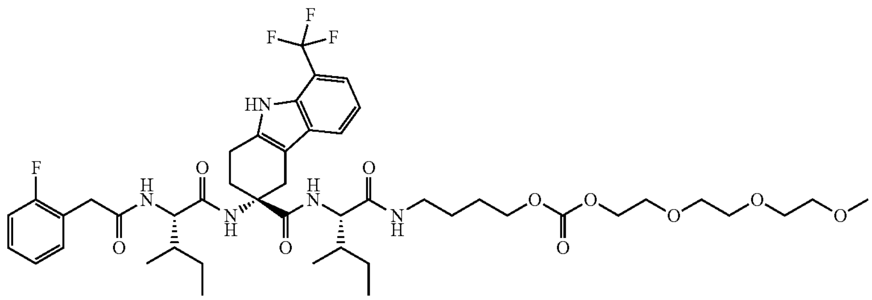 [SMILES: CCC(C)[C@H](NC(=O)Cc1ccccc1F)C(=O)N[C@]1(C(=O)N[C@H](C(=O)NCCCCOC(=O)OCCOCCOCCOC)C(C)CC)CCc2[nH]c3c(C(F)(F)F)cccc3c2C1] | Carbonic acid 4-{(S)-2-[((R)-3-{(S)-2-[2-(2-fluoro-phenyl)-acetylamino]-3-methyl-pentanoylamino}-8-trifluoromethyl-2,3,4,9-tetrahydro-1H-carbazole-3-carbonyl)-amino]-3-methyl-pentanoylamino}-butyl ester 2-[2-(2-methoxy-ethoxy)-ethoxy]-ethyl ester |
| 225 | 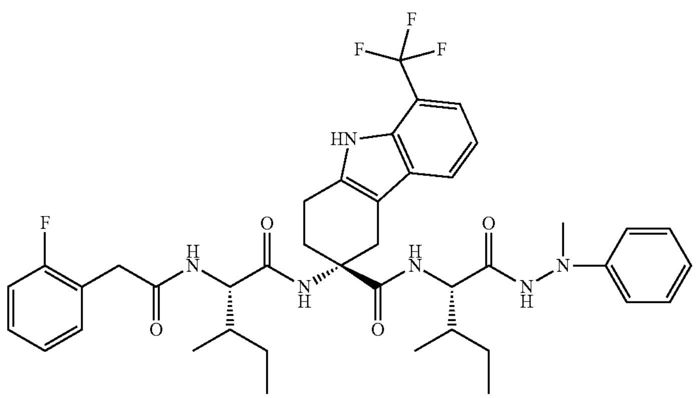 [SMILES: CCC(C)[C@H](NC(=O)Cc1ccccc1F)C(=O)N[C@]1(C(=O)N[C@H](C(=O)NN(C)c2ccccc2)C(C)CC)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(N'-methyl-N'-phenyl-hydrazinocarbonyl)-butyl]-amide |
| 226 | 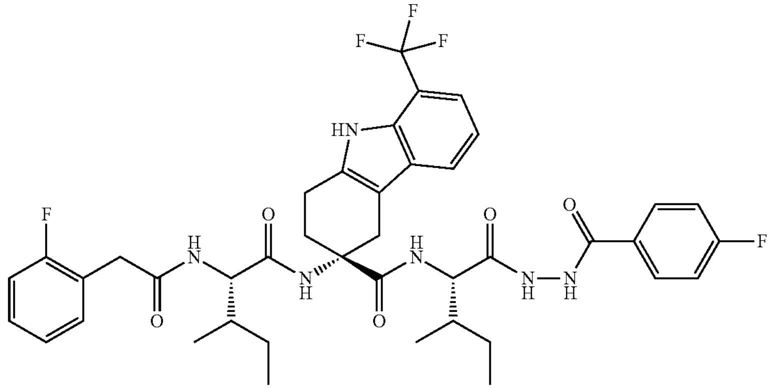 [SMILES: CCC(C)[C@H](NC(=O)Cc1ccccc1F)C(=O)N[C@]1(C(=O)N[C@H](C(=O)NNC(=O)c2ccc(F)cc2)C(C)CC)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[N'-(4-fluoro-benzoyl)-hydrazinocarbonyl]-2-methyl-butyl}-amide |

-continued

| Compound | Structure | Chemical name |
|---|---|---|
| 227 | 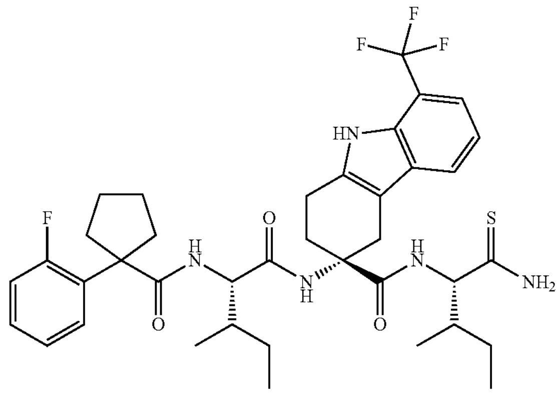 [SMILES: CCC(C)[C@H](NC(=O)C1(c2ccccc2F)CCCC1)C(=O)N[C@]1(C(=O)N[C@H](C(N)=S)C(C)CC)CCc2[nH]c3c(C(F)(F)F)cccc3c2C1] | (R)-3-((S)-2-{[1-(2-Fluoro-phenyl)-cyclopentanecarbonyl]-amino}-3-methyl-pentanoylamino)-8-trifluoromethyl-2,3,4,9-tetrahydro-1H-carbazole-3-carboxylic acid ((S)-2-methyl-1-thiocarbamoyl-butyl)-amide |
| 228 | 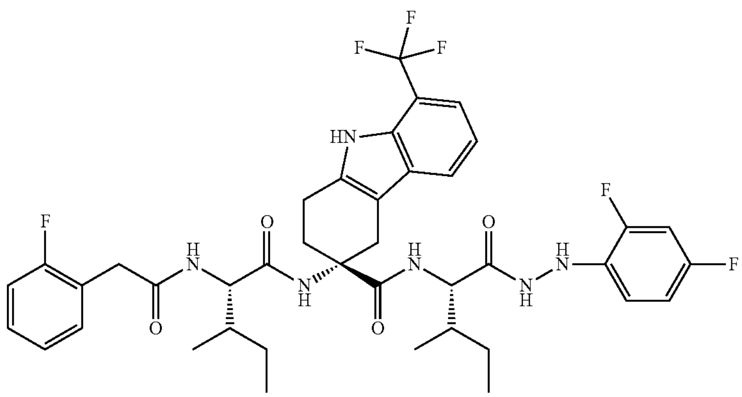 [SMILES: CCC(C)[C@H](NC(=O)Cc1ccccc1F)C(=O)N[C@]1(C(=O)N[C@H](C(=O)NNc2ccc(F)cc2F)C(C)CC)CCc2[nH]c3c(C(F)(F)F)cccc3c2C1] | R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[N'-(2,4-difluoro-phenyl)-hydrazinocarbonyl]-2-methyl-butyl}-amide |
| 229 | 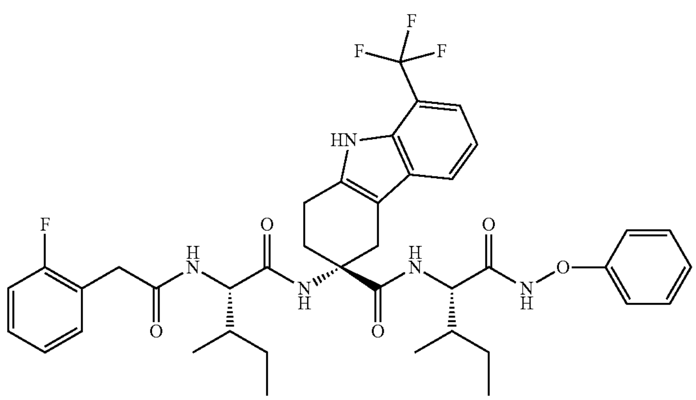 [SMILES: CCC(C)[C@H](NC(=O)Cc1ccccc1F)C(=O)N[C@]1(C(=O)N[C@H](C(=O)NOc2ccccc2)C(C)CC)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid ((S)-2-methyl-1-phenoxycarbamoyl-butyl)-amide |
| 230 | 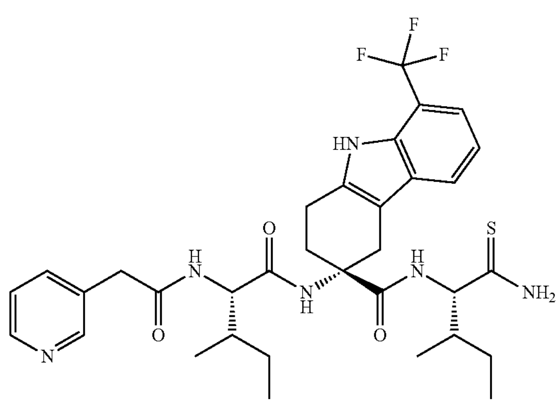 [SMILES: CCC(C)[C@H](NC(=O)Cc1cccnc1)C(=O)N[C@]1(C(=O)N[C@H](C(N)=S)C(C)CC)CCc2[nH]c3c(C(F)(F)F)cccc3c2C1] | (R)-3-[(S)-3-Methyl-2-(2-pyridin-3-yl-acetylamino)-pentanoylamino]-8-trifluoromethyl-2,3,4,9-tetrahydro-1H-carbazole-3-carboxylic acid ((S)-2-methyl-1-thiocarbamoyl-butyl)-amide |

-continued

| Compound | Structure | Chemical name |
|---|---|---|
| 231 | 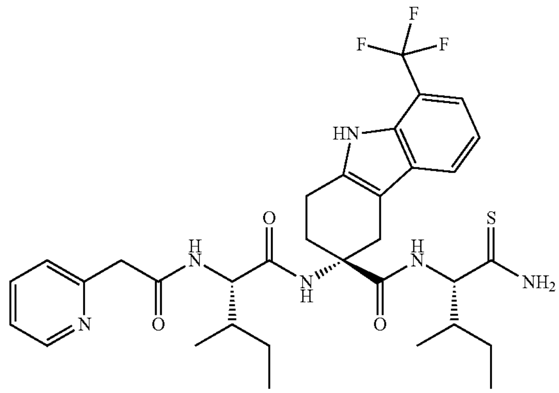 [SMILES: CCC(C)[C@H](NC(=O)Cc1ccccn1)C(=O)N[C@]1(C(=O)N[C@H](C(N)=S)C(C)CC)CCc2[nH]c3c(C(F)(F)F)cccc3c2C1] | (R)-3-[(S)-3-Methyl-2-(2-pyridin-2-yl-acetylamino)-pentanoylamino]-8-trifluoromethyl-2,3,4,9-tetrahydro-1H-carbazole-3-carboxylic acid ((S)-2-methyl-1-thiocarbamoyl-butyl)-amide |
| 232 | 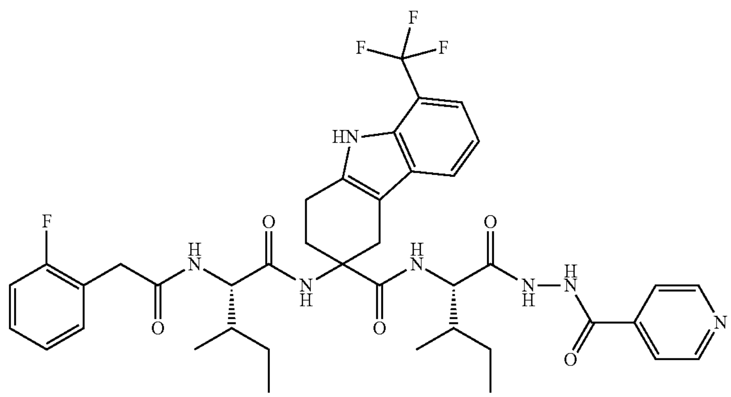 [SMILES: CCC(C)[C@H](NC(=O)Cc1ccccc1F)C(=O)NC1(C(=O)N[C@H](C(=O)NNC(=O)c2ccncc2)C(C)CC)CCc2[nH]c3c(C(F)(F)F)cccc3c2C1] | 3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[N'-(pyridine-4-carbonyl)-hydrazinocarbonyl]-butyl}-amide |
| 233 | 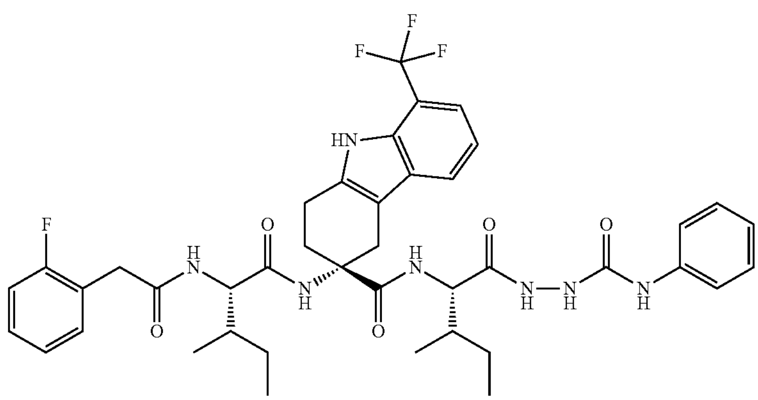 [SMILES: CCC(C)[C@H](NC(=O)Cc1ccccc1F)C(=O)N[C@]1(C(=O)N[C@H](C(=O)NNC(=O)Nc2ccccc2)C(C)CC)CCc2[nH]c3c(C(F)(F)F)cccc3c2C1] | 3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid |
| 234 | 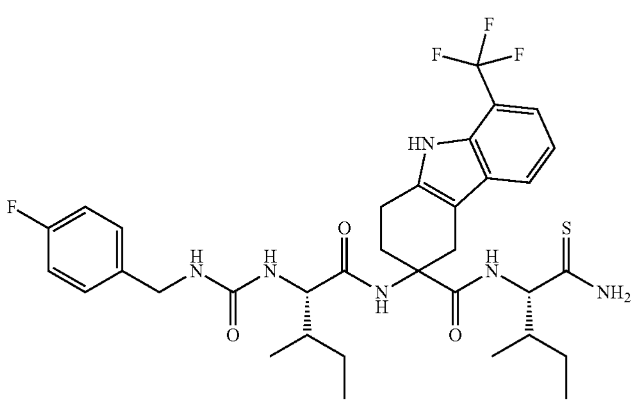 [SMILES: CCC(C)[C@H](NC(=O)NCc1ccc(F)cc1)C(=O)NC1(C(=O)N[C@H](C(N)=S)C(C)CC)CCc2[nH]c3c(C(F)(F)F)cccc3c2C1] | 3-{(S)-2-[3-(4-Fluoro-benzyl)-ureido]-3-methyl-pentanoylamino}-8-trifluoromethyl-2,3,4,9-tetrahydro-1H-carbazole-3-carboxylic acid ((S)-2-methyl-1-thiocarbamoyl-butyl)-amide |

| Compound | Structure | Chemical name |
|---|---|---|
| 235 | 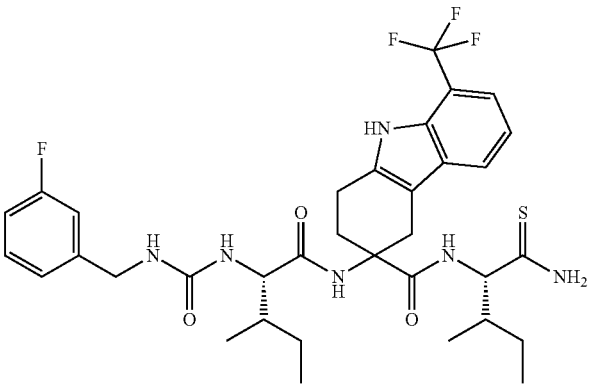 [SMILES: CCC(C)[C@H](NC(=O)NCc1cccc(F)c1)C(=O)NC1(C(=O)N[C@H](C(N)=S)C(C)CC)CCc2[nH]c3c(C(F)(F)F)cccc3c2C1] | 3-{(S)-2-[3-(3-Fluoro-benzyl)-ureido]-3-methyl-pentanoylamino}-8-trifluoromethyl-2,3,4,9-tetrahydro-1H-carbazole-3-carboxylic acid ((S)-2-methyl-1-thiocarbamoyl-butyl)-amide |
| 236 | 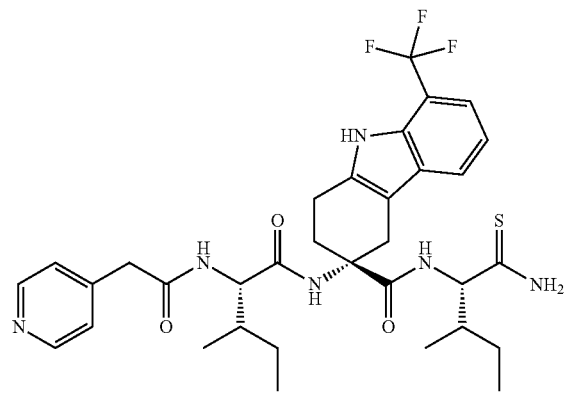 [SMILES: CCC(C)[C@H](NC(=O)Cc1ccncc1)C(=O)N[C@]1(C(=O)N[C@H](C(N)=S)C(C)CC)CCc2[nH]c3c(C(F)(F)F)cccc3c2C1] | (R)-3-[(S)-3-Methyl-2-(2-pyridin-4-yl-acetylamino)-pentanoylamino]-8-trifluoromethyl-2,3,4,9-tetrahydro-1H-carbazole-3-carboxylic acid ((S)-2-methyl-1-thiocarbamoyl-butyl)-amide |
| 237 | 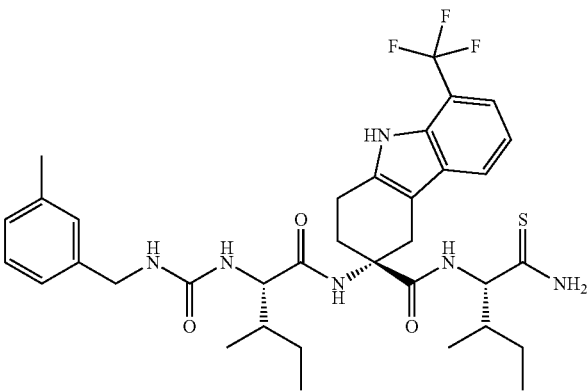 [SMILES: CCC(C)[C@H](NC(=O)NCc1cccc(C)c1)C(=O)N[C@]1(C(=O)N[C@H](C(N)=S)C(C)CC)CCc2[nH]c3c(C(F)(F)F)cccc3c2C1] | (R)-3-{(S)-3-Methyl-2-[3-(3-methyl-benzyl)-ureido]-pentanoylamino}-8-trifluoromethyl-2,3,4,9-tetrahydro-1H-carbazole-3-carboxylic acid ((S)-2-methyl-1-thiocarbamoyl-butyl)-amide |
| 238 | 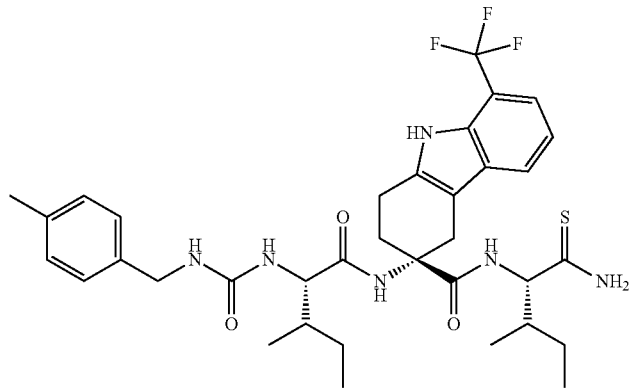 [SMILES: CCC(C)[C@H](NC(=O)NCc1ccc(C)cc1)C(=O)N[C@]1(C(=O)N[C@H](C(N)=S)C(C)CC)CCc2[nH]c3c(C(F)(F)F)cccc3c2C1] | (R)-3-{(S)-3-Methyl-2-[3-(4-methyl-benzyl)-ureido]-pentanoylamino}-8-trifluoromethyl-2,3,4,9-tetrahydro-1H-carbazole-3-carboxylic acid ((S)-2-methyl-1-thiocarbamoyl-butyl)-amide |

-continued

| Compound | Structure | Chemical name |
|---|---|---|
| 239 | 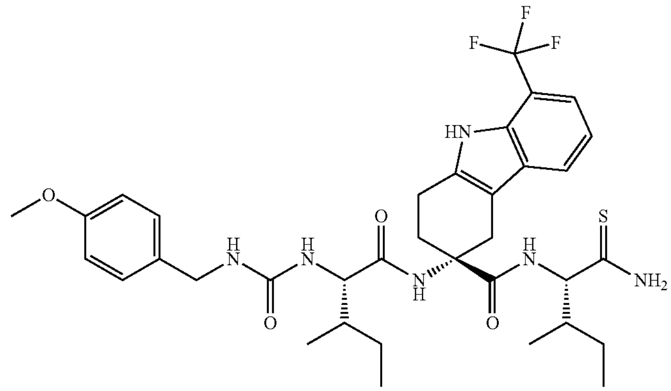 [SMILES: CCC(C)[C@H](NC(=O)NCc1ccc(OC)cc1)C(=O)N[C@]1(C(=O)N[C@H](C(N)=S)C(C)CC)CCc2[nH]c3c(C(F)(F)F)cccc3c2C1] | (R)-3-{(S)-2-[3-(4-Methoxy-benzyl)-ureido]-3-methyl-pentanoylamino}-8-trifluoromethyl-2,3,4,9-tetrahydro-1H-carbazole-3-carboxylic acid ((S)-2-methyl-1-thiocarbamoyl-butyl)-amide |
| 240 | 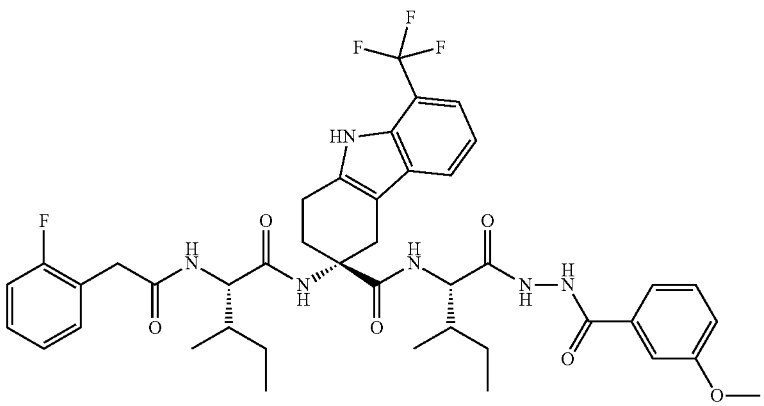 [SMILES: CCC(C)[C@H](NC(=O)Cc1ccccc1F)C(=O)N[C@]1(C(=O)N[C@H](C(=O)NNC(=O)c2cccc(OC)c2)C(C)CC)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[N'-(3-methoxy-benzoyl)-hydrazinocarbonyl]-2-methyl-butyl}-amid |
| 241 | 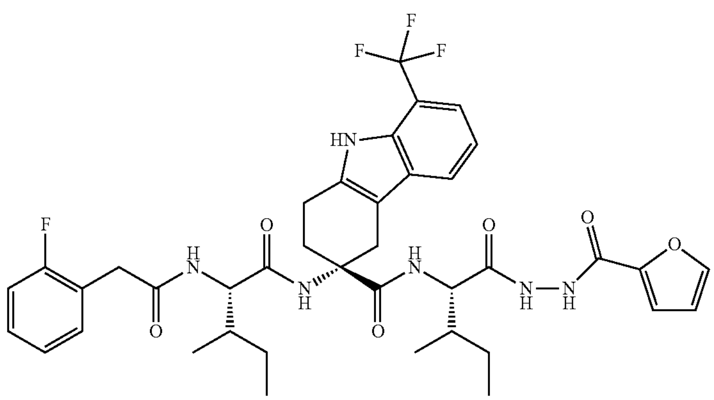 [SMILES: CCC(C)[C@H](NC(=O)Cc1ccccc1F)C(=O)N[C@]1(C(=O)N[C@H](C(=O)NNC(=O)c2ccco2)C(C)CC)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[N'-(furan-2-carbonyl)-hydrazinocarbonyl]-2-methyl-butyl}-amide |
| 242 | 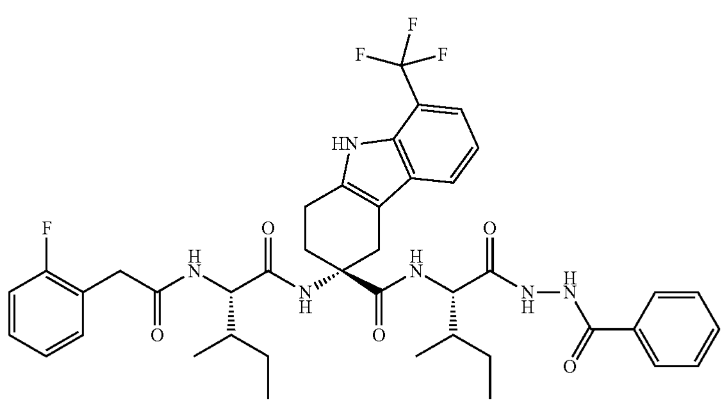 [SMILES: CCC(C)[C@H](NC(=O)Cc1ccccc1F)C(=O)N[C@]1(C(=O)N[C@H](C(=O)NNC(=O)c2ccccc2)C(C)CC)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(N'-benzoyl-hydrazinocarbonyl)-2-methyl-butyl]-amide |

-continued

| Compound | Structure | Chemical name |
|---|---|---|
| 243 | 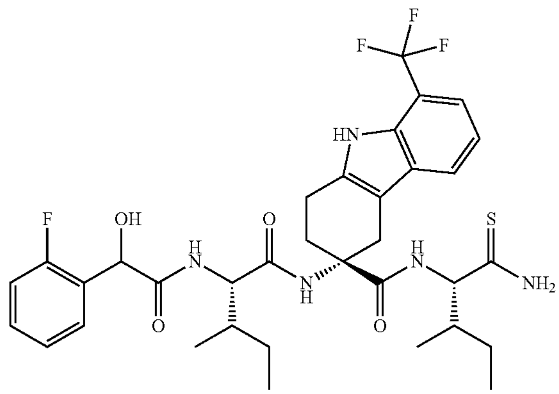 [SMILES: CCC(C)[C@H](NC(=O)C(O)c1ccccc1F)C(=O)N[C@]1(C(=O)N[C@H](C(N)=S)C(C)CC)CCc2[nH]c3c(C(F)(F)F)cccc3c2C1] | (R)-3-{(S)-2-[2-(2-Fluoro-phenyl)-2-hydroxy-acetylamino]-3-methyl-pentanoylamino}-8-trifluoromethyl-2,3,4,9-tetrahydro-1H-carbazole-3-carboxylic acid ((S)-2-methyl-1-thiocarbamoyl-butyl)-amide |
| 244 | 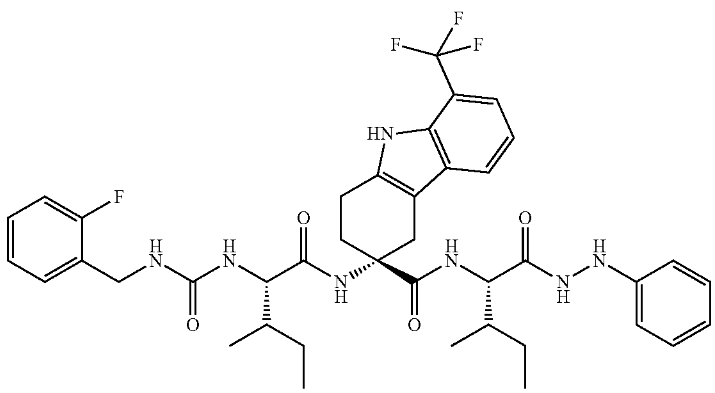 [SMILES: CCC(C)[C@H](NC(=O)NCc1ccccc1F)C(=O)N[C@]1(C(=O)N[C@H](C(=O)NNc2ccccc2)C(C)CC)CCc2[nH]c3c(C(F)(F)F)cccc3c2C1] | (R)-3-{(S)-2-[3-(2-Fluoro-benzyl)-ureido]-3-methyl-pentanoylamino}-8-trifluoromethyl-2,3,4,9-tetrahydro-1H-carbazole-3-carboxylic acid [(S)-2-methyl-1-(N'-phenyl-hydrazinocarbonyl)-butyl]-amide |
| 245 | 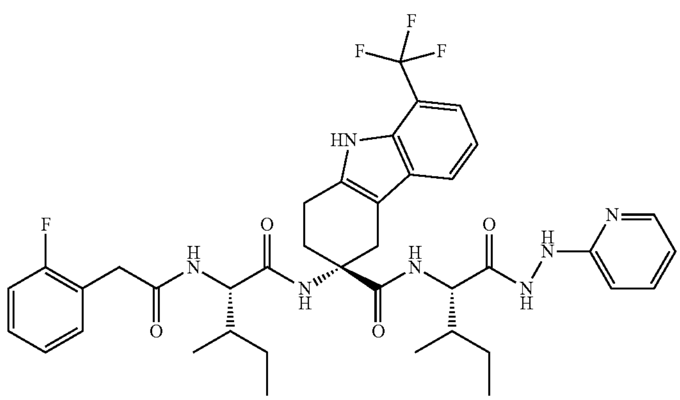 [SMILES: CCC(C)[C@H](NC(=O)Cc1ccccc1F)C(=O)N[C@]1(C(=O)N[C@H](C(=O)NNc2ccccn2)C(C)CC)CCc2[nH]c3c(C(F)(F)F)cccc3c2C1] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(N'-pyridin-2-yl-hydrazinocarbonyl)-butyl]-amide |
| 246 | 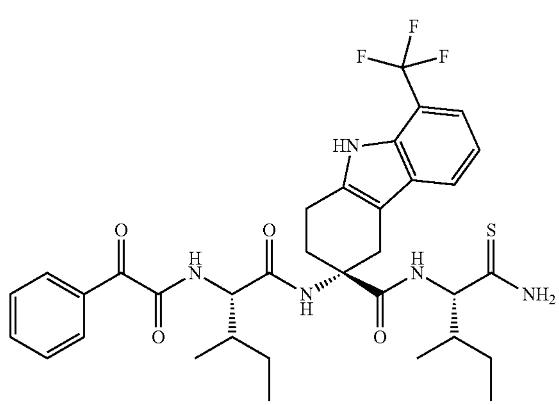 [SMILES: CCC(C)[C@H](NC(=O)C(=O)c1ccccc1)C(=O)N[C@]1(C(=O)N[C@H](C(N)=S)C(C)CC)CCc2[nH]c3c(C(F)(F)F)cccc3c2C1] | (R)-3-[(S)-3-Methyl-2-(2-oxo-2-phenyl-acetylamino)-pentanoylamino]-8-trifluoromethyl-2,3,4,9-tetrahydro-1H-carbazole-3-carboxylic acid ((S)-2-methyl-1-thiocarbamoyl-butyl)-amide |

-continued

| Compound | Structure | Chemical name |
|---|---|---|
| 247 | 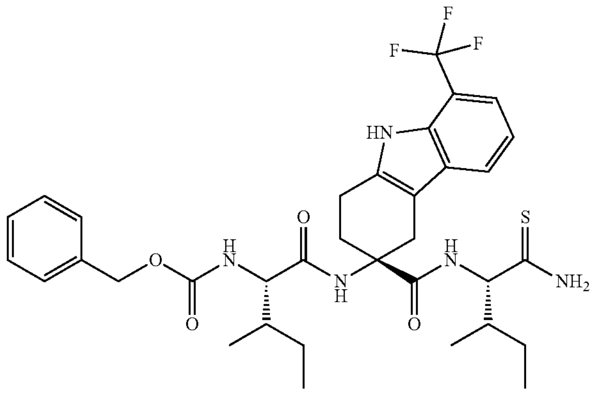 [SMILES: CCC(C)[C@H](NC(=O)OCc1ccccc1)C(=O)N[C@]1(C(=O)N[C@H](C(N)=S)C(C)CC)CCc2[nH]c3c(C(F)(F)F)cccc3c2C1] | {(S)-2-Methyl-1-[(R)-3-((S)-2-methyl-1-thiocarbamoyl-butylcarbamoyl)-8-trifluoromethyl-2,3,4,9-tetrahydro-1H-carbazol-3-ylcarbamoyl]-butyl}-carbamic acid benzyl ester |
| 248 | 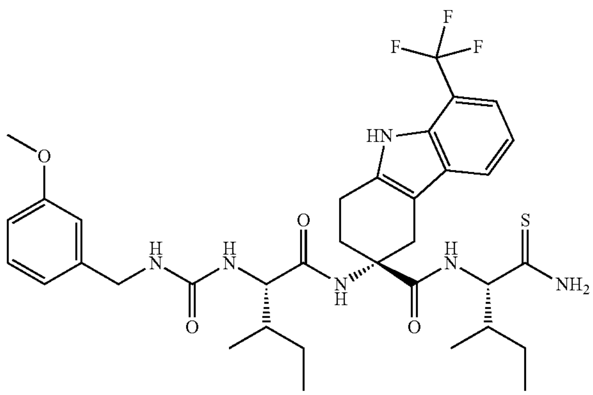 [SMILES: CCC(C)[C@H](NC(=O)NCc1cccc(OC)c1)C(=O)N[C@]1(C(=O)N[C@H](C(N)=S)C(C)CC)CCc2[nH]c3c(C(F)(F)F)cccc3c2C1] | (R)-3-{(S)-2-[3-(3-Methoxy-benzyl)-ureido]-3-methyl-pentanoylamino}-8-trifluoromethyl-2,3,4,9-tetrahydro-1H-carbazole-3-carboxylic acid ((S)-2-methyl-1-thiocarbamoyl-butyl)-amide |
| 249 | 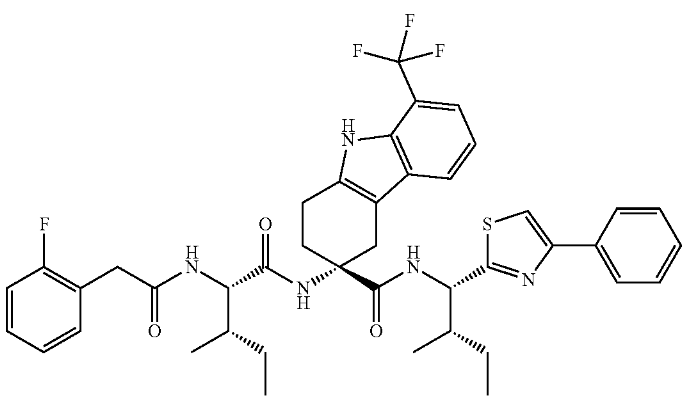 [SMILES: CC[C@H](C)[C@H](NC(=O)Cc1ccccc1F)C(=O)N[C@]1(C(=O)N[C@H](c2nc(-c3ccccc3)cs2)[C@@H](C)CC)CCc2[nH]c3c(C(F)(F)F)cccc3c2C1] | (R)-3-{(2S,3S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(1S,2S)-2-methyl-1-(4-phenyl-thiazol-2-yl)-butyl]-amide |
| 250 | 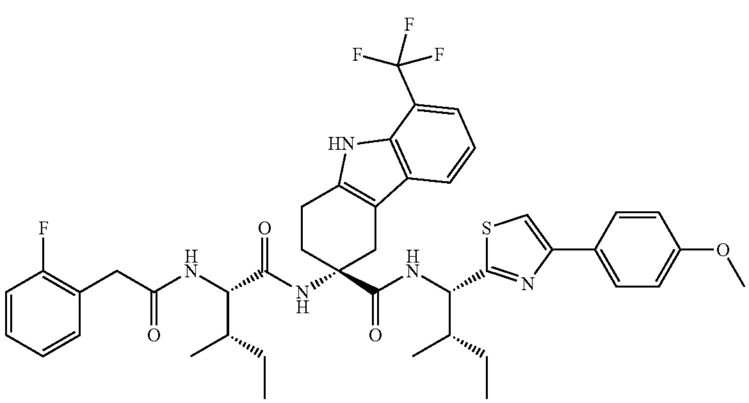 [SMILES: CC[C@H](C)[C@H](NC(=O)Cc1ccccc1F)C(=O)N[C@]1(C(=O)N[C@H](c2nc(-c3ccc(OC)cc3)cs2)[C@@H](C)CC)CCc2[nH]c3c(C(F)(F)F)cccc3c2C1] | (R)-3-{(2S,3S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(1S,2S)-1-[4-(4-methoxy-phenyl)-thiazol-2-yl]-2-methyl-butyl}-amide |

| Compound | Structure | Chemical name |
|---|---|---|
| 251 | 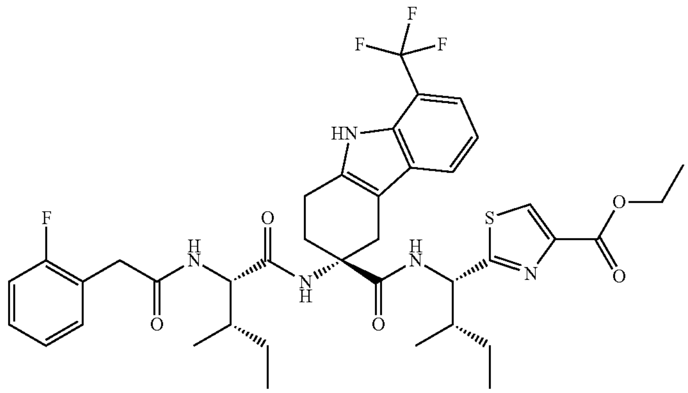 [SMILES: CCOC(=O)c1csc([C@@H](NC(=O)[C@@]2(NC(=O)[C@@H](NC(=O)Cc3ccccc3F)[C@@H](C)CC)CCc3[nH]c4c(C(F)(F)F)cccc4c3C2)[C@@H](C)CC)n1] | 2-{(1R,2S)-1-[((R)-3-{(2S,3S)-2-[2-(2-Fluoro-phenyl)-acetylamino]-3-methyl-pentanoylamino}-8-trifluoromethyl-2,3,4,9-tetrahydro-1H-carbazole-3-carbonyl)-amino]-2-methyl-butyl}-thiazole-4-carboxylic acid ethyl ester |
| 252 | 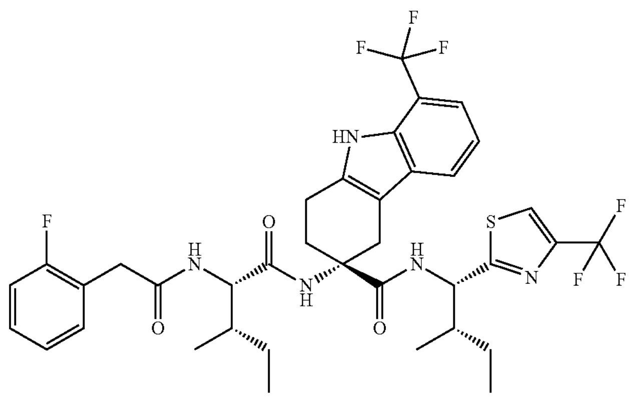 [SMILES: CC[C@H](C)[C@H](NC(=O)Cc1ccccc1F)C(=O)N[C@]1(C(=O)N[C@H](c2nc(C(F)(F)F)cs2)[C@@H](C)CC)CCc2[nH]c3c(C(F)(F)F)cccc3c2C1] | (R)-3-{(2S,3S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(1S,2S)-2-methyl-1-(4-trifluoromethyl-thiazol-2-yl)-butyl]-amide |
| 253 | 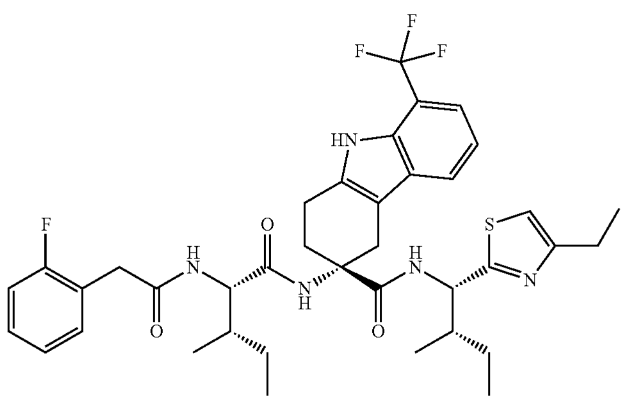 [SMILES: CCc1csc([C@@H](NC(=O)[C@@]2(NC(=O)[C@@H](NC(=O)Cc3ccccc3F)[C@@H](C)CC)CCc3[nH]c4c(C(F)(F)F)cccc4c3C2)[C@@H](C)CC)n1] | (R)-3-{(2S,3S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(1S,2S)-1-(4-ethyl-thiazol-2-yl)-2-methyl-butyl]-amide |
| 254 | 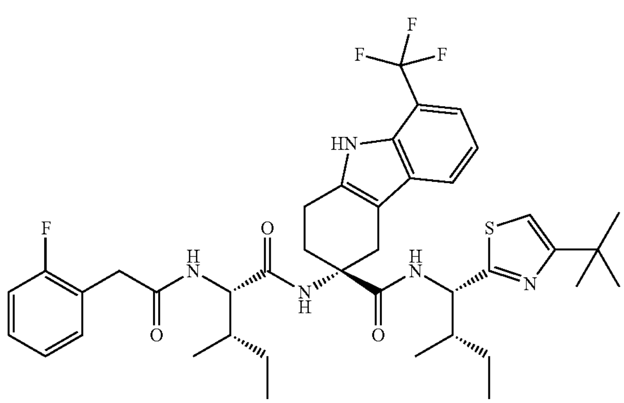 [SMILES: CC[C@H](C)[C@H](NC(=O)Cc1ccccc1F)C(=O)N[C@]1(C(=O)N[C@H](c2nc(C(C)(C)C)cs2)[C@@H](C)CC)CCc2[nH]c3c(C(F)(F)F)cccc3c2C1] | (R)-3-{(2S,3S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(1S,2S)-1-(4-tert-butyl-thiazol-2-yl)-2-methyl-butyl]-amide |

-continued

| Compound | Structure | Chemical name |
|---|---|---|
| 255 | 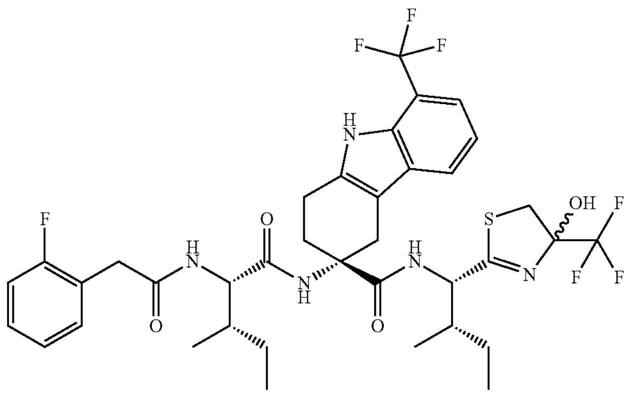 [SMILES: CC[C@H](C)[C@H](NC(=O)Cc1ccccc1F)C(=O)N[C@]1(C(=O)N[C@H](C2=NC(O)(C(F)(F)F)CS2)[C@@H](C)CC)CCc2[nH]c3c(C(F)(F)F)cccc3c2C1] | (R)-3-{(2S,3S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(1S,2S)-1-(4-hydroxy-4-trifluoromethyl-4,5-dihydro-thiazol-2-yl)-2-methyl-butyl]-amide |
| 256 | 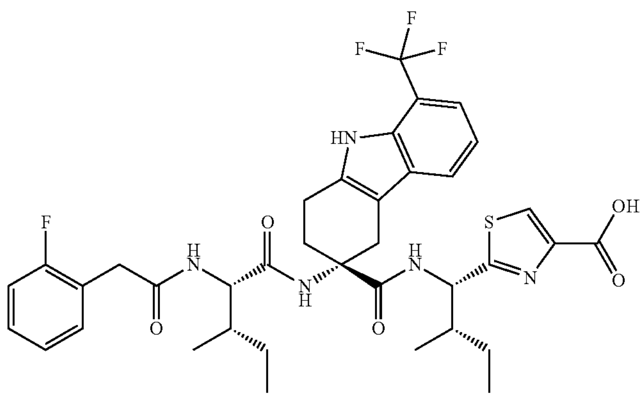 [SMILES: CC[C@H](C)[C@H](NC(=O)Cc1ccccc1F)C(=O)N[C@]1(C(=O)N[C@H](c2nc(C(=O)O)cs2)[C@@H](C)CC)CCc2[nH]c3c(C(F)(F)F)cccc3c2C1] | 2-{(1S,2S)-1-[((R)-3-{(2S,3S)-2-[2-(2-Fluoro-phenyl)-acetylamino]-3-methyl-pentanoylamino}-8-trifluoromethyl-2,3,4,9-tetrahydro-1H-carbazole-3-carbonyl)-amino]-2-methyl-butyl}-thiazole-4-carboxylic acid |
| 257 | 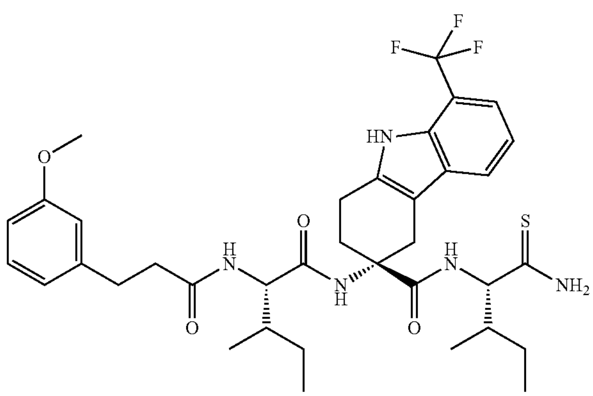 [SMILES: CCC(C)[C@H](NC(=O)CCc1cccc(OC)c1)C(=O)N[C@]1(C(=O)N[C@H](C(N)=S)C(C)CC)CCc2[nH]c3c(C(F)(F)F)cccc3c2C1] | (R)-3-{(S)-2-[3-(3-Methoxy-phenyl)-propionylamino]-3-methyl-pentanoylamino}-8-trifluoromethyl-2,3,4,9-tetrahydro-1H-carbazole-3-carboxylic acid ((S)-2-methyl-1-thiocarbamoyl-butyl)-amide |
| 258 | 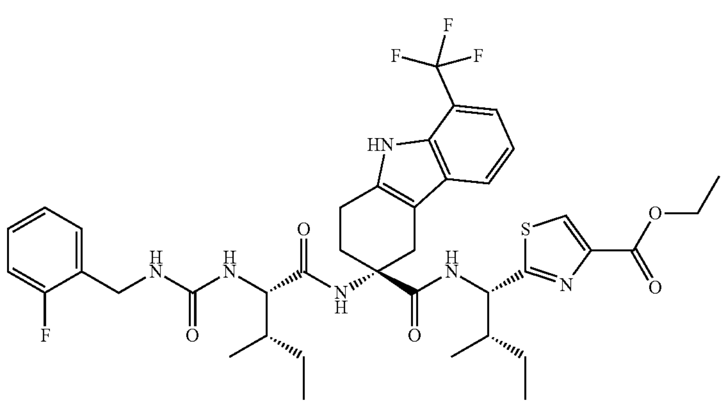 [SMILES: CCOC(=O)c1csc([C@@H](NC(=O)[C@@]2(NC(=O)[C@@H](NC(=O)NCc3ccccc3F)[C@@H](C)CC)CCc3[nH]c4c(C(F)(F)F)cccc4c3C2)[C@@H](C)CC)n1] | 2-{(1S,2S)-1-[((R)-3-{(2S,3S)-2-[3-(2-Fluoro-benzyl)-ureido]-3-methyl-pentanoylamino}-8-trifluoromethyl-2,3,4,9-tetrahydro-1H-carbazole-3-carbonyl)-amino]-2-methyl-butyl}-thiazole-4-carboxylic acid ethyl ester |

| Compound | Structure | Chemical name |
|---|---|---|
| 259 | 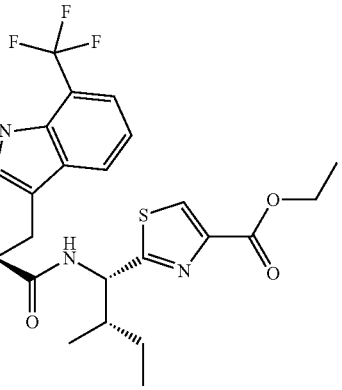 | 2-{(1S,2S)-1-[((R)-3-{(2S,3S)-2-[3-(4-Methoxy-benzyl)-ureido]-3-methyl-pentanoylamino}-8-trifluoromethyl-2,3,4,9-tetrahydro-1H-carbazole-3-carbonyl)-amino]-2-methyl-butyl}-thiazole-4-carboxylic acid ethyl ester |
| 260 | 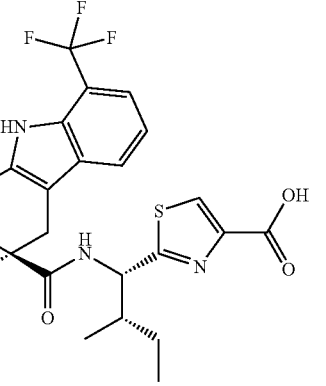 | 2-{(1S,2S)-1-[((R)-3-{(2S,3S)-2-[3-(4-Methoxy-benzyl)-ureido]-3-methyl-pentanoylamino}-8-trifluoromethyl-2,3,4,9-tetrahydro-1H-carbazole-3-carbonyl)-amino]-2-methyl-butyl}-thiazole-4-carboxylic acid |
| 261 | 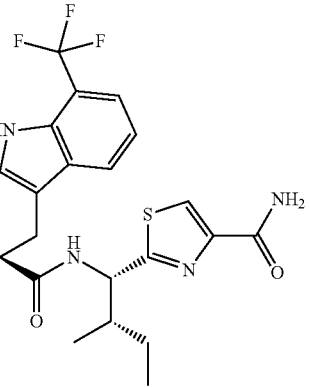 | (R)-3-{(2S,3S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(1S,2S)-1-(4-carbamoyl-thiazol-2-yl)-2-methyl-butyl]-amide |
| 262 | 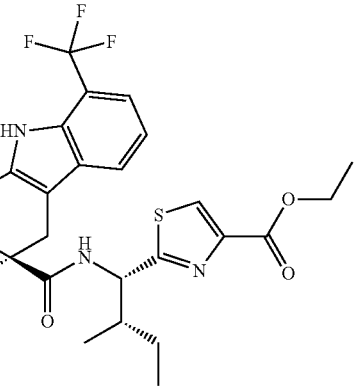 | 2-{(1S,2S)-1-[((R)-3-{(2S,3S)-2-[3-(2-Fluoro-benzyl)-thioureido]-3-methyl-pentanoylamino}-8-trifluoromethyl-2,3,4,9-tetrahydro-1H-carbazole-3-carbonyl)-amino]-2-methyl-butyl}-thiazole-4-carboxylic acid ethyl ester |

| Compound | Structure | Chemical name |
|---|---|---|
| 263 | 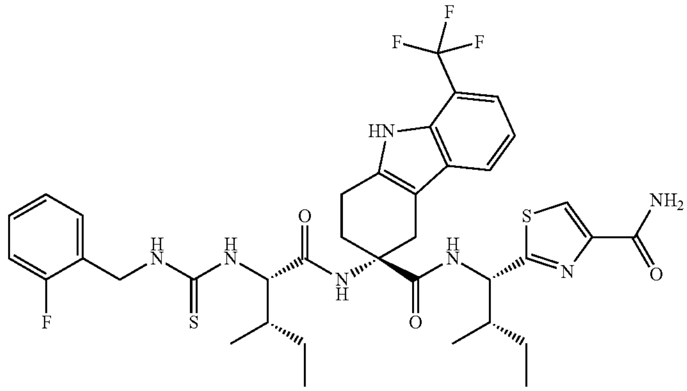 [SMILES: CC[C@H](C)[C@H](NC(=S)NCc1ccccc1F)C(=O)N[C@]1(C(=O)N[C@H](c2nc(C(N)=O)cs2)[C@@H](C)CC)CCc2[nH]c3c(C(F)(F)F)cccc3c2C1] | (R)-3-{(2S,3S)-2-[3-(2-Fluoro-benzyl)-thioureido]-3-methyl-pentanoylamino}-8-trifluoromethyl-2,3,4,9-tetrahydro-1H-carbazole-3-carboxylic acid [(1S,2S)-1-(4-carbamoyl-thiazol-2-yl)-2-methyl-butyl]-amide |
| 264 | 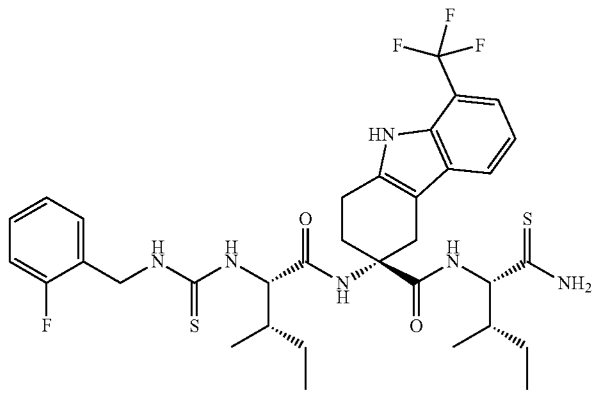 [SMILES: CC[C@H](C)[C@H](NC(=S)NCc1ccccc1F)C(=O)N[C@]1(C(=O)N[C@H](C(N)=S)[C@@H](C)CC)CCc2[nH]c3c(C(F)(F)F)cccc3c2C1] | (R)-3-{(2S,3S)-2-[3-(2-Fluoro-benzyl)-thioureido]-3-methyl-pentanoylamino}-8-trifluoromethyl-2,3,4,9-tetrahydro-1H-carbazole-3-carboxylic acid ((1S,2S)-2-methyl-1-thiocarbamoyl-butyl)-amide |
| 265 | 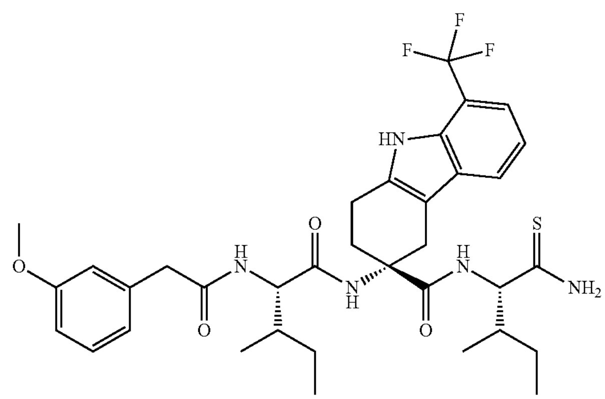 [SMILES: CCC(C)[C@H](NC(=O)Cc1cccc(OC)c1)C(=O)N[C@]1(C(=O)N[C@H](C(N)=S)C(C)CC)CCc2[nH]c3c(C(F)(F)F)cccc3c2C1] | (R)-3-{(S)-2-[2-(3-Methoxy-phenyl)-acetylamino]-3-methyl-pentanoylamino}-8-trifluoromethyl-2,3,4,9-tetrahydro-1H-carbazole-3-carboxylic acid ((S)-2-methyl-1-thiocarbamoyl-butyl)-amide |
| 266 | 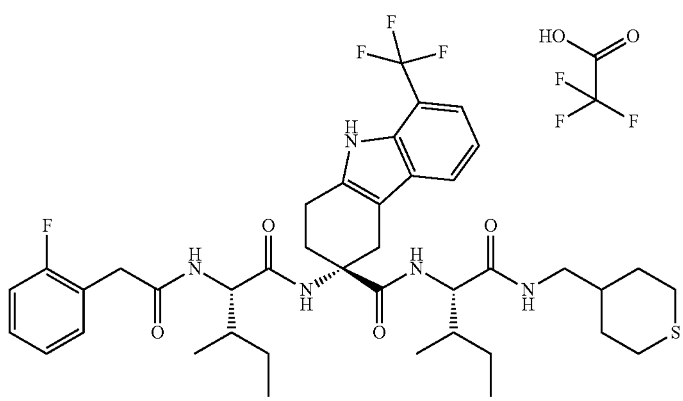 [SMILES: CCC(C)[C@H](NC(=O)Cc1ccccc1F)C(=O)N[C@]1(C(=O)N[C@H](C(=O)NCC2CCSCC2)C(C)CC)CCc2[nH]c3c(C(F)(F)F)cccc3c2C1 ; O=C(O)C(F)(F)F] | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(tetrahydro-thiopyran-4-ylmethyl)-carbamoyl]-butyl}-amide |

For the avoidance of doubt, if chemical name and chemical structure of the above illustrated compounds do not correspond by mistake, the chemical structure is regarded to unambiguously define the compound.

All the above generically or explicitly disclosed tetrahydrocarbazole compounds, including preferred subsets/embodiments of formula (I) and Compounds 1 to 266, are hereinafter referred to as compounds of the (present) invention.

The terms indicated for explanation of the above compounds of the invention aways, unless indicated otherwise in the description or in the claims, have the following meanings:

The term "unsubstituted" means that the corresponding radical, group or moiety has no substituents.

The term "substituted" means that the corresponding radical, group or moiety has one or more substituents. Where a radical has a plurality of substituents, and a selection of various substituents is specified, the substituents are selected independently of one another and do not need to be identical.

The term "alkyl" for the purposes of this invention refers to acyclic saturated or unsaturated hydrocarbon radicals which may be branched or straight-chain and have 1 to 8 carbon atoms, i.e. $C_{1-8}$-alkanyls, $C_{2-8}$-alkenyls and $C_{2-8}$-alkynyls. Alkenyls have at least one C=C double bond and alkynyls at least one C=C triple bond. Alkynyls may additionally also have at least one C=C double bond. Examples of suitable alkyl radicals are methyl, ethyl, n-propyl, isopropyl, n-butyl, isobutyl, sec-butyl, tert-butyl, n-pentyl, iso-pentyl, neo-pentyl, tert-pentyl, 2- or 3-methyl-pentyl, n-hexyl, 2-hexyl, isohexyl, n-heptyl, n-octyl, n-nonyl, n-decyl, n-undecyl, n-dodecyl, n-tetradecyl, n-hexadecyl, n-octadecyl, n-icosanyl, n-docosanyl, ethylenyl (vinyl), propenyl (—$CH_2CH=CH_2$; —CH=CH—$CH_3$, —C(=$CH_2$)—$CH_3$), butenyl, pentenyl, hexenyl, heptenyl, octenyl, octadienyl, octadecenyl, octadec-9-enyl, icosenyl, icos-11-enyl, (Z)-icos-11-enyl, docosnyl, docos-13-enyl, (Z)-docos-13-enyl, ethynyl, propynyl (—$CH_2$—C≡H, —C≡$CH_3$), butynyl, pentynyl, hexynyl, heptynyl, octynyl, The term "($C_9$-$C_{30}$)alkyl" for the purposes of this invention refers to acyclic saturated or unsaturated hydrocarbon radicals which may be branched or straight-chain and have 9 to 30 carbon atoms, i.e. $C_{9-30}$-alkanyls, $C_{9-30}$-alkenyls and $C_{9-30}$-alkynyls. $C_{9-30}$-Alkenyls have at least one C=C double bond and $C_{9-30}$-alkynyls at least one C=C triple bond. $C_{9-30}$-Alkynyls may additionally also have at least one C=C double bond. Examples of suitable ($C_9$-$C_{30}$)alkyl radicals are tetradecyl, hexadecyl, octadecyl, eicosanyl, cis-13-docosenyl (erucyl), trans-13-docosenyl (brassidyl), cis-15-tetracosenyl (nervonyl) and trans-15-tetracosenyl.

The term "cycloalkyl" for the purposes of this invention refers to saturated and partially unsaturated non-aromatic cyclic hydrocarbon groups/radicals, having 1 to 3 rings, that contain 3 to 20, preferably 3 to 12, most preferably 3 to 8 carbon atoms. The cycloalkyl radical may also be part of a bi- or polycyclic system, where, for example, the cycloalkyl radical is fused to an aryl, heteroaryl or heterocyclyl radical as defined herein by any possible and desired ring member(s). The bonding to the compounds of the general formula (I) can be effected via any possible ring member of the cycloalkyl radical. Examples of suitable cycloalkyl radicals are cyclopropyl, cyclobutyl, cyclopentyl, cyclohexyl, cycloheptyl, cyclooctyl, cyclodecyl, cyclohexenyl, cyclopentenyl and cyclooctadienyl.

The term "heterocyclyl" for the purposes of this invention refers to a mono- or poly-cyclic system of 3 to 20, preferably 5 or 6 to 14 ring atoms comprising carbon atoms and 1, 2, 3, 4, or 5 heteroatoms, in particular nitrogen, oxygen and/or sulfur which are identical or different. The cyclic system may be saturated, mono- or polyunsaturated but may not be aromatic. In the case of a cyclic system consisting of at least two rings the rings may be fused or Spiro- or otherwise connected. Such "heterocyclyl" radicals can be linked via any ring member. The term "heterocyclyl" also includes systems in which the heterocycle is part of a bi- or polycyclic saturated, partially unsaturated and/or aromatic system, such as where the heterocycle is fused to an "aryl", "cycloalkyl", "heteroaryl" or "heterocyclyl" group as defined herein via any desired and possible ring member of the heterocycyl radical. The bonding to the compounds of the general formula (I) can be effected via any possible ring member of the heterocycyl radical. Examples of suitable "heterocyclyl" radicals are pyrrolidinyl, thiapyrrolidinyl, piperidinyl, piperazinyl, oxapiperazinyl, oxapiperidinyl, oxadiazolyl, tetrahydrofuryl, imidazolidinyl, thiazolidinyl, tetrahydropyranyl, morpholinyl, tetrahydrothiophenyl, dihydropyranyl.

The term "aryl" for the purposes of this invention refers to aromatic hydrocarbon systems having 3 to 14, preferably 5 to 14, more preferably 6 to 14 carbon atoms. The term "aryl" also includes systems in which the aromatic cycle is part of a bi- or poly-cyclic saturated, partially unsaturated and/or aromatic system, such as where the aromatic cycle is fused to an "aryl", "cycloalkyl", "heteroaryl" or "heterocyclyl" group as defined herein via any desired and possible ring member of the aryl radical. The bonding to the compounds of the general formula (I) can be effected via any possible ring member of the aryl radical. Examples of suitable "aryl" radicals are phenyl, biphenyl, naphthyl and anthracenyl, but likewise indanyl, indenyl, or 1,2,3,4-tetrahydronaphthyl.

The term "heteroaryl" for the purposes of this invention refers to a 3 to 14, preferably 5 to 14, more preferably 5-, 6- or 7-membered cyclic aromatic hydrocarbon radical which comprises at least 1, where appropriate also 2, 3, 4 or 5 heteroatoms, preferably nitrogen, oxygen and/or sulfur, where the heteroatoms are identical or different. The number of nitrogen atoms is preferably 0, 1, 2, or 3, and that of the oxygen and sulfur atoms is independently 0 or 1. The term "heteroaryl" also includes systems in which the aromatic cycle is part of a bi- or polycyclic saturated, partially unsaturated and/or aromatic system, such as where the aromatic cycle is fused to an "aryl", "cycloalkyl", "heteroaryl" or "heterocyclyl" group as defined herein via any desired and possible ring member of the heteroaryl radical. The bonding to the compounds of the general formula (I) can be effected via any possible ring member of the heteroaryl radical. Examples of suitable "heteroaryl" are pyrrolyl, thienyl, furyl, imidazolyl, thiazolyl, isothiazolyl, oxazolyl, oxadiazolyl, isoxazolyl, pyrazolyl, pyridinyl, pyrimidinyl, pyridazinyl, pyrazinyl, indolyl, quinolinyl, isoquinolinyl, imidazolyl, triazolyl, triazinyl, tetrazolyl, phthalazinyl, indazolyl, indolizinyl, quinoxalinyl, quinazolinyl, pteridinyl, carbazolyl, phenazinyl, phenoxazinyl, phenothiazinyl, acridinyl.

For the purposes of the present invention, the terms "alkylcycloalkyl", "cycloalkylalkyl", "alkyl-heterocyclyl", "heterocyclylalkyl", "alkyl-aryl", "arylalkyl", "alkyl-heteroaryl" and "heteroarylalkyl" mean that alkyl, cycloalkyl, heterocycl, aryl and heteroaryl are each as defined above, and the cycloalkyl, heterocyclyl, aryl and heteroaryl radical is bonded to the compounds of the general formula (I) via an alkyl radical, preferably $C_1$-$C_8$-alkyl radical, more preferably $C_1$-$C_4$-alkyl radical.

The term "halogen", "halogen atom" or "halogen substituent" (Hal-) for the purposes of this invention refers to one, where appropriate, a plurality of fluorine (F, fluoro), bromine (Br, bromo), chlorine (Cl, chloro), or iodine (I, iodo) atoms. The designations "dihalogen", "trihalogen" and "perhalogen" refer respectively to two, three and four substituents, where each substituent can be selected independently from the group consisting of fluorine, chlorine, bromine and iodine. "Halogen" preferably means a fluorine, chlorine or bromine atom.

All stereoisomers of the compounds of the invention are contemplated, either in a mixture or in pure or substantially pure form. The compounds of the invention can have asymmetric centers at any of the carbon atoms. Consequently, they can exist in the form of their racemates, in the form of the pure enantiomers and/or diastereomers or in the form of mixtures of these enantiomers and/or diastereomers. The mixtures may have any desired mixing ratio of the stereoisomers.

Thus, for example, the compounds of the invention which have one or more centers of chirality and which occur as racemates or as diastereomer mixtures can be fractionated by methods known per se into their optical pure isomers, i.e. enantiomers or diastereomers. The separation of the compounds of the invention can take place by column separation on chiral or nonchiral phases or by recrystallization from an optionally optically active solvent or with use of an optically active acid or base or by derivatization with an optically active reagent such as, for example, an optically active alcohol, and subsequent elimination of the radical.

The compounds of the invention may be present in the form of their double bond isomers as "pure" E or Z isomers, or in the form of mixtures of these double bond isomers.

Where possible, the compounds of the invention may be in the form of the tautomers.

It is likewise possible for the compounds of the invention to be in the form of any desired prodrugs such as, for example, esters, carbonates, carbamates, ureas, amides or phosphates, in which cases the actually biologically active form is released only through metabolism. Any compound that can be converted in vivo to provide the bioactive agent (i.e. compounds of the invention) is a prodrug within the scope and spirit of the invention.

Various forms of prodrugs are well known in the art and are described for instance in:
  (i) Wermuth C G et al., Chapter 31: 671-696, The Practice of Medicinal Chemistry, Academic Press 1996;
  (ii) Bundgaard H, Design of Prodrugs, Elsevier 1985; and
  (iii) Bundgaard H, Chapter 5: 131-191, A Textbook of Drug Design and Development, Harwood Academic Publishers 1991.

Said references are incorporated herein by reference.

It is further known that chemical substances are converted in the body into metabolites which may where appropriate likewise elicit the desired biological effect—in some circumstances even in more pronounced form.

Any biologically active compound that was converted in vivo by metabolism from any of the compounds of the invention is a metabolite within the scope and spirit of the invention.

The compounds of the invention can, if they have a sufficiently basic group such as, for example, a secondary or tertiary amine, be converted with inorganic and organic acids into salts. The pharmaceutically acceptable salts of the compounds of the invention are preferably formed with hydrochloric acid, hydrobromic acid, iodic acid, sulfuric acid, phosphoric acid, methanesulfonic acid, p-toluenesulfonic acid, carbonic acid, formic acid, acetic acid, sulfoacetic acid, trifluoroacetic acid, oxalic acid, malonic acid, maleic acid, succinic acid, tartaric acid, racemic acid, malic acid, embonic acid, mandelic acid, fumaric acid, lactic acid, citric acid, taurocholic acid, glutaric acid, stearic acid, glutamic acid or aspartic acid. The salts which are formed are, inter alfa, hydrochlorides, chlorided, hydrobromides, bromides, iodides, sulfates, phosphates, methanesulfonates, tosylates, carbonates, bicarbonates, formates, acetates, sulfoacetates, triflates, oxalates, malonates, maleates, succinates, tartrates, malates, embonates, mandelates, fumarates, lactates, citrates, glutarates, stearates, aspartates and glutamates. The stoichiometry of the salts formed from the compounds of the invention may moreover be an integral or non-integral multiple of one.

The compounds of the invention can, if they contain a sufficiently acidic group such as, for example, the carboxy, sulfonic acid, phosphoric acid or a phenolic group, be converted with inorganic and organic bases into their physiologically tolerated salts. Examples of suitable inorganic bases are ammonium, sodium hydroxide, potassium hydroxide, calcium hydroxide, and of organic bases are ethanolamine, diethanolamine, triethanolamine, ethylenediamine, t-butylamine, t-octylamine, dehydroabietylamine, cyclohexylamine, dibenzylethylene-diamine and lysine. The stoichiometry of the salts formed from the compounds of the invention can moreover be an integral or non-integral multiple of one.

It is likewise possible for the compounds of the invention to be in the form of their solvates and, in particular, hydrates which can be obtained for example by crystallization from a solvent or from aqueous solution. It is moreover possible for one, two, three or any number of solvate or water molecules to combine with the compounds of the invention to give solvates and hydrates.

It is known that chemical substances form solids which exist in different order states which are referred to as polymorphic forms or modifications. The various modifications of a polymorphic substance may differ greatly in their physical properties. The compounds of the invention can exist in various polymorphic forms and certain modifications may moreover be metastable. All these polymorphic forms of the compounds are to be regarded as belonging to the invention.

According to a further aspect, the object of the invention has surprisingly been solved by providing a process for manufacturing the compounds of the invention.

The tetrahydrocarbazole derivatives (compounds of the invention) as illustrated herein are ligands of G-protein coupled receptors (GPCRs).

Thus, the aforementioned compounds of the invention are suitable for the treatment and/or prophylaxis of physiological and/or pathological conditions mediated by G-protein coupled receptors or physiological and/or pathological conditions which can be influenced by modulation of these receptors, and thus prevented, treated and/or alleviated.

For the purpose of the present invention, the term "treatment" is also intended to include prophylactic treatment or alleviation.

The term "(GPCR) receptor ligand" or "ligand" is intended to refer for the purposes of the present invention to every compound which binds in any way to a receptor (the receptors in the present invention being GPCR receptors) and induces activation, inhibition and/or another conceivable effect at this receptor. The term "(GPCR) receptor ligand" or "ligand" thus includes agonists, antagonists, partial agonists/antagonists, inverse agonists and other ligands which cause an effect at the receptor which is similar to the effect of agonists, antagonists, partial agonists/antagonists or inverse agonists.

The term "modulation" or "modulated" is intended to refer for the purposes of the present invention to as follows: "activation, partial activation, inhibition, partial inhibition". In this case, it is within the specialist knowledge of the average person skilled in the art to measure and determine such activation, partial activation, inhibition, partial inhibition by means of the usual methods of measurement and determination. Thus, a partial activation can be measured and determined in relation to a complete activation; likewise, a partial inhibition in relation to a complete inhibition.

The terms "inhibiting, inhibition and/or retardation" are intended to refer for the purposes of the present invention to as follows: "partial or complete inhibiting, inhibition and/or retardation". In this case, it is within the specialist knowledge of the average person skilled in the art to measure and determine such inhibiting, inhibition, and/or retardation by means of the usual methods of measurement and determination. Thus, a partial inhibiting, inhibition and/or retardation, for example, can be measured and determined in relation to a complete inhibiting, inhibition and/or retardation.

The compounds of the invention being ligands of GPCR receptors are surprisingly characterized by a strong binding affinity to such receptors, preferably to the GnRH/LHRH receptor, compared to known prior art compounds.

Due to their surprisingly strong receptor binding, the compounds of the invention can be advantageously administered at lower doses compared to other less potent binders while still achieving equivalent or even superior desired biological effects. In addition, such a dose reduction may advantageously lead to less or even no medicinal adverse effects. Further, the high binding specificity of the compounds of the invention may translate into a decrease of undesired side effects on its own regardless of the dose applied.

The compounds of the invention being ligands of GPCR receptors are surprisingly characterized by a strong inhibition of luteinizing hormone (LH) secretion, which is at least equivalent or even superior to that of known prior art compounds.

In addition, the compounds of the invention being ligands of GPCR receptors surprisingly show more advantageous hormone suppression. Thus, for example, in the treatment of endometriosis or uterine myomas in women, a reliable, therapeutically effective and controlled reduction in the estradiol level may be achieved without chemical castration being brought about and hormone withdrawal manifestation which are disadvantageous for the patients recurring. In the treatment of benign prostate hyperplasia (BPH) in men, for example, a pronounced, deeper and/or longer-lasting reduction in the testosterone level may be achieved, but likewise without reaching the castration level and/or causing disadvantageous hormone withdrawal manifestations.

Furthermore, the compounds of the invention, being of non-peptidic nature, are resistant to degradation by enzymes of the gastro-intestinal tract. Hence, they offer the advantage to be given by oral route. They surprisingly display an improved metabolic stability, in particular microsomal stability, an improved solubility, in particular in acidic milieus such as gastric juice, and/or an improved bioavailability. Hence, again an advantageous dose reduction may be achievable which may cause less or even no adverse medicinal effects.

The compounds of the invention, being characterized by novel C-terminus modifications, advantageously show improved receptor binding affinity, improved metabolic stability as well as improved solubility, each and all of which are supposed to be attributable to the novel C-terminus modifications.

According to a further aspect, the object of the invention has surprisingly been solved by providing the compounds of the present invention or pharmaceutical compositions as described herein for use as a medicament.

According to another aspect, the object of the present invention has surprisingly been solved by providing the use of the compounds of the invention or pharmaceutical compositions as described herein for the manufacture of a medicament for the treatment and/or prophylaxis of physiological and/or pathological conditions mediated by G-protein coupled receptors or of physiological and/or pathological conditions which can be treated by modulation of these receptors. Likewise, corresponding medicaments comprising at least one compound of the invention or at least one pharmaceutical composition as described herein for use in the treatment and/or prophylaxis of physiological and/or pathological conditions mediated by G-protein coupled receptors or of physiological and/or pathological conditions which can be treated by modulation of these receptors are also comprised by the present invention.

In a preferred embodiment, these G-protein coupled receptors are selected from the group consisting of "GnRH receptor, LHRH receptor, neurokinin family receptor, $NK_1$ receptor, $NK_2$ receptor". Particularly preferred is the GnRH/LHRH receptor.

As illustrated supra, the compounds of the invention can acts as modulators of these GPCR receptors. In a preferred embodiment, the compounds of the invention act as GnRH receptor antagonists, LHRH receptor antagonists, $NK_1$ receptor antagonists and/or $NK_2$ receptor antagonists. Most preferably, the compounds of the invention are antagonists of the GnRH/LHRH receptor.

The compounds of the invention and pharmaceutical compositions as described herein can be administered for the treatment and/or prophylaxis of physiological and/or pathological conditions mediated by G-protein coupled receptors or physiological and/or pathological conditions which can be influenced by modulation of these receptors.

For the purpose of the present invention, all physiological and/or pathological conditions are intended to be comprised that are known to be mediated by G-protein coupled receptors or that are known to be able to be influenced by modulation of these receptors.

Preferably, these conditions are benign and malignant neoplastic diseases, male fertility control, hormone therapy, hormone replacement therapy, controlled ovarian stimulation (COS) in the context of in-vitro fertilization (IVF), female sub- and infertility, female contraception, nausea and vomiting, for example as a consequence of emetogenic chemotherapy, pain, inflammations, rheumatic and arthritic pathological conditions as well as the following conditions: chronic pain, panic disorder, disturbances of mood and sleep, depression, fibromyalgia, post-traumatic stress disorder, tension headache, migraine headache, anxiety, generalized anxiety disorder, bowel syndrome, irritable bowel sysndrome, stress-induced hypertension, asthma, emesis, cough, cystitis of the bladder, pancreatitis, atopic dermatitis (refer to Rupniak N M, Chapter 4.3: Substance P(NK1 receptor) antagonists, in Steckler T, Kalin N H, Reul J M H M (Eds.) Handbook of Stress and Brain, Vol. 15, 2005; Duffy R A, Expert Opin. Emerg. Drugs 2004, 9(1):9-21).

Hormone therapy in this connection includes, inter alia, the treatment of endometriosis, uterine leiomyomas, uterine fibroids and benign prostate hyperplasia (BPH). In male fertility control, the compounds of the invention bring about a reduction in spermatogenesis. Combined administration with androgens, e.g. testosterone or testosterone derivatives, such as, for example, testosterone esters, is preferred. The testosterone derivatives can in this case be administered for example by injection, e.g. by intramuscular depot injection.

Female hormone therapy in this connection includes, inter alia, for example, the treatment of benign hormone-dependent disorders such as endometriosis, uterine fibroids, uterine myomas (uterine leiomyomas), endometrium hyperplasia, dysmenorrhea, and dysfunctional uterine bleeding (menorrhagia, metrorrhagia), where appropriate in combination with other hormones, e.g. estrogens or/and progestins. Particularly preferred are combinations of the LHRH receptor antagonists of the invention and tissue-selective partial estrogen agonists, such as Raloxifene®.

The compounds of the invention can also be employed in hormone replacement therapy, for example for treating hot flushes, in the control of female fertility, for example by switching off the endogenous hormone cycle for controlled induction of ovulation (controlled ovarian stimulation, COS), and for the treatment of sterility within the scope of assisted reproduction techniques (ART) such as in-vitro fertilization (IVF), as well as in female contraception.

Thus, an LHRH receptor antagonist of the invention can be administered on days 1 to 15 of the female cycle together with estrogen, preferably with very low estrogen dosages. On days 16 to 21 of the cycle of intake, progestagen is added to the combination of estrogen and LHRH receptor antagonist. The LHRH receptor antagonist of the invention can be administered continuously throughout the cycle. It is possible in this way to achieve a reduction in the hormone dosage and thus a reduction in the side effects of non-physiological hormone levels. It is additionally possible to achieve advantageous effects in women suffering from polycystic ovary syndrome and androgen-dependent disorders, such as acne, seborrhea and hirsutism. An improved cycle control compared with previous administration methods is also to be expected.

Further preferred conditions that can be treated and/or prevented by administering the compounds of the invention and/or pharmaceutical compositions as described herein are malignant hormone-dependent tumor diseases, such as premenopausal breast cancer, prostate cancer, ovarian cancer, uterine cancer, cervical cancer and endometrial cancer, benign prostate hyperplasia (BPH), gonadal protection during chemotherapy, developmental disturbances in early childhood, e.g. pubertas praecox, HIV infections or AIDS, neurological or neurodegenerative disorders, ARC (AIDS related complex), Kaposi sarcoma, tumors originating in the brain and/or nervous system and/or meninges (refer to WO 99/01764), dementia and Alzheimer's disease.

In a further preferred embodiment, the physiological and/or pathological conditions are selected from the group consisting of: "benign tumor diseases, malignant tumor diseases, male fertility control, hormone therapy, hormone replacement therapy, female sub- or infertility, controlled ovarian stimulation in in vitro fertilization (COS/ART), female contraception, side effects due to chemotherapy, prostate cancer, breast cancer, uterine cancer, endometrial cancer, cervical cancer, ovarian cancer, benign prostate hyperplasia (BPH), endometriosis, uterine fibroids, uterine myomas, endometrium hyperplasia, dysmenorrhoea, dysfunctional uterine bleeding (menorrhagia, metrorrhagia), pubertas praecox, hirsutism, polycystic ovary syndrome, hormone-dependent tumor diseases, HIV infections or AIDS, neurological or neurodegenerative disorders, ARC (AIDS related complex), Kaposi sarcoma, tumors originating from the brain and/or nervous system and/or meninges, dementia, Alzheimer's disease, nausea, vomiting, pain, inflammations, such as appendicitis, arteritis, arthritis, blepharitis, bronchiolitis, bronchitis, bursitis, cervicitis, cholangitis, cholecystitis, chorioamnionitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, gingivitis, glossitis, hepatitis, hidradenitis suppurativa, ileitis, iritis, laryngitis, mastitis, meningitis, myelitis, myocarditis, myositis, nephritis, omphalitis, oophoritis, orchitis, osteitis, otitis, pancreatitis, parotitis, pericarditis, peritonitis, pharyngitis, pleuritis, phlebitis, pneumonitis, proctitis, prostatitis, pyelonephritis, rhinitis, salpingitis, sinusitis, stomatitis, synovitis, tendonitis, tonsillitis, uveitis, vaginitis, vasculitis, vulvitis but also asthma, irritable bowel syndrome and cystitis of the bladder, chronic inflammations, acute inflammations, rheumatic and arthritic pathological states, such as arthritis, rheumatoid arthritis, lupus erythematosus, Sjögren's syndrome, scleroderma (systemic sclerosis), dermatomyositis, polychondritis, polymyositis, polymyalgia rheumatica, osteoarthritis (arthrosis), septic arthritis, fibromyalgia, gout, pseudogout, spondyloarthropathies, ankylosing spondylitis, reactive arthritis (Reiter's syndrome), psoriatic arthropathy, enteropathic spondylitis, reactive arthropathy, vasculitis, polyarteritis nodosa, Henoch-Schönlein purpura, serum sickness, Wegener's granulomatosis, giant cell arteritis, temporal arteritis, Takayasu's arteritis, Behçet's syndrome, Kawasaki's disease (mucocutaneous lymph node syndrome) and Buerger's disease (thromboangiitis obliterans), chronic pain, panic disorder, disturbances of mood and sleep, depression, fibromyalgia, post-traumatic stress disorder, tension headache, migraine headache, anxiety, generalized anxiety disorder, bowel syndrome, irritable bowel sysndrome, stress-induced hypertension, asthma, emesis, cough, cystitis of the bladder, pancreatitis and/or atopic dermatitis.

Likewise, corresponding medicaments comprising at least one compound of the invention or at least one pharmaceutical composition as described herein for use in the treatment and/or prophylaxis of the herein disclosed physiological and/or pathological conditions are also comprised by the present invention.

As illustrated supra, the compounds of the invention are ligands of GPCR receptors. They can be administered to various mammalian species, including human, for the treatment and/or prophylaxis of physiological and/or pathological conditions in such mammals.

For the purpose of the present invention, all mammalian species are regarded as being comprised. Preferably, such mammals are selected from the group consisting of "human, domestic animals, cattle, livestock, pets, cow, sheep, pig, goat, horse, pony, donkey, hinny, mule, hare, rabbit, cat, dog, guinea pig, hamster, rat, mouse". More preferably, such mammals are human.

In a further aspect of the present invention, the compounds of the invention or pharmaceutical compositions as described herein are used in combination with at least one additional pharmacologically active substance.

Such additional pharmacologically active substance may be other compounds of the present invention and/or other suitable therapeutic agents useful in the treatment and/or prophylaxis of the aforementioned physiological and/or pathological conditions. The additional pharmacologically active substance may be an antagonist of GPCRs and/or an agonist of GPCRs depending on the purpose of the combined use. Selection and combination of the additional pharmacologically active substance(s) can be easily performed by the skilled artisan on the basis of his expert knowledge and depending on the purpose of the combined use and physiological and/or pathological conditions targeted.

In a preferred embodiment, the compounds of the invention or pharmaceutical compositions as described herein are used for the treatment and/or prophylaxis of the aforementioned physiological and/or pathological conditions in the form of a medicament, where such medicament comprises at least one additional pharmacologically active substance.

In another preferred embodiment, the compounds of the invention or pharmaceutical compositions as described herein are used for the treatment and/or prophylaxis of the aforementioned physiological and/or pathological conditions in the form of a medicament, where the medicament is applied before and/or during and/or after treatment with at least one additional pharmacologically active substance.

In a further preferred embodiment, the additional pharmacologically active substance being selected from the group consisting of: "androgens, estrogens, progestins, progestagens, selective estrogen receptor modulator (SERM), selective androgen receptor modulator (SARM), receptor-type tyrosine kinase inhibitor, 5alpha-reductase inhibitors, 5alpha-reductase 1 inhibitors, 5alpha-reductase 2 inhibitors, alpha-receptor inhibitors (alpha blockers), alpha1-adrenergic receptor antagonists, aromatase inhibitors, lyase inhibitors, GnRH/LHRH receptor agonists, GnRH/LHRH receptor antagonists, $NK_1$ receptors antagonists, $NK_2$ receptors antagonists, $NK_1$ receptors agonists, $NK_2$ receptors agonists".

In a yet further preferred embodiment, the additional pharmacologically active substance being selected from the group consisting of: "testosterone, oestradiol, oestriol, oestrone, progesterone, raloxifene {[2-(4-hydroxyphenyl)-6-hydrobenzo[b]thien-3-yl][4-(2-(1-piperidinyl)ethoxy)phenyl]-methanone; Chemical Abstract Services Registry No. 84449-90-1}, arzoxifene [2-(4-methoxyphenyl)-3-[4-[2-(1-piperidinyl)ethoxy]phenoxy]-Benzo[b]thiophene-6-ol, Chemical Abstract Services Registry No. 182133-25-1], lasofoxifene[5,6,7,8-tetrahydro-6-phenyl-5-[4-[2-(1-pyrrolidinyl)ethoxy]phenyl]-(5R,6S)-2-Naphthalenol, Chemical Abstract Services Registry No. 180916-16-9], ospemifene {2-[4-[(1Z)-4-chloro-1,2-diphenyl-1-buten-1-yl]phenoxy]-Ethanol, Chemical Abstract Services Registry No. 128607-22-7}, TSE-424 {1-[[4-[2-(hexahydro-1H-azepin-1-yl)ethoxy]phenyl]methyl]-2-(4-hydroxyphenyl)-3-Methyl-1H-Indol-5-ol acetate (1:1), Chemical Abstract Services Registry No. 198481-33-3}, HMR-3339, SERM-3339, SPC-8490, HM-101 {2-[2-[4-[(1Z)-4-chloro-1,2-diphenyl-1-buten-1-yl]phenoxy]ethoxy]-Ethanol, Chemical Abstract Services Registry No. 341524-89-8}, bazedoxifene (WAY 140424) {1-[[4-[2-(hexahydro-1H-azepin-1-yl)ethoxy]phenyl]methyl]-2-(4-hydroxyphenyl)-3-methyl-1H-Indol-5-ol, Chemical Abstract Services Registry No. 198481-32-2}, flutamide {2-methyl-N-[4-nitro-3-(trifluoromethyl)phenyl]-Propanamide, Chemical Abstract Services Registry No. 13311-84-7}, casodex {N-[4-cyano-3-(trifluoromethyl)phenyl]-3-[(4-fluorophenyl)sulfonyl]-2-hydroxy-2-methyl-Propanamide, Chemical Abstract Services Registry No. 90357-06-5}, nilutamide {5,5-dimethyl-3-[4-nitro-3-(trifluoromethyl)phenyl]-2,4-Imidazolidinedione, Chemical Abstract Services Registry No. 63612-50-0}, tamoxifen {2-[4-[(1Z)-1,2-diphenyl-1-buten-1-yl]phenoxy]-N,N-dimethyl-Ethanamine, Chemical Abstract Services Registry No. 10540-29-1}, fulvestrant {7-[9-[(4,4,5,5,5-pentafluoropentyl)sulfinyl]nonyl]-, (7alpha, 17beta)-Estra-1,3,5(10)-triene-3,17-diol, Chemical Abstract Services Registry No. 129453-61-8}, finasteride {N-(1,1-dimethylethyl)-2,4a,4b,5,6,6a,7,8,9,9a,9b,10,11,11a-tetradecahydro-4a,6a-dimethyl-2-oxo-(4aR,4bS,6aS,7S,9aS,9bS,11aR)-1H-Indeno[5,4-f]quinoline-7-carboxamide, Chemical Abstract Services Registry No. 98319-26-7}, dutasteride {N-[2,5-bis(trifluoromethyl)phenyl]-2,4a,4b,5,6,6a,7,8,9,9a,9b,10,11,11a-tetradecahydro-4a,6a-dimethyl-2-oxo-(4aR,4bS,6aS,7S,9aS,9bS,11aR)-1H-Indeno[5,4-f]quinoline-7-carboxamide, Chemical Abstract Services Registry No. 164656-23-9}, izonsteride {8-[(4-ethyl-2-benzothiazolyl)thio]-1,4,4a,5,6,10b-hexahydro-4,10b-dimethyl-(4aR,10bR)-(9Cl) Benzo[f]quinolin-3(2H)-one, Chemical Abstract Services Registry No. 176975-26-1}, epristeride {17-[[(1,1-dimethylethyl)amino]carbonyl]-(17beta)-Androsta-3,5-diene-3-carboxylic acid, Chemical Abstract Services Registry No. 119169-78-7}, tamsulosin {5-[(2R)-2-[[2-(2-ethoxyphenoxy)ethyl]amino]propyl]-2-methoxy-Benzenesulfonamide, Chemical Abstract Services Registry No. 106133-20-4}, prazosin {[4-(4-amino-6,7-dimethoxy-2-quinazolinyl)-1-piperazinyl]-2-furanyl-Methanone, Chemical Abstract Services Registry No. 19216-56-9}, terazosin {[4-(4-amino-6,7-dimethoxy-2-quinazolinyl)-1-piperazinyl](tetrahydro-2-furanyl)-methanone, Chemical Abstract Services Registry No. 63590-64-7}, doxazosin {[4-(4-amino-6,7-dimethoxy-2-quinazolinyl)-1-piperazinyl](2,3-dihydro-1,4-benzodioxin-2-yl)-Methanone, Chemical Abstract Services Registry No. 74191-85-8}, silodosin {2,3-dihydro-1-(3-hydroxypropyl)-5-[(2R)-2-[[2-[2-(2,2,2-trifluoroethoxy)phenoxy]ethyl]amino]propyl]-1H-Indole-7-carboxamide, Chemical Abstract Services Registry No. 160970-54-7}, alfuzosin {N-[3-[(4-amino-6,7-dimethoxy-2-quinazolinyl)methylamino]propyl]tetrahydro-2-Furancarboxamide, Chemical Abstract Services Registry No. 81403-80-7}, anastrozole {alpha1, alpha1, alpha3, alpha3-tetramethyl-5-(1H-1,2,4-triazol-1-ylmethyl)-1,3-Benzenediacetonitrile, Chemical Abstract Services Registry No. 120511-73-1}, letrozole {4,4'-(1H-1,2,4-triazol-1-ylmethylene)bis-Benzonitrile, Chemical Abstract Services Registry No. 112809-51-5}, finrozole {4-[(1R,2S)-3-(4-fluorophenyl)-2-hydroxy-1-(1H-1,2,4-triazol-1-yl)propyl]-Benzonitrile, Chemical Abstract Services Registry No. 160146-17-8}, exemestane {6-methylene-Androsta-1,4-diene-3,17-dione, Chemical Abstract Services Registry No. 107868-30-4}, gefitinib {N-(3-chloro-4-fluorophenyl)-7-methoxy-6-[3-(4-morpholinyl)propoxy]-4-Quinazolinamine, Chemical Abstract Services Registry No. 184475-35-2}, imatinib {4-[(4-methyl-1-piperazinyl)methyl]-N-[4-methyl-3-[[4-(3-pyridinyl)-2-pyrimidinyl]amino]phenyl]-Benzamide, Chemical Abstract Services Registry No. 152459-95-5}, semaxanib {3-[(3,5-dimethyl-1H-pyrrol-2-yl)methylene]-1,3-dihydro-(3Z)-2H-Indol-2-one, Chemical Abstract Services Registry No. 194413-58-6}, SU-6668 {5-[(1,2-dihydro-2-oxo-3H-indol-3-ylidene)methyl]-2,4-dimethyl-1H-Pyrrole-3-propanoic acid, Chemical Abstract Services Registry No. 252916-29-3}, SU-101 {5-methyl-N-[4-(trifluoromethyl)phenyl]-4-Isoxazolecarboxamide, Chemical Abstract Services Registry No. 75706-12-6}, Cl-1033 {N-[4-[(3-chloro-4-fluorophenyl)amino]-7-[3-(4-morpholinyl)propoxy]-6-quinazolinyl]-2-Propenamide hydrochloride (1:2), Chemical Abstract Services Registry No. 289499-45-2}, E-6006 {N,N-dimethyl-2-[(1-methyl-1H-pyrazol-5-yl)-2-thienylmethoxy]-eEthanamine, Chemical Abstract Services Registry No. 247046-52-2}, R-116301 {4-[(2R,4S)-1-[3,5-bis(trifluoromethyl)benzoyl]-2-(phenylmethyl)-4-piperidinyl]-N-(2,6-dimethylphenyl)-1-piperazineacetamide with hydroxy-(S)-Butanedioic acid (1:1), Chemical Abstract Services Registry No. 257888-24-7}, aprepitant {5-[[(2R,3S)-2-[(1R)-1-[3,5-bis(trifluoromethyl)phenyl]ethoxy]-3-(4-fluorophenyl)-4-morpholinyl]methyl]-1,2-dihydro-3H-1,2,4-Triazol-3-one, Chemical Abstract Services Registry No. 170729-80-3}, GW-2016, ZD-4794, BL-1832, BL-1833, GW-597599, GW-679769, KRP-103, TKA-457, L-758298, L-760735, L-759274, NIP-530, CJ-17493, R-1124, ezlopitant {2-(diphenylmethyl)-N-[[2-methoxy-5-(1-methylethyl)phenyl]methyl]-(2S,3S)-1-Azabicyclo[2.2.2]octan-3-amine, Chemical Abstract Services Registry No. 147116-64-1}, CP-122721 {N-[[2-methoxy-5-(trifluoromethoxy)phenyl]methyl]-2-phenyl- (2S,3S)-3-Piperidinamine, Chemical Abstract Services Registry No. 145742-28-5}, PD-154075 {[(1R)-1-(1H-indol-3-ylmethyl)-1-methyl-2-oxo-2-[[(1S)-1-phenylethyl]amino]ethyl]-Carbamic acid 2-benzofuranylmethyl ester, Chemical Abstract Services Registry No. 158991-23-2}, CP-96345 {2-(diphenylmethyl)-N-[(2-methoxyphenyl)methyl]-(2S,3S)-1-Azabicyclo[2.2.2]octan-3-amine, Chemical Abstract Services Registry No. 132746-60-2}, R-673 {N,alpha,alpha-trimethyl-N-[4-(2-methylphenyl)-2-(4-methyl-1-piperazinyl)-5-pyrimidinyl]-3,5-bis(trifluoromethyl)-Benzeneacetamide, Chemical Abstract Services Registry No. 311340-66-6}, SSR 240600 {1-[2-[(2R)-4-[[3,5-bis(trifluoromethyl)phenyl]acetyl]-2-(3,4-dichlorophenyl)-2-morpholinyl]ethyl]-alpha,alpha-dimethyl-4-Piperidineacetamide, Chemical Abstract Services Registry No. 537034-22-3}, MK-0869 {5-[[(2R,3S)-2-[(1R)-1-[3,5-bis(trifluoromethyl)phenyl]ethoxy]-3-(4-fluorophenyl)-4-morpholinyl]methyl]-1,2-dihydro-3H-1,2,4-Triazol-3-one, Chemical Abstract Services Registry No. 170729-80-3}, SR 140333 {1-[2-[(3S)-3-(3,4-dichlorophenyl)-1-[[3-(1-methylethoxy)phenyl]acetyl]-3-piperidinyl]ethyl]-4-phenyl-1-Azoniabicyclo[2.2.2]octane, Chemical Abstract Services Registry No. 155418-05-6}, CP-99,994 {(2R,3R)—N-[(2-methoxyphenyl)methyl]-2-phenyl-3-Piperidinamine dihydrochloride, Chemical Abstract Services Registry No. 872726-33-5}, NKP-608 {N-[(2R,4S)-1-[3,5-bis(trifluoromethyl)benzoyl]-2-[(4-chlorophenyl)methyl]-4-piperidinyl]-4-Quinolinecarboxamide, Chemical Abstract Services Registry No. 177707-12-9}, TAK-637 {7-[[3,5-bis(trifluoromethyl)phenyl]methyl]-8,9,10,11-tetrahydro-9-methyl-5-(4-methylphenyl)-7H-[1,4]Diazocino[2,1-g][1,7]naphthyridine-6,13-dione, Chemical Abstract Services Registry No. 217185-75-6}, MEN-11467 {N-[(1S,2R)-2-[[(2R)-2-[methyl[(4-methylphenyl)acetyl]amino]-3-(2-naphthalenyl)-1-oxopropyl]amino]cyclohexyl]-1H-Indole-3-carboxamide, Chemical Abstract Services Registry No. 214487-46-4}, GR 73632 {N-(5-amino-1-oxopentyl)-L-phenylalanyl-L-phenylalanyl-L-prolyl-N-methyl-L-leucyl-L-Methioninamide, Chemical Abstract Services Registry No. 133156-06-6}, phenoxybenzamine {N-(2-chloroethyl)-N-(1-methyl-2-phenoxyethyl)-Benzenemethanamine, Chemical Abstract Services Registry No. 59-96-1}, sildenafil {5-[2-ethoxy-5-[(4-methyl-1-piperazinyl)sulfonyl]phenyl]-1,6-dihydro-1-methyl-3-propyl-7H-Pyrazolo[4,3-d]pyrimidin-7-one, Chemical Abstract Services Registry No. 139755-83-2}, bicalutamide {N-[4-cyano-3-(trifluoromethyl)phenyl]-3-[(4-fluorophenyl)sulfonyl]-2-hydroxy-2-methyl-Propanamide, Chemical Abstract Services Registry No. 90357-06-5}, cyproterone acetate {(1beta,2beta)-17-(acetyloxy)-6-chloro-1,2-dihydro-3'H-Cyclopropa[1,2]pregna-1,4,6-triene-3,20-dione, Chemical Abstract Services Registry No. 427-51-0}, ketoconazole {1-[4-[4-[[(2R,4S)-2-(2,4-dichlorophenyl)-2-(1H-imidazol-1-ylmethyl)-1,3-dioxolan-4-yl]methoxy]phenyl]-1-piperazinyl]-Ethanone, Chemical Abstract Services Registry No. 65277-42-1}, aminoglutethimide {3-(4-aminophenyl)-3-ethyl-2,6-Piperidinedione, Chemical Abstract Services Registry No. 125-84-8}, danazol {(17alpha)-Pregna-2,4-dien-20-yno[2,3-d]isoxazol-17-ol, Chemical Abstract Services Registry No. 17230-88-5}".

According to a further aspect of the present invention, the object of the invention has surprisingly been achieved by providing a kit comprising a pharmacologically active amount of at least one compound of the invention and/or at least one pharmaceutical composition as described herein and a pharmacologically active amount of at least one further pharmacologically active substance as defined herein.

The compounds of the present invention and/or where appropriate additional pharmacologically active substances or pharmaceutical compositions as described herein can be administered in a known manner. The route of administration may thereby be any route which effectively transports the active compound to the appropriate or desired site of action, for example orally or non-orally, in particular topically, transdermally, pulmonary, rectally, intravaginally, nasally or parenteral or by implantation. Oral administration is preferred.

The compounds of the present invention and/or where appropriate additional pharmacologically active substances or pharmaceutical compositions as described herein can be administered as liquid, semisolid and solid medicinal forms. This takes place in the manner suitable in each case in the form of aerosols, powders, dusting powders and epipastics, tablets including coated tablets, emulsions, foams, solutions, suspensions, gels, ointments, pastes, pills, pastilles, capsules or suppositories. They can be administered in a suitable dosage form to the skin, epicutaneously as solution, suspension, emulsion, foam, ointment, paste or plaster; via the oral and lingual mucosa, buccally, lingually or sublingually as tablet, pastille, coated tablet, linctus or gargle; via the gastric and intestinal mucosa, enterally as tablet, coated tablet, capsule, solution, suspension or emulsion; via the rectal mucosa, rectally as suppository, rectal capsule or ointment; via the nasal mucosa, nasally as drops, ointments or spray; via the bronchial and alveolar epithelium, by the pulmonary route or by inhalation as aerosol or inhalant; via the conjunctiva, conjunctivally as eyedrops, eye ointment, eye tablets, lamellae or eye lotion; via the mucosa of the genital organs, intravaginally as vaginal suppositories, ointments and douche, by the intrauterine route as uterine pessary; via the urinary tract, intraurethrally as irrigation, ointment or bougie; into an artery, intraarterially as injection; into a vein, intravenously as injection or infusion; into the skin, intracutaneously as injection or implant; under the skin, subcutaneously as injection or implant; into the muscle, intramuscularly as injection or implant; into the abdominal cavity, intraperitoneally as injection or infusion.

As already explained above, the compounds of the invention can also be combined with other pharmaceutically active substances. It is possible for the purpose of a combination therapy to administer the individual active ingredients simultaneously or separately, in particular either by the same route (for example orally) or by separate routes (for example orally and as injection). They may be present and administered in identical or different amounts in a unit dose. It is also possible to use a particular dosage regimen when this appears appropriate. It is also possible in this way to combine a plurality of the novel compounds according to the invention with one another.

The compounds of the invention and/or where appropriate additional pharmacologically active substances are converted into a form which can be administered and are mixed where appropriate with pharmaceutically acceptable carriers and/or auxiliaries and/or diluents. Suitable excipients and carriers are described for example in Zanowiak P, Ullmann's Encyclopedia of Industrial Chemistry 2005, Pharmaceutical Dosage Forms, 1-33; Spiegel A J et al., Journal of Pharmaceutical Sciences 1963, 52: 917-927; Czetsch-Lindenwald H, Pharm. Ind. 1961, 2: 72-74; Fiedler H P, Lexikon der Hilfsstoffe für Pharmazie, Kosmetik and angrenzende Gebiete 2002, Editio Cantor Verlag, p65-68.

Oral administration can take place for example in solid form as tablet, capsule, gel capsule, coated tablet, granulation or powder, but also in the form of a drinkable solution or emulsion. The compounds of the invention can for oral administration be combined with known and ordinarily used, physiologically acceptable auxiliaries and carriers, such as, for example, gum arabic, talc, starch, sugars such as, for example, mannitol, methylcellulose, lactose, gelatin, surface-active agents, magnesium stearate, cyclodextrins, aqueous or nonaqueous carriers, diluents, dispersants, emulsifiers, lubricants, preservatives and flavorings (e.g. essential oils). The compounds of the invention can also be dispersed in a microparticulate, e.g. nanoparticulate, composition.

Non-oral administration can take place for example by intravenous, subcutaneous, intramuscular injection of sterile aqueous or oily solutions, suspensions or emulsions, by means of implants or by ointments, creams or suppositories. Administration as sustained release form is also possible where appropriate. Implants may comprise inert materials, e.g. biodegradable polymers or synthetic silicones such as, for example, silicone rubber. Intravaginal administration is possible for example by means of vaginal rings. Intrauterine administration is possible for example by means of diaphragms or other suitable intrauterine devices. Transdermal administration is additionally provided, in particular by means of a formulation suitable foi this purpose and/or suitable means such as, for example, patches.

The dosage may vary within a wide range depending on type and/or severity of the disease, physiological and/or pathological condition, the mode of administration, the age, gender, bodyweight and sensitivity of the subject to be treated. It is within the ability of a skilled worker to determine a "pharmacologically effective amount" of a compound of the invention and/or additional pharmacologically active substance. Administration can take place in a single dose or a plurality of separate dosages.

A suitable unit dose is, for example, from 0.001 mg to 100 mg of the active ingredient, i.e. at least one compound of the invention and, where appropriate, at least one additional pharmacologically active substance, per kg of a patient's bodyweight.

In another aspect, the present invention relates to a pharmaceutical composition comprising a pharmacologically active amount of at least one compound of the invention, preferably a compound of the invention selected from the group consisting of: compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 66, 67, 68, 69, 70, 71, 72, 73, 74, 75, 76, 77, 78, 80, 81, 82, 83, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265 and/or compound 266.

In a further aspect, such a pharmaceutical composition additionally comprises at least one pharmaceutically acceptable carrier and/or auxiliary and/or comprises at least one further pharmacologically active substance.

In a preferred embodiment, such further pharmacologically active substance is selected from the group consisting of: "androgens, estrogens, progestins, progestagens, selective estrogen receptor modulator (SERM), selective androgen receptor modulator (SARM), receptor-type tyrosine kinase inhibitor, 5alpha-reductase inhibitors, 5alpha-reductase 1 inhibitors, 5alpha-reductase 2 inhibitors, alpha-receptor inhibitors (alpha blockers), alpha1-adrenergic receptor antagonists, aromatase inhibitors, lyase inhibitors, GnRH/LHRH receptor agonists, GnRH/LHRH receptor antagonists, $NK_1$ receptors antagonists, $NK_2$ receptors antagonists, NK, receptors agonists, $NK_2$ receptors agonists" and preferably is selected from the group consisting of: "testosterone, oestradiol, oestriol, oestrone, progesterone, raloxifene, arzoxifene, lasofoxifene, ospemifene, TSE-424, HMR-3339, SERM-3339, SPC-8490, HM-101, bazedoxifene (WAY 140424), flutamide, casodex, nilutamide, tamoxifen, fulvestrant, finasteride, dutasteride, izonsteride, epristeride, tamsulosin, prazosin, terazosin, doxazosin, silodosin, alfuzosin, anastrozole, letrozole, finrozole, exemestane, gefitinib, imatinib, semaxanib, SU-6668, SU-101, CI-1033, E-6006, R-116301, aprepitant, GW-2016, ZD-4794, BL-1832, BL-1833, GW-597599, GW-679769, KRP-103, TKA-457, L-758298, L-760735, L-759274, NIP-530, CJ-17493, R-1124, ezlopitant, CP-122721, PD-154075, CP-96345, R-673, SSR 240600, MK-0869, SR 140333, CP-99,994, NKP-608, TAK-637, MEN-11467, GR 73632, phenoxybenzamine, sildenafil, bicalutamide, cyproterone acetate, ketoconazole, aminoglutethimide, danazol".

Concerning the pharmaceutical compositions of the invention, at least one of the compounds of the invention is present in a pharmacologically effective amount, preferably in a unit dose, e.g. the aforementioned unit dose, specifically and preferably in an administration form which makes oral administration possible. Furthermore, reference may be made to that already said in connection with the possible uses and administrations of the compounds of the invention.

Chemical Synthesis:
General Methods for Synthesizing the Embodiments of the Invention The compounds of the invention can be prepared for example in the following way:

Firstly, the compounds of the invention can be synthesized by preparing the depicted central tetrahydrocarbazole structure

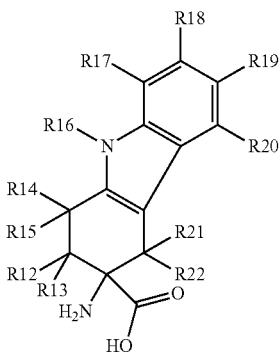

where this optionally protected tetrahydrocarbazole structure already contains the required substituents where appropriate as precursors or in protected form.

The central tetrahydrocarbazole structure is obtainable, for example, by a Fischer indole synthesis, known per se. For this purpose, a suitably substituted cyclohexanone derivative which is provided where appropriate with protective groups is condensed with the particular desired phenylhydrazine derivative which is likewise suitably substituted and, where appropriate, provided with protective groups (e.g. as described by Britten & Lockwood, *J. Chem. Soc. Perkin Trans. I* 1974, 1824 or Maki et al., *Chem. Pharm. Bull.* 1973, 21, 240). The cyclohexane structure is substituted in the 4,4' position by the radicals —COOH and —NH$_2$ or where appropriate by the (protected) precursors thereof. The phenylhydrazine structure is substituted where appropriate by the radicals R17 to R20. Phenylhydrazine derivatives which are not commercially available can be prepared by processes known to the skilled worker. Positional isomers resulting where appropriate in the condensation of the cyclohexanone derivative and the phenylhydrazine derivative can be separated by chromatographic methods such as, for example, HPLC.

The derivatization of the terahydrocarbazole unit can in principle be achieved in various ways known to the skilled worker, and as indicated for example in WO 03/051837 or in WO 2006/005484.

The embodiments of the invention or intermediates thereof were synthesized either by conventional liquid phase synthesis in solution (see below) or else wholly or partly on a solid phase as described in WO 2006/005484.

The synthesis of relevant building blocks like tert-butyl ((S)-1-carbamoyl-2-methylbutyl)carbamate (Boc-Ile-NH$_2$), tert-butyl ((S)-2-methyl-1-thiocarbamoylbutyl)-carbamate (Boc-Ile thioamide), (S)-2-amino-3-methylpentanamide (H-Ile thioamide), (R/S)-3-((S)-2-benzyloxycarbonyl-amino-3-methylpentanoylamino)-6,8-dichloro-2,3,4,9-tetrahydro-1H-carbazole-3-carboxylic acid (Z—(S)-Ile-(R/S)-(6,8-Cl)-Thc-OH) and the synthesis of C-terminal substituted amides in solution as exemplified by the synthesis of (S)-2-{[(R/S)-3-((S)-2-benzyloxycarbonylamino-3-methylpentanoylamino)-6,8-dichloro-2,3,4,9-tetrahydro-1H-carbazole-3-carbonyl]amino}-3-methylpentanoic acid ((S)—Z-Ile-(R/S)-(6,8-Cl)-Thc-(S)-Ile-OH)+R1-NH—R2 has been described in WO 2006/005484, Purification of the Crude Reaction Products (i.e. Mixtures of Diastereoisomers) by Semipreparative HPLC Analytical and semipreparative HPLC systems from Shimadzu; column 250-50, LiChrospher® 100, RP18 (12 µm) from Merck; flow rate 60 ml/min.

Eluents: A=970 ml of water+30 ml of ACN+1 ml of TFA
B=300 ml of water+700 ml of ACN+1 ml of TFA
UV detector 220 nm.

All products were isolated by gradient elution.

The crude products are dissolved in eluent B (DMF added for products of low solubility) and purified in portions on the column (e.g. dissolve 500 mg of crude product in 15 ml of B and separate in one portion). The separation conditions in this case depend on the peptide sequence and nature and amount of the impurities and are established experimentally beforehand on the analytical column.

A typical gradient is: 60% B-100% B in 30 minutes.

If the crude products are mixtures of diastereomers, they are separated by this method.

The isolated fractions are checked by analytical HPLC. ACN and TFA are removed in a rotary evaporator, and the remaining aqueous concentrate is lyophilized.

The compounds of the present invention were prepared as indicated below. The analytical characterization of the compounds of the invention took place by $^1$H-NMR spectroscopy and/or mass spectrometry.

The chemicals and solvents employed were obtained commercially from usual suppliers (Acros, Avocado, Aldrich, Bachem, Fluka, Lancaster, Maybridge, Merck, Sigma, TCI etc.) or synthesized by processes known to the skilled worker.

For the exemplary embodiments indicated below, chiral building blocks were usually employed in enantiopure form. In the case of the tetrahydrocarbazole precursor, the racemic building block was employed. Final products were purified by semipreparative HPLC and characterized in the form of the pure diastereomers.

List of Abbreviations Used:
e.g. for example
DBU 1,8-diazabicyclo[5.4.0]undec-7-ene
HOBt 1-hydroxybenzotriazole
Fmoc 9-fluoroenylmethoxycarbonyl
Boc tert-butyloxycarbonyl
Z benzyloxycarbonyl
Z—Cl benzyloxycarbonyl chloride
Boc$_2$O di-tert-butyl dicarbonate
Bzl benzyl
AA amino acid
EDT 1,2-ethanedithiol
DEAD diethyl azodicarboxylate
DIC N,N'-diisopropylcarbodiimide
DCC N,N'-dicyclohexylcarbodiimide
HATU N,N,N',N'-tetramethyl-O-(7-azabenzotriazol-1-yl)uronium hexafluorophosphate
HOAt 1-hydroxy-7-azabenzotriazole
PyBop (benzotriazol-1-yloxy)tripyrrolidinophosphonium hexafluorophosphate
OSu N-hydroxysuccinimidyl
DIPEA diisopropylethylamine
DMAP N,N'-dimethylaminopyridine
DBU 1,8-diazabicyclo[5.4.0]undec-7-ene
NMM N-methylmorpholine
TFA trifluoroacetic acid
DCM dichloromethane
DMF N,N'-dimethylformamide
DMA N,N'-dimethylacetamide
ACN acetonitrile
THF tetrahydrofuran
Me methyl
MeOH methanol
Lawesson's reagent 2,4-bis(4-methoxyphenyl)-1,3-dithia-2,4-diphosphetane 2,4-disulfide
Thc 3-amino-2,3,4,9-tetrahydro-1H-carbazole-3-carboxylic acid
Ala alanine(yl)
Val valine(yl)
Ile isoleucine(yl)
Leu leucine(yl)
Gln glutamine(yl)
Asn asparagine(yl)
Tyr tyrosine(yl)
hTyr homo-tyrosine(yl)
Arg arginine(yl)
Lys lysine(yl)
RT room temperature
m.p. melting point
ml milliliter
min minute
h hour ELISA enzyme linked immunosorbent assay
HEPES N-(2-hydroxyethyl)piperazine-N'-2-ethanesulfonic acid
DMEM Dulbecco's modified Eagles medium
RIA radio immuno assay
LHRH luteinizing hormone releasing hormone
LH luteinizing hormone
NK1 neurokinin 1
NK2 neurokinin 2
PG protecting group The compounds of the invention were named using the AutoNom 2000 software (ISIS™/Draw 2.5; MDL).

The contents of all cited references and patents are hereby incorporated by reference in their entirety. The invention is explained in more detail by means of the following examples without, however, being restricted thereto.

EXAMPLES

I) Synthesis and Physicochemical Characterization of Selected Compounds of the Invention Examples 1 and 2

((S)-1-{(R)-3-[(R)-1-(5-Amino-[1,3,4]oxadiazol-2-yl)-2-methyl-butylcarbamoyl]-6,8-dichloro-2,3,4,9-tetrahydro-1H-carbazol-3-ylcarbamoyl}-2-methyl-butyl)-carbamic acid benzyl ester (1) and ((S)-1-{(R)-3-[(R)-1-(5-Amino-[1,3,4]oxadiazol-2-yl)-2-methyl-butylcarbamoyl]-6,8-dichloro-2,3,4,9-tetrahydro-1H-carbazol-3-ylcarbamoyl}-2-methyl-butyl)-carbamic acid benzyl ester (2)

0.200 g (0.37 mmol) of (R/S)-3-((S)-2-Benzyloxycarbonylamino-3-methyl-pentanoylamino)-6,8-dichloro-2,3,4,9-tetrahydro-1H-carbazole-3-carboxylic acid, 0.104 g (0.37 mmol) of (S)-1-(5-amino-[1,3,4]oxadiazol-2-yl)-2-methyl-butyl-ammonium-trifluoro-acetate, 0.139 g (0.37 mmol) of HATU and 0.4 mL (2.35 mmol) of DIPEA were heated in 5 mL of DMF in a microwave at 110° C. and 100 watt for 5 min. The reaction solution was separated on a preparative HPLC column.

Compound 1

Yield: 0.056 g (20% of theory).
$^1$H-NMR (DMSO-$d_6$, 600 MHz): $\delta$ =11.36 (s, 1H); 7.76 (s, 1H); 7.68 (d, 1H); 7.41 (s, 1H); 7.22-7.37 (m, 6H); 7.14 (s, 1H); 7.02 (s, 2H); 5.02 (d, 1H); 4.87 (dd, 1H); 4.80 (d, 1H); 3.81 (dd, 1H); 2.98 (d, 1H); 2.86 (d, 1H); 2.75-2.82 (m, 2H); 2.56-2.61 (m, 1H); 2.11-2.18 (m, 1H); 1.90-1.96 (m, 1H); 1.56-1.63 (m, 1H); 1.44-1.51 (m, 1H); 1.30-1.37 (m, 1H); 1.11-1.18 (m, 1H); 0.99-1.07 (m, 1H); 0.78-0.85 (m, 6H); 0.75 (d, 3H); 0.72 (t, 3H) ppm.
ESI-MS: found: 698.5 (M+H$^+$). calculated: 697 g/mol.

Compound 2

Yield: 0.035 g (13% of theory).
$^1$H-NMR (DMSO-$d_6$, 600 MHz): $\delta$ =11.26 (s, 1H); 8.04 (s, 1H); 7.64 (d, 1H); 7.44 (d, 1H); 7.30-7.39 (m, 6H); 7.11 (s, 1H); 6.98 (s, 2H); 5.07 (d, 1H); 4.98 (d, 1H); 4.86 (dd, 1H); 3.77 (dd, 1H); 3.53 (d, 1H); 3.07 (d, 1H); 2.95-3.03 (m, 1H); 2.74 (dd, 1H); 2.21-2.27 (m, 1H); 2.04-2.11 (m, 1H); 1.95-2.00 (m, 1H); 1.44-1.51 (m, 1H); 1.35-1.41 (m, 1H); 1.08-1.20 (m, 2H); 0.84 (d, 3H); 0.81 (t, 3H); 0.72-0.80 (m, 1H); 0.48 (d, 3H); 0.33 (t, 3H) ppm.
ESI-MS: found: 698.5 (M+H$^+$). calculated: 697 g/mol.

By the above procedure, the following compounds were also prepared:

Examples 3 and 4

((S)-1-{(R)-6,8-Dichloro-3-[(S)-2-methyl-1-(3-methyl-[1,2,4]oxadiazol-5-yl)-butylcarbamoyl]-2,3,4,9-tetrahydro-1H-carbazol-3-ylcarbamoyl}-2-methyl-butyl)-carbamic acid benzyl ester and ((S)-1-{(S)-6,8-Dichloro-3-[(S)-2-methyl-1-(3-methyl-[1,2,4]oxadiazol-5-yl)-butylcarbamoyl]-2,3,4,9-tetrahydro-1H-carbazol-3-ylcarbamoyl}-2-methyl-butyl)-carbamic acid benzyl ester Compound 3

$^1$H-NMR (DMSO-$d_6$, 600 MHz): $\delta$ =11.36 (s, 1H); 7.92 (d, 1H), 7.80 (s, 1H); 7.40 (s, 1H); 7.23-7.36 (m, 6H); 7.14 (s, 1H); 5.00-5.08 (m, 2H), 4.79 (d, 1H), 3.84 (dd, 1H) 2.99 (d, 1H), 2.88 (d, 1H), 2.73-2.82 (m, 2H), 2.55-2.64 (m, 1H), 2.35 (s, 3H), 2.12-2.18 (m, 1H), 1.99-2.05 (m, 1H), 1.57-1.63 (m, 1H), 1.41-1.49 (m, 1H), 1.30-1.37 (m, 1H), 1.14-1.22 (m, 1H), 0.99-1.07 (m, 1H), 0.81 (t, 3H), 0.78 (d, 3H), 0.76 (d, 3H), 0.72 (t, 3H) ppm.
ESI-MS: found: 697.3 (M+H$^+$). calculated: 696 g/mol.

Compound 4

$^1$H-NMR (DMSO-$d_6$, 600 MHz): $\delta$ =11.26 (s, 1H); 8.08 (s, 1H); 7.86 (d, 1H); 7.45 (d, 1H); 7.30-7.39 (m, 6H); 7.12 (s, 1H); 5.02-5.09 (m, 2H); 4.96 (d, 1H); 3.80 (dd, 1H); 3.54 (d, 1H); 3.05 (d, 1H); 2.96-3.03 (m, 1H); 2.79 (dd, 1H); 2.34 (s, 3H); 2.22-2.26 (m, 1H); 2.03-2.11 (m, 2H); 1.42-1.49 (m, 1H); 1.36-1.42 (m, 1H); 1.08-1.23 (m, 2H); 0.79-0.84 (m, 6H); 0.71-0.79 (m, 1H); 0.48 (d, 3H); 0.35 (t, 3H) ppm.
ESI-MS: found: 697.4 (M+H$^+$). calculated: 696 g/mol.

Data on further exemplary embodiments are compiled in Table 1 below:

TABLE 1

Further exemplary embodiments with MS data

| Compound | Name (Autonom) | Mass (calc.). | Mass (found) |
|---|---|---|---|
| 5 | 5-((S)-1-{[(R)-3-((S)-2-Benzyloxycarbonylamino-3-methyl-pentanoylamino)-6,8-dichloro-2,3,4,9-tetrahydro-1H-carbazole-3-carbonyl]-amino}-2-methyl-butyl)-[1,2,4]oxadiazole-3-carboxylic acid ethyl ester | 754.0 | 755.6 |
| 6 | 5-((S)-1-{[(S)-3-((S)-2-Benzyloxycarbonylamino-3-methyl-pentanoylamino)-6,8-dichloro-2,3,4,9-tetrahydro-1H-carbazole-3-carbonyl]-amino}-2-methyl-butyl)-[1,2,4]oxadiazole-3-carboxylic acid ethyl ester | 754.0 | 755.3 |
| 7 | ((S)-1-{(S)-6,8-Dichloro-3-[(S)-2-methyl-1-(5-oxo-4,5-dihydro-[1,3,4]oxadiazol-2-yl)-butylcarbamoyl]-2,3,4,9-tetrahydro-1H-carbazol-3-ylcarbamoyl}-2-methyl-butyl)-carbamic acid benzyl ester | 698.0 | 699.5 |
| 8 | {(S)-1-[(R)-6,8-Dichloro-3-((S)-2-methyl-1-[1,3,4]oxadiazol-2-yl-butylcarbamoyl)-2,3,4,9-tetrahydro-1H-carbazol-3-ylcarbamoyl]-2-methyl-butyl}-carbamic acid benzyl ester | 682.0 | 683.4 |

TABLE 1-continued

Further exemplary embodiments with MS data

| Compound | Name (Autonom) | Mass (calc.). | Mass (found) |
|---|---|---|---|
| 9 | {(S)-1-[(S)-6,8-Dichloro-3-((S)-2-methyl-1-[1,3,4]oxadiazol-2-yl-butylcarbamoyl)-2,3,4,9-tetrahydro-1H-carbazol-3-ylcarbamoyl]-2-methyl-butyl}-carbamic acid benzyl ester | 682.0 | 683.4 |
| 10 | ((S)-1-{(R)-3-[(S)-1-(3-Carbamoyl-[1,2,4]oxadiazol-5-yl)-2-methyl-butylcarbamoyl]-6,8-dichloro-2,3,4,9-tetrahydro-1H-carbazol-3-ylcarbamoyl}-2-methyl-butyl)-carbamic acid benzyl ester | 725.0 | 726.2 |
| 11 | ((S)-1-{(S)-3-[(S)-1-(3-Carbamoyl-[1,2,4]oxadiazol-5-yl)-2-methyl-butylcarbamoyl]-6,8-dichloro-2,3,4,9-tetrahydro-1H-carbazol-3-ylcarbamoyl}-2-methyl-butyl)-carbamic acid benzyl ester | 725.0 | 726.3 |
| 12 | 5-{(S)-1-[((R)-3-{(S)-2-[2-(2,6-Difluoro-phenyl)-acetylamino]-3-methyl-pentanoylamino}-8-trifluoromethyl-2,3,4,9-tetrahydro-1H-carbazole-3-carbonyl)-amino]-2-methyl-butyl}-[1,2,4]oxadiazole-3-carboxylic acid ethyl ester | 774.0 | 775.2 |
| 13 | 5-((S)-1-{[(R)-3-((S)-2-Benzyloxycarbonylamino-3-methyl-pentanoylamino)-6,8-dichloro-2,3,4,9-tetrahydro-1H-carbazole-3-carbonyl]-amino}-2-methyl-butyl)-[1,3,4]oxadiazole-2-carboxylic acid ethyl ester | 754.0 | 755.3 |
| 14 | ((S)-1-{(R)-3-[(S)-1-(5-Acetylamino-[1,3,4]oxadiazol-2-yl)-2-methyl-butylcarbamoyl]-6,8-dichloro-2,3,4,9-tetrahydro-1H-carbazol-3-ylcarbamoyl}-2-methyl-butyl)-carbamic acid benzyl ester | 739.0 | 740.2 |
| 15 | 5-((S)-1-{[(S)-3-((S)-2-Benzyloxycarbonylamino-3-methyl-pentanoylamino)-6,8-dichloro-2,3,4,9-tetrahydro-1H-carbazole-3-carbonyl]-amino}-2-methyl-butyl)-[1,3,4]oxadiazole-2-carboxylic acid ethyl ester | 754.0 | 755.3 |
| 16 | ((S)-1-{(S)-3-[(S)-1-(5-Acetylamino-[1,3,4]oxadiazol-2-yl)-2-methyl-butylcarbamoyl]-6,8-dichloro-2,3,4,9-tetrahydro-1H-carbazol-3-ylcarbamoyl}-2-methyl-butyl)-carbamic acid benzyl ester | 739.0 | 740.3 |
| 17 | ((S)-1-{(R)-6,8-Dichloro-3-[(S)-2-methyl-1-(5-oxo-4,5-dihydro-[1,3,4]oxadiazol-2-yl)-butylcarbamoyl]-2,3,4,9-tetrahydro-1H-carbazol-3-ylcarbamoyl}-2-methyl-butyl)-carbamic acid benzyl ester | 698.0 | 699.3 |
| 18 | 5-((S)-1-{[(R)-3-((S)-2-Benzyloxycarbonylamino-3-methyl-pentanoylamino)-6,8-dichloro-2,3,4,9-tetrahydro-1H-carbazole-3-carbonyl]-amino}-2-methyl-butyl)-[1,2,4]oxadiazole-3-carboxylic acid propyl ester | 768.0 | 769.5 |
| 19 | 5-((S)-1-{[(S)-3-((S)-2-Benzyloxycarbonylamino-3-methyl-pentanoylamino)-6,8-dichloro-2,3,4,9-tetrahydro-1H-carbazole-3-carbonyl]-amino}-2-methyl-butyl)-[1,2,4]oxadiazole-3-carboxylic acid propyl ester | 768.0 | 769.5 |
| 20 | ((S)-1-{(R)-6,8-Dichloro-3-[(S)-1-(3-diethylcarbamoyl-[1,2,4]oxadiazol-5-yl)-2-methyl-butylcarbamoyl]-2,3,4,9-tetrahydro-1H-carbazol-3-ylcarbamoyl}-2-methyl-butyl)-carbamic acid benzyl ester | 781.0 | 782.7 |
| 21 | ((S)-1-{(R)-6,8-Dichloro-3-[(S)-1-(3-cyano-[1,2,4]oxadiazol-5-yl)-2-methyl-butylcarbamoyl]-2,3,4,9-tetrahydro-1H-carbazol-3-ylcarbamoyl}-2-methyl-butyl)-carbamic acid benzyl ester | 707.0 | 708.5 |
| 22 | ((S)-1-{(S)-6,8-Dichloro-3-[(S)-1-(3-cyano-[1,2,4]oxadiazol-5-yl)-2-methyl-butylcarbamoyl]-2,3,4,9-tetrahydro-1H-carbazol-3-ylcarbamoyl}-2-methyl-butyl)-carbamic acid benzyl ester | 707.0 | 708.5 |
| 23 | ((S)-1-{(R)-6,8-Dichloro-3-[(S)-2-methyl-1-(5-methyl-[1,3,4]oxadiazol-2-yl)-butylcarbamoyl]-2,3,4,9-tetrahydro-1H-carbazol-3-ylcarbamoyl}-2-methyl-butyl)-carbamic acid benzylester | 696.0 | 697.4 |
| 24 | ((S)-1-{(S)-6,8-Dichloro-3-[(S)-2-methyl-1-(5-methyl-[1,3,4]oxadiazol-2-yl)-butylcarbamoyl]-2,3,4,9-tetrahydro-1H-carbazol-3-ylcarbamoyl}-2-methyl-butyl)-carbamic acid benzyl ester | 696.0 | 697.4 |
| 25 | 5-((S)-1-{[(R)-3-((S)-2-Benzyloxycarbonylamino-3-methyl-pentanoylamino)-6,8-dichloro-2,3,4,9-tetrahydro-1H-carbazole-3-carbonyl]-amino}-2-methyl-butyl)-[1,2,4]oxadiazole-3-carboxylic acid methyl ester | 740.0 | 741.4 |
| 26 | 5-((S)-1-{[(S)-3-((S)-2-Benzyloxycarbonylamino-3-methyl-pentanoylamino)-6,8-dichloro-2,3,4,9-tetrahydro-1H-carbazole-3-carbonyl]-amino}-2-methyl-butyl)-[1,2,4]oxadiazole-3-carboxylic acid methyl ester | 740.0 | 741.4 |
| 27 | [(S)-1-((R)-6,8-Dichloro-3-{(S)-1-[5-(3-ethyl-ureido)-[1,3,4]oxadiazol-2-yl]-2-methyl-butylcarbamoyl}-2,3,4,9-tetrahydro-1H-carbazol-3-ylcarbamoyl)-2-methyl-butyl]-carbamic acid benzyl ester | 768.0 | 769.2 |
| 28 | 5-{(S)-1-[((R)-3-{(S)-2-[2-(2-Fluoro-phenyl)-acetylamino]-3-methyl-pentanoylamino}-8-trifluoromethyl-2,3,4,9-tetrahydro-1H-carbazole-3-carbonyl)-amino]-2-methyl-butyl}-[1,2,4]oxadiazole-3-carboxylic acid ethyl ester | 756.0 | 758.0 |

TABLE 1-continued

Further exemplary embodiments with MS data

| Compound | Name (Autonom) | Mass (calc.). | Mass (found) |
|---|---|---|---|
| 29 | 5-{(S)-1-[((S)-3-{(S)-2-[2-(2-Fluoro-phenyl)-acetylamino]-3-methyl-pentanoylamino}-8-trifluoromethyl-2,3,4,9-tetrahydro-1H-carbazole-3-carbonyl)-amino]-2-methyl-butyl}-[1,2,4]oxadiazole-3-carboxylic acid ethyl ester | 756.0 | 757.5 |
| 30 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[5-(3-ethyl-ureido)-[1,3,4]oxadiazol-2-yl]-2-methyl-butyl}-amide | 770.0 | 771.6 |
| 31 | (S)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[5-(3-ethyl-ureido)-[1,3,4]oxadiazol-2-yl]-2-methyl-butyl}-amide | 770.0 | 771.5 |
| 32 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(5-amino-[1,3,4]oxadiazol-2-yl)-2-methyl-butyl]-amide | 699.0 | 700.4 |
| 33 | Name not generated by AutoNom | 772.0 | 773.7 |
| 34 | Name not generated by AutoNom | 845.0 | 846.4 |
| 80 | 5-{(S)-1-[(3-{2-[2-(2-Fluoro-phenyl)-acetylamino]-3-methyl-pentanoylamino}-8-trifluoromethyl-2,3,4,9-tetrahydro-1H-carbazole-3-carbonyl)-amino]-2-methyl-butyl}-[1,2,4]oxadiazole-3-carboxylic acid ethyl ester | 756.0 | 757.4 |
| 81 | 5-{(S)-1-[((R)-3-{(R)-2-[2-(2-Fluoro-phenyl)-acetylamino]-3-methyl-pentanoylamino}-8-trifluoromethyl-2,3,4,9-tetrahydro-1H-carbazole-3-carbonyl)-amino]-2-methyl-butyl}-[1,2,4]oxadiazole-3-carboxylic acid ethyl ester | 756.0 | 757.4 |
| 82 | (R)-3-{(R)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[5-(3-ethyl-ureido)-[1,3,4]oxadiazol-2-yl]-2-methyl-butyl}-amide | 770.0 | 771.6 |
| 83 | (S)-3-{(R)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[5-(3-ethyl-ureido)-[1,3,4]oxadiazol-2-yl]-2-methyl-butyl}-amid | 770.0 | 771.6 |

The embodiments presented in Table 1 were synthesized according to the following general reaction scheme:

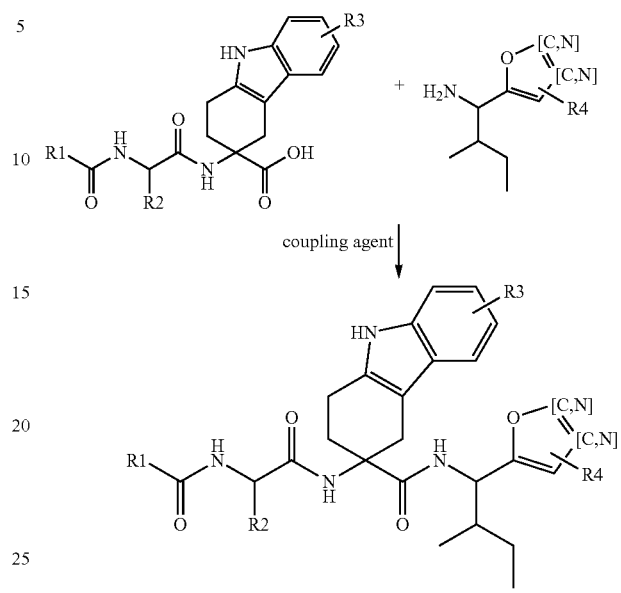

The definition of the R radicals shown in the above reaction scheme and further herein disclosed general reaction schemes corresponds to the substituents (e.g. R radicals) defined above in connection with the general formula (I) and preferred subsets/embodiments. For the avoidance of doubt, the R radicals shown in the above reaction scheme and further herein disclosed general reaction schemes can be identical, but do not need to be identical with the substituents (e.g. R radicals) defined above in connection with the general formula (I) and preferred subsets/embodiments. The individual assignment can be accomplished in a simple manner by the person skilled in the art on the basis of his or her average technical knowledge.

The building blocks (intermediates) were prepared from commercially available starting materials according to WO 06/005484 and the literature cited herein. The oxadiazole building blocks were synthesized according the following literature:

1) Houben-Weyl Vol. E8c: 409.
2) Houben-Weyl Vol. EBd: 189.
3) J. Org. Chem. 1995, 60: 3112.

Compound 35

(R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(pyrrolidin-1-ylmethyl)-carbamoyl] butyl}-amide 0.500 g (0.76 mmol) of (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid ((S)-1-carbamoyl-2-methyl-butyl)-amide (described in WO 2006/005484) and 0.5 mL (6.68) of formaldehyde (37% in water) were suspended in 20 mL methanol. After 30 min 65 mg (0.91 mmol) of pyrrolidine were added and the reaction mixture was heated under reflux for 5 h. The solvents were removed under vacuum and the residue purified by chromatography.

Yield: 0.220 g (39% of theory).

¹H-NMR (DMSO-d₆, 600 MHz): δ=11.13 (s, 1H); 8.16 (s, 1H); 8.11 (d, 1H); 7.86 (s, 1H); 7.60 (d, 1H); 7.34 (d, 1H); 7.19-7.27 (m, 3H); 7.06-7.12 (m, 3H); 4.11-4.20 (m, 3 H); 3.95 (dd, 1H); 3.52 (d, 1H); 3.30 (d, 1H); 3.04 (d, 1H); 2.96 (d, 1H); 2.82 (dd, 1H); 2.60-2.67 (m, 2H); 2.52-2.53 (m, 4H); 2.12-2.17 (m, 1H); 1.62-1.69 (m, 6H); 1.34-1.38 (m, 2H); 0.98-1.05 (m, 2H); 0.80 (d, 3H); 0.76-0.78 (m, 6H); 0.72 (t, 3H) ppm.

ESI-MS: found: 743.4 (M+H⁺). calculated: 742 g/mol.

The described procedure can be based on carboxamides or on thioamides as starting materials. By the above procedure, but with morpholine instead of pyrrolidine the follwing compounds were also prepared:

Compound 36

(R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(morpholin-4-ylmethyl)-carbamoyl]-butyl}-amide ¹H-NMR (DMSO-d₆, 600 MHz): δ =11.13 (s, 1H); 8.10-8.14 (m, 2H); 7.86 (s, 1H); 7.62 (d, 1H); 7.34 (d, 1H); 7.19-7.27 (m, 3H); 7.07-7.12 (m, 3H); 4.17-4.20 (m, 2H); 4.01 (dd, 1H); 3.83 (dd, 1H); 3.51-3.55 (m, 5H); 3.31 (d, 1H); 3.05 (d, 1H); 2.97 (d, 1H); 2.82 (dd, 1H); 2.60-2.68 (m, 2H); 2.39-2.45 (m, 4H); 2.12-2.17 (m, 1H); 1.69-1.70 (m, 1H); 1.62-1.63 (m, 1H); 1.32-1.39 (m, 2H); 1.00-1.06 (m, 2H); 0.75-0.81 (m, 9H); 0.72 (t, 3H) ppm.

ESI-MS: found: 759.4 (M+H⁺). calculated: 758 g/mol.

Compound 37

(R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(morpholin-4-ylmethyl)-thiocarbamoyl]-butyl}-amide ¹H-NMR (DMSO-d₆, 600 MHz): δ =11.14 (s, 1H); 10.20 (s, 1H); 8.01 (d, 1H); 7.86 (s, 1H); 7.59 (d, 1H); 7.34 (d, 1H); 7.31 (d, 1H); 7.24-7.27 (m, 1H); 7.19 (t, 1H); 7.06-7.12 (m, 3H); 4.60 (dd, 1H); 4.52 (dd, 1H); 4.32 (dd, 1H); 4.21 (dd, 1H), 3.55-3.57 (m, 4H); 3.49 (d, 1H); 3.27 (d, 1H); 3.04 (d, 1H); 2.91 (d, 1H); 2.81 (dd, 1H); 2.68 (dd, 1H); 2.53-2.62 (m, 5H); 2.11-2.15 (m, 1H); 1.75-1.78 (m, 1H); 1.63-1.64 (m, 1H); 1.45-1.48 (m, 1H); 1.34-1.38 (m, 1H); 1.00-1.07 (m, 2H); 0.81 (d, 3H); 0.76-0.78 (m, 6H); 0.73 (t, 3H) ppm.

ESI-MS: found: 775.4 (M+H⁺). calculated: 774 g/mol.

Compound 38

(R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid ((S)-1-methoxycarbamoyl-2-methyl-butyl)-amide 0.500 g (0.91 mmol) of (R/S)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid (synthesized in according to WO 2006/005484), 0.521 g (1.37 mmol) of HATU and 2.0 mL (11.76 mmol) of DIPEA were dissolved in DMF and stirred for 30 min at room temperature. 0.220 g (1.37 mmol) of (S)-2-Amino-3-methyl-pentanoic acid methoxy-amide were added and the reaction mixture and heated at 110° C. for 3 h. The solvent was removed under vacuum and the residue was purified by high performance liquid chromatography.

Yield: 0.177 g (28% of theory).

¹H-NMR (DMSO-d₆, 600 MHz): δ =11.15 (s, 1H); 11.12 (s, 1H), 8.07 (d, 1H), 7.86 (s, 1H); 7.64 (d, 1H); 7.34 (d, 1H); 7.19-7.23 (m, 3H); 7.07-7.12 (m, 3H); 4.17 (dd, 1H), 4.01 (dd, 1H); 3.57 (s, 3H); 3.51 (d, 1H); 3.28 (d, 1H); 3.02 (d, 1H); 2.94 (d, 1H); 2.81 (d, 1H); 2.67-2.74 (m, 1H); 2.57-2.63 (m, 1H); 2.11-2.17 (m, 1H); 1.61-1.68 (m, 2H); 1.32-1.40 (m, 2H); 0.98-1.07 (m, 2H); 0.77-0.81 (m, 9H); 0.72 (t, 3H) ppm.

ESI-MS: found: 690.4 (M+H⁺). calculated: 689 g/mol.

According to the procedure described for the synthesis of compound 38, the following compounds were also prepared:

Compound 39

(R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(morpholine-4-carbonyl)-butyl]-amide ¹H-NMR (DMSO-d₆, 600 MHz): δ =11.12 (s, 1H); 7.98 (d, 1H); 7.82 (s, 1H); 7.64 (d, 1H); 7.32-7.35 (m, 2H); 7.18-7.26 (m, 2H); 7.05-7.12 (m, 3H); 4.64 (dd, 1H); 4.22 (m, 1 H); 3.44-3.57 (m, 9H); 3.23 (d, 1H); 3.00 (d, 1H); 2.94 (d, 1H); 2.81 (dd, 1H); 2.72 (dd, 1H); 2.60 (d, 1H); 2.13-2.18 (m, 1H); 1.75-1.76 (m, 1H); 1.60-1.61 (m, 1H); 1.33-1.39 (m, 2H); 0.97-1.05 (m, 2H); 0.83 (d, 3H), 0.76-0.79 (m, 6H); 0.73 (t, 3H) ppm.

ESI-MS: found: 730.5 (M+H⁺). calculated: 729 g/mol.

Compound 41

(R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid ((S)-1-ethoxycarbamoyl-2-methyl-butyl)-amide ¹H-NMR (DMSO-d₆, 600 MHz): δ =11.12 (s, 1H); 11.03 (s, 1H), 8.06 (d, 1H), 7.86 (s, 1H); 7.63 (d, 1H); 7.34 (d, 1H); 7.20-7.26 (m, 3H); 7.06-7.12 (m, 3H); 4.18 (dd, 1H), 4.03 (dd, 1H); 3.78 (q, 2H); 3.51 (d, 1H); 3.29 (d, 1H); 3.02 (d, 1H); 2.94 (d, 1H); 2.81 (d, 1H); 2.69 (d, 1H); 2.54-2.62 (m, 1H); 2.12-2.17 (m, 1H); 1.61-1.67 (m, 2H); 1.33-1.39 (m, 2H); 1.14 (t, 3H); 0.99-1.07 (m, 2H); 0.77-0.89 (m, 9H); 0.73 (t, 3H) ppm.

ESI-MS: found: 704.3 (M+H⁺). calculated: 703 g/mol.

Compound 42

(R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(2-morpholin-4-yl-ethylcarbamoyl)-butyl]-amide ¹H-NMR (DMSO-d₆, 600 MHz): δ =11.12 (s, 1H); 8.10 (d, 1H); 7.85 (s, 1H); 7.78 (s, 1H); 7.62 (d, 1H); 7.34 (d, 1H); 7.23-7.27 (m, 1H); 7.18-7.20 (m, 2H); 7.06-7.11 (m, 3 H); 4.13-4.17 (m, 2H); 3.46-3.56 (m, 5H), 3.24-3.30 (m, 2H); 3.10-3.17 (m, 1H); 2.97-3.04 (m, 2H); 2.81 (dd, 1H); 2.57-2.67 (m, 2H); 2.28-2.47 (m, 5H); 2.1-2.15 (m, 1H); 1.61-1.67 (m, 2H); 1.30-1.38 (m, 2H); 0.98-1.06 (m, 2H); 0.85-0.87 (m, 1H); 0.75-0.80 (m, 9H); 0.71 (t, 3H) ppm.

ESI-MS: found: 773.3 (M+H⁺). calculated: 772 g/mol.

Compound 43

(R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(4-hydroxybutylcarbamoyl)-2-methyl-butyl]amide $^1$H-NMR (DMSO-$d_6$, 600 MHz): δ =11.12 (s, 1H); 8.12 (d, 1H); 7.93 (s, 1H); 7.71 (t, 1H); 7.64 (d, 1H); 7.34 (d, 1H); 7.23-7.27 (m, 1H); 7.16-7.20 (m, 2H); 7.06-7.12 (m, 3 H); 4.39-4.40 (m, 1H); 4.12-4.20 (m, 2H); 3.50 (d, 1H); 3.37-3.40 (m, 2H); 3.29 (d, 1H); 2.96-3.12 (m, 4H); 2.82 (dd, 1H); 2.60-2.67 (m, 2H); 2.11-2.16 (m, 1H); 1.62-1.67 (m, 2H); 1.30-1.44 (m, 6H); 0.97-1.06 (m, 2H); 0.75-0.78 (m, 9H); 0.71 (t, 3H) ppm.

ESI-MS: found: 732.6 (M+H$^+$). calculated: 731 g/mol.

Compound 44

(R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(3-morpholin-4-yl-propylcarbamoyl)-butyl]-amide $^1$H-NMR (DMSO-$d_6$, 600 MHz): δ =11.12 (s, 1H); 8.12 (d, 1H); 7.81 (s, 1H); 7.79 (s, 1H); 7.62 (d, 1H); 7.34 (d, 1H); 7.23-7.26 (m, 1H); 7.16-7.21 (m, 2H); 7.06-7.12 (m, 3 H); 4.11-4.16 (m, 2H); 3.53-3.59 (m, 4H); 3.50 (d, 1H); 3.29 (d, 1H); 3.09-3.14 (m, 1H); 2.98-3.06 (m, 3H); 2.82 (dd, 1H); 2.61-2.65 (m, 2H); 2.25-2.45 (m, 5H); 2.12-2.15 (m, 1H); 1.54-1.68 (m, 4H); 1.32-1.35 (m, 2H); 0.98-1.04 (m, 2H); 0.81-0.88 (m, 1H); 0.74-0.78 (m, 9H); 0.71 (t, 3H) ppm.

ESI-MS: found: 787.7 (M+H$^+$). calculated: 786 g/mol.

Data on further exemplary embodiments synthesized according or in analogy to compound 38 are compiled in Table 2 below:

TABLE 2

Further exemplary embodiments with MS data

| Compound | Name (Autonom) | Mass (calc.) | Mass (found) |
|---|---|---|---|
| 45 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(1-methyl-piperidin-4-ylmethyl)-carbamoyl]-butyl}-amide | 770.0 | 771.8 |
| 46 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(tetrahydro-pyran-4-ylmethyl)-carbamoyl]-butyl}-amide | 757.0 | 758.7 |
| 47 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(2-morpholin-4-yl-ethylthiocarbamoyl)-butyl]-amide | 788.0 | 789.7 |
| 48 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[(1-formyl-piperidin-4-ylmethyl)-carbamoyl]-2-methyl-butyl}-amide | 784.0 | 785.5 |
| 49 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[(1-acetyl-piperidin-4-ylmethyl)-carbamoyl]-2-methyl-butyl}-amide | 798.0 | 799.7 |
| 50 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(pyridin-4-ylmethyl)-carbamoyl]-butyl}-amide | 750.0 | 751.6 |
| 51 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(2-diethylamino-ethylcarbamoyl)-2-methyl-butyl]-amide | 758.0 | 759.4 |
| 52 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(tetrahydro-pyran-4-ylmethyl)-thiocarbamoyl]-butyl}-amide | 773.0 | 774.7 |
| 53 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(4-hydroxy-butylthiocarbamoyl)-2-methyl-butyl]-amide | 747.0 | 748.7 |
| 54 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(2-morpholin-4-yl-ethylthiocarbamoyl)-butyl]-amide | 788.0 | 789.6 |
| 55 | (R)-8-Chloro-6-fluoro-3-{(S)-2-[2-(2-fluoro-phenyl)-acetylamino]-3-methyl-pentanoylamino}-2,3,4,9-tetrahydro-1H-carbazole-3-carboxylic acid [(S)-2-methyl-1-(2-morpholin-4-yl-ethylcarbamoyl)-butyl]-amide | 756.0 | 757.6 |
| 56 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(piperidin-4-ylmethyl)-carbamoyl]-butyl}-amide | 756.0 | 757.7 |
| 57 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(2-hydroxy-ethylcarbamoyl)-2-methyl-butyl]-amide | 703.0 | 704.5 |
| 58 | (R)-8-Chloro-6-fluoro-3-{(S)-2-[2-(2-fluoro-phenyl)-acetylamino]-3-methyl-pentanoylamino}-2,3,4,9-tetrahydro-1H-carbazole-3-carboxylic acid {(S)-2-methyl-1-[(pyridin-4-ylmethyl)-carbamoyl]-butyl}-amide | 734.0 | 735.5 |
| 59 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(5-hydroxy-pentylcarbamoyl)-2-methyl-butyl]-amide | 745.0 | 746.6 |

TABLE 2-continued

Further exemplary embodiments with MS data

| Compound | Name (Autonom) | Mass (calc.). | Mass (found) |
|---|---|---|---|
| 60 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(pyridin-4-ylmethyl)-thiocarbamoyl]-butyl}-amide | 766.0 | 767.3 |
| 61 | (R)-8-Chloro-6-fluoro-3-{(S)-2-[2-(2-fluoro-phenyl)-acetylamino]-3-methyl-pentanoylamino}-2,3,4,9-tetrahydro-1H-carbazole-3-carboxylic acid [(S)-2-methyl-1-(2-morpholin-4-yl-ethylthiocarbamoyl)-butyl]-amide | 772.0 | 773.6 |
| 63 | (4-{(S)-2-[((R)-3-{(S)-2-[2-(2-Fluoro-phenyl)-acetylamino]-3-methyl-pentanoylamino}-8-trifluoromethyl-2,3,4,9-tetrahydro-1H-carbazole-3-carbonyl)-amino]-3-methyl-pentanoylamino}-butyl)-phosphonic acid diethyl ester | 851.0 | 852.6 |
| 64 | (4-{(S)-2-[((R)-3-{(S)-2-[2-(2-Fluoro-phenyl)-acetylamino]-3-methyl-pentanoylamino}-8-trifluoromethyl-2,3,4,9-tetrahydro-1H-carbazole-3-carbonyl)-amino]-3-methyl-pentanoylamino}-butyl)-phosphonic acid | 795.0 | 796.6 |
| 67 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(4-hydroxy-phenylcarbamoyl)-2-methyl-butyl]-amide | 751.0 | 752.4 |
| 68 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(4-methoxy-phenylcarbamoyl)-2-methyl-butyl]-amide | 765.0 | 766.5 |
| 69 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(3-hydroxy-4-methoxy-phenylcarbamoyl)-2-methyl-butyl]-amide | 781.0 | 782.5 |
| 70 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(2,4-dihydroxy-phenylcarbamoyl)-2-methyl-butyl]-amide | 767.0 | 768.4 |
| 71 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(2-hydroxy-4-methoxy-phenylcarbamoyl)-2-methyl-butyl]-amide | 781.0 | 782.5 |
| 72 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(2,4,6-trimethoxy-phenylcarbamoyl)-butyl]-amide | 825.0 | 826.5 |
| 73 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(4-hydroxy-cyclohexylcarbamoyl)-2-methyl-butyl]-amide | 757.0 | 758.6 |
| 74 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(3-imidazol-1-yl-propylthiocarbamoyl)-2-methyl-butyl]-amide | 783.0 | 784.4 |
| 75 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(R)-1-(3-imidazol-1-yl-propylthiocarbamoyl)-2-methyl-butyl]-amide | 783.0 | 784.4 |
| 76 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(2-thiophen-2-yl-ethylthiocarbamoyl)-butyl]-amide | 785.0 | 786.3 |
| 77 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(pyridin-3-ylmethyl)-thiocarbamoyl]-butyl}-amide | 766.0 | 767.3 |
| 85 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(2-diethylamino-ethylcarbamoyl)-methyl]-amide | 702.0 | 703.4 |
| 86 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(2-morpholin-4-yl-ethylcarbamoyl)-methyl]-amide | 716.0 | 717.4 |
| 87 | (S)-8-Chloro-6-fluoro-3-{(S)-2-[2-(2-fluoro-phenyl)-acetylamino]-3-methyl-pentanoylamino}-2,3,4,9-tetrahydro-1H-carbazole-3-carboxylic acid {(S)-2-methyl-1-[(pyridin-4-ylmethyl)-carbamoyl]-butyl}-amide | 734.0 | 735.5 |
| 88 | (R)-8-Chloro-6-fluoro-3-{(S)-2-[2-(2-fluoro-phenyl)-thioacetylamino]-3-methyl-pentanoylamino}-2,3,4,9-tetrahydro-1H-carbazole-3-carboxylic acid {(S)-2-methyl-1-[(pyridin-4-ylmethyl)-carbamoyl]-butyl}-amide | 750.0 | 751.5 |
| 89 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(2-pyridin-4-yl-ethylthiocarbamoyl)-butyl]-amide | 780.0 | 781.4 |
| 90 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(4-hydroxy-cyclohexylthiocarbamoyl)-2-methyl-butyl]-amide | 773.0 | 775.0 |

TABLE 2-continued

Further exemplary embodiments with MS data

| Compound | Name (Autonom) | Mass (calc.) | Mass (found) |
|---|---|---|---|
| 91 | 2-{(S)-2-[((R)-3-{(S)-2-[2-(2-Fluoro-phenyl)-acetylamino]-3-methyl-pentanoylamino}-8-trifluoromethyl-2,3,4,9-tetrahydro-1H-carbazole-3-carbonyl)-amino]-3-methyl-pentanoylamino}-5-methoxy-benzoic acid | 809.0 | 810.5 |
| 92 | Phosphoric acid diethyl ester 5-{(S)-2-[((R)-3-{(S)-2-[2-(2-fluoro-phenyl)-acetylamino]-3-methyl-pentanoylamino}-8-trifluoromethyl-2,3,4,9-tetrahydro-1H-carbazole-3-carbonyl)-amino]-3-methyl-pentanoylamino}-2-methoxy-phenyl ester | 917.0 | 918.5 |
| 93 | Dimethylamino-acetic acid 4-{(S)-2-[((R)-3-{(S)-2-[2-(2-fluoro-phenyl)-acetylamino]-3-methyl-pentanoylamino}-8-trifluoromethyl-2,3,4,9-tetrahydro-1H-carbazole-3-carbonyl)-amino]-3-methyl-pentanoylamino}-butyl ester | 816.0 | 816.9 |
| 94 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(4-hydroxy-benzylcarbamoyl)-2-methyl-butyl]-amide | 765.0 | 766.5 |
| 95 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(3-hydroxy-4-methoxy-benzylcarbamoyl)-2-methyl-butyl]-amide | 795.0 | 796.7 |
| 96 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(4-hydroxy-3-methoxy-benzylcarbamoyl)-2-methyl-butyl]-amide | 795.0 | 796.7 |
| 97 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(4-methoxy-phenylthiocarbamoyl)-2-methyl-butyl]-amide | 781.0 | 782.4 |
| 102 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(3-hydroxy-propylcarbamoyl)-2-methyl-butyl]-amide | 717.0 | 718.3 |
| 103 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid ((S)-1-benzylthiocarbamoyl-2-methyl-butyl)-amide | 765.0 | 766.3 |
| 107 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[(6-chloro-pyridin-3-ylmethyl)-thiocarbamoyl]-2-methyl-butyl}-amide | 800.0 | 801.3 |
| 108 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(2-pyridin-3-yl-ethylthiocarbamoyl)-butyl]-amide | 780.0 | 781.5 |
| 109 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(pyrimidin-4-ylmethyl)-thiocarbamoyl]-butyl}-amide | 767.0 | 768.4 |
| 110 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(2-imidazol-1-yl-ethylthiocarbamoyl)-2-methyl-butyl]-amide | 769.0 | |
| 111 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(2-pyrazol-1-yl-ethylthiocarbamoyl)-butyl]-amide | 769.0 | |
| 112 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(2-[1,2,4]triazol-1-yl-ethylthiocarbamoyl)-butyl]-amide | 770.0 | 771.6 |
| 121 | 5-{(S)-2-[((R)-3-{(S)-2-[2-(2-Fluoro-phenyl)-acetylamino]-3-methyl-pentanoylamino}-8-trifluoromethyl-2,3,4,9-tetrahydro-1H-carbazole-3-carbonyl)-amino]-3-methyl-pentanoylamino}-2-hydroxy-benzoic acid | 795.0 | 796.7 |
| 122 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(3-fluoro-4-hydroxy-phenylcarbamoyl)-2-methyl-butyl]-amide | 769.0 | 770.5 |
| 123 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(3-hydroxy-4-methoxy-benzylthiocarbamoyl)-2-methyl-butyl]-amide | 811.0 | 812.4 |
| 124 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid ((S)-1-hydrazinocarbonyl-2-methyl-butyl)-amide | 674.0 | 675.4 |
| 125 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(3-hydroxy-4-methoxy-phenylthiocarbamoyl)-2-methyl-butyl]-amide | 797.0 | 798.6 |

TABLE 2-continued

Further exemplary embodiments with MS data

| Compound | Name (Autonom) | Mass (calc.). | Mass (found) |
|---|---|---|---|
| 127 | (S)-2-[((R)-3-{(S)-2-[2-(2-Fluoro-phenyl)-acetylamino]-3-methyl-pentanoylamino}-8-trifluoromethyl-2,3,4,9-tetrahydro-1H-carbazole-3-carbonyl)-amino]-3-methyl-pentanoic acid 3-imidazol-1-yl-propyl ester | 768.0 | 769.3 |
| 128 | (R)-2-[((R)-3-{(S)-2-[2-(2-Fluoro-phenyl)-acetylamino]-3-methyl-pentanoylamino}-8-trifluoromethyl-2,3,4,9-tetrahydro-1H-carbazole-3-carbonyl)-amino]-3-methyl-pentanoic acid 3-imidazol-1-yl-propyl ester | 768.0 | 769.5 |
| 129 | ((S)-1-{(R)-6,8-Dichloro-3-[(S)-1-(4-hydroxy-benzylcarbamoyl)-2-methyl-butylcarbamoyl]-2,3,4,9-tetrahydro-1H-carbazol-3-ylcarbamoyl}-2-methyl-butyl)-carbamic acid benzyl ester | 763.0 | 764.6 |
| 130 | ((S)-1-{(S)-6,8-Dichloro-3-[(S)-1-(4-hydroxy-benzylcarbamoyl)-2-methyl-butylcarbamoyl]-2,3,4,9-tetrahydro-1H-carbazol-3-ylcarbamoyl}-2-methyl-butyl)-carbamic acid benzyl ester | 763.0 | 764.6 |
| 131 | (S)-2-[((R)-3-{(S)-2-[2-(2-Fluoro-phenyl)-acetylamino]-3-methyl-pentanoylamino}-8-trifluoromethyl-2,3,4,9-tetrahydro-1H-carbazole-3-carbonyl)-amino]-3-methyl-pentanoic acid pyridin-4-ylmethyl ester | 751.0 | 752.5 |
| 132 | (R)-2-[((R)-3-{(S)-2-[2-(2-Fluoro-phenyl)-acetylamino]-3-methyl-pentanoylamino}-8-trifluoromethyl-2,3,4,9-tetrahydro-1H-carbazole-3-carbonyl)-amino]-3-methyl-pentanoic acid pyridin-4-ylmethyl ester | 751.0 | 752.5 |
| 133 | 2-[((R)-3-{(S)-2-[2-(2-Fluoro-phenyl)-acetylamino]-3-methyl-pentanoylamino}-8-trifluoromethyl-2,3,4,9-tetrahydro-1H-carbazole-3-carbonyl)-amino]-3-methyl-pentanoic acid 2-dimethylamino-ethyl ester | 732.0 | 732.7 |
| 134 | (S)-2-[((R)-3-{(S)-2-[2-(2-Fluoro-phenyl)-acetylamino]-3-methyl-pentanoylamino}-8-trifluoromethyl-2,3,4,9-tetrahydro-1H-carbazole-3-carbonyl)-amino]-3-methyl-pentanoic acid 3-hydroxy-4-methoxy-benzyl ester | 796.0 | 797.6 |
| 135 | (R)-2-[((R)-3-{(S)-2-[2-(2-Fluoro-phenyl)-acetylamino]-3-methyl-pentanoylamino}-8-trifluoromethyl-2,3,4,9-tetrahydro-1H-carbazole-3-carbonyl)-amino]-3-methyl-pentanoic acid 3-hydroxy-4-methoxy-benzyl ester | 796.0 | 797.5 |
| 136 | [(S)-1-((S)-6,8-Dichloro-3-{(S)-2-methyl-1-[(tetrahydro-pyran-4-ylmethyl)-carbamoyl]-butylcarbamoyl}-2,3,4,9-tetrahydro-1H-carbazol-3-ylcarbamoyl)-2-methyl-butyl]-carbamic acid benzyl ester | 755.0 | 756.6 |
| 137 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(quinolin-6-ylcarbamoyl)-butyl]-amide | 786.0 | 787.5 |
| 138 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(R)-2-methyl-1-(quinolin-6-ylcarbamoyl)-butyl]-amide | 786.0 | 787.7 |
| 139 | [(S)-1-((R)-6,8-Dichloro-3-{(S)-2-methyl-1-[(tetrahydro-pyran-4-ylmethyl)-thiocarbamoyl]-butylcarbamoyl}-2,3,4,9-tetrahydro-1H-carbazol-3-ylcarbamoyl)-2-methyl-butyl]-carbamic acid benzyl ester | 771.0 | 772.6 |
| 140 | ((S)-1-{(R)-6,8-Dichloro-3-[(S)-1-(4-hydroxy-3-methoxy-phenylcarbamoyl)-2-methyl-butylcarbamoyl]-2,3,4,9-tetrahydro-1H-carbazol-3-ylcarbamoyl}-2-methyl-butyl)-carbamic acid benzyl ester | 779.0 | 780.7 |
| 141 | ((S)-1-{(S)-6,8-Dichloro-3-[(S)-1-(4-hydroxy-3-methoxy-phenylcarbamoyl)-2-methyl-butylcarbamoyl]-2,3,4,9-tetrahydro-1H-carbazol-3-ylcarbamoyl}-2-methyl-butyl)-carbamic acid benzyl ester | 779.0 | 780.6 |
| 143 | [(S)-1-((R)-6,8-Dichloro-3-{(S)-2-methyl-1-[(tetrahydro-pyran-4-ylmethyl)-carbamoyl]-butylcarbamoyl}-2,3,4,9-tetrahydro-1H-carbazol-3-ylcarbamoyl)-2-methyl-butyl]-carbamic acid benzyl ester | 755.0 | 756.7 |
| 144 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(N'-phenyl-hydrazinocarbonyl)-butyl]-amide | 750.0 | 751.6 |
| 145 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid ((S)-3-methylsulfanyl-1-thiocarbamoyl-propyl)-amide | 693.0 | 694.4 |
| 146 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(quinolin-5-ylcarbamoyl)-butyl]-amide | 786.0 | 787.6 |
| 147 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(isoquinolin-5-ylcarbamoyl)-2-methyl-butyl]-amide | 786.0 | 787.6 |
| 148 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(2-tetrahydro-pyran-4-yl-acetylamino)-methyl]-butyl}-amide | 771.0 | 772.8 |
| 149 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid ((S)-2-methyl-1-{[(tetrahydro-pyran-4-carbonyl)-amino]-methyl}-butyl)-amide | 757.0 | 758.7 |
| 152 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[3-(tetrahydro-pyran-4-ylmethyl)-ureidomethyl]-butyl}-amide | 786.0 | 787.4 |

TABLE 2-continued

Further exemplary embodiments with MS data

| Compound | Name (Autonom) | Mass (calc.) | Mass (found) |
|---|---|---|---|
| 153 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(2-tetrahydro-pyran-4-yl-acetylamino)-butyl]-amide | 757.0 | 758.3 |
| 157 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(R)-2-methyl-1-[3-(tetrahydro-pyran-4-ylmethyl)-ureido]-butyl}-amide | 772.0 | |
| 158 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid ((R)-2-methyl-1-{[(tetrahydro-pyran-4-ylmethyl)-carbamoyl]-methyl}-butyl)-amide | 771.0 | 772.6 |
| 160 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[N'-(4-methoxy-phenyl)-hydrazinocarbonyl]-2-methyl-butyl}-amide | 780.0 | |
| 163 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(N'-acetyl-hydrazinocarbonyl)-2-methyl-butyl]-amide | 716.0 | |
| 164 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(N'-aminocarbonyl-hydrazinocarbonyl)-2-methyl-butyl]-amide | 717.0 | |
| 165 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[N'-(4-hydroxy-benzoyl)-hydrazinocarbonyl]-2-methyl-butyl}-amide | 794.0 | |
| 166 | (R)-3-{(S)-2-[2-(2-Fluoro-phenyl)-acetylamino]-3-methyl-pentanoylamino}-8-trifluormethyl-2,3,4,9-tetrahydro-1H-carbazole-3-carboxylic acid [(S)-1-(acetylamino-methyl)-2-methyl-butyl]-amide | 687.0 | 688.5 |
| 167 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[(3-ethyl-ureido)-methyl]-2-methyl-butyl}-amide | 716.0 | 717.6 |
| 168 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(2-imidazol-1-yl-ethylcarbamoyl)-2-methyl-butyl]-amide | 753.0 | 754.6 |
| 169 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(pyrazin-2-ylmethyl)-carbamoyl]-butyl}-amide | 751.0 | 752.6 |
| 170 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid ((1S,2S)-1-acetylamino-2-methyl-butyl)-amide | 673.0 | 674.4 |
| 171 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(isoquinolin-8-ylcarbamoyl)-2-methyl-butyl]-amide | 786.0 | 787.6 |
| 172 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[3-(3-hydroxy-propyl)-ureidomethyl]-2-methyl-butyl}-amide | 746.0 | 747.9 |
| 173 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[(3-ethyl-thioureido)-methyl]-2-methyl-butyl}-amide | 732.0 | 733.7 |
| 174 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(3-pyridin-4-yl-ureido)-methyl]-butyl}-amide | 765.0 | 766.6 |
| 175 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[3-(1H-tetrazol-5-yl)-propylcarbamoyl]-butyl}-amide | 769.0 | 770.3 |
| 176 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(1H-tetrazol-5-ylmethyl)-carbamoyl]-butyl}-amide | 741.0 | 742.6 |
| 177 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[(2-tert-butyl-2H-tetrazol-5-ylmethyl)-carbamoyl]-2-methyl-butyl}-amide | 797.0 | 798.5 |
| 178 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(2-tert-butyl-2H-tetrazol-5-ylcarbamoyl)-2-methyl-butyl]-amide | 783.0 | 784.4 |
| 179 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(1-tert-butyl-1H-tetrazol-5-ylcarbamoyl)-2-methyl-butyl]-amide | 783.0 | 784.5 |
| 180 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(2-pyridin-4-yl-acetylamino)-methyl]-butyl}-amide | 764.0 | 765.6 |
| 181 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[2-(1-methyl-1H-tetrazol-5-ylsulfanyl)-ethylcarbamoyl]-butyl}-amide | 801.0 | 802.3 |
| 182 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(1S,2S)-2-methyl-1-(2-pyridin-4-yl-acetylamino)-butyl]-amide | 750.0 | 751.6 |

TABLE 2-continued

Further exemplary embodiments with MS data

| Compound | Name (Autonom) | Mass (calc.). | Mass (found) |
|---|---|---|---|
| 183 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid (S)-2-methyl-1-[(pyrimidin-5-ylmethyl)-carbamoyl]-butyl}-amide | 751.0 | 752.4 |
| 184 | | 865.0 | 866.5 |
| 185 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(2-tetrazol-1-yl-ethylcarbamoyl)-butyl]-amide | 755.0 | 756.6 |
| 186 | {(S)-2-[((R)-3-{(S)-2-[2-(2-Fluoro-phenyl)-acetylamino]-3-methyl-pentanoylamino}-8-trifluoromethyl-2,3,4,9-tetrahydro-1H-carbazole-3-carbonyl)-amino]-3-methyl-pentyl}-carbamic acid tetrahydro-pyran-4-yl ester | 773.0 | 774.4 |
| 187 | {(S)-2-[((R)-3-{(S)-2-[2-(2-Fluoro-phenyl)-acetylamino]-3-methyl-pentanoylamino}-8-trifluoromethyl-2,3,4,9-tetrahydro-1H-carbazole-3-carbonyl)-amino]-3-methyl-pentyl}-carbamic acid methyl ester | 703.0 | 704.4 |
| 188 | 1-tert-butyl-4-(3-{(S)-2-[((R)-3-{(S)-2-[2-(2-fluoro-phenyl)-acetylamino]-3-methyl-pentanoylamino}-8-trifluoromethyl-2,3,4,9-tetrahydro-1H-carbazole-3-carbonyl)-amino]-3-methyl-pentanoylamino}-propyl)-4H-tetrazol-1-ium; Trifluoro-acetate | 826.0 | 826.4 |
| 189 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(3-tetrazol-1-yl-propylcarbamoyl)-butyl]-amide | 769.0 | 770.2 |
| 190 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(3-pyridin-4-ylmethyl-ureidomethyl)-butyl]-amide | 779.0 | 780.6 |
| 191 | | 972.0 | 973.5 |
| 192 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(1H-tetrazol-5-ylcarbamoyl)-butyl]-amide | 727.0 | 728.3 |
| 193 | (R)-3-{(S)-2-[(Bicyclo[4.2.0]octa-1(6),2,4-triene-7-carbonyl)-amino]-3-methyl-pentanoylamino}-8-trifluoromethyl-2,3,4,9-tetrahydro-1H-carbazole-3-carboxylic acid ((S)-2-methyl-1-thiocarbamoyl-butyl)-amide | 669.0 | 670.4 |
| 194 | (R)-3-{(S)-2-[2-(2-Chloro-phenyl)-acetylamino]-3-methyl-pentanoylamino}-8-trifluoromethyl-2,3,4,9-tetrahydro-1H-carbazole-3-carboxylic acid ((S)-2-methyl-1-thiocarbamoyl-butyl)-amide | 691.0 | 692.4 |
| 195 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(4-tetrazol-1-yl-butylcarbamoyl)-butyl]-amide | 783.0 | 784.4 |
| 196 | (R)-3-((S)-3-Methyl-2-phenylacetylamino-pentanoylamino)-8-trifluoromethyl-2,3,4,9-tetrahydro-1H-carbazole-3-carboxylic acid ((S)-2-methyl-1-thiocarbamoyl-butyl)-amide | 657.0 | 658.3 |
| 197 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid ((S)-2-methyl-1-{[(morpholine-4-carbonyl)-amino]-methyl}-butyl)-amide | 758.0 | 759.4 |
| 198 | R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid ((S)-2-methyl-1-{[3-(tetrahydro-pyran-4-yl)-ureido]-methyl}-butyl)-amide | 772.0 | 773.4 |
| 199 | (R)-3-{(S)-3-Methyl-2-[2-(2-trifluoromethyl-phenyl)-acetylamino]-pentanoylamino}-8-trifluoromethyl-2,3,4,9-tetrahydro-1H-carbazole-3-carboxylic acid ((S)-2-methyl-1-thiocarbamoyl-butyl)-amide | 725.0 | 726.5 |
| 200 | (R)-3-[(S)-3-Methyl-2-(2-methyl-2-phenyl-propionylamino)-pentanoylamino]-8-trifluoromethyl-2,3,4,9-tetrahydro-1H-carbazole-3-carboxylic acid ((S)-2-methyl-1-thiocarbamoyl-butyl)-amide | 685.0 | 686.5 |
| 201 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[3-(2-pyridin-4-yl-ethyl)-ureidomethyl]-butyl}-amide | 793.0 | 794.4 |
| 202 | (R)-3-[(S)-3-Methyl-2-((S)-2-phenyl-propionylamino)-pentanoylamino]-8-trifluoromethyl-2,3,4,9-tetrahydro-1H-carbazole-3-carboxylic acid ((S)-2-methyl-1-thiocarbamoyl-butyl)-amide | 671.0 | 672.3 |
| 203 | (R)-3-[(S)-3-Methyl-2-((R)-2-phenyl-propionylamino)-pentanoylamino]-8-trifluoromethyl-2,3,4,9-tetrahydro-1H-carbazole-3-carboxylic acid ((S)-2-methyl-1-thiocarbamoyl-butyl)-amide | 671.0 | 672.4 |
| 204 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(methanesulfonylamino-methyl)-2-methyl-butyl]-amide | 723.0 | 724.3 |
| 205 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(3-pyridin-4-ylmethyl-thioureidomethyl)-butyl]-amide | 795.0 | 796.6 |
| 206 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[3-(tetrahydro-pyran-4-ylmethyl)-thioureidomethyl]-butyl}-amide | 802.0 | 803.3 |
| 207 | (R)-3-[(S)-3-Methyl-2-((R)-2-phenyl-butyrylamino)-pentanoylamino]-8-trifluoromethyl-2,3,4,9-tetrahydro-1H-carbazole-3-carboxylic acid ((S)-2-methyl-1-thiocarbamoyl-butyl)-amide | 685.0 | 686.4 |
| 208 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid ((S)-2-methyl-1-{3-[2-(tetrahydro-pyran-4-yl)-ethyl]-ureidomethyl}-butyl)-amide | 800.0 | 801.3 |
| 209 | R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[3-(2-morpholin-4-yl-ethyl)-ureidomethyl]-butyl}-amide | 801.0 | 802.3 |

TABLE 2-continued

Further exemplary embodiments with MS data

| Compound | Name (Autonom) | Mass (calc.) | Mass (found) |
|---|---|---|---|
| 210 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid ((S)-1-benzylthiocarbamoyl-2-methyl-butyl)-amide | 765.0 | 766.3 |
| 211 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(3-hydroxy-propylcarbamoyl)-2-methyl-butyl]-amide | 717.0 | 718.3 |
| 212 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid ((S)-2-oxo-azepan-3-yl)-amide | 657.0 | 658.3 |
| 213 | (R)-3-{(S)-2-[2-(2-Fluoro-phenyl)-acetylamino]-4-methylsulfanyl-butyrylamino}-8-trifluoromethyl-2,3,4,9-tetrahydro-1H-carbazole-3-carboxylic acid ((S)-2-methyl-1-thiocarbamoyl-butyl)-amide | 693.0 | 694.5 |
| 214 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid ((R)-1-carbamoyl-2-methylsulfanyl-ethyl)-amide | 663.0 | 664.4 |
| 215 | (R)-3-{(R)-2-[2-(2-Fluoro-phenyl)-acetylamino]-3-methylsulfanyl-propionylamino}-8-trifluoromethyl-2,3,4,9-tetrahydro-1H-carbazole-3-carboxylic acid ((S)-2-methyl-1-thiocarbamoyl-butyl)-amide | 679.0 | 680.4 |
| 216 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[(2-methoxy-pyridin-4-ylmethyl)-thiocarbamoyl]-2-methyl-butyl}-amide | 796.0 | 797.6 |
| 217 | (R)-3-{(R)-2-[2-(2-Fluoro-phenyl)-acetylamino]-3-thiophen-2-yl-propionylamino}-8-trifluoromethyl-2,3,4,9-tetrahydro-1H-carbazole-3-carboxylic acid ((S)-2-methyl-1-thiocarbamoyl-butyl)-amide | 715.0 | 716.5 |
| 218 | (R)-3-((S)-2-{[2-(2-Fluoro-phenyl)-acetyl]-methyl-amino}-3-methyl-pentanoylamino)-8-trifluoromethyl-2,3,4,9-tetrahydro-1H-carbazole-3-carboxylic acid ((S)-2-methyl-1-thiocarbamoyl-butyl)-amide | 689.0 | 690.6 |
| 219 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(morpholin-4-ylcarbamoyl)-butyl]-amide | 744.0 | 745.8 |
| 220 | (R)-3-((S)-2-{[2-(2-Fluoro-phenyl)-acetyl]-methyl-amino}-3-methyl-pentanoylamino)-8-trifluoromethyl-2,3,4,9-tetrahydro-1H-carbazole-3-carboxylic acid ((S)-1-carbamoyl-2-methyl-butyl)-amide | 673.0 | 674.7 |
| 221 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(piperidin-1-ylcarbamoyl)-butyl]-amide | 742.0 | 743.3 |
| 222 | (R)-3-{(S)-2-[3-(2-Fluoro-phenyl)-ureido]-3-methyl-pentanoylamino}-8-trifluoromethyl-2,3,4,9-tetrahydro-1H-carbazole-3-carboxylic acid ((S)-2-methyl-1-thiocarbamoyl-butyl)-amide | 676.0 | 677.5 |
| 223 | (R)-3-{(S)-2-[3-(2-Fluoro-benzyl)-ureido]-3-methyl-pentanoylamino}-8-trifluoromethyl-2,3,4,9-tetrahydro-1H-carbazole-3-carboxylic acid ((S)-2-methyl-1-thiocarbamoyl-butyl)-amide | 690.0 | 691.8 |
| 224 | Carbonic acid 4-{(S)-2-[((R)-3-{(S)-2-[2-(2-fluoro-phenyl)-acetylamino]-3-methyl-pentanoylamino}-8-trifluoromethyl-2,3,4,9-tetrahydro-1H-carbazole-3-carbonyl)-amino]-3-methyl-pentanoylamino}-butyl ester 2-[2-(2-methoxy-ethoxy)-ethoxy]-ethyl ester | 921.0 | 922.6 |
| 225 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(N'-methyl-N'-phenyl-hydrazinocarbonyl)-butyl]-amide | 764.0 | 765.6 |
| 226 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[N'-(4-fluoro-benzoyl)-hydrazinocarbonyl]-2-methyl-butyl}-amide | 796.0 | 797.6 |
| 227 | (R)-3-((S)-2-{[1-(2-Fluoro-phenyl)-cyclopentanecarbonyl]-amino}-3-methyl-pentanoylamino)-8-trifluoromethyl-2,3,4,9-tetrahydro-1H-carbazole-3-carboxylic acid ((S)-2-methyl-1-thiocarbamoyl-butyl)-amide | 729.0 | 730.6 |
| 228 | R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[N'-(2,4-difluoro-phenyl)-hydrazinocarbonyl]-2-methyl-butyl}-amide | 786.0 | 787.6 |
| 229 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid ((S)-2-methyl-1-phenoxycarbamoyl-butyl)-amide | 751.0 | 752.6 |
| 230 | (R)-3-[(S)-3-Methyl-2-(2-pyridin-3-yl-acetylamino)-pentanoylamino]-8-trifluoromethyl-2,3,4,9-tetrahydro-1H-carbazole-3-carboxylic acid ((S)-2-methyl-1-thiocarbamoyl-butyl)-amide | 658.0 | 659.5 |
| 231 | (R)-3-[(S)-3-Methyl-2-(2-pyridin-2-yl-acetylamino)-pentanoylamino]-8-trifluoromethyl-2,3,4,9-tetrahydro-1H-carbazole-3-carboxylic acid ((S)-2-methyl-1-thiocarbamoyl-butyl)-amide | 658.0 | 659.5 |
| 232 | 3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[N'-(pyridine-4-carbonyl)-hydrazinocarbonyl]-butyl}-amide | 779.0 | 780.5 |
| 233 | | 793.0 | 794.7 |
| 234 | 3-{(S)-2-[3-(4-Fluoro-benzyl)-ureido]-3-methyl-pentanoylamino}-8-trifluoromethyl-2,3,4,9-tetrahydro-1H-carbazole-3-carboxylic acid ((S)-2-methyl-1-thiocarbamoyl-butyl)-amide | 690.0 | 691.5 |
| 235 | 3-{(S)-2-[3-(3-Fluoro-benzyl)-ureido]-3-methyl-pentanoylamino}-8-trifluoromethyl-2,3,4,9-tetrahydro-1H-carbazole-3-carboxylic acid ((S)-2-methyl-1-thiocarbamoyl-butyl)-amide | 690.0 | 691.6 |
| 236 | (R)-3-[(S)-3-Methyl-2-(2-pyridin-4-yl-acetylamino)-pentanoylamino]-8-trifluoromethyl-2,3,4,9-tetrahydro-1H-carbazole-3-carboxylic acid ((S)-2-methyl-1-thiocarbamoyl-butyl)-amide | 658.0 | 659.6 |

TABLE 2-continued

Further exemplary embodiments with MS data

| Compound | Name (Autonom) | Mass (calc.). | Mass (found) |
|---|---|---|---|
| 237 | (R)-3-{(S)-3-Methyl-2-[3-(3-methyl-benzyl)-ureido]-pentanoylamino}-8-trifluoromethyl-2,3,4,9-tetrahydro-1H-carbazole-3-carboxylic acid ((S)-2-methyl-1-thiocarbamoyl-butyl)-amide | 686.0 | 687.6 |
| 238 | (R)-3-{(S)-3-Methyl-2-[3-(4-methyl-benzyl)-ureido]-pentanoylamino}-8-trifluoromethyl-2,3,4,9-tetrahydro-1H-carbazole-3-carboxylic acid ((S)-2-methyl-1-thiocarbamoyl-butyl)-amide | 686.0 | 687.5 |
| 239 | (R)-3-{(S)-2-[3-(4-Methoxy-benzyl)-ureido]-3-methyl-pentanoylamino}-8-trifluoromethyl-2,3,4,9-tetrahydro-1H-carbazole-3-carboxylic acid ((S)-2-methyl-1-thiocarbamoyl-butyl)-amide | 702.0 | 703.5 |
| 240 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[N'-(3-methoxy-benzoyl)-hydrazinocarbonyl]-2-methyl-butyl}-amid | 808.0 | 809.6 |
| 241 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[N'-(furan-2-carbonyl)-hydrazinocarbonyl]-2-methyl-butyl}-amide | 768.0 | 769.4 |
| 242 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(N'-benzoyl-hydrazinocarbonyl)-2-methyl-butyl]-amide | 778.0 | 779.7 |
| 243 | (R)-3-{(S)-2-[2-(2-Fluoro-phenyl)-2-hydroxy-acetylamino]-3-methyl-pentanoylamino}-8-trifluoromethyl-2,3,4,9-tetrahydro-1H-carbazole-3-carboxylic acid ((S)-2-methyl-1-thiocarbamoyl-butyl)-amide | 691.0 | 692.5 |
| 244 | (R)-3-{(S)-2-[3-(2-Fluoro-benzyl)-ureido]-3-methyl-pentanoylamino}-8-trifluoromethyl-2,3,4,9-tetrahydro-1H-carbazole-3-carboxylic acid [(S)-2-methyl-1-(N'-phenyl-hydrazinocarbonyl)-butyl]-amide | 765.0 | 766.4 |
| 245 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(N'-pyridin-2-yl-hydrazinocarbonyl)-butyl]-amide | 751.0 | 752.2 |
| 246 | (R)-3-[(S)-3-Methyl-2-(2-oxo-2-phenyl-acetylamino)-pentanoylamino]-8-trifluoromethyl-2,3,4,9-tetrahydro-1H-carbazole-3-carboxylic acid ((S)-2-methyl-1-thiocarbamoyl-butyl)-amide | 671.0 | 672.4 |
| 247 | {(S)-2-Methyl-1-[(R)-3-((S)-2-methyl-1-thiocarbamoyl-butylcarbamoyl)-8-trifluoromethyl-2,3,4,9-tetrahydro-1H-carbazol-3-ylcarbamoyl]-butyl}-carbamic acid benzyl ester | 673.0 | 674.4 |
| 248 | (R)-3-{(S)-2-[3-(3-Methoxy-benzyl)-ureido]-3-methyl-pentanoylamino}-8-trifluoromethyl-2,3,4,9-tetrahydro-1H-carbazole-3-carboxylic acid ((S)-2-methyl-1-thiocarbamoyl-butyl)-amide | 702.0 | 703.6 |
| 249 | (R)-3-{(2S,3S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(1S,2S)-2-methyl-1-(4-phenyl-thiazol-2-yl)-butyl]-amide | 775.0 | 776.2 |
| 250 | (R)-3-{(2S,3S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(1S,2S)-1-[4-(4-methoxy-phenyl)-thiazol-2-yl]-2-methyl-butyl}-ami | 805.0 | 806.3 |
| 251 | 2-{(1R,2S)-1-[((R)-3-{(2S,3S)-2-[2-(2-Fluoro-phenyl)-acetylamino]-3-methyl-pentanoylamino}-8-trifluoromethyl-2,3,4,9-tetrahydro-1H-carbazole-3-carbonyl)-amino]-2-methyl-butyl}-thiazole-4-carboxylic acid ethyl ester | 771.0 | 772.2 |
| 252 | (R)-3-{(2S,3S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(1S,2S)-2-methyl-1-(4-trifluoromethyl-thiazol-2-yl)-butyl]-amide | 767.0 | 768.3 |
| 253 | (R)-3-{(2S,3S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(1S,2S)-1-(4-ethyl-thiazol-2-yl)-2-methyl-butyl]-amide | 727.0 | 728.0 |
| 254 | (R)-3-{(2S,3S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(1S,2S)-1-(4-tert-butyl-thiazol-2-yl)-2-methyl-butyl]-amide | 755.0 | 756.2 |
| 255 | (R)-3-{(2S,3S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(1S,2S)-1-(4-hydroxy-4-trifluoromethyl-4,5-dihydro-thiazol-2-yl)-2-methyl-butyl]-amide | 785.0 | 786.3 |
| 256 | 2-{(1S,2S)-1-[((R)-3-{(2S,3S)-2-[2-(2-Fluoro-phenyl)-acetylamino]-3-methyl-pentanoylamino}-8-trifluoromethyl-2,3,4,9-tetrahydro-1H-carbazole-3-carbonyl)-amino]-2-methyl-butyl}-thiazole-4-carboxylic acid | 743.0 | 744.2 |
| 257 | (R)-3-{(S)-2-[3-(3-Methoxy-phenyl)-propionylamino]-3-methyl-pentanoylamino}-8-trifluoromethyl-2,3,4,9-tetrahydro-1H-carbazole-3-carboxylic acid ((S)-2-methyl-1-thiocarbamoyl-butyl)-amide | 701.0 | 702.5 |
| 258 | 2-{(1S,2S)-1-[((R)-3-{(2S,3S)-2-[3-(2-Fluoro-benzyl)-ureido]-3-methyl-pentanoylamino}-8-trifluoromethyl-2,3,4,9-tetrahydro-1H-carbazole-3-carbonyl)-amino]-2-methyl-butyl}-thiazole-4-carboxylic acid ethyl ester | 786.0 | 787.6 |
| 259 | 2-{(1S,2S)-1-[((R)-3-{(2S,3S)-2-[3-(4-Methoxy-benzyl)-ureido]-3-methyl-pentanoylamino}-8-trifluoromethyl-2,3,4,9-tetrahydro-1H-carbazole-3-carbonyl)-amino]-2-methyl-butyl}-thiazole-4-carboxylic acid ethyl ester | 798.0 | 799.3 |
| 260 | 2-{(1S,2S)-1-[((R)-3-{(2S,3S)-2-[3-(4-Methoxy-benzyl)-ureido]-3-methyl-pentanoylamino}-8-trifluoromethyl-2,3,4,9-tetrahydro-1H-carbazole-3-carbonyl)-amino]-2-methyl-butyl}-thiazole-4-carboxylic acid | 770.0 | 771.3 |
| 261 | (R)-3-{(2S,3S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(1S,2S)-1-(4-carbamoyl-thiazol-2-yl)-2-methyl-butyl]-amide | 742.0 | 743.5 |

TABLE 2-continued

Further exemplary embodiments with MS data

| Compound | Name (Autonom) | Mass (calc.). | Mass (found) |
|---|---|---|---|
| 262 | 2-{(1S,2S)-1-[((R)-3-{(2S,3S)-2-[3-(2-Fluoro-benzyl)-thioureido]-3-methyl-pentanoylamino}-8-trifluoromethyl-2,3,4,9-tetrahydro-1H-carbazole-3-carbonyl)-amino]-2-methyl-butyl}-thiazole-4-carboxylic acid ethyl ester | 802.0 | 803.3 |
| 263 | (R)-3-{(2S,3S)-2-[3-(2-Fluoro-benzyl)-thioureido]-3-methyl-pentanoylamino}-8-trifluoromethyl-2,3,4,9-tetrahydro-1H-carbazole-3-carboxylic acid [(1S,2S)-1-(4-carbamoyl-thiazol-2-yl)-2-methyl-butyl]-amide | 773.0 | 774.5 |
| 264 | (R)-3-{(2S,3S)-2-[3-(2-Fluoro-benzyl)-thioureido]-3-methyl-pentanoylamino}-8-trifluoromethyl-2,3,4,9-tetrahydro-1H-carbazole-3-carboxylic acid ((1S,2S)-2-methyl-1-thiocarbamoyl-butyl)-amide | 706.0 | 707.3 |
| 265 | (R)-3-{(S)-2-[2-(3-Methoxy-phenyl)-acetylamino]-3-methyl-pentanoylamino}-8-trifluoromethyl-2,3,4,9-tetrahydro-1H-carbazole-3-carboxylic acid ((S)-2-methyl-1-thiocarbamoyl-butyl)-amide | 687.0 | 688.5 |
| 266 | (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(tetrahydro-thiopyran-4-ylmethyl)-carbamoyl]-butyl}-amide | 773.0 | 774.5 |

The presented embodiments were synthesized according to the following, well known, general reaction scheme:

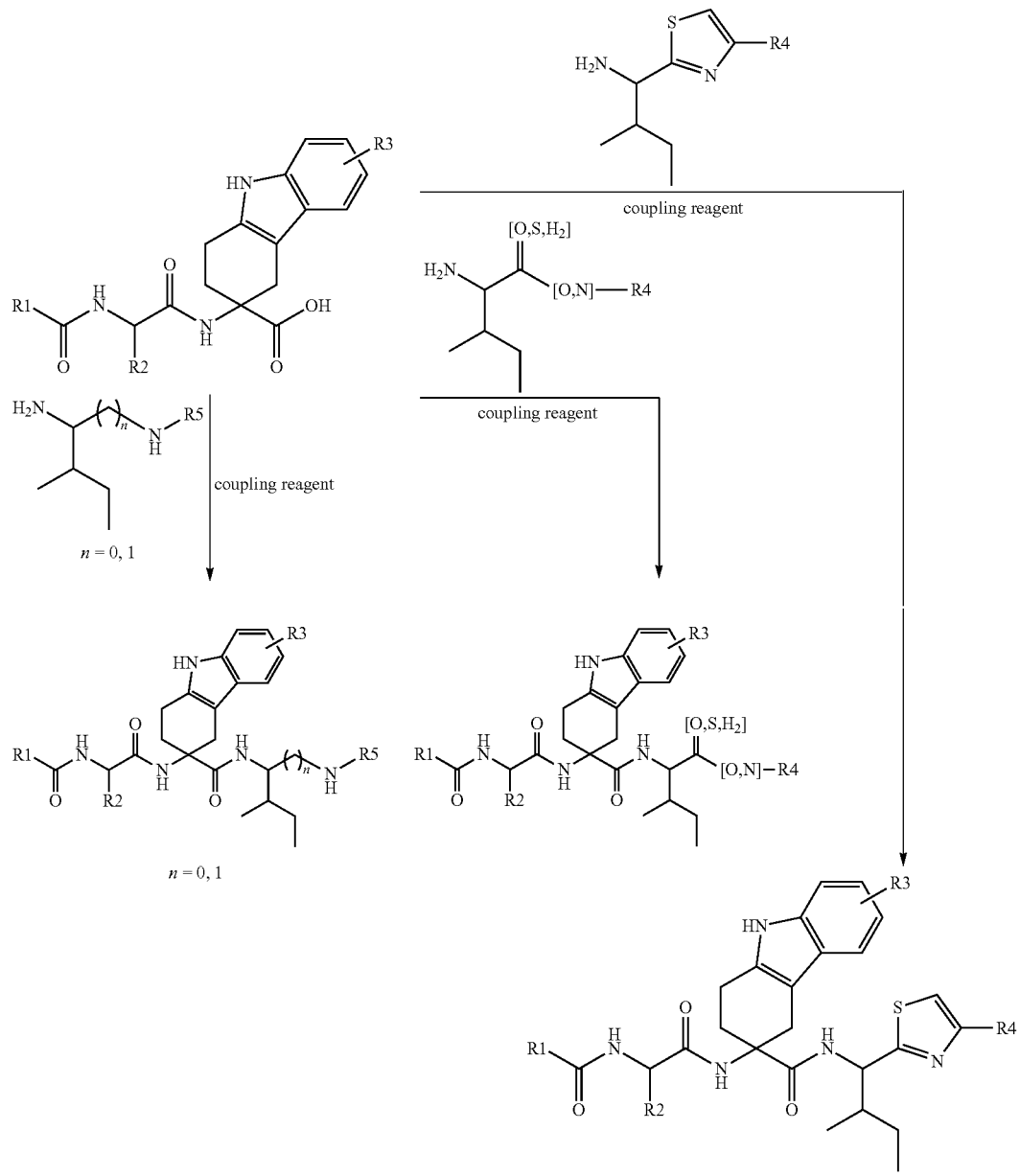

The definition of the R radicals shown in the above reaction scheme and further herein disclosed general reaction schemes corresponds to the substituents (e.g. R radicals) defined above in connection with the general formula (I) and preferred subsets/embodiments. For the avoidance of doubt, the R radicals shown in the above reaction scheme and further herein disclosed general reaction schemes can be identical, but do not need to be identical with the substituents (e.g. R radicals) defined above in connection with the general formula (I) and preferred subsets/embodiments. The individual assignment can be accomplished in a simple manner by the person skilled in the art on the basis of his or her average technical knowledge.

The building blocks (intermediates) were synthesized from commercially available starting materials in analogy to well known literature procedures.

Amino acids with thiazole-C-termini were synthesized according to D. F. W. Cross et al. (*J. Chem. Soc.* 1963, 2143-2150) or R. Houssin et al. (*J. Org. Chem.* 1985, 50, 2787-2788) from the corresponding amino acid thioamide and alpha-halogen ketone derivatives.

Hydrazide or substituted thioamide building blocks were synthesized from commercially available starting materials in analogy to well known literature procedures outlined in the following reaction schemes:

preferred subsets/embodiments. The individual assignment can be accomplished in a simple manner by the person skilled in the art on the basis of his or her average technical knowledge.

Synthesis of ester derivatized building blocks from protected amino acids and alcohols in analogy to well known standard procedures:

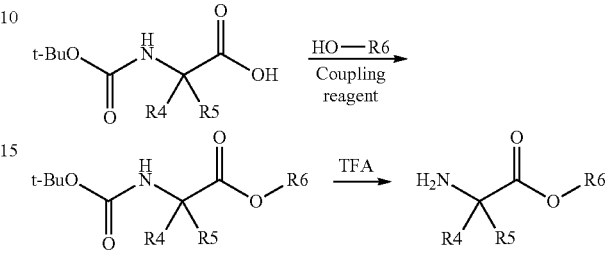

The definition of the R radicals shown in the above reaction scheme and further herein disclosed general reaction schemes corresponds to the substituents (e.g. R radicals) defined above in connection with the general formula (I) and preferred subsets/embodiments. For the avoidance of doubt, the R radicals shown in the above reaction scheme and further herein disclosed general reaction schemes can be identical, but do not

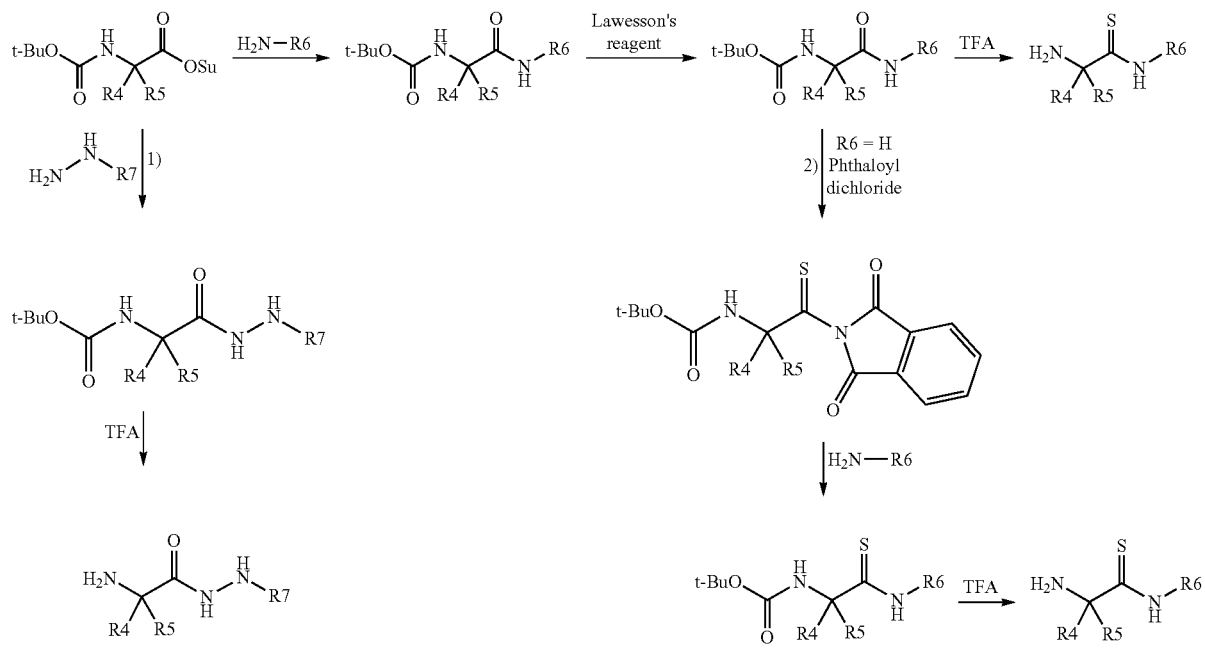

1) U.S. Pat. No. 2,908,688 (Hoffmann-La Roche 1958).
Ekegren et al *J. Med. Chem.* 2006; 1828-1832.
2) Brain et al: *J. Org Chem.* 1997, 62: 3808.

The definition of the R radicals shown in the above reaction scheme and further herein disclosed general reaction schemes corresponds to the substituents (e.g. R radicals) defined above in connection with the general formula (I) and preferred subsets/embodiments. For the avoidance of doubt, the R radicals shown in the above reaction scheme and further herein disclosed general reaction schemes can be identical, but do not need to be identical with the substituents (e.g. R radicals) defined above in connection with the general formula (I) and need to be identical with the substituents (e.g. R radicals) defined above in connection with the general formula (I) and preferred subsets/embodiments. The individual assignment can be accomplished in a simple manner by the person skilled in the art on the basis of his or her average technical knowledge.

Synthesis of diamino building blocks from protected amides in analogy to well known standard procedures:

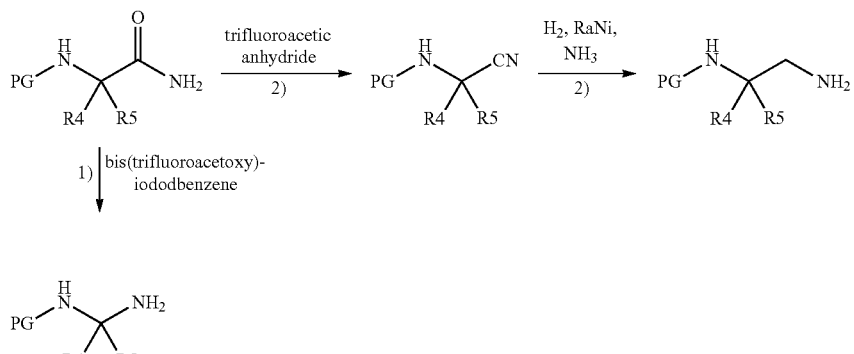

1) a. Louden et al. *J. Org. Chem.* 1984, 42: 4272.
   b. Guerlavais et al. *J. Med. Chem.* 2003, 46: 1191.
2) Boeijen et al. *Eur. J. Org. Chem.* 1999: 2127.

The definition of the R radicals shown in the above reaction scheme and further herein disclosed general reaction schemes corresponds to the substituents (e.g. R radicals) defined above in connection with the general formula (I) and preferred subsets/embodiments. For the avoidance of doubt, the R radicals shown in the above reaction scheme and further herein disclosed general reaction schemes can be identical, but do not need to be identical with the substituents (e.g. R radicals) defined above in connection with the general formula (I) and preferred subsets/embodiments. The individual assignment can be accomplished in a simple manner by the person skilled in the art on the basis of his or her average technical knowledge.

These diamino building blocks were further modified according to well known standard procedures:

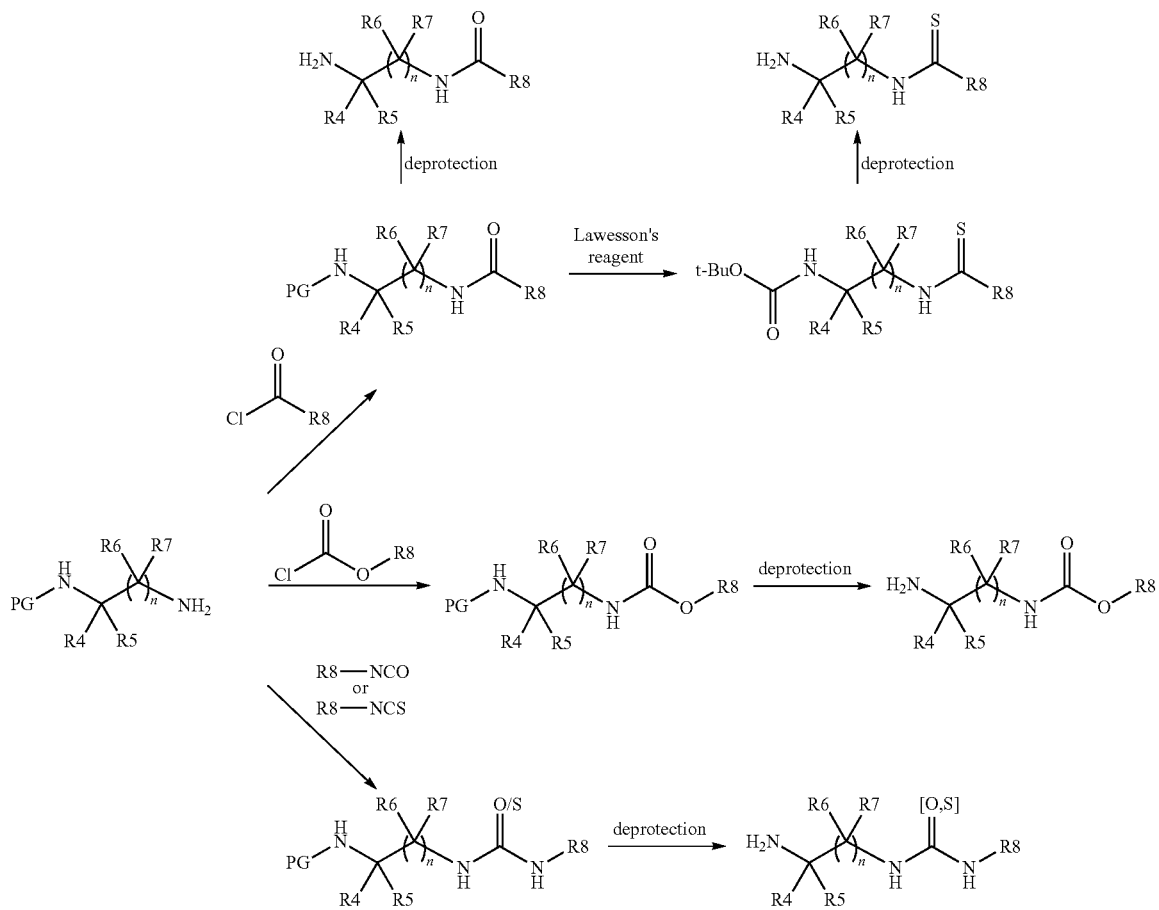

$n = 0, 1$
PG = Protecting group

Compound 62

(R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid ((S)-2-methyl-1-{[(tetrahydro-pyran-4-ylmethyl)-amino]-methyl}-butyl)-amide 0.050 g (0.06 mmol) of (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(tetrahydro-pyran-4-ylmethyl)-thibcarbamoyl]-butyl}-amide were dissolved in 7 mL of THF/Methanol (1:1). 0.123 g (0.52 mmol) of nickel(ll)chloride hexahydrate were added at room temperature. The mixture was stirred for 10 min at this temperature. At 0° C. 0.059 g (1.55 mmol) sodium borhydrate were added. Stirring was continued for 18 h at room temperature. The mixture was filtered over silica gel and the silica gel layer was washed with MeOH. The filtrate and washes were combined, concentrated and the residue purified by HPLC.

Yield: 0.030 g (62% of theory).

$^1$H-NMR (DMSO-d$_6$, 600 MHz): δ=11.08 (s, 1H); 8.26 (bs, 1H); 7.72 (bs, 1H); 7.58 (d, 1H); 7.34 (d, 1H); 7.21-7.31 (m, 2H); 7.05-7.14 (m, 4H); 3.94 (t, 1H); 3.75-3.86 (m, 3H); 3.56 (d, 1H); 3.37-3.46 (m, 2H); 3.01-3.13 (m, 2H); 2.82 (d, 2H); 2.70 (m, 1H); 2.14 (m, 1H); 1.57-1.70 (m, 3H); 1.27-1.42 (m, 3H); 1.13-1.20 (m, 2H); 1.01 (sept, 2H); 0.79 (t, 3H); 0.74 (d, 3H); 0.72 (d, 3H); 0.69 (t, 3H) ppm.

ESI-MS: found: 744.6 (M+H$^+$). calculated: 743 g/mol.

According to the procedure described for the synthesis of compound 62, the following compound was also prepared:

Compound 66

(R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(2-morpholin-4-yl-ethylamino)-methyl]-butyl}-amide $^1$H-NMR (DMSO-d$_6$, 600 MHz): δ=11.11 (s, 1H); 8.37 (d, 2H); 7.99 (s, 1H); 7.58 (d, 2H); 7.35 (d, 2H); 7.28-7.32 (m, 2H); 7.24 (d, 2H); 7.13-7.17 (m, 2H); 7.11 (t, 1H); 3.91-4.00 (m, 3H); 3.63 (d, 1H); 3.54 (d, 1H); 3.15-3.23 (m, 2H); 3.03 (t, 1H); 2.92 (t, 2H); 2.81 (bs, 1H); 2.12 (m, 1H); 1.64 (m, 1H); 1.23-1.43 (m, 4H); 1.03 (m, 1H); 0.79 (t, 3H); 0.76 (d, 3H); 0.70-0.73 (m, 6H) ppm.

ESI-MS: found: 759.5 (M+H$^+$). calculated: 758 g/mol.

Compound 78

((S)-1-{(R)-6,8-Dichloro-3-[(S)-3-methyl-1-(1H-tetrazol-5-yl)-butylcarbamoyl]-2,3,4,9-tetrahydro-1H-carbazol-3-ylcarbamoyl}-2-methyl-butyl)-carbamic acid benzyl ester 0.122 g (0.19 mmol) of {(5)-1-[(R)-6,8-Dichloro-3-((S)-1-cyano-3-methyl-butylcarbamoyl)-2,3,4,9-tetrahydro-1H-carbazol-3-ylcarbamoyl]-2-methyl-butyl}-carbamic acid benzyl ester synthesized according to 84 (see below), 0.028 g (0.44 mmol) of sodium azide and 0.026 (0.48 mmol) of ammonium chloride were heated in 2 mL of DMF in a microwave at 110° C. and 100 watt for 6 h. The reaction solution was separated on a preparative HPLC column.

Yield: 0.035 g (26% of theory).

$^1$H-NMR (DMSO-d$_6$, 600 MHz): δ=15.98 (bs, 1H); 11.35 (s, 1H); 7.88 (bs, 1H); 7.85 (s, 1H); 7.38 (s, 1H); 7.26 (d, 2H); 7.29-7.35 (m, 4H); 7.15 (s, 1H); 5.29 (q, 1H); 5.03 (d, 1H); 4.83 (d, 1H); 3.81 (t, 1H); 2.98 (d, 1H); 2.86 (d, 1H); 2.79 (dd, 1H); 2.73 (dd, 1H); 2.57 (m, 1H); 2.15 (m, 1H); 1.75-1.84 (m, 2H); 1.57-1.65 (m, 2H); 1.35 (m, 1H); 1.04 (m, 1H); 0.86 (t, 6H); 0.76 (d, 3H); 0.73 (t, 3H) ppm.

ESI-MS: found: 683.6 (M+H$^+$). calculated: 682 g/mol.

Compound 84

(R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid ((S)-1-cyano-2-methyl-butyl)-amide 1.649 g (2.50 mmol) of (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid ((S)-1-carbamoyl-2-methyl-butyl)-amide were dissolved in 10 mL of pyridine. At 0° C. 0.70 mL (5.0 mmol) of trifluoroacetic anhydride were added and the mixture was stirred for 20 h at room temperature. The reaction mixture was concentrated and the residue purified by HPLC Yield: 0.530 g (54% of theory).

$^1$H-NMR (DMSO-d$_6$, 600 MHz): δ=11.12 (s, 1H); 8.24 (d, 1H); 8.20 (d, 1H); 7.95 (s, 1H); 7.68 (d, 1H); 7.34 (d, 1H); 7.26-7.29 (m, 2H); 7.09-7.15 (m, 3H); 4.56 (t, 1H); 4.08 (t, 1H); 3.58 (d, 1H); 3.41 (d, 1H); 3.03 (d, 1H); 3.96 (d; 1H); 2.82 (dd, 1H); 2.70 (dd, 1H); 2.60 (m, 1H); 2.16 (m, 1H); 1.74 (m, 1H); 1.63 (m, 1H); 1.35-1.41 (m, 2H); 0.98-1.12 (m, 3H); 0.91 (d, 3H); 0.77-0.80 (m, 6H); 0.74 (t, 3H) ppm.

ESI-MS: found: 642.4 (M+H$^+$). calculated: 641 g/mol.

II) LHRH-Receptor Binding Assay

For LHRH receptor binding studies, an assay system using alpha T3-1 cell line with endogenous GnRH receptor expression was employed (Windle et al., Mol. Endocrinol. 1990, 4(4): 597-603).

Iodinated cetrorelix was used as a tracer with about 80% of peptide capable of specific receptor association.

For displacement binding assays, the cells were incubated with approximately 200 pM [$^{125}$I] cetrorelix and different concentrations of unlabeled test compounds as competitor. The cell suspension in binding medium was layered on top of silicon/paraffin oil, incubated for 60 min at 37° C. and separated by centrifugation. The tips of the tubes containing the cell pellet were cut off, subsequently cell pellet and supernatant were analyzed by gamma-radiation analysis.

The amount of unspecific binding was determined by including unlabeled cetrorelix at 1 µM final concentration and was typically ≦10% of total binding. $IC_{50}$ values were calculated by using the GraphPad Prism analysis program (GraphPad Software Inc.).

Table 3 shows the receptor binding data (absolute/normalized) of selected compounds of the invention in comparison with pertinent prior art examples.

From the experimental data presented in the table it is evident that the selected compounds of the invention show an up to 529% higher receptor binding affinity compared to the pertinent prior art examples.

TABLE 3

LHRH rezeptor-binding assay - $EC_{50}$ values for selected compounds

| Compounds | $EC_{50}$ [nM] | Normalized Affinity |
|---|---|---|
| compound 52 | 17 | 218% |
| compound 54 (TFA salt) | 15 | 247% |
| compound 60 | 15 | 247% |
| compound 69 | 7 | 529% |
| compound 71 | 9 | 411% |
| compound 74 | 15 | 247% |
| compound 118 | 13 | 285% |
| compound 178 | 10 | 370% |
| WO 2006/005484-substance 75 | 37 | 100% |
| WO 2006/005484-substance 76 | 38 | 97% |
| WO 2006/005484-substance 66 | 39 | 95% |
| WO 2006/005484-substance 67 | 151 | 25% |
| WO 2006/005484-substance 7 | 179 | 21% |

III) Metabolic Stability Testing in Liver Microsomes

Subcellular fractions of different tissues can be prepared easily by ultracentrifugation. Most commonly these are prepared from the liver of animals and human donors to gain information about the potential hepatic clearance of compounds (first-pass elimination of drugs). Human or animal (e.g. dog, mouse, rat) subcellular fraction like liver microsomes, or possibly the fraction called S9 have therefore become a very commonly and widely used as an in vitro model to investigate mainly cytochrome P450 dependent phase I (but also phase II) metabolism that takes place in the liver. As enzymatic activities are stable during a prolonged storage of the microsomes (at −80° C.), microsomes do not need to be freshly prepared and are commercially available.

In order to reflect the standard proportion of the enzymes in human and animal livers, liver microsomes are usually pooled from a number of species of the same sex (or mixed-gender). By supplementing the liver microsomes with relevant cofactors and other components it is possible to investigate and distinguish between CYPs, flavin-containing monooxygenase (FMO) and UDP-glucuronosyltransferase (UGT) activities.

Selected compounds of the invention were tested for their stability in mixed-gender human liver microsomes and compared to pertinent prior art compounds.

Under the test conditions applied (1 mg microsomal protein/mL, initial concentration of 10 µM, and incubation for 60 minutes at 37° C.) the following normalized results were obtained.

Table 4 shows the normalized microsomal stability of selected compounds of the invention in comparison with pertinent prior art examples.

From the experimental data presented in the table it is evident that the selected compounds of the invention show an up to 1948% higher microsomal stability compared to the pertinent prior art examples.

TABLE 4

Normalized microsomal stability for selected compounds

| Compounds | Normalized microsomal stability |
|---|---|
| compound 52 | 178% |
| compound 167 | 274% |
| compound 31 | 276% |
| compound 173 | 285% |
| compound 239 | 307% |
| compound 219 | 452% |
| compound 114 | 537% |
| compound 54 | 611% |
| compound 73 | 624% |
| compound 190 | 665% |
| compound 36 | 774% |
| compound 205 | 800% |
| compound 251 | 1033% |
| compound 69 | 1041% |
| compound 244 | 1096% |
| compound 256 | 1194% |
| compound 258 | 1215% |
| compound 164 | 1230% |
| compound 188 | 1259% |
| compound 137 | 1296% |
| compound 242 | 1322% |
| compound 236 | 1328% |
| compound 183 | 1350% |
| compound 144 | 1352% |
| compound 250 | 1491% |
| compound 249 | 1580% |
| compound 74 | 1889% |
| compound 230 | 1948% |
| WO 2006/005484-substance 7 | 100% |
| WO 2006/005484-substance 68 | 93% |
| WO 2006/005484-substance 76 | 61% |

IV) Pharmacokinetic Study

Adult male Wistar rats weighing 278-290 g (Jinvier, France) were used in the study. Animals were housed in a temperature-controlled room (20-24° C.) and maintained in a 12 h light/12 h dark cycle. Food and water were available ad libitum.

For surgery, rats were anaesthetised with a ketamine (90 mg/kg)/xylazine (10 mg/kg) mixture, and cannulated with silicone tubing via the right jugular vein. Prior to the first blood sampling, animals were connected to a counterbalanced system and tubing to perform blood sampling in the freely moving rat.

Separate stock solutions (5 mg/ml) of compound 52 of the invention and prior art substance WO 2006/005484—substance 76 were prepared in Solutol HS 15/PEG300 (3:1). The whole process was performed under constant stirring. Half of the volume of the vehicle was added first. After sonication (5 minutes), the second half of the vehicle was added and the vials were again sonicated. All the solutions were clear and free of particles or agglomerates.

Immediately before application, the dosing mixture was prepared by adding equal volumes of the stock solutions to end up with a final concentration of 1 mg/ml for each compound. The mixture was applied orally to rats with an application volume of 5 ml/kg.

Blood samples (200 μl) were taken 1 hour before application and 1, 2, 4, 6, 8, 12 and 24 hours after. They were centrifuged at 650 g for 10 minutes at 4° C. and then the plasma was harvested and kept at −20° C. until LC/MS analysis.

The following results displayed in table 5 were obtained. FIG. 1 depicts the area-under-the-curve (AUC) which is indicative for bioavailability of the compounds. As can be seen from table 5 and FIG. 1, compared to the pertinent prior art substance compound 52 of the invention shows a more than 300% higher AUC indicative for a higher bioavailability.

TABLE 5

Results of the pharmacokinetic study

|  | Compound 52 | WO 2006/005484-substance 76 |
|---|---|---|
| Dose (mg/kg) | 5 | 5 |
| Cmax obs (ng/ml) | 38.2 | 12.5 |
| tmax obs (h) | 4.0 | 4.0 |
| AUC0-tz (ng * h/ml) | 305.9 | 96.2 |

V) Testosterone Suppression Experiment

Male Wistar rats weighing 248-296 g (Janvier, France) were used in the present study. Animals were housed in a temperature-controlled room (20-22° C.) and maintained in a 12 h light/12 h dark cycle. Food and water were available ad libitum.

Rats were anaesthetised with a ketamine (135 mg/kg)/xylazine (10 mg/kg) mixture, and cannulated with silicone tubing via the right jugular vein. Prior to the first blood sampling, animals were connected to a counterbalanced system and tubing, to perform blood sampling in the freely moving rat.

The dosing solutions were prepared immediately before application. The po solution was obtained by dissolving the compound 54 (TFA salt) of the invention in Solutol HS15/PEG300 (3:1).

A group of control rats was applied with the po vehicle (5 ml/kg) and the compound 54 of the invention. A baseline of testosterone level was established by two blood samples taken at −1 and 0 h. At time 0 (0 h), the compound was applied and blood samples (200 μl) were taken 1, 2, 4, 6, 8, 12, and 24 h post-dose after po.

The blood samples were collected in heparinized tubes and stored on ice. They were centrifuged at 3000 g (10 min, 4° C.). Plasma was harvested and kept at −20° C. until being assayed.

The concentrations of testosterone in the rat plasma samples were determined using the Testosterone ELISA (EIA-1559) from DRG Instruments according to the manufacturer's instructions. This assay is based on the competition between unlabeled testosterone from the sample and a fixed amount of horse-radish peroxidase conjugated testosterone for the binding sites of a monoclonal testosterone antibody bound to the plate. In detail, 25 μl/well of blank, standards (in duplicate) and samples (in singula) without special pre-treatment were added to the microtiter plate. After 1 h of incubation together with 200 μl/well of enzyme conjugate, the plate was washed 3 times with wash buffer, provided with the kit. For the colour reaction, 200 μl of substrate solution were added to each well. The reaction was stopped after 15 min by adding 100 μl of stop solution (0.5 M $H_2SO_4$) to each well. The plate was read within the next 30 min with a Spectramax Plus (Molecular Devices) at 450 nm. The concentration of testosterone in the samples was calculated from the standard curve and is inversely proportional to the optical density measured.

Due to the pulsatile release of testosterone in intact rats, two pre-treatment samples ere collected to establish baseline values prior the administration of the compound. For data analysis, the pre-treatment time points (−1 and 0 h) were averaged. A paired t-test (SigmaStat software; SPSS; Erkrath, Germany) was performed to determine whether or not the treatment had an effect. This repeated measure procedure is used to test differences of testosterone levels in the same individual before and after treatment. The pre-treatment mean value was compared to the testosterone levels measured after application.

Figure 2:
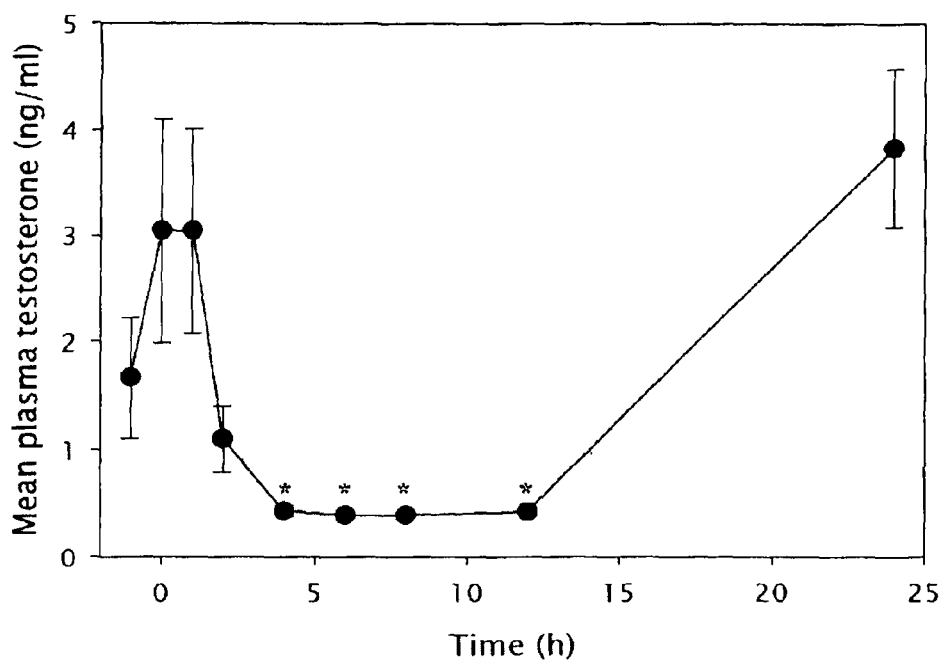
FIG. 2 depicts the mean plasma testosterone concentration (ng/mL) over time upon administration of compound 54 (TFA salt) of the invention.

FIG. 2 shows the achieved testosterone suppression for the administration of compound 54 (TFA salt) of the invention.

The invention claimed is:

1. A method of treating a condition in a subject in need of such treatment, the method comprising administering a therapeutically effective amount of at least one tetrahydrocarbazole to the subject to treat the condition, wherein the condition is a benign tumor disease, a malignant tumor disease, male fertility control, controlled ovarian stimulation in in vitro fertilization (COS/ART), prostate cancer, breast cancer, endometrial cancer, ovarian cancer, benign prostate hyperplasia (BPH), endometriosis, uterine fibroids, uterine myomas, endometrium hyperplasia, pubertas praecox, polycystic ovary syndrome, or a hormone-dependent tumor disease, wherein the at least one tetrahydrocarbozole is selected from the group consisting of:

Compound 31 (S)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[5-(3-ethyl-ureido)-[1,3,4]oxadiazol-2-yl]-2-methyl-butyl}-amide;

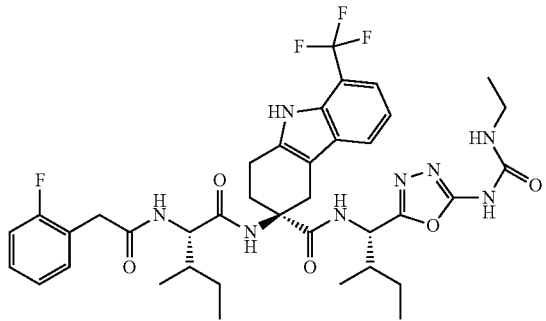 [SMILES: CCNC(=O)Nc1nnc([C@@H](NC(=O)[C@]2(NC(=O)[C@@H](NC(=O)Cc3ccccc3F)C(C)CC)CCc3[nH]c4c(C(F)(F)F)cccc4c3C2)C(C)CC)o1]

Compound 36 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(morpholin-4-ylmethyl)-carbamoyl]-butyl}amide

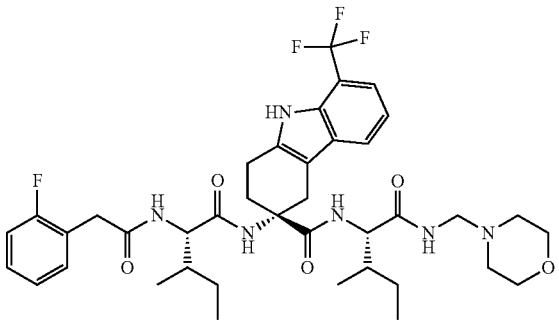 [SMILES: CCC(C)[C@H](NC(=O)Cc1ccccc1F)C(=O)N[C@]1(C(=O)N[C@H](C(=O)NCN2CCOCC2)C(C)CC)CCc2[nH]c3c(C(F)(F)F)cccc3c2C1]

Compound 51 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(2-diethylamino-ethylcarbamoyl)-2-methyl-butyl]-amide;

Compound 60 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(pyridin-4-ylmethyl)-thiocarbamoyl]-butyl}-amide;

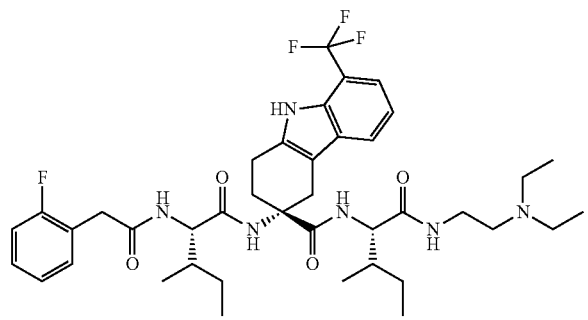 [SMILES: CCC(C)[C@H](NC(=O)Cc1ccccc1F)C(=O)N[C@]1(C(=O)N[C@H](C(=O)NCCN(CC)CC)C(C)CC)CCc2[nH]c3c(C(F)(F)F)cccc3c2C1]

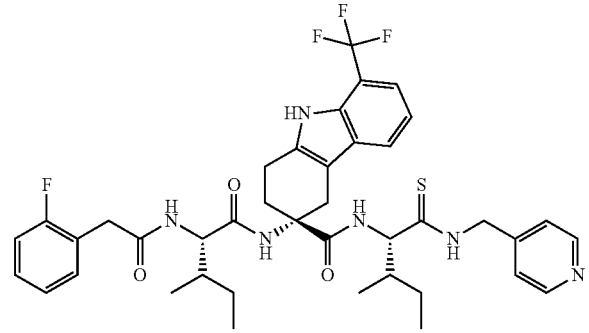

Compound 52 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(tetrahydro-pyran-4-ylmethyl)-thiocarbamoyl]-butyl}-amide;

Compound 69 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(3-hydroxy-4-methoxy-phenylcarbamoyl)-2-methyl-butyl]-amide;

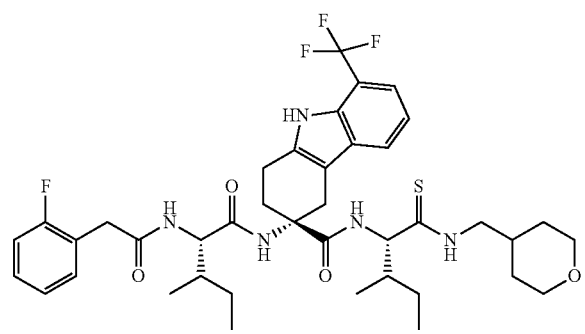 [SMILES: CCC(C)[C@H](NC(=O)Cc1ccccc1F)C(=O)N[C@]1(C(=O)N[C@H](C(=S)NCC2CCOCC2)C(C)CC)CCc2[nH]c3c(C(F)(F)F)cccc3c2C1]

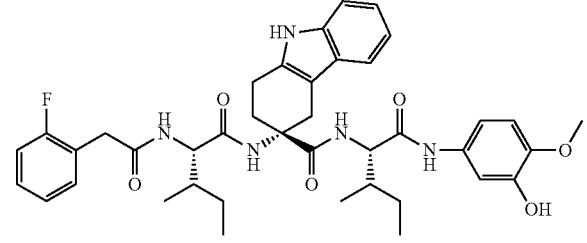

Compound 54 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(2-morpholin-4-yl-ethylthiocarbamoyl)-butyl]-amide;

Compound 71 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(2-hydroxy-4-methoxy-phenylcarbamoyl)-2-methyl-butyl]-amide;

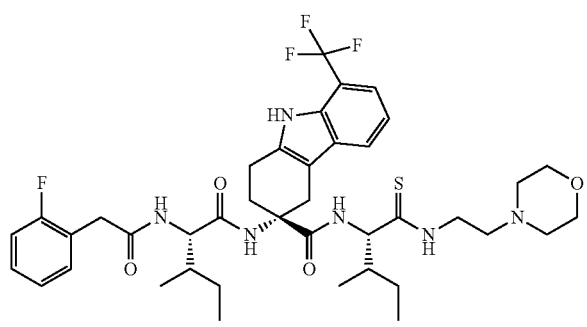 [SMILES: CCC(C)[C@H](NC(=O)Cc1ccccc1F)C(=O)N[C@]1(C(=O)N[C@H](C(=S)NCCN2CCOCC2)C(C)CC)CCc2[nH]c3c(C(F)(F)F)cccc3c2C1]

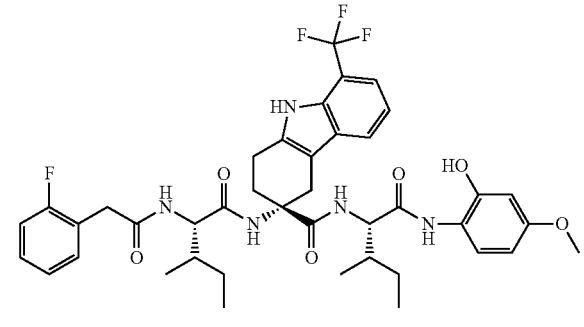 [SMILES: CCC(C)[C@H](NC(=O)Cc1ccccc1F)C(=O)N[C@]1(C(=O)N[C@H](C(=O)Nc2ccc(OC)cc2O)C(C)CC)CCc2[nH]c3c(C(F)(F)F)cccc3c2C1]

Compound 73 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(4-hydroxy-cyclohexylcarbamoyl)-2-methyl-butyl]-amide;

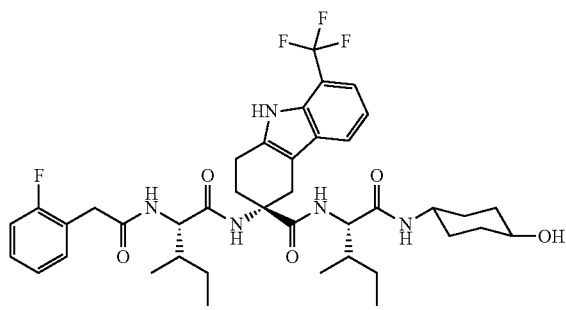 [SMILES: CCC(C)[C@H](NC(=O)Cc1ccccc1F)C(=O)N[C@]1(C(=O)N[C@H](C(=O)NC2CCC(O)CC2)C(C)CC)CCc2[nH]c3c(C(F)(F)F)cccc3c2C1]

Compound 74 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(3-imidazol-1-yl-propylthiocarbamoyl)-2-methyl-butyl]-amide;

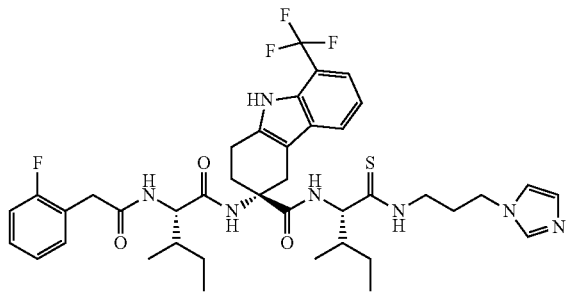 [SMILES: CCC(C)[C@H](NC(=O)Cc1ccccc1F)C(=O)N[C@]1(C(=O)N[C@H](C(=S)NCCCn2ccnc2)C(C)CC)CCc2[nH]c3c(C(F)(F)F)cccc3c2C1]

Compound 114 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(4-[1,2,4]triazol-1-yl-butylthiocarbamoyl)-butyl]-amide;

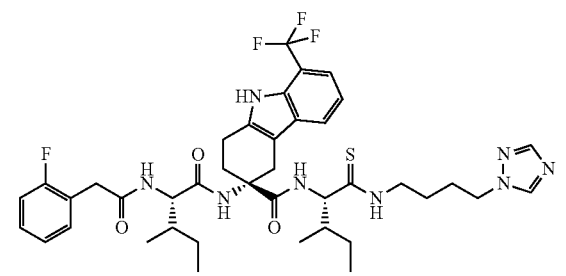 [SMILES: CCC(C)[C@H](NC(=O)Cc1ccccc1F)C(=O)N[C@]1(C(=O)N[C@H](C(=S)NCCCCn2cncn2)C(C)CC)CCc2[nH]c3c(C(F)(F)F)cccc3c2C1]

Compound 118 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(5-methyl-[1,3,4]oxadiazol-2-ylmethyl)-thiocarbamoyl]-butyl}-amide;

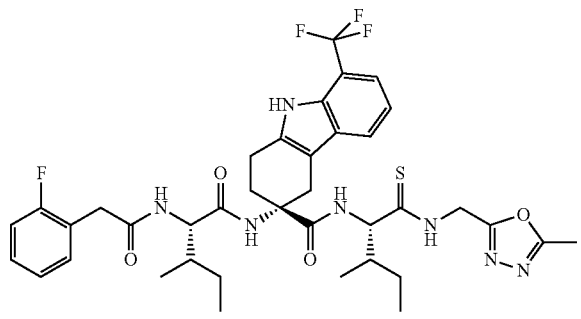 [SMILES: CCC(C)[C@H](NC(=O)Cc1ccccc1F)C(=O)N[C@]1(C(=O)N[C@H](C(=S)NCc2nnc(C)o2)C(C)CC)CCc2[nH]c3c(C(F)(F)F)cccc3c2C1]

Compound 137 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(quinolin-6-ylcarbamoyl)-butyl]-amide;

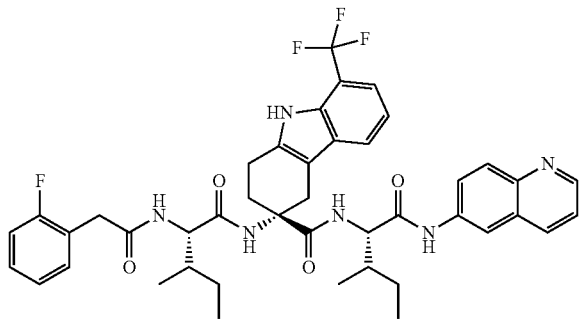 [SMILES: CCC(C)[C@H](NC(=O)Cc1ccccc1F)C(=O)N[C@]1(C(=O)N[C@H](C(=O)Nc2ccc3ncccc3c2)C(C)CC)CCc2[nH]c3c(C(F)(F)F)cccc3c2C1]

Compound 144 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(N'-phenyl-hydrazinocarbonyl)-butyl]-amide;

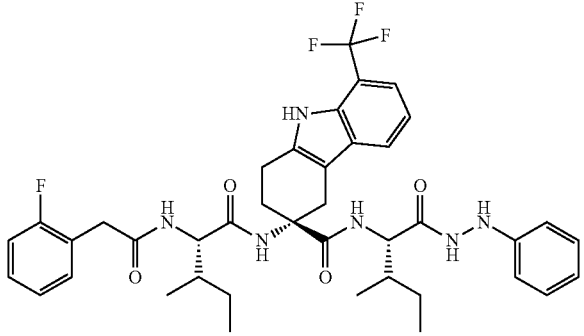 [SMILES: CCC(C)[C@H](NC(=O)Cc1ccccc1F)C(=O)N[C@]1(C(=O)N[C@H](C(=O)NNc2ccccc2)C(C)CC)CCc2[nH]c3c(C(F)(F)F)cccc3c2C1]

Compound 164

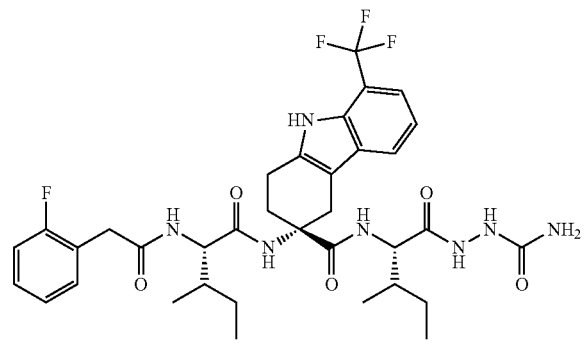 [SMILES: CCC(C)[C@H](NC(=O)Cc1ccccc1F)C(=O)N[C@]1(C(=O)N[C@H](C(=O)NNC(N)=O)C(C)CC)CCc2[nH]c3c(C(F)(F)F)cccc3c2C1]

Compound 167

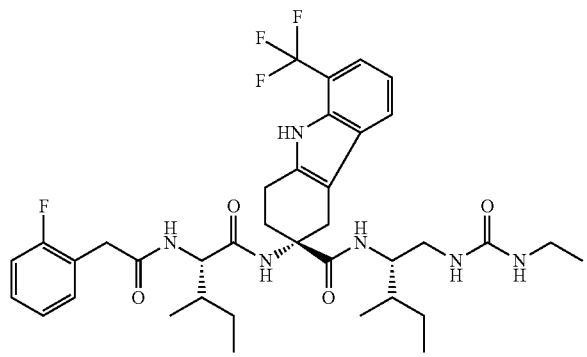 [SMILES: CCNC(=O)NC[C@@H](NC(=O)[C@@]1(NC(=O)[C@@H](NC(=O)Cc2ccccc2F)C(C)CC)CCc2[nH]c3c(C(F)(F)F)cccc3c2C1)C(C)CC]

(R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[(3-ethyl-ureido)-methyl]-2-methyl-butyl}-amide;

Compound 173

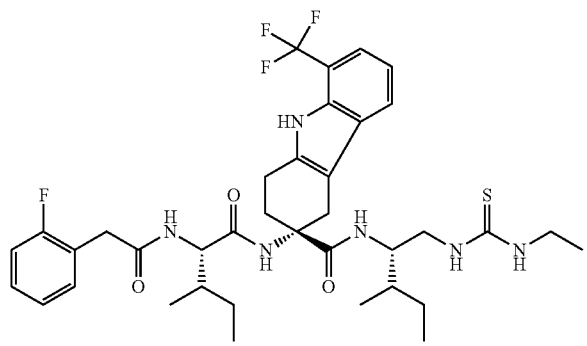 [SMILES: CCNC(=S)NC[C@@H](NC(=O)[C@@]1(NC(=O)[C@@H](NC(=O)Cc2ccccc2F)C(C)CC)CCc2[nH]c3c(C(F)(F)F)cccc3c2C1)C(C)CC]

(R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-1-[(3-ethyl-thioureido)-methyl]-2-methyl-butyl}-amide;

Compound 178

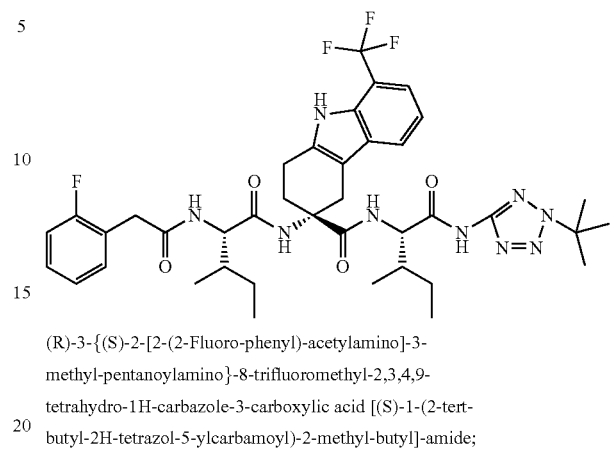

(R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(2-tert-butyl-2H-tetrazol-5-ylcarbamoyl)-2-methyl-butyl]-amide;

Compound 183

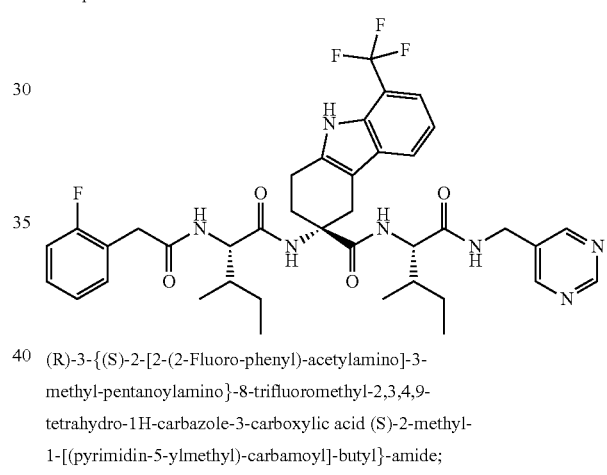

(R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid (S)-2-methyl-1-[(pyrimidin-5-ylmethyl)-carbamoyl]-butyl}-amide;

Compound 188

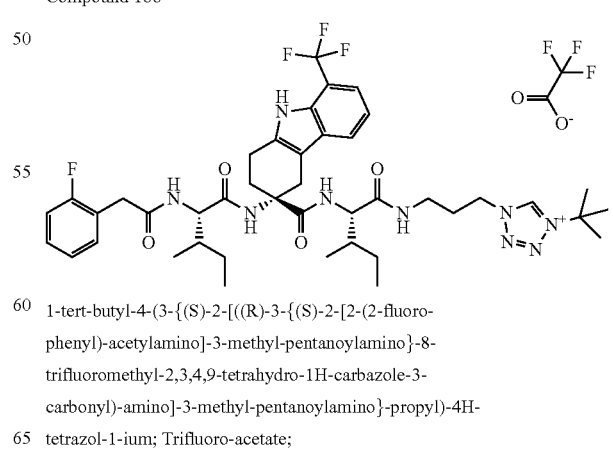

1-tert-butyl-4-(3-{(S)-2-[((R)-3-{(S)-2-[2-(2-fluoro-phenyl)-acetylamino]-3-methyl-pentanoylamino}-8-trifluoromethyl-2,3,4,9-tetrahydro-1H-carbazole-3-carbonyl)-amino]-3-methyl-pentanoylamino}-propyl)-4H-tetrazol-1-ium; Trifluoro-acetate;

Compound 190

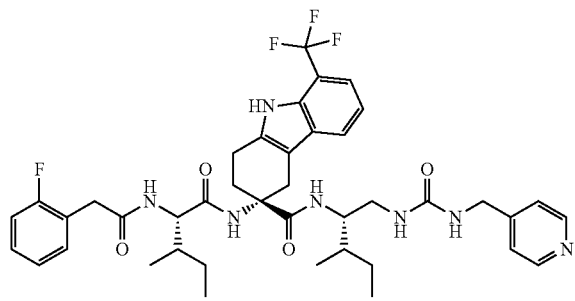 [SMILES: CCC(C)[C@H](NC(=O)Cc1ccccc1F)C(=O)N[C@]1(C(=O)N[C@H](CNC(=O)NCc2ccncc2)C(C)CC)CCc2[nH]c3c(C(F)(F)F)cccc3c2C1]

(R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(3-pyridin-4-ylmethyl-ureidomethyl)-butyl]-amide;

Compound 205

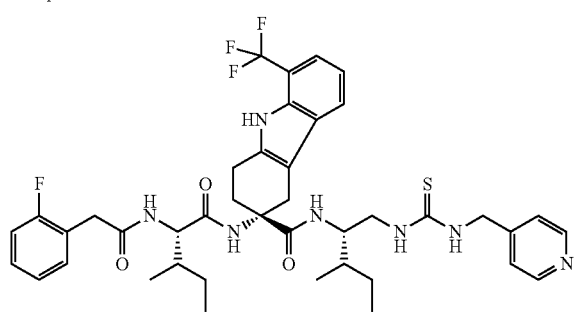

(R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(3-pyridin-4-ylmethyl-thioureidomethyl)-butyl]-amide;

Compound 219

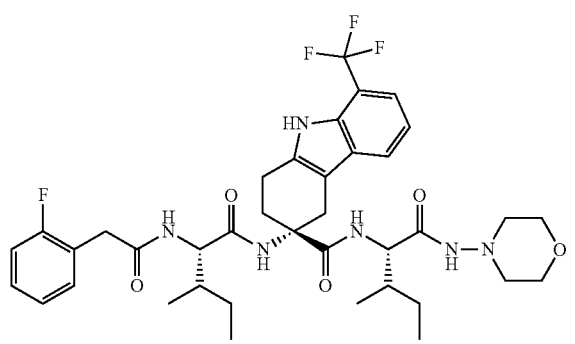 [SMILES: CCC(C)[C@H](NC(=O)Cc1ccccc1F)C(=O)N[C@]1(C(=O)N[C@H](C(=O)NN2CCOCC2)C(C)CC)CCc2[nH]c3c(C(F)(F)F)cccc3c2C1]

(R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-2-methyl-1-(morpholin-4-ylcarbamoyl)-butyl]-amide;

Compound 230

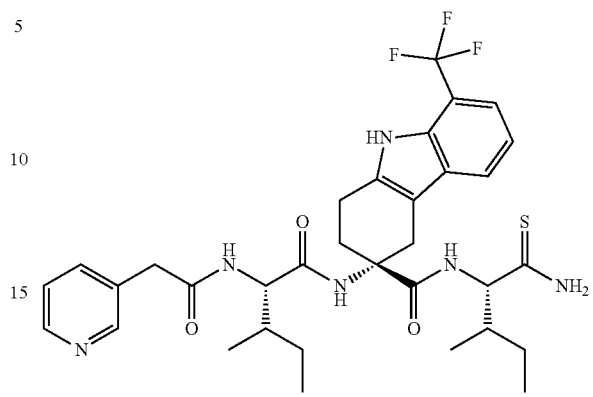

(R)-3-[(S)-3-Methyl-2-(2-pyridin-3-yl-acetylamino)-pentanoylamino]-8-trifluoromethyl-2,3,4,9-tetrahydro-1H-carbazole-3-carboxylic acid ((S)-2-methyl-1-thiocarbamoyl-butyl)-amide;

Compound 236

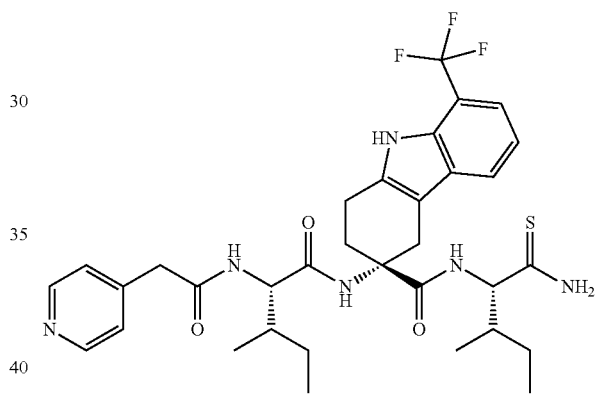

(R)-3-[(S)-3-Methyl-2-(2-pyridin-4-yl-acetylamino)-pentanoylamino]-8-trifluoromethyl-2,3,4,9-tetrahydro-1H-carbazole-3-carboxylic acid ((S)-2-methyl-1-thiocarbamoyl-butyl)-amide;

Compound 239

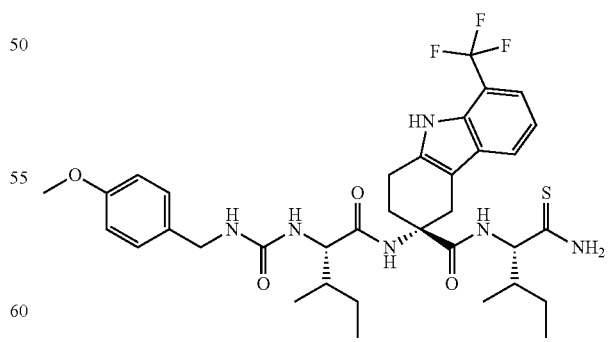

(R)-3-{(S)-2-[3-(4-Methoxy-benzyl)-ureido]-3-methyl-pentanoylamino}-8-trifluoromethyl-2,3,4,9-tetrahydro-1H-carbazole-3-carboxylic acid ((S)-2-methyl-1-thiocarbamoyl-butyl)-amide;

Compound 242

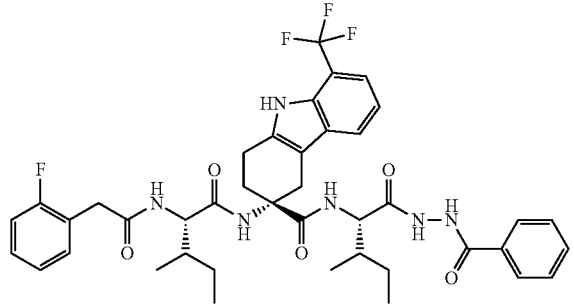 [SMILES: CCC(C)[C@H](NC(=O)Cc1ccccc1F)C(=O)N[C@]1(C(=O)N[C@H](C(=O)NNC(=O)c2ccccc2)C(C)CC)CCc2[nH]c3c(C(F)(F)F)cccc3c2C1]

(R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(S)-1-(N'-benzoyl-hydrazinocarbonyl)-2-methyl-butyl]-amide;

Compound 244

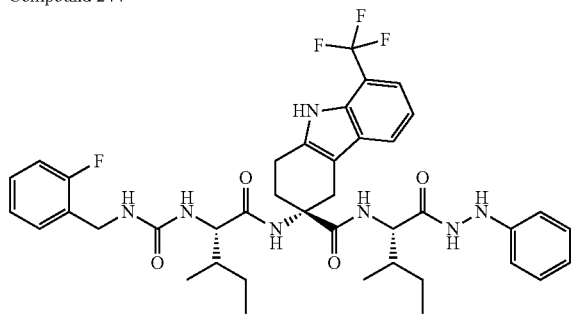

(R)-3-{(S)-2-[3-(2-Fluoro-benzyl)-ureido]-3-methyl-pentanoylamino}-8-trifluoromethyl-2,3,4,9-tetrahydro-1H-carbazole-3-carboxylic acid [(S)-2-methyl-1-(N'-phenyl-hydrazinocarbonyl)-butyl]-amide;

Compound 249

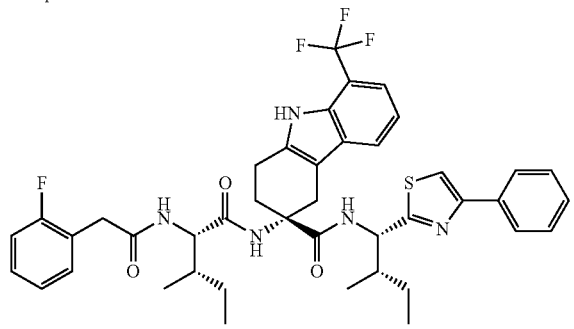

(R)-3-{(2S,3S)-2-[2-(2-Fluoro-phenyl)-acetylamino]-3-methyl-pentanoylamino}-8-trifluoromethyl-2,3,4,9-tetrahydro-1H-carbazole-3-carboxylic acid [(1S,2S)-2-methyl-1-(4-phenyl-thiazol-2-yl)-butyl]-amide;

Compound 250

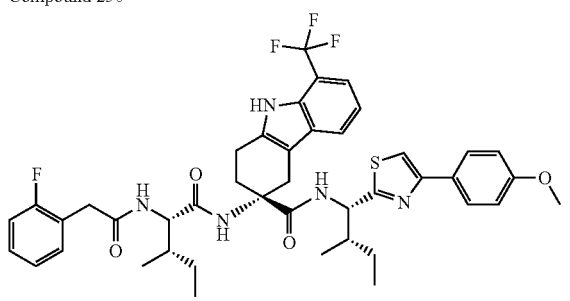

(R)-3-{(2S, 3S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(1S,2S)-1-[4-(4-methoxy-phenyl)-thiazol-2-yl]-2-methyl-butyl}-amide;

Compound 251

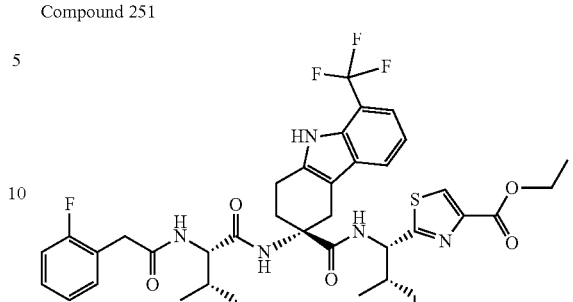

2-{(1R,2S)-1-[((R)-3-{(2S,3S)-2-[2-(2-Fluoro-phenyl)-acetylamino]-3-methyl-pentanoylamino}-8-trifluoromethyl-2,3,4,9-tetrahydro-1H-carbazole-3-carbonyl)-amino]-2-methyl-butyl}-thiazole-4-carboxylic acid ethyl ester;

Compound 256

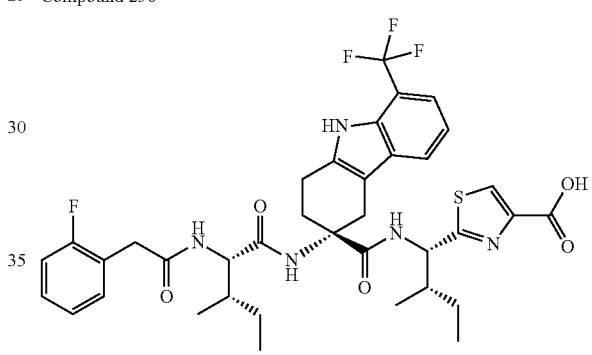

2-{(1S,2S)-1-[((R)-3-{(2S,3S)-2-[2-(2-Fluoro-phenyl)-acetylamino]-3-methyl-pentanoylamino}-8-trifluoromethyl-2,3,4,9-tetrahydro-1H-carbazole-3-carbonyl)-amino]-2-methyl-butyl}-thiazole-4-carboxylic acid; and Compound 258

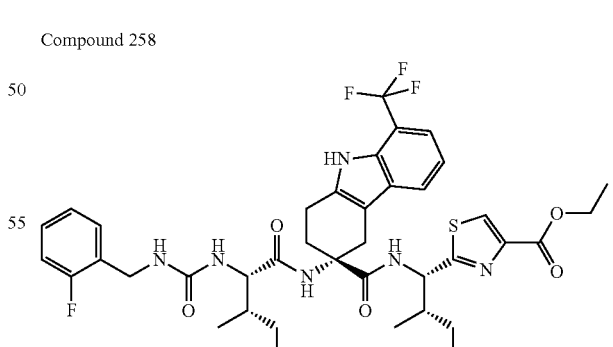

2-{(1S,2S)-1-[((R)-3-{(2S,3S)-2-[3-(2-Fluoro-benzyl)-ureido]-3-methyl-pentanoylamino}-8-trifluoromethyl-2,3,4,9-tetrahydro-1H-carbazole-3-carbonyl)-amino]-2-methyl-butyl}-thiazole-4-carboxylic acid ethyl ester.

2. The method of claim 1, wherein the at least one compound is

Compound 52 (R)-3-{(S)-2-[2-(2-Fluoro-phenyl)-acetylamino]-3-methyl-pentanoylamino}-8-trifluoromethyl-2,3,4,9-tetrahydro-1H-carbazole-3-carboxylic acid {(S)-2-methyl-1-[(tetrahydro-pyran-4-ylmethyl)-thiocarbamoyl]-butyl}-amide.

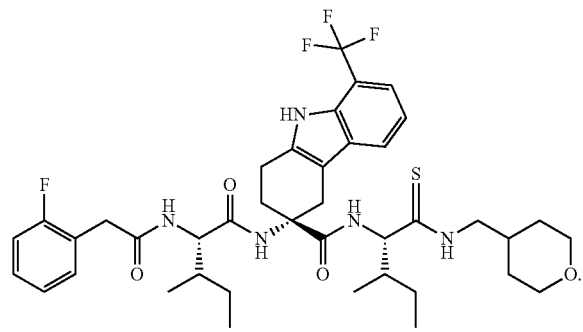 [SMILES: CCC(C)[C@H](NC(=O)Cc1ccccc1F)C(=O)N[C@]1(C(=O)N[C@H](C(=S)NCC2CCOCC2)C(C)CC)CCc2[nH]c3c(C(F)(F)F)cccc3c2C1]

3. The method of claim 1, where the at least one compound is administered in a unit dose of from 0.001 mg to 100 mg per kg of body weight of the subject.

4. The method of claim 1, where the at least one compound is administered in a unit dose of from 0.001 mg to 100 mg per kg of body weight of the subject.

5. The method of claim 2, wherein the condition is a benign tumor disease.

6. The method of claim 2, wherein the condition is a malignant tumor disease.

7. The method of claim 2, wherein the condition is male fertility control.

8. The method of claim 2, wherein the condition is controlled ovarian stimulation in in vitro fertilization (COS/ART).

9. The method of claim 2, wherein the condition is prostate cancer.

10. The method of claim 2, wherein the condition is breast cancer.

11. The method of claim 2, wherein the condition is endometrial cancer.

12. The method of claim 2, wherein the condition is ovarian cancer.

13. The method of claim 2, wherein the condition is benign prostate hyperplasia (BPH).

14. The method of claim 2, wherein the condition is endometriosis.

15. The method of claim 2, wherein the condition is uterine fibroids.

16. The method of claim 2, wherein the condition is uterine myomas.

17. The method of claim 2, wherein the condition is endometrium hyperplasia.

18. The method of claim 2, wherein the condition is pubertas praecox.

19. The method of claim 2, wherein the condition is polycystic ovary syndrome.

20. The method of claim 2, wherein the condition is a hormone-dependent tumor disease.

* * * * *